United States Patent [19]
Baker et al.

[11] Patent Number: 5,783,593
[45] Date of Patent: Jul. 21, 1998

[54] INHIBITORS OF SQUALENE SYNTHETASE AND PROTEIN FARNESYLTRANSFERASE

[75] Inventors: William R. Baker, Bellevue, Wash.; Saul H. Rosenberg, Grayslake, Ill.; Anthony K. L. Fung, Gurnee, Ill.; Todd W. Rockway, Grayslake, Ill.; Stephen A. Fakhoury, Mundelein, Ill.; David S. Garvey, Dover, Mass.; B. Gregory Donner, Mundelein, Ill.; Stephen J. O'Connor, Wilmette, Ill.; Rajnandan N. Prasad, Vernon Hills, Ill.; Wang Shen, Skokie, Ill.; David M. Stout, Mettawa, Ill.; Gerard M. Sullivan, Round Lake Beach, Ill.

[73] Assignee: Abbott Laboratories, Abbott Park, Ill.

[21] Appl. No.: 633,262

[22] Filed: Apr. 29, 1996

Related U.S. Application Data

[63] Continuation-in-part of Ser. No. 429,095, May 3, 1995, abandoned, which is a continuation-in-part of Ser. No. 322,783, Oct. 18, 1994, abandoned, which is a continuation-in-part of Ser. No. 289,711, Aug. 12, 1994, abandoned, which is a continuation-in-part of Ser. No. 147,708, Nov. 4, 1993, abandoned.

[51] Int. Cl.$^6$ .................. A61K 31/16; A61K 31/19; A61K 31/215; A61K 31/41
[52] U.S. Cl. .................. 514/381; 514/18; 514/19; 514/533; 514/542; 514/557; 514/559; 514/561; 514/562; 514/563; 514/572; 514/613; 514/616; 514/617; 514/619; 514/621; 514/729; 530/330; 530/331; 548/251; 548/253; 548/254; 560/19; 560/37; 560/45; 560/48; 560/49; 560/76; 560/123; 562/405; 562/426; 562/433; 562/442; 562/443; 562/452; 562/465; 562/480; 562/488; 562/489; 562/505; 562/553; 562/607; 564/57; 564/152; 564/153; 564/155; 564/161; 564/163; 564/164; 564/169; 564/180
[58] Field of Search .................. 514/18, 19, 381, 514/533, 542, 557, 559, 561, 562, 563, 572, 613, 616, 617, 619, 621, 729; 530/330, 331; 548/251, 253, 254; 560/19, 37, 45, 48, 49, 76, 123; 562/405, 426, 433, 442, 443, 452, 465, 480, 488, 489, 505, 553, 607; 564/57, 152, 153, 155, 161, 163, 164, 169, 180

[56] References Cited

U.S. PATENT DOCUMENTS

| | | | |
|---|---|---|---|
| 3,236,801 | 2/1966 | Rhum et al. | 524/285 |
| 3,720,712 | 3/1973 | Largman | 564/155 |
| 3,786,156 | 1/1974 | Rynbrandt et al. | 514/530 |
| 4,202,902 | 5/1980 | Carr et al. | 514/519 |
| 4,220,795 | 9/1980 | Kluender et al. | 560/118 |
| 4,340,715 | 7/1982 | Gounder et al. | 528/99 |
| 4,349,564 | 9/1982 | Bühler et al. | 514/421 |
| 4,387,106 | 6/1983 | De Vries et al. | 564/49 |
| 5,025,003 | 6/1991 | Biller | 514/120 |
| 5,064,961 | 11/1991 | Bisacchi et al. | 544/276 |
| 5,095,136 | 3/1992 | Biller et al. | 560/124 |
| 5,102,907 | 4/1992 | Bergstrom et al. | 514/456 |
| 5,130,462 | 7/1992 | Slusarchyk et al. | 558/58 |
| 5,245,061 | 9/1993 | Singh et al. | 554/121 |
| 5,260,465 | 11/1993 | Singh et al. | 554/134 |
| 5,260,479 | 11/1993 | Singh et al. | 560/190 |
| 5,631,401 | 5/1997 | Stein et al. | 562/451 |

FOREIGN PATENT DOCUMENTS

| | | |
|---|---|---|
| 0448393 | 9/1991 | European Pat. Off. . |
| 0503520 | 9/1992 | European Pat. Off. . |
| 526936 | 2/1993 | European Pat. Off. . |
| 0611749 | 8/1994 | European Pat. Off. . |
| 9212158 | 7/1992 | WIPO . |
| 9418167 | 8/1994 | WIPO . |
| 9422870 | 10/1994 | WIPO . |
| 9504025 | 2/1995 | WIPO . |
| 9521815 | 8/1995 | WIPO . |

OTHER PUBLICATIONS

CA67:100098q Hydrogenolysis . . . borohydride, Kunieda et al., p. 9417, 1967.
CA75:76726K Hydrogenolysis . . . thymidine, Witkop, et al. p. 461, 1971.
J.A. Moore, Chemistry of Materials, (1989) vol. 1, 163–166 "An Intrinsically Photosensitive Polyimide".
Richter et al, Synthesis of trans/syn– and trans/anti–Dimeric Uracil. Angew. Chem. Int. Edit., vol. 8, No. 3, 1969, pp. 208–209.
Nakanishi et al. Aliphatic poly(amino acids) and polymides . . . Polymer, Sep. 1973, vol. 14, pp. 440–444.
Kuneida et al. Hydrogenolysis of Thymine Dimer to Cyclobutanes . . . J. Am. Chem. Soc. 02 Aug. 1967, vol. 89, No. 16, pp. 4232–4233.

*Primary Examiner*—Jeffrey E. Russel
*Attorney, Agent, or Firm*—Gregory W. Steele; Steven R. Crowley

[57] ABSTRACT

The present invention provides a compound of the formula

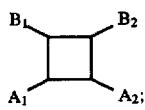

which inhibit squalene synthetase and cholesterol biosynthesis and are useful in the treatment of e.g., hyperlipidaemia, atherosclerosis, or fungal infections, processes for the preparation of the compounds of the invention, intermediates useful in these processes, and pharmaceutical compositions containing the compounds.

26 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE:
( A ) DESCRIPTION: peptide ( x i ) SEQUENCE DESCRIPTION: SEQ ID NO:1:

Lys Lys Ser Lys Thr Lys Cys Val Ile Met
1               5                   1 0

INHIBITORS OF SQUALENE SYNTHETASE AND PROTEIN FARNESYLTRANSFERASE

This is a continuation-in-part of U.S. patent application Ser. No. 08/429,095, filed May 3, 1995, now abandoned, which is a continuation-in-part of U.S. patent application Ser. No. 322,783, filed Oct. 18, 1994, now abandoned, which is a continuation-in-part of U.S. patent application Ser. No. 289,711, filed Aug. 12, 1994, now abandoned, which is a continuation-in-part of U.S. patent application Ser. No. 147,708, filed Nov. 4, 1993, now abandoned.

TECHNICAL FIELD

The present invention relates to new cyclobutane dicarboxylic acid compounds which are useful in inhibiting de novo squalene production or inhibiting protein farnesyltransferase and the farnesylation of the oncogene protein Ras or inhibiting fungal growth and to chemotherapeutic, antifungal, hypolipidaemic and antiatherosclerotic compositions containing such compounds and to a method of using such compounds for inhibiting cholesterol biosynthesis and atherosclerosis, for inhibiting protein farnesyl-transferase and the farnesylation of the oncogene protein Ras and as antifungals.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate, reduced form, (NADPH) to form squalene (Poulter, C. D., Rilling, H. C., in "Biosynthesis of Isoprenoid Compounds", Vol. I, Chapter 8, pp. 413–441, J. Wiley and Sons, 1981 and references therein). This enzyme is the first committed step of the de novo cholesterol biosynthetic pathway. Thus inhibition of squalene synthetase will lead to inhibition of cholesterol biosynthesis and thus will act as a hypocholesterolemic. Thus squalene synthetase inhibitors ultimately should be useful for the treatment and prevention of hyperlipidaemia or atherosclerosis or other disorders resulting from an excess of cholesterol.

Transformed protein Ras is involved in the proliferation of cancer cells. The Ras must be farnesylated before this proliferation can occur. Farnesylation of Ras by farnesyl pyrophosphate (FPP) is effected by protein farnesyltransferase. Inhibition of protein farnesyltransferase and, thereby, of farnesylation of the Ras protein, blocks the ability of transformed cells to proliferate.

Activation of Ras also partially mediates smooth muscle cell proliferation (Circulation), I-3: 88 (1993). Inhibition of protein farnesyltransferase and, thereby, of farnesylation of the Ras protein, would aid in the prevention of restenosis.

Inhibition of squalene synthetase also results in the inhibition of fungal growth.

DISCLOSURE OF THE INVENTION

In accordance with the present invention there are provided substituted cyclobutanes of formula (I):

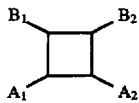

(1)

wherein $A_1$ and $A_2$ are independently selected from (1) —X—C(O)—G or —X—C(S)—G wherein at each occurrence X is independently selected from (a) a covalent bond, (b) —$CH_2$—, (c) —O—, (d) —S— and (e) —N($R_a$)— wherein $R_a$ is hydrogen, loweralkyl, cycloalkyl or cycloalkylalkyl and at each occurrence G is independently selected from —$R_2$, —N($R_1$)($R_2$), —$OR_2$ and —$SR_2$ wherein at each occurrence $R_1$ is independently selected from (a) hydrogen, (b) loweralkyl, (c) alkenyl, (d) alkynyl, (e) cycloalkyl, (f) cycloalkylalkyl, (g) alkoxycarbonylalkyl, (h) alkoxyalkyl, (i) thioalkoxyalkyl, (j) haloalkyl, (k) aryl, (l) heterocyclic, (m) arylalkyl, (n) aryl-substituted cycloalkylalkyl, (o) (heterocyclic)alkyl, (p) heterocyclic-substituted cycloalkylalkyl and (q) aryl, heterocyclic, arylalkyl, aryl-substituted cycloalkylalkyl, (heterocyclic)alkyl or heterocyclic-substituted cycloalkylalkyl wherein the aryl group, the aryl part of the arylalkyl group, the aryl part of the aryl-substituted cycloalkylalkyl group, the heterocyclic group, the heterocyclic part of the (heterocyclic)alkyl group or the heterocyclic part of the heterocyclic-substituted cycloalkylalkyl group is substituted with —Y—$R_3$ wherein at each occurrence Y is independently selected from (i) a covalent bond, (ii) —C(O)—, (iii) —$CH_2$—, (iv) —O—, (v) —S(O)$_m$— wherein m is 0, 1 or 2, (vi) —N($R_b$)— wherein $R_b$ is hydrogen or loweralkyl, (vii) —$CH_2$O—, (viii) —$CH_2$S(O)$_m$— wherein m is 0, 1 or 2, and (ix) —$CH_2$N($R_b$)— wherein $R_b$ is hydrogen or loweralkyl and at each occurrence $R_3$ is independently selected from (i) aryl, (ii) arylalkyl, (iii) cycloalkyl, (iv) cycloalkylalkyl, (v) heterocyclic and (vi) (heterocyclic)alkyl and at each occurrence $R_2$ is independently selected from (i) alkenyl, (ii) alkynyl, (iii) aryl, (iv) arylalkyl, (v) arylalkenyl, (vi) heterocyclic, (vii) (heterocyclic)alkyl and (viii) aryl, heterocyclic, arylalkyl or (heterocyclic)alkyl wherein the aryl group, the aryl part of the arylalkyl group, the heterocyclic group or the heterocyclic part of the (heterocyclic)alkyl group is substituted with —Z—$R_4$ wherein at each occurrence Z is independently selected from (i) a covalent bond, (ii) —C(O)—, (iii) —$CH_2$—, (iv) —O—, (v) —S(O)$_p$— wherein p is 0, 1 or 2, (vi) —N($R_c$)— wherein $R_c$ is hydrogen or loweralkyl, (vii) —$CH_2$O—, (viii) —$CH_2$S(O)$_p$— wherein p is 0, 1 or 2 and (ix) —$CH_2$N($R_c$)— wherein $R_c$ is hydrogen or loweralkyl and at each occurrence $R_4$ is independently selected from (i) aryl, (ii) arylalkyl, (iii) cycloalkyl, (iv) cycloalkylalkyl, (v) heterocyclic and (vi) (heterocyclic)alkyl and (2) —(CH$_2$)$_q$—N(R$_1$)(R$_2$) wherein q is 0, 1 or 2 and at each occurrence $R_1$ and $R_2$ are independently defined as above; and $B_1$ and $B_2$ are independently selected from (1) —$CH_2$OH or —$CH_2CH_2$OH, (2) —CH=NOH, —CHO or —$CH_2$CHO, (3) —W—$R_5$ wherein at each occurrence W is independently selected from (a) a covalent bond, (b) alkylene, (c) alkenylene, (d) —C(O)NH— and (e) —NHC(O)NH— and $R_5$ is independently selected from 5-tetrazolyl, (a)

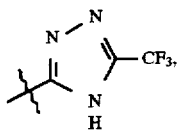 (b)

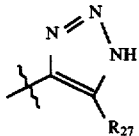 (c)

wherein R$_{27}$ is —CN, —NO$_2$, or —CO$_2$R$_{28}$ wherein R$_{28}$ is hydrogen, aryl or loweralkyl,

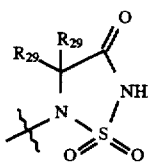 (d)

wherein at each occurrence R$_{29}$ is selected from hydrogen and loweralkyl,

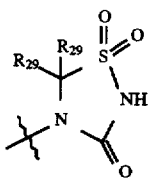 (e)

wherein R$_{29}$ is as defined above,

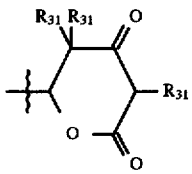 (f)

wherein at each occurrence R$_{31}$ is selected from hydrogen, loweralkyl, alkenyl, alkoxyalkyl and benzyl,

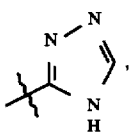 (g)

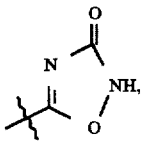 (h)

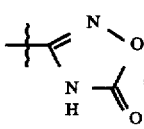 (i)

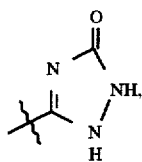 (j)

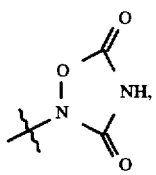 (k)

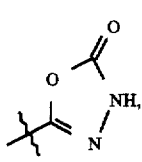 (l)

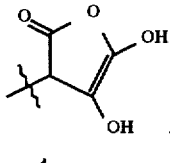 (m)

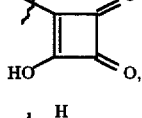, and

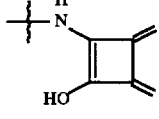 (n)

 (4)

(5) —Q—C(O)R$_6$ wherein at each occurrence Q is independently selected from (a) a covalent bond, (b) alkylene, (c) alkenylene, (d) —CH(OH)— and (e) —NHC(O)(CH$_2$)$_r$— wherein r is 0 to 4 and at each occurrence R$_6$ is independently selected from (a) —OR$_7$ wherein R$_7$ is hydrogen or a carboxy-protecting group, (b) —NH$_2$, (c) —NHOH, (d) —NHSO$_2$CF$_3$ (e) an alpha-amino acid or a beta-amino acid which is bonded via the alpha- or beta-amino group and (f) a di-, tri- or tetra-peptide which is bonded via the amino terminal amino group, (6) —CH$_2$—N(OH)—C(O)—R$_{25}$ wherein R$_{25}$ is hydrogen, methyl or trifluoromethyl, and (7) —C(O)—NH—S(O)$_2$—R$_{26}$ wherein R$_{26}$ is aryl, heterocyclic, arylalkyl, (heterocyclic)alkyl, C$_3$-C$_7$-cycloalkyl, C$_1$-C$_8$-alkyl or perfluoro-C$_1$-C$_4$-alkyl, or a pharmaceutically acceptable salt thereof.

Preferred compounds of the invention are compounds of formula (II):

 (II)

wherein A$_1$, A$_2$, B$_1$ and B$_2$ are defined as above;
or a pharmaceutically acceptable salt thereof.

Preferred compounds of the invention are compounds of formula (I) or (II) wherein A$_1$ and A$_2$ are independently selected from —C(O)—G wherein G is defined as above and B$_1$ and B$_2$ are independently selected from (a) —W—R$_5$ wherein W is a covalent bond or alkylene and R$_5$ is 5-tetrazolyl or

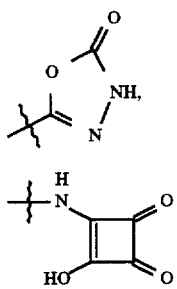

and (c) —Q—C(O)—R$_6$ wherein at each occurrence Q is independently selected from a covalent bond and alkylene and at each occurrence R$_6$ is independently selected from (1) —OR$_7$ wherein R$_7$ is hydrogen or a carboxy-protecting group, (2) an alpha-amino acid or a beta-amino acid which is bonded via the alpha- or beta-amino group and (3) a di-, tri- or tetra-peptide which is bonded via the amino terminal amino group.

More preferred compounds of the invention are compounds of formula (I) or (II) wherein A$_1$ and A$_2$ are independently selected from —C(O)—G wherein G is —N(R$_1$)(R$_2$) wherein R$_1$ and R$_2$ are as defined above and B$_1$ and B$_2$ are independently selected from (a) —W—R$_5$ wherein W is a covalent bond or alkylene and R$_5$ is 5-tetrazolyl or

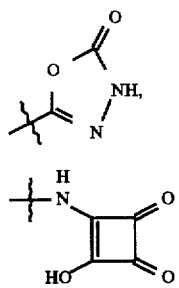

and (c) —Q—C(O)—R$_6$ wherein at each occurrence Q is independently selected from a covalent bond and alkylene and at each occurrence R$_6$ is independently selected from (1) —OR$_7$ wherein R$_7$ is hydrogen or a carboxy-protecting group, (2) an alpha-amino acid or a beta-amino acid which is bonded via the alpha- or beta-amino group and (3) a di-, tri- or tetra-peptide which is bonded via the amino terminal amino group.

Even more preferred compounds of the invention are compounds of formula (I) or (II) wherein A$_1$ and A$_2$ are independently selected from —C(O)—G wherein G is —N(R$_1$)(R$_2$) wherein R$_1$ is independently selected from (a) hydrogen, (b) loweralkyl, (c) cycloalkyl, (d) cycloalkylalkyl, (e) alkoxyalkyl, (f) thioalkoxyalkyl, (g) aryl, (h) heterocyclic, (i) arylalkyl, (j) (heterocyclic)alkyl, (k) aryl-substituted cycloalkylalkyl, (l) heterocyclic-substituted cycloalkylalkyl and (m) aryl, heterocyclic, arylalkyl, (heterocyclic)alkyl, aryl-substituted cycloalkylalkyl or heterocyclic-substituted cycloalkylalkyl wherein the aryl group, the aryl part of the arylalkyl group, the aryl part of the aryl-substituted cycloalkylalkyl, the heterocyclic group, the heterocyclic part of the (heterocyclic)alkyl group or the heterocyclic part of the heterocyclic-substituted cycloalkylalkyl group is substituted with —Y—R$_3$ wherein at each occurrence Y is independently selected from (i) —O—, (ii) —S(O)$_m$— wherein m is 0, 1 or 2 and (iii) —N(R$_b$)— wherein R$_b$ is hydrogen or loweralkyl and at each occurrence R$_3$ is independently selected from (i) aryl, (ii) arylalkyl, (iii) cycloalkyl, (iv) cycloalkylalkyl, (v) heterocyclic and (vi) (heterocyclic)alkyl and at each occurrence R$_2$ is independently selected from aryl, heterocyclic, arylalkyl and (heterocyclic)alkyl wherein the aryl group, aryl part of the arylalkyl group, heterocyclic group or heterocyclic part of the (heterocyclic)alkyl group is substituted with —Z—R$_4$ wherein at each occurrence Z is independently selected from (i) —O—, (ii) —S(O)$_p$— wherein p is 0, 1 or 2 and (iii) —N(R$_c$)— wherein R$_c$ is hydrogen or loweralkyl and at each occurrence R$_4$ is independently selected from (i) aryl, (ii) arylalkyl, (iii) cycloalkyl, (iv) cycloalkylalkyl, (v) heterocyclic and (vi) (heterocyclic)alkyl and B$_1$ and B$_2$ are independently selected from (a) —W—R$_5$ wherein W is a covalent bond or alkylene and R$_5$ is 5-tetrazolyl or

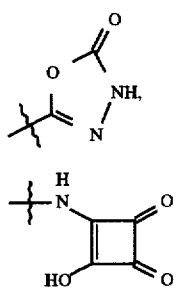

and (c) —Q—C(O)—R$_6$ wherein at each occurrence Q is independently selected from a covalent bond and alkylene and at each occurrence R$_6$ is independently selected from (1) —OR$_7$ wherein R$_7$ is hydrogen or a carboxy-protecting group, (2) an alpha-amino acid or a beta-amino acid which is bonded via the alpha- or beta-amino group and (3) a di-, tri- or tetra-peptide which is bonded via the amino terminal amino group.

Yet even more preferred compounds of the invention are compounds of formula (I) or (II) wherein A$_1$ and A$_2$ are independently selected from —C(O)—G wherein G is —N(R$_1$)(R$_2$) wherein at each occurrence R$_1$ is independently selected from (a) loweralkyl, (b) cycloalkyl and (c) cycloalkylalkyl and at each occurrence R$_2$ is independently selected from aryl and arylalkyl wherein the aryl group or aryl part of the arylalkyl group is substituted with —Z—R$_4$ wherein at each occurrence Z is independently selected from (i) —O— and (ii) —S— and at each occurrence R$_4$ is independently selected from (i) aryl, (ii) arylalkyl, (iii) cycloalkyl, (iv) cycloalkylalkyl, (v) heterocyclic and (vi) (heterocyclic)alkyl and B$_1$ and B$_2$ are independently selected from —Q—C(O)—R$_6$, —W—R$_5$ and

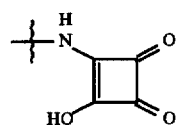

wherein at each occurrence Q and W are independently selected from a covalent bond and alkylene, R$_6$ is —OR$_7$ wherein R$_7$ is hydrogen or a carboxy-protecting group and R$_5$ is 5-tetrazolyl or

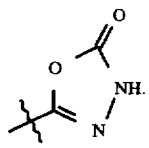

Most preferred compounds of the invention are compounds of formula (I) or (II) wherein $A_1$ and $A_2$ are independently selected from —C(O)—G wherein G is —N($R_1$)($R_2$) wherein at each occurrence $R_1$ is independently selected from (a) loweralkyl, (b) cycloalkyl and (c) cycloalkylalkyl and at each occurrence $R_2$ is independently selected from phenyl and benzyl wherein the phenyl group or the phenyl ring of the benzyl group is substituted with —Z—$R_4$ wherein at each occurrence Z is independently selected from (i) —O— and (ii) —S— and at each occurrence $R_4$ is independently selected from (i) aryl, (ii) arylalkyl, (iii) heterocyclic and (iv) (heterocyclic)alkyl and $B_1$ and $B_2$ are independently selected from —Q—C(O)—$R_6$, —W—$R_5$ and

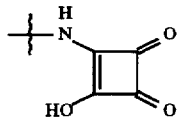

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

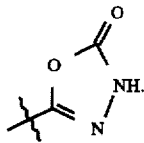

Most highly preferred compounds of the invention are compounds of formula (I) or (II) wherein $A_1$ and $A_2$ are independently selected from —C(O)—G wherein G is —N($R_1$)($R_2$) wherein at each occurrence $R_1$ is independently selected from (a) loweralkyl, (b) cycloalkyl and (c) cycloalkylalkyl and $R_2$ is benzyl wherein the phenyl ring of the benzyl group is substituted with —Z—$R_4$ wherein at each occurrence Z is independently selected from (i) —O— and (ii) —S— and $R_4$ is aryl and $B_1$ and $B_2$ are independently selected from —Q—C(O)—$R_6$, —W—$R_5$ and

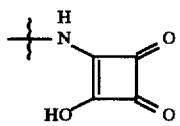

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

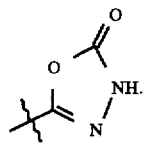

Other most highly preferred compounds of the invention are compounds of formula (I) or (II) wherein $A_1$ and $A_2$ are independently selected from —C(O)—G wherein G is —N($R_1$)($R_2$) wherein at each occurrence $R_1$ is (a) loweralkyl, (b) cycloalkyl and (c) cycloalkylalkyl and $R_2$ is benzyl wherein the phenyl ring of the benzyl group is substituted with —Z—$R_4$ wherein at each occurrence Z is independently selected from (i) —O— and (ii) —S— and $R_4$ is heterocyclic and $B_1$ and $B_2$ are independently selected from —Q—C(O)—$R_6$, —W—$R_5$ and

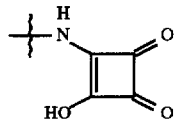

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

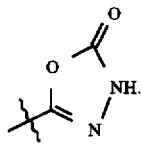

Another aspect of this invention relates to the use of compounds of the formula:

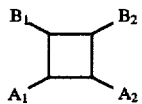 (III)

or

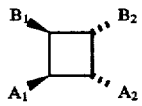 (IV)

wherein $A_1$ and $A_2$ are independently selected from —X—C(O)—G or —X—C(S)—G wherein at each occurrence X is independently selected from (a) a covalent bond, (b) —$CH_2$—, (c) —O—, (d) —S— and (e) —N($R_a$)— wherein $R_a$ is hydrogen, loweralkyl, cycloalkyl or cycloalkylalkyl and at each occurrence G is independently selected from —$R_2$, —N($R_1$)($R_2$), —$OR_2$ and —$SR_2$ wherein at each occurrence $R_1$ is independently selected from (a) hydrogen, (b) loweralkyl, (c) alkenyl, (d) alkynyl, (e) cycloalkyl, (f) cycloalkylalkyl, (g) alkoxycarbonylalkyl, (h) alkoxyalkyl, (i) thioalkoxyalkyl, (j) haloalkyl, (k) aryl, (l) heterocyclic, (m) arylalkyl, (n) aryl-substituted cycloalkylalkyl, (o) (heterocyclic)alkyl, (p) heterocyclic-substituted cycloalkylalkyl and (q) aryl, heterocyclic, arylalkyl, aryl-substituted cycloalkylalkyl, (heterocyclic)alkyl or heterocyclic-substituted cycloalkylalkyl wherein the aryl group, the aryl part of the arylalkyl group, the aryl part of the aryl-substituted cycloalkylalkyl group, the heterocyclic group, the heterocyclic part of the (heterocyclic)alkyl group or the heterocyclic part of the heterocyclic-substituted cycloalkylalkyl group is substituted with —Y—$R_3$ wherein at each occurrence Y is independently selected from (i) a covalent bond, (ii) —C(O)—, (iii) —$CH_2$—, (iv) —O—, (v) —S(O)$_m$— wherein m is 0, 1 or 2, (vi) —N($R_b$)— wherein $R_b$ is hydrogen or loweralkyl, (vii) —$CH_2$O—, (viii) —$CH_2$S(O)$_m$— wherein m is 0, 1 or 2, and (ix) —$CH_2$N($R_b$)— wherein $R_b$ is hydrogen or loweralkyl and at each occurrence $R_3$ is independently selected from (i) aryl, (ii) arylalkyl, (iii) cycloalkyl, (iv) cycloalkylalkyl, (v) heterocyclic and (vi) (heterocyclic) alkyl and at each occurrence $R_2$ is independently selected from (i) alkenyl, (ii) alkynyl, (iii) aryl, (iv) arylalkyl, (v) arylalkenyl, (vi) heterocyclic, (vii) (heterocyclic)alkyl and (viii) aryl, heterocyclic, arylalkyl or (heterocyclic)alkyl wherein the aryl group, the aryl part of the arylalkyl group, the heterocyclic group or the heterocyclic part of the (heterocyclic)alkyl group is substituted with —Z—$R_4$ wherein at each occurrence Z is independently selected from (i) a covalent bond, (ii) —C(O)—, (iii) —$CH_2$—, (iv) —O—, (v) —S(O)$_p$— wherein p is 0, 1 or 2, (vi) —N($R_c$)— wherein $R_c$ is hydrogen or loweralkyl, (vii) —$CH_2$O—, (viii) —$CH_2$S(O)$_p$— wherein p is 0, 1 or 2 and (ix) —$CH_2$N($R_c$)— wherein $R_c$ is hydrogen or loweralkyl and at each occurrence $R_4$ is independently selected from (i) aryl, (ii) arylalkyl, (iii) cycloalkyl, (iv) cycloalkylalkyl, (v) heterocyclic and (vi) (heterocyclic)alky; and $B_1$ and $B_2$ are independently selected from
(1) —$CH_2$OH or —$CH_2CH_2$OH,
(2) —CH=NOH, —CHO or —$CH_2$CHO,
(3) —W—$R_5$ wherein at each occurrence W is independently selected from (a) a covalent bond, (b) alkylene, (c) alkenylene, (d) —C(O)NH— and (e) —NHC(O)NH— and $R_5$ is independently selected from 5-tetrazolyl, (a)

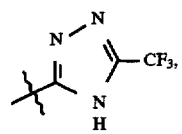

(b)

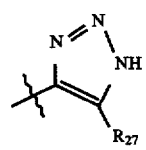

(c)

wherein $R_{27}$ is —CN, —$NO_2$, or —$CO_2R_{28}$ wherein $R_{28}$ is hydrogen, aryl or loweralkyl,

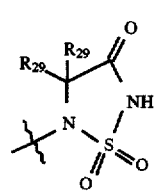

(d)

wherein at each occurrence $R_{29}$ is selected from hydrogen and loweralkyl,

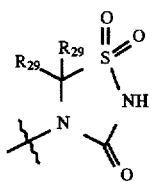

(e)

wherein $R_{29}$ is as defined above,

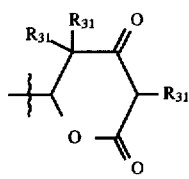

(f)

wherein at each occurrence $R_{31}$ is selected from hydrogen, loweralkyl, alkenyl, alkoxyalkyl and benzyl,

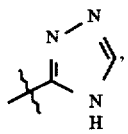

(g)

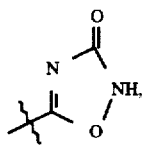

(h)

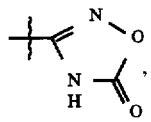

(i)

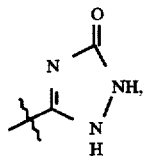

(j)

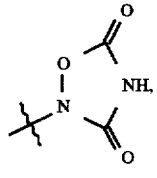

(k)

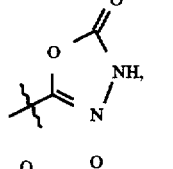

(l)

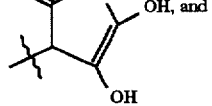

(m)

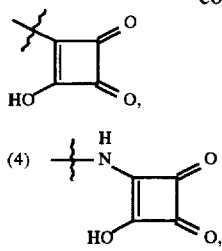

(5) —Q—C(O)R$_6$ wherein at each occurrence Q is independently selected from (a) a covalent bond, (b) alkylene, (c) alkenylene, (d) —CH(OH)— and (e) —NHC(O)(CH$_2$)$_r$— wherein r is 0 to 4 and at each occurrence R$_6$ is independently selected from (a) —OR$_7$ wherein R$_7$ is hydrogen or a carboxy-protecting group, (b) —NH$_2$, (c) —NHOH, (d) —NHSO$_2$CF$_3$ (e) an alpha-amino acid or a beta-amino acid which is bonded via the alpha- or beta-amino group and (f) a di-, tri- or tetra-peptide which is bonded via the amino terminal amino group, (6) —CH$_2$—N(OH)—C(O)—R$_{25}$ wherein R$_{25}$ is hydrogen, methyl or trifluoromethyl, and (7) —C(O)—NH—S(O)$_2$—R$_{26}$ wherein R$_{26}$ is aryl, heterocyclic, arylalkyl, (heterocyclic)alkyl, C$_3$–C$_7$-cycloalkyl, C$_1$–C$_8$-alkyl or perfluoro-C$_1$–C$_4$-alkyl, or a pharmaceutically acceptable salt thereof;

as inhibitors of protein farnesyltransferase.

Preferred inhibitors of protein farnesyltransferase are compounds of formula (III) or (IV) wherein A$_1$ and A$_2$ are independently —C(O)—NR$_1$R$_2$ wherein at each occurrence R$_1$ is independently selected from (k) aryl, (l) heterocyclic, (m) arylalkyl, (n) aryl-substituted cycloalkylalkyl, (o) (heterocyclic)alkyl, (p) heterocyclic-substituted cycloalkylalkyl and (q) aryl, heterocyclic, arylalkyl, aryl-substituted cycloalkylalkyl, (heterocyclic)alkyl or heterocyclic-substituted cycloalkylalkyl wherein the aryl group, the aryl part of the arylalkyl group, the aryl part of the aryl-substituted cycloalkylalkyl group, the heterocyclic group, the heterocyclic part of the (heterocyclic)alkyl group or the heterocyclic part of the heterocyclic-substituted cycloalkylalkyl group is substituted with —Y—R$_3$ wherein at each occurrence Y is independently selected from (i) a covalent bond, (ii) —C(O)—, (iii) —CH$_2$—, (iv) —O—, (v) —S(O)$_m$— wherein m is 0, 1 or 2, (vi) —N(R$_b$)— wherein R$_b$ is hydrogen or loweralkyl, (vii) —CH$_2$O—, (viii) —CH$_2$S(O)$_m$— wherein m is 0, 1 or 2, and (ix) —CH$_2$N(R$_b$)— wherein R$_b$ is hydrogen or loweralkyl and at each occurrence R$_3$ is independently selected from (i) aryl, (ii) arylalkyl, (iii) cycloalkyl, (iv) cycloalkylalkyl, (v) heterocyclic and (vi) (heterocyclic)alkyl, and at each occurrence R$_2$ is independently selected from arylalkyl and (heterocyclic)alkyl; and B$_1$ and B$_2$ are independently selected from (1) —W—R$_5$ wherein at each occurrence W is independently selected from (a) a covalent bond, (b) alkylene, (c) alkenylene, (d) —C(O)NH— and (e) —NHC(O)NH— and R$_5$ is 5-tetrazolyl, (2) —Q—C(O)R$_6$ wherein at each occurrence Q is independently selected from (a) a covalent bond, (b) alkylene, (c) alkenylene, (d) —CH(OH)— and (e) —NHC(O)(CH$_2$)$_r$— wherein r is 0 to 4 and at each occurrence R$_6$ is independently selected from (a) —OR$_7$ wherein R$_7$ is hydrogen or a carboxy-protecting group, (b) —NH$_2$, (c) —NHOH, (d) —NHSO$_2$CF$_3$ (e) an alpha-amino acid or a beta-amino acid which is bonded via the alpha- or beta-amino group and (f) a di-, tri- or tetra-peptide which is bonded via the amino terminal amino group, and (3) —C(O)—NH—S(O)$_2$—R$_{26}$ wherein R$_{26}$ is aryl, heterocyclic, arylalkyl, (heterocyclic)alkyl, C$_3$–C$_7$-cycloalkyl, C$_1$–C$_8$-alkyl or perfluoro-C$_1$–C$_4$-alkyl, or a pharmaceutically acceptable salt thereof.

The present invention also relates to processes for preparing the compounds of formula (I), (II), (III) or (IV) and to the synthetic intermediates useful in such processes.

In a further aspect of the present invention are disclosed pharmaceutical compositions which comprise a compound of the present invention in combination with a pharmaceutically acceptable carrier.

In yet another aspect of the present invention are disclosed pharmaceutical compositions which comprise a compound of the present invention in combination with another antihyperlipoproteinemic agent and/or with one or more other serum cholesterol lowering agents or HMG CoA reductase inhibitors and a pharmaceutically acceptable carrier.

In yet another aspect of the present invention are disclosed pharmaceutical compositions which comprise a compound of the present invention in combination with another chemotherapeutic agent and a pharmaceutically acceptable carrier.

In yet another aspect of the present invention is disclosed a method for inhibiting squalene synthase in a human or lower mammal, comprising administering to the patient a therapeutically effective amount of a compound of the invention.

In yet another aspect of the present invention is disclosed a method for inhibiting or treating atherosclerosis or inhibiting or treating hyperlipidemia which would inhibit the development of atherosclerosis in a human or lower mammal, comprising administering to the patient a therapeutically effective amount of a compound of the invention alone or in combination with another cardiovascular agent.

Also disclosed is a method of treating fungal infections in a human or lower mammal, comprising administering to the patient a therapeutically effective amount of a compound of the invention.

In yet another aspect of the present invention is disclosed a method for inhibiting protein farnesyltransferase in a human or lower mammal, comprising administering to the patient a therapeutically effective amount of a compound of the invention.

In yet another aspect of the present invention is disclosed a method for inhibiting or treating cancer in a human or lower mammal, comprising administering to the patient a therapeutically effective amount of a compound of the invention alone or in combination with another chemotherapeutic agent.

In yet another aspect of the present invention is disclosed a method of preventing restenosis in a human or lower mammal, comprising administering to the patient a therapeutically effective amount of a compound of the invention.

The compounds of the invention comprise asymmetrically substituted carbon atoms. As a result, all stereoisomers of the compounds of the invention are meant to be included in the invention, including racemic mixtures, mixtures of diastereomers, as well as single diastereomers of the compounds of the invention. The terms "S" and "R" configuration, as used herein, are as defined by the IUPAC 1974 Recommendations for Section E, Fundamental Stereochemistry, Pure Appl. Chem. (1976) 45, 13–30.

The terms α and β are employed to describe relative orientation for ring substituents on cyclic compounds, i.e., substituted cyclobutanes in the present invention. The α-side of the reference plane (the plane formed by the cyclobutane ring) is that side on which the highest ranking substituent (according to the Cahn-Ingold-Prelog Sequence Rule) lies at the lowest-numbered stereogenic carbon atom. All substituents lying on the same side of the reference plane as the highest-ranking substituent are assigned an α descriptor. Those substituents lying on the opposite side of the reference plane are assigned a β descriptor. It should be noted that this usage does not describe absolute configuration. The terms α and β configuration, as used herein, are as defined by the Chemical Abstracts Index Guide-Appendix IV (1987) ¶ 203.

The term "α-amino acid" or "alpha-amino acid" refers to an α-amino acid selected from the group consisting of alanine, arginine, asparagine, aspartic acid, cysteine, glutamine, glutamic acid, glycine, histidine, isoleucine, leucine, lysine, methionine, norleucine, ornithine, phenylalanine, proline, sarcosine, serine, threonine, tryptophan, tyrosine and valine. The stereochemistry at the asymmetric center can be of the D- or L-configuration.

The term "β-amino acid" or "beta-amino acid" refers to an amino acid wherein the amino group is β to the carboxylic acid functionality. Examples of β-amino acids include β-alanine, β-phenylalanine and the like.

The term "dipeptide" as used herein refers to $AA_1-AA_2$ wherein $AA_1$ and $AA_2$ are independently selected from α- and β-amino acids as described above coupled together by an amide bond (—C(O)—NH—) between the carboxy terminus of $AA_1$ and the amino terminus of $AA_2$. Examples of dipeptides include H-Glycyl-Alanine-OH, H-Glycyl-β-Alanine-OH, H-Leucyl-Glycine-OH and the like.

The term "tripeptide" as used herein refers to $AA_1-AA_2-AA_3$ wherein $AA_1$, $AA_2$ and $AA_3$ are independently selected from α- and β-amino acids as described above coupled together by amide bonds (—C(O)—NH—) between the carboxy terminus of $AA_1$ and the amino terminus of $AA_2$ and the carboxy terminus of $AA_2$ and the amino terminus of $AA_3$. Examples of tripeptides include H-Glycyl-Alanyl-Leucine-OH, H-Glycyl-β-Alanyl-Sarcosine-OH, H-Leucyl-Glycyl-Alanine-OH and the like.

The term "tetrapeptide" as used herein refers to $AA_1-AA_2-AA_3-AA_4$ wherein $AA_1$, $AA_2$, $AA_3$ and $AA_4$ are independently selected from α- and β-amino acids as described above coupled together by amide bonds (—C(O)—NH—) between the carboxy terminus of $AA_1$ and the amino terminus of $AA_2$, the carboxy terminus of $AA_2$ and the amino terminus of $AA_3$, and the carboxy terminus of $AA_3$ and the amino terminus of $AA_4$.

The term "carboxy protecting group" as used herein refers to a carboxylic acid protecting ester group employed to block or protect the carboxylic acid functionality while the reactions involving other functional sites of the compound are carried out. Carboxy-protecting groups are disclosed in Greene, "Protective Groups in Organic Synthesis" pp. 152–186 (1981), which is hereby incorporated herein by reference. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975), which is hereby incorporated herein by reference. Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are hereby incorporated herein by reference. Examples of esters useful as prodrugs for compounds containing carboxyl groups can be found on pages 14–21 of "Bioreversible Carriers in Drug Design: Theory and Application", edited by E. B. Roche, Pergamon Press, New York (1987), which is hereby incorporated herein by reference. Representative carboxy protecting groups are $C_1$ to $C_8$ loweralkyl (e.g., methyl, ethyl or tertiary butyl and the like); arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl or cycloalkyloxycarbonylalkyl, such as methoxycarbonylmethyl, cyclohexyloxycarbonylmethyl, 1-methoxycarbonyl-1-ethyl, and the like; alkoxycarbonyloxyalkyl or cycloalkyloxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; aryloxycarbonyloxyalkyl, such as 2-(phenoxycarbonyloxy)ethyl, 2-(5-indanyloxycarbonyloxy)ethyl and the like; alkoxyalkylcarbonyloxyalkyl, such as 2-(1-methoxy-2-methylpropan-2-oyloxy)ethyl and like; arylalkyloxycarbonyloxyalkyl, such as 2-(benzyloxycarbonyloxy)ethyl and the like; arylalkenyloxycarbonyloxyalkyl, such as 2-(3-phenylpropen-2-yloxycarbonyloxy)ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(loweralkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred N-protecting groups are formyl, acetyl, benzoyl, pivaloyl, t-butylacetyl, phenylsulfonyl, benzyl, t-butyloxycarbonyl (Boc) and benzyloxycarbonyl (Cbz).

The term "loweralkyl" as used herein refers to branched or straight chain alkyl groups comprising one to ten carbon atoms, including methyl, ethyl, propyl, isopropyl, n-butyl, t-butyl, neopentyl and the like.

The term "alkoxy" as used herein refers to RO— wherein R is loweralkyl as defined above. Representative examples of alkoxy groups include methoxy, ethoxy, t-butoxy and the like.

The term "alkoxyalkoxy" as used herein refers to $R_{80}O-R_{81}O-$ wherein $R_{80}$ is loweralkyl as defined above and $R_{81}$ is an alkylene group. Representative examples of alkoxyalkoxy groups include methoxymethoxy, ethoxymethoxy, t-butoxymethoxy and the like.

The term "alkoxyalkyl" as used herein refers to an alkoxy group as previously defined appended to an alkyl group as previously defined. Examples of alkoxyalkyl include, but are not limited to, methoxymethyl, methoxyethyl, isopropoxymethyl and the like.

The term "alkoxycarbonyl" as used herein refers to an alkoxy group as previously defined appended to the parent molecular moiety through a carbonyl group. Examples of alkoxycarbonyl include methoxycarbonyl, ethoxycarbonyl, isopropoxycarbonyl and the like.

The term "alkoxycarbonylalkyl" as used herein refers to an alkoxylcarbonyl group as previously defined appended to a loweralkyl group. Examples of alkoxycarbonylalkyl include methoxycarbonylmethyl, 2-ethoxycarbonylethyl and the like.

The term "alkylene" denotes a divalent group derived from a straight or branched chain saturated hydrocarbon having from 1 to 10 carbon atoms by the removal of two hydrogen atoms, for example methylene, 1,2-ethylene, 1,1-ethylene, 1,3-propylene, 2,2-dimethylpropylene, and the like.

The term "alkenyl" as used herein refers to a branched or straight hydrocarbon chain comprising two to twenty carbon atoms which also comprises one or more carbon-carbon double bonds. Representative alkenyl groups include 2-propenyl (i.e., allyl), 3-methyl-2-butenyl, 3,7-dimethyl-2,6-octadienyl, 4,8-dimethyl-3,7-nonadienyl, 3,7,11-trimethyl-2,6,10-dodecatrienyl and the like.

The term "alkenylene" denotes a divalent group derived from a straight or branched chain hydrocarbon containing from 2 to 10 carbon atoms and also containing at least one carbon-carbon double bond. Examples of alkenylene include —CH=CH—, —CH$_2$CH=CH—, —C(CH$_3$)=CH—, —CH$_2$CH=CHCH$_2$—, and the like.

The term "alkynyl" as used herein refers to a branched or straight hydrocarbon chain comprising two to twenty carbon atoms which also comprises one or more carbon-carbon triple bonds. Representative alkynyl groups include ethynyl, 2-propynyl (propargyl), 1-propynyl and the like.

The term "amino" as used herein refers to —NH$_2$.

The term "alkylamino" as used herein refers to $R_{51}NH-$ wherein $R_{51}$ is a loweralkyl group, for example, methylamino, ethylamino, butylamino, and the like.

The term "dialkylamino" as used herein refers to $R_{56}R_{57}N-$ wherein $R_{56}$ and $R_{57}$ are independently selected from loweralkyl, for example dimethylamino, diethylamino, methyl propylamino, and the like.

The term "aryl" as used herein refers to a mono- or bicyclic carbocyclic ring system having one or two aromatic rings including, but not limited to, phenyl, naphthyl, tetrahydronaphthyl, indanyl, indenyl and the like. Aryl groups (including bicyclic aryl groups) can be unsubstituted or substituted with one, two or three substituents independently selected from loweralkyl, haloalkyl, alkoxy, thioalkoxy, amino, alkylamino, dialkylamino, hydroxy, halo, mercapto, nitro, carboxaldehyde, carboxy, alkoxycarbonyl and carboxamide. In addition, substituted aryl groups include tetrafluorophenyl and pentafluorophenyl.

The term "arylalkyl" as used herein refers to a loweralkyl radical to which is appended an aryl group. Representative arylalkyl groups include benzyl, phenylethyl, hydroxybenzyl, fluorobenzyl, fluorophenylethyl and the like.

The term "arylalkenyl" as used herein refers to an aryl group as previously defined appended to an alkenyl group as previously defined. Examples of arylalkenyl include styryl (i.e., 2-phenylethenyl), 2-(1-naphthyl)ethenyl and the like.

The term "aryl-substituted cycloalkylalkyl" as used herein refers to a cycloalkylalkyl radical in which the alkyl portion of the radical is substituted with an aryl group. Examples of aryl-substituted cycloalkylalkyl include α-(cyclopropylmethyl)benzyl, α-(cyclobutylmethyl)benzyl and the like.

The term "carboxaldehyde" as used herein refers to the group —C(O)H.

The term "carboxamide" as used herein refers to the group —C(O)NH$_2$.

The term "cycloalkyl" as used herein refers to an alicyclic group comprising from 3 to 7 carbon atoms including, but not limited to, cyclopropyl, cyclobutyl, cyclopentyl, cyclohexyl and the like.

The term "cycloalkylalkyl" as used herein refers to a loweralkyl radical to which is appended a cycloalkyl group. Representative examples of cycloalkylalkyl include cyclopropylmethyl, cyclohexylmethyl, 2-(cyclopropyl)ethyl and the like.

The term "1,2,3,4-cyclobutanetetracarboxylic dianhydride" as used herein refers to the (1,2/3,4) compound wherein the two anhydride rings are trans (i.e., on opposite sides of the plane formed by the cyclobutane ring) to one another.

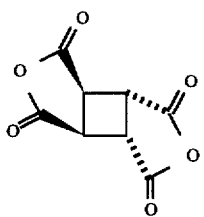

The relative stereochemistry is as shown.

The term "halogen" or "halo" as used herein refers to I, Br, Cl or F.

The term "haloalkyl" as used herein refers to a lower alkyl radical, as defined above, bearing at least one halogen substituent, for example, chloromethyl, fluoroethyl or trifluoromethyl and the like.

The term "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one oxygen atom; one sulfur atom; one nitrogen and one sulfur atom; one nitrogen and one oxygen atom; two oxygen atoms in non-adjacent positions; one oxygen and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, benzofuryl or benzothienyl and the like). Heterocyclics include: azetidinyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, isoxazolyl, oxadiazolyl, thiadiazolyl, pyrrolyl, pyrimidyl and benzothienyl. Heterocyclics also include compounds of the formula

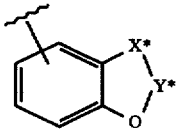

where X* is —CH$_2$— or —O— and Y* is —C(O)— or [—C(R")$_2$—]$_v$ where R" is hydrogen or C$_1$–C$_4$-alkyl and v is 1, 2 or 3 such as 1,3-benzodioxolyl, 1,4-benzodioxanyl and the like.

Heterocyclics can be unsubstituted or monosubstituted or disubstituted with substituents independently selected from hydroxy, halo, oxo (=O), alkylimino (R*N=wherein R* is a loweralkyl group), amino, alkylamino, dialkylamino, alkoxy, alkoxyalkoxy, haloalkyl, cycloalkyl, aryl, arylalkyl, —COOH, —SO$_3$H and loweralkyl. In addition, nitrogen containing heterocycles can be N-protected.

The term "(heterocyclic)alkyl" as used herein refers to a heterocyclic group as defined above appended to a loweralkyl radical as defined above. Examples of heterocyclic alkyl include 2-pyridylmethyl, 4-pyridylmethyl, 4-quinolinylmethyl and the like.

The term "heterocyclic-substituted cycloalkylalkyl" as used herein refers to a cycloalkylalkyl radical in which the alkyl portion of the radical is substituted with a heterocyclic group. Examples of heterocyclic-substituted cycloalkylalkyl include α-(cyclopropylmethyl)furan-2-ylmethyl, α-(cyclobutylmethyl)thien-2-ylmethyl and the like.

The term "mercapto" as used herein refers to the group —SH.

The term "perfluoro-C$_1$–C$_4$-alkyl" as used herein refers to an alkyl radical of 1 to 4 carbon atoms in which all hydrogen atoms have been replaced with fluorine atoms. Examples of perfluoro-C$_1$–C$_4$-alkyl include trifluoromethyl, pentafluoroethyl and the like.

The term "tetrazolyl" or "5-tetrazolyl" as used herein refers to a radical of the formula

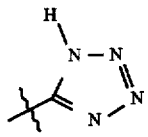

or a tautomer thereof.

The term "thioalkoxy" as used herein refers to R$_{70}$S— wherein R$_{70}$ is loweralkyl. Examples of thioalkoxy include, but are not limited to, methylthio, ethylthio and the like.

The term "thioalkoxyalkyl" as used herein refers to a thioalkoxy group as previously defined appended to a loweralkyl group as previously defined. Examples of thioalkoxyalkyl include thiomethoxymethyl, 2-thiomethoxyethyl and the like.

Representative compounds of the invention include:

(1α,2β,3β,4α)-1,2-Di[N-methyl-N-(4-phenoxybenzyl) aminocarbonyl]cyclobutane-3,4-dicarboxylic acid;

(1α,2β,3β,4α)-1,2-Di[N-methyl-N-(4-benzyloxybenzyl) aminocarbonyl]cyclobutane-3,4-dicarboxylic acid;

(1α,2β,3β,4α)-1,2-Di[N-benzyl-N-(4-phenoxybenzyl) aminocarbonyl]cyclobutane-3,4-dicarboxylic acid;

(1α,2β,3β,4α)-1,2-Di[N-ethyl-N-(4-phenoxybenzyl) aminocarbonyl]cyclobutane-3,4-dicarboxylic acid;

(1α,2β,3β,4α)-1,2-Di[N-propyl-N-(4-phenoxybenzyl) aminocarbonyl]cyclobutane-3,4-dicarboxylic acid;

(1α,2β,3β,4α)-1,2-Di[N-methyl-N-(3-phenoxybenzyl) aminocarbonyl]cyclobutane-3,4-dicarboxylic acid;

(1α,2β,3β,4α)-1,2-Di[N,N-di(4-phenoxybenzyl) aminocarbonyl]cyclobutane-3,4-dicarboxylic acid;

(1α,2β,3β,4α)-1,2-Di[N-methyl-N-(4-[4-fluorophenoxy] benzyl)aminocarbonyl]cyclobutane-3,4-dicarboxylic acid;

(1α,2β,3β,4α)-1,2-Di[N-methyl-N-(3-[4-fluorophenoxy] benzyl)aminocarbonyl]cyclobutane-3,4-dicarboxylic acid;

(1α,2β,3β,4α)-1,2-Di[N-methyl-N-biphenylaminocarbonyl]cyclobutane-2,4-dicarboxylic acid;

(1α,2β,3β,4α)-1,2-Di[N-isopropyl-N-biphenylaminocarbonyl]cyclobutane-3,4-dicarboxylic acid;

(1α,2β,3β,4α)-1,2-Di[N-isobutyl-N-(4-phenoxybenzyl) aminocarbonyl]cyclobutane-3,4-dicarboxylic acid;

(1α,2β,3β,4α)-1,2-Di[N-propyl-N-(4-benzylbenzyl) aminocarbonyl]cyclobutane-3,4-dicarboxylic acid;

(1α,2β,3β,4α)-1,2-Di[N-butyl-N-(4-phenoxybenzyl) aminocarbonyl]cyclobutane-3,4-dicarboxylic acid;

(1α,2β,3β,4α)-1,2-Di[N-propargyl-N-(4-phenoxybenzyl) aminocarbonyl]cyclobutane-3,4-dicarboxylic acid;

(1α,2β,3β,4α)-1,2-Di[N-pentyl-N-(4-phenoxybenzyl) aminocarbonyl]cyclobutane-3,4-dicarboxylic acid;

(1α,2β,3β,4α)-1,2-Di[N-allyl-N-(4-phenoxybenzyl)
aminocarbonyl]cyclobutane-3,4-dicarboxylic acid;

(1α,2β,3β,4α)-1,2-Di[N-cyclopropyl-N-(4-phenoxybenzyl)
aminocarbonyl]cyclobutane-3,4-dicarboxylic acid;

(1α,2β,3β,4α)-1,2-Di[N-cyclohexylmethyl-N-
phenoxybenzyl)aminocarbonyl]cyclobutane-3,4-
dicarboxylic acid;

(1α,2β,3β,4α)-1,2-Di[N-phenyl-N-phenoxybenzyl)
aminocarbonyl]cyclobutane-3,4-dicarboxylic acid;

(1α,2β,3β,4α)-1,2-Di[N-4-methoxybenzyl-N-4-
phenoxybenzyl)aminocarbonyl]cyclobutane-3,4-
dicarboxylic acid;

(1α,2β,3β,4α)-1,2-Di[N-(S)-α-methylbenzyl-N-4-
phenoxybenzyl)aminocarbonyl]cyclobutane-3,4-
dicarboxylic acid;

(1α,2β,3β,4α)-1,2-Di[N-(R)-α-methylbenzyl-N-4-
phenoxybenzyl)aminocarbonyl]cyclobutane-3,4-
dicarboxylic acid;

(1α,2β,3β,4α)-1,2-Di[N-benzyl-N-(5-phenyl-2,4-
pentadienyl)aminocarbonyl]cyclobutane-3,4-
dicarboxylic acid;

(−)-(1α,2β,3β,4α)-1,2-Di[N-propyl-N-(phenoxybenzyl)
aminocarbonyl]cyclobutane-3,4-dicarboxylic acid;

(1α,2β,3β,4α)-1,2-Di[N-propyl-N-(2-(4-phenoxyphenyl)
ethyl)aminocarbonyl]cyclobutane-3,4-dicarboxylic acid;

(1α,2β,3β,4α)-1,2-Di[N-propyl-N-(4-phenoxyphenyl)
aminocarbonyl]cyclobutane-3,4-dicarboxylic acid;

(1α,2β,3β,4α)-1,2-Di[N-(2-methoxyethyl)-N-(4-
phenoxybenzyl)aminocarbonyl]cyclobutane-3,4-
dicarboxylic acid;

(1α,2β,3β,4α)-1,2-Di[N-(2-methylthioethyl)-N-(4-
phenoxybenzyl)aminocarbonyl]cyclobutane-3,4-
dicarboxylic acid;

(1α,2β,3β,4α)-1,2-Di[N-(2-ethylthioethyl)-N-(4-
phenoxybenzyl)aminocarbonyl]cyclobutane-3,4-
dicarboxylic acid;

(1α,2β,3β,4α)-1,2-Di[N-(2-fluoroethyl)-N-(4-
phenoxybenzyl)aminocarbonyl]cyclobutane-3,4-
dicarboxylic acid;

(1α,2β,3β,4α)-1,2-Di[N-(furan-2-ylmethyl)-N-(4-
phenoxybenzyl)aminocarbonyl]cyclobutane-3,4-
dicarboxylic acid;

(1α,2β,3β,4α)-1,2-Di[N-(thien-2-ylmethyl)-N-(4-
phenoxybenzyl)aminocarbonyl]cyclobutane-3,4-
dicarboxylic acid;

(1α,2β,3β,4α)-1,2-Di[N-(2-ethylthioethyl)-N-(4-
phenylthiobenzyl)aminocarbonyl]cyclobutane-3,4-
dicarboxylic acid;

(1α,2β,3β,4α)-1,2-Di[N-(cyclopropylmethyl)-N-(4-
phenoxybenzyl)aminocarbonyl]cyclobutane-3,4-
dicarboxylic acid;

(1α,2β,3β,4α)-1,2-Di[N-cyclobutyl-N-(4-phenoxybenzyl)
aminocarbonyl]cyclobutane-3,4-dicarboxylic acid;

(1α,2β,3β,4α)-1,2-Di[N-cyclopentyl-N-(4-phenoxybenzyl)
aminocarbonyl]cyclobutane-3,4-dicarboxylic acid;

(1α,2β,3β,4α)-1,2-Di[N-cyclohexyl-N-(4-phenoxybenzyl)
aminocarbonyl]cyclobutane-3,4-dicarboxylic acid;

(1α,2β,3β,4α)-1,2-Di[N-(cyclopentylmethyl)-N-(4-
phenoxybenzyl)aminocarbonyl]cyclobutane-3,4-
dicarboxylic acid;

(1α,2β,3β,4α)-1,2-Di[N-(cyclobutylmethyl)-N-(4-
phenoxybenzyl)aminocarbonyl]cyclobutane-3,4-
dicarboxylic acid;

(1α,2β,3β,4α)-1,2-Di[N-(4-fluorobenzyl)-N-(4-
phenoxybenzyl)aminocarbonyl]cyclobutane-3,4-
dicarboxylic acid;

(1α,2β,3β,4α)-1,2-Di[N-(4-phenoxybenzyl)-N-(3-
methoxyphenethyl)aminocarbonyl]cyclobutane-3,4-
dicarboxylic acid;

(1α,2β,3β,4α)-1,2-Di[N-(4-phenoxybenzyl)-N-(3,4-
dimethoxyphenethyl)aminocarbonyl]cyclobutane-3,4-
dicarboxylic acid;

(1α,2β,3β,4α)-1,2-Di[N-(4-phenoxybenzyl)-N-
phenethylaminocarbonyl]cyclobutane-3,4-dicarboxylic
acid;

(1α,2β,3β,4α)-1,2-Di[N-(p-phenoxybenzyl)-N-(3-phenyl-
1-propyl)aminocarbonyl]cyclobutane-3,4-dicarboxylic
acid;

(1α,2β,3β,4α)-1,2-Di[N-(4-phenoxybenzyl)-N-(4-phenyl-
1-butyl)aminocarbonyl]cyclobutane-3,4-dicarboxylic
acid;

(1α,2β,3β,4α)-1,2-Di[N-(4-phenoxybenzyl)-N-
(methoxycarbonylmethyl)aminocarbonyl]cyclobutane-3,
4-dicarboxylic acid;

(1α,2β,3β,4α)-1,2-Di[N-(4-phenoxybenzyl)-N-
(ethoxycarbonylethyl)aminocarbonyl]cyclobutane-3,4-
dicarboxylic acid;

(1α,2β,3β,4α)-1,2-Di[N-propyl-N-(4-
cyclohexyloxybenzyl)aminocarbonyl]cyclobutane-3,4-
dicarboxylic acid;

(1α,2β,3β,4α)-1-[N-Propyl-N-(4-phenoxybenzyl)
aminocarbonyl]-2-[N-methyl-N-(homogeranyl)
aminocarbonyl]cyclobutane-3,4-dicarboxylic acid;

(1α,2β,3β,4α)-1-[N-Propyl-N-(4-phenoxybenzyl)
aminocarbonyl]-2-[N-benzyl-N-(4-phenoxybenzyl)
aminocarbonyl]cyclobutane-3,4-dicarboxylic acid;

(1α,2β,3β,4α)-1-[N-Propyl-N-(4-phenoxybenzyl)
aminocarbonyl]-2-[N-(4-phenoxybenzyl)aminocarbonyl]
cyclobutane-3,4-dicarboxylic acid;

(1α,2β,3β,4α)-1,2-Di-(4-phenoxybenzyloxycarbonyl)-3,4-
dicarboxylic acid;

(1α,2β,3β,4α)-1,2-Di[N-propyl-N-(4-phenylaminophenyl)
aminocarbonyl]cyclobutane-3,4-dicarboxylic acid;

(1α,2β,3β,4α)-1,2-Di[N-propyl-N-(4-phenylaminobenzyl)
aminocarbonyl]cyclobutane-3,4-dicarboxylic acid;

(1α,2β,3β,4α)-1,2-Di[N-propyl-N-(4-phenylthiobenzyl)
aminocarbonyl]cyclobutane-3,4-dicarboxylic acid;

(1α,2β,3β,4α)-1,2-Di[N-propyl-N-[4-
phenoxymethylbenzyl]aminocarbonyl]cyclobutane-3,4-
dicarboxylic acid;

(1α,2β,3β,4α)-1,2-Di[N-propyl-N-(4-phenoxybenzyl)
aminocarbonyl]-4-hydroxymethyl-cyclobutane-3-
carboxylic acid;

(1α,2β,3β,4α)-1,2-Di[N-propyl-N-(4-phenoxybenzyl)
aminocarbonyl]-4-[(hydroxyimino)methyl]-cyclobutane-
3-carboxylic acid;

(1α,2β,3β,4α)-1,2-Di[N-propyl-N-(4-phenoxybenzyl)
aminocarbonyl]-4-tetrazolyl-cyclobutane-3-carboxylic
acid;

(1α,2β,3β,4α)-1,2-Di[N-propyl-N-(4-phenoxybenzyl)
aminocarbonyl-4-tetrazolylmethyl-cyclobutane-3-
carboxylic acid;

(1α,2β,3β,4α)-1,2-Di[N-propyl-N-(4-phenoxybenzyl)
aminocarbonyl]-4-(carboxycarbonylamino)cyclobutane-
3-carboxylic acid;

(1α,2β,3β,4α)-1,2-Di[N-propyl-N-(4-phenoxybenzyl)
aminocarbonyl]-4-(3-carboxypropionylamino)
cyclobutane-3-carboxylic acid;

(1α,2β,3β,4α)-1,2-Di[N-propyl-N-(4-phenoxybenzyl)
aminocarbonyl-4-(E-2-carboxyethenyl-cyclobutane-3-
carboxylic acid;

(1α,2β,3β,4α)-1,2-Di[N-propyl-N-(4-phenoxybenzyl)
aminocarbonyl-4-(2-carboxyethyl)-cyclobutane-3-
carboxylic acid;

(1α,2β,3β,4α)-1,2-Di[N-propyl-N-(4-phenoxybenzyl)
aminocarbonyl]-4-(1-carboxy-1-hydroxymethyl)
cyclobutane-3-carboxylic acid;

(1α,2β,3β,4α)-1,2-Di[N-propyl-N-(4-phenoxybenzyl)aminocarbonyl]-3,4-di[(hydroxyimino)methyl]cyclobutane;

(1α,2β,3β,4α)-1,2-Di[N-methyl-N-(4-phenoxybenzyl)aminocarbonyl]cyclobutane-3,4-dicarboxylic acid dimethyl ester;

(1α,2β,3β,4α)-1,2-Di[N-propyl-N-(3-phenoxybenzyl)aminocarbonyl]cyclobutane-3,4-dicarboxylic acid;

(1α,2β,3β,4α)-1,2-Di[N-propyl-N-(5-phenoxyfurfuryl)aminocarbonyl}cyclobutane-3,4-dicarboxylic acid;

(1α,2β,3β,4α)-1,2-Di[N-propyl-N-(5-phenoxythien-2-ylmethyl)aminocarbonyl]cyclobutane-3,4-dicarboxylic acid;

(1α,2β,3β,4α)-1,2-Di[N-propyl-N-(4-(furan-2-yloxybenzyl)aminocarbonyl]cyclobutane-3,4-dicarboxylic acid;

(1α,2β,3β,4α)-1,2-Di[N-propyl-N-(4-(thiazol-2-yloxybenzyl)aminocarbonyl]cyclobutane-3,4-dicarboxylic acid;

(1α,2β,3β,4α)-1,2-Di[N-propyl-N-(4-(pyrrol-1-ylmethyl)benzyl)aminocarbonyl]cyclobutane-3,4-dicarboxylic acid;

(1α,2β,3β,4α)-1,2-Di[N-propyl-N-(3-methyl-4-phenoxybenzyl)aminocarbonyl]cyclobutane-3,4-dicarboxylic acid;

(1α,2β,3β,4α)-1,2-Di[N-propyl-N-(4-naphth-2-yloxybenzyl)aminocarbonyl]cyclobutane-3,4-dicarboxylic acid;

(1α,2β,3β,4α)-1,2-Di[N-propyl-N-(4-(3-methyl-1-phenoxy)benzyl)aminocarbonyl]cyclobutane-3,4-dicarboxylic acid;

(1α,2β,3β,4α)-1,2-Di[N-propyl-N-(4-(4-methyl-1-phenoxy)benzyl)aminocarbonyl]cyclobutane-3,4-dicarboxylic acid;

(1α,2β,3β,4α)-1,2-Di[N-propyl-N-(4-naphth-1-yloxybenzyl)aminocarbonyl]cyclobutane-3,4-dicarboxylic acid;

(1α,2β,3β,4α)-1,2-Di[N-propyl-N-(4-phenoxybenzyl)aminocarbonyl]cyclobutane-3-[N-(5-tetrazolyl)]carboxamide-4-carboxylic acid;

(1α,2β,3β,4α)-1,2-Di[N-propyl-N-(4-phenoxybenzyl)aminocarbonyl]cyclobutane-3-(N-(5-tetrazolyl)aminocarbonylamino)-4-carboxylic acid;

(1α,2β,3β,4α)-1,2-Di[N-propyl-N-(4-phenoxybenzyl)aminocarbonyl]cyclobutane-3,4-dicarboxylic acid dimethyl ester;

(1α,2β,3β,4α)-1,2-Di[N-propyl-N-(4-phenoxybenzyl)aminocarbonyl]-3-(methoxycarbonyl)cyclobutane-4-carboxylic acid;

(1α,2β,3α,4α)-1,2-Di[-N-propyl-N-(4-phenoxybenzyl)aminocarbonyl]cyclobutane-3,4-dicarboxylic acid;

(1α,2β,3α,4β)-1,2-Di[N-propyl-N-(4-phenoxybenzyl)aminocarbonyl]cyclobutane-3,4-dicarboxylic acid;

(1α,2β,3β,4α)-1,2-Di[N-propyl-N-(4-phenoxybenzyl)aminocarbonyl]-3-[(hydroxyamino)carbonyl]cyclobutane-4-carboxylic acid;

(1α,2β,3β,4α)-3-(Amino)carbonyl-1,2-Di[N-propyl-N-(4-phenoxybenzyl)aminocarbonyl]cyclobutane-4-carboxylic acid;

(1α,2β,3β,4α)-1,2-Di[N-propyl-N-(4-phenoxybenzyl)aminocarbonyl]-3-(trifluoromethanesulfonylamino)cyclobutane-4-carboxylic acid;

(1α,2β,3β,4α)-4-(Carboxy)methyl)-1,2-Di[N-propyl-N-(4-phenoxybenzyl)aminocarbonyl]cyclobutane-3-carboxylic acid;

(1α,2β,3β,4α)-3,4-Bis(diazoacetyl)-1,2-Di[N-propyl-N-(4-phenoxybenzyl)aminocarbonyl]cyclobutane;

(1α,2β,3β,4α)-1,2-Di[N-propyl-N-(4-phenoxybenzyl)aminocarbonyl]cyclobutane-3,4-diacetic acid;

(1α,2β,3β,4α)-1,2-Di[N-propyl-N-(4-phenoxybenzyl)aminocarbonyl]cyclobutane-3,4-dicarboxylic acid mono-Norleucine amide;

(1α,2β,3β,4α)-1,2-Di[N-propyl-N-(4-phenoxybenzyl)aminocarbonyl]cyclobutane-3-phenoxycarbonyl-4-dicarboxylic acid;

(1α,2β,3β,4α)-1,2-Di[N-propyl-N-(4-phenoxybenzyl)aminocarbonyl]cyclobutane-3,4-dicarboxylic acid mono-Glycine amide;

(1α,2β,3β,4α)-1,2-Di[N-propyl-N-(4-phenoxybenzyl)aminocarbonyl]cyclobutane-3,4-dicarboxylic acid mono-d,l-Proline amide;

(1α,2β,3β,4α)-1,2-Di[N-propyl-N-(4-phenoxybenzyl)aminocarbonyl]cyclobutane-3,4-dicarboxylic acid mono-Sarcosine amide;

(1α,2β,3β,4α)-1,2-Di[N-propyl-N-(4-phenoxybenzyl)aminocarbonyl]cyclobutane-3,4-dicarboxylic acid mono-d,l-Aspartic acid amide;

(1α,2β,3β,4α)-1,2-Di[N-propyl-N-(4-phenoxybenzyl)aminocarbonyl]cyclobutane-3,4-dicarboxylic acid mono-Serine amide;

(1α,2β,3β,4α)-1,2-Di[N-propyl-N-(4-phenoxybenzyl)aminocarbonyl]cyclobutane-3,4-dicarboxylic acid mono-β-Alanine amide;

(1α,2β,3β,4α)-1,2-Di[N-propyl-N-(4-phenoxybenzyl)aminocarbonyl]cyclobutane-3,4-dicarboxylic acid mono-d-Norleucine amide;

(1α,2β,3β,4α)-1,2-Di[N-propyl-N-(4-phenoxybenzyl)aminocarbonyl]cyclobutane-3,4-dicarboxylic acid mono-l-Norleucine amide;

(1α,2β,3β,4α)-1,2-Di[N-(4-pyridyl)methyl-N-(phenoxybenzyl)aminocarbonyl]cyclobutane-3,4-dicarboxylic acid;

(1α,2α,3β,4β)-1,2-Di[N-propyl-N-(phenoxybenzyl)aminocarbonyl]cyclobutane-3,4-dicarboxylic acid;

(1α,2α,3α,4α)-1,2-Di[N-propyl-N-(phenoxybenzyl)aminocarbonyl]cyclobutane-3,4-dicarboxylic acid;

(1α,2α,3α,4β)-1,2-Di[N-propyl-N-(4-phenoxybenzyl)aminocarbonyl]cyclobutane-3,4-dicarboxylic acid;

(1α,2β,3β,4α)-1,2-Di-N-propyl-N-(4-benzoylbenzyl)aminocarbonyl]cyclobutane-3,4-carboxylic acid;

(1α,2β,3β,4α)-1,2-Di[N-propyl-N-(4-(3,4-methylenedioxyphenoxy)benzyl)-aminocarbonyl]cyclobutane-3,4-carboxylic acid;

(1α,2β,3β,4α)-1,2-Di[N-methyl-N-(4-phenoxybenzyl)aminocarbonylamino]cyclobutane-3,4-dicarboxylic acid;

(1α,2β,3β,4α)-1,2-Di[N,N-dibenzylaminocarbonyl]cyclobutane-3,4-dicarboxylic acid;

(1α,2β,3β,4α)-1,2-Di(N-benzyl-N-(4-chlorobenzyl)aminocarbonyl)cyclobutane-3,4-dicarboxylic acid;

(1α,2β,3β,4α)-1,2-Di[(4-phenoxybenzyl)carbonylamino]cyclobutane-3,4-dicarboxylic acid;

(1α,2β,3β,4α)-1,2-Di[N-propyl-N-(4-phenoxybenzyl)carbonylamino]cyclobutane-3,4-dicarboxylic acid;

(1α,2β,3β,4α)-1,2-Di-[N-propyl-N-(4-phenoxybenzyl)aminocarbonyl]-3,4-bis(tetrazolylmethyl)cyclobutane;

(1α,2β,3β,4α)-1,2-Di-[N-propyl-N-(4-phenoxybenzyl)aminocarbonylmethyl]-cyclobutane-3,4-dicarboxylic acid;

(1α,2β,3β,4α)-1,2-Di{N-benzyl-N-[(4-phenoxy)benzyl]aminocarbonyl}cyclobutane-3,4-diacetic acid;

(−)-(1α,2β,3β,4α)-1,2-Di[N-cyclopropylmethyl-N-(4-phenoxybenzyl)aminocarbonyl]cyclobutane-3,4-dicarboxylic acid;

(1α,2β,3β,4α)-1,2-Di[N-propyl-N-(4-phenoxybenzyl)aminothiocarbonyl]cyclobutane-3,4-dicarboxylic acid;

(1α,2β,3β,4α)-1,2-Di[N-(S)-α-(cyclopropylmethyl)benzyl-N-(4-phenoxybenzyl)-aminocarbonyl]cyclobutane-3,4-dicarboxylic acid;

(1α,2β,3β,4α)-1,2-Di[N-(R)-α-(cyclopropylmethyl)benzyl-N-(4-phenoxybenzyl)-aminocarbonyl]cyclobutane-3,4-dicarboxylic acid;

(1α,2β,3β,4α)-1,2-Di[N-propyl-N-(S)-α-(cyclopropylmethyl)-(4-phenoxybenzyl)-aminocarbonyl]cyclobutane-3,4-dicarboxylic acid;

(1α,2β,3β,4α)-1,2-Di[N-propyl-N-(R)-α-(cyclopropylmethyl)-(4-phenoxybenzyl)-aminocarbonyl]cyclobutane-3,4-dicarboxylic acid;

(1α,2β,3β,4α)-1,2-Di[N-(R)-α-ethylbenzyl-N-(4-phenoxyphenyl)aminocarbonyl]-cyclobutane-3,4-dicarboxylic acid;

(1α,2β,3β,4α)-1,2-Di[N-(S)-α-ethylbenzyl-N-(4-phenoxyphenyl)aminocarbonyl]-cyclobutane-3,4-dicarboxylic acid;

(1α,2β,3β,4α)-1,2-Di[N-(R)-α-(cyclopropylmethyl)benzyl-N-(4-phenoxybenzyl)-aminocarbonyl]cyclobutane-3,4-dicarboxylic acid;

(1α,2β,3β,4α)-1,2-Di[N-(S)-α-(cyclopropylmethyl)benzyl-N-(4-phenoxybenzyl)-aminocarbonyl]cyclobutane-3,4-dicarboxylic acid;

(1α,2β,3β,4α)-1,2-Di[N-(R)-α-propyl-(4-phenoxybenzyl)aminocarbonyl]cyclobutane-3,4-dicarboxylic acid;

(1α,2β,3β,4α)-1,2-Di[N-(S)-α-propyl-(4-phenoxybenzyl)aminocarbonyl]cyclobutane-3,4-dicarboxylic acid;

(1α,2β,3β,4α)-1,2-Di[N-propyl-N-(R)-α-propyl-(4-phenoxybenzyl)aminocarbonyl]-cyclobutane-3,4-dicarboxylic acid;

(1α,2β,3β,4α)-1,2-Di[N-propyl-N-(S)-α-propyl-(4-phenoxybenzyl)aminocarbonyl]-cyclobutane-3,4-dicarboxylic acid;

(1α,2β,3β,4α)-1,2-Di[N-benzyl-N-(R)-α-propyl-(4-phenoxybenzyl)-aminocarbonyl]-cyclobutane-3,4-dicarboxylic acid;

(1α,2β,3β,4α)-1,2-Di[N-benzyl-N-(S)-α-propyl-(4-phenoxybenzyl)-aminocarbonyl]-cyclobutane-3,4-dicarboxylic acid;

(1α,2β,3β,4α)-1,2-Di[N-(cyclopropylmethyl)-N-(R)-α-propyl-(4-phenoxybenzyl)-aminocarbonyl]cyclobutane-3,4-dicarboxylic acid;

(1α,2β,3β,4α)-1,2-Di[N-(cyclopropylmethyl)-N-(S)-α-propyl-(4-phenoxybenzyl)-aminocarbonyl]cyclobutane-3,4-dicarboxylic acid;

(1α,2β,3β,4α)-1,2-Di[N-propyl-N-(4-phenoxybenzyl)-aminocarbonyl]-3-(ethoxycarbonyl)cyclobutane-4-carboxylic acid;

(1α,2β,3β,4α)-1,2-Di[N-propyl-N-(4-phenoxybenzyl) aminocarbonyl]-3-(propoxycarbonyl)cyclobutane-4-carboxylic acid;

(1α,2β,3β,4α)-1,2-Di[N-propyl-N-(4-phenoxybenzyl) aminocarbonyl]-3-(butoxycarbonyl)cyclobutane-4-carboxylic acid;

(1α,2β,3β,4α)-1,2-Di[N-propyl-N-(4-phenoxybenzyl) aminocarbonyl]-3-(isobutoxycarbonyl)cyclobutane-4-carboxylic acid;

(1α,2β,3β,4α)-1,2-Di[N-propyl-N-(4-phenoxybenzyl) aminocarbonyl]-3-(pentoxycarbonyl)cyclobutane-4-carboxylic acid;

(1α,2β,3β,4α)-1,2-Di[N-propyl-N-(4-phenoxybenzyl) aminocarbonyl]-3-(1-methylpropoxycarbonyl) cyclobutane-4-carboxylic acid;

(1α,2β,3β,4α)-1,2-Di[N-propyl-N-(4-phenoxybenzyl) aminocarbonyl]-3-(tert-butyloxycarbonyl)cyclobutane-4-carboxylic acid;

(1α,2β,3β,4α)-1,2-Di[N-propyl-N-(4-phenoxybenzyl) aminocarbonyl]-3-(isopropoxycarbonyl)cyclobutane-4-carboxylic acid;

(1α,2β,3β,4α)-1,2-Di[N-propyl-N-(4-phenoxybenzyl) aminocarbonyl]-3-(isoamyloxycarbonyl)cyclobutane-4-carboxylic acid;

(1α,2β,3β,4α)-1,2-Di[N-propyl-N-(4-phenoxybenzyl) aminocarbonyl]-3-(1S)-1-methoxycarbonyl-1-ethoxycarbonyl)cyclobutane-4-carboxylic acid;

(1α,2β,3β,4α)-1,2-Di[N-propyl-N-(4-phenoxybenzyl) aminocarbonyl]-3-(butoxycarbonylmethyl)cyclobutane-4-acetic acid;

(1α,2β,3β,4α)-1,2-Di[N-propyl-N-(4-phenoxybenzyl) aminocarbonyl]-3-((1S)-1-methoxycarbonyl-1-ethoxycarbonylmethyl)cyclobutane-4-acetic acid;

(1α,2β,3β,4α)-1,2-Di[N-propyl-N-(4-phenoxybenzyl) aminocarbonyl]-3-(N,N-diethylacetamidocarbonylmethyl)cyclobutane-4-acetic acid;

(1α,2β,3β,4α)-1,2-Di[N-propyl-N-(4-phenoxybenzyl) aminocarbonyl]-3-(acetoxymethoxycarbonyl) cyclobutane-4-carboxylic acid;

(1α,2β,3β,4α)-1,2-Di[N-propyl-N-(4-phenoxybenzyl) aminocarbonyl]-3,4-di(acetoxymethoxycarbonyl) cyclobutane;

(1α,2β,3β,4α)-1,2-Di[N-propyl-N-(4-phenoxybenzyl) aminocarbonyl]-3-(propionyloxymethoxycarbonyl) cyclobutane-4-carboxylic acid;

(1α,2β,3β,4α)-1,2-Di[N-propyl-N-(4-phenoxybenzyl) aminocarbonyl]-3,4-di(propionyloxymethoxycarbonyl) cyclobutane;

(1α,2β,3β,4α)-1,2-Di[N-propyl-N-(4-phenoxybenzyl) aminocarbonyl]-3-(butyryloxymethoxycarbonyl) cyclobutane-4-carboxylic acid;

(1α,2β,3β,4α)-1,2-Di[N-propyl-N-(4-phenoxybenzyl) aminocarbonyl]-3,4-di(butyryloxymethoxycarbonyl) cyclobutane;

(1α,2β,3β,4α)-1,2-Di[N-propyl-N-(4-phenoxybenzyl) aminocarbonyl]-3-(isobutyryloxymethoxycarbonyl) cyclobutane-4-carboxylic acid;

(1α,2β,3β,4α)-1,2-Di[N-propyl-N-(4-phenoxybenzyl) aminocarbonyl]-3,4-di(isobutyryloxymethoxycarbonyl) cyclobutane;

(1α,2β,3β,4α)-1,2-Di[N-propyl-N-(4-phenoxybenzyl) aminocarbonyl]-3-(pivaloyloxymethoxycarbonyl) cyclobutane-4-carboxylic acid;

(1α,2β,3β,4α)-1,2-Di[N-propyl-N-(4-phenoxybenzyl) aminocarbonyl]-3,4-di(pivaloyloxymethoxycarbonyl) cyclobutane;

(1α,2β,3β,4α)-1,2-Di[N-propyl-N-(4-phenoxybenzyl) aminocarbonyl]-3,4-di(cyclopropylcarboxymethoxycarbonyl)cyclobutane;

(1α,2β,3β,4α)-1,2-Di[N-propyl-N-(4-phenoxybenzyl) aminocarbonyl]-3-(cyclobutylcarboxymethoxycarbonyl) cyclobutane-4-carboxylic acid;

(1α,2β,3β,4α)-1,2-Di[N-propyl-N-(4-phenoxybenzyl) aminocarbonyl]-3,4-di(cyclobutylcarboxymethoxycarbonyl)cyclobutane;

(1α,2β,3β,4α)-1,2-Di[N-propyl-N-(4-phenoxybenzyl) aminocarbonyl]-3-(cyclopentylcarboxymethoxycarbonyl)cyclobutane-4-carboxylic acid;

(1α,2β,3β,4α)-1,2-Di[N-propyl-N-(4-phenoxybenzyl) aminocarbonyl]-3,4-di(cyclopentylcarboxymethoxycarbonyl)cyclobutane;

(1α,2β,3β,4α)-1,2-Di[N-propyl-N-(4-phenoxybenzyl) aminocarbonyl]-3-(cyclohexylcarboxymethoxycarbonyl) cyclobutane-4-carboxylic acid;

(1α,2β,3β,4α)-1,2-Di[N-propyl-N-(4-phenoxybenzyl) aminocarbonyl]-3,4-di(cyclohexylcarboxymethoxycarbonyl)cyclobutane;

(1α,2β,3β,4α)-1,2-Di[N-propyl-N-(4-phenoxybenzyl) aminocarbonyl]-3-(cyclohexylcarboxymethoxycarbonyl)cyclobutane-4-carboxylic acid;

(1α,2β,3β,4α)-1,2-Di[N-propyl-N-(4-phenoxybenzyl) aminocarbonyl]-3,4-di(cyclohexylcarboxymethoxycarbonyl)cyclobutane;

(1α,2β,3β,4α)-1,2-Di[N-propyl-N-(4-phenoxybenzyl) aminocarbonyl]-3-(1-propionyloxyethoxycarbonyl)cyclobutane-4-carboxylic acid;

(1α,2β,3β,4α)-1,2-Di[N-propyl-N-(4-phenoxybenzyl) aminocarbonyl]-3-(1-pivaloyloxyethoxycarbonyl)cyclobutane-4-carboxylic acid;

(1α,2β,3β,4α)-1,2-Di[N-propyl-N-(4-phenoxybenzyl) aminocarbonyl]-3,4-di(1-pivaloyloxyethoxycarbonyl))cyclobutane;

(1α,2β,3β,4α)-1,2-Di[N-propyl-N-(4-phenoxybenzyl) aminocarbonyl]-3-(1-methyl-1-propionyloxyethoxycarbonyl)cyclobutane-4-carboxylic acid;

(1α,2β,3β,4α)-1,2-Di[N-propyl-N-(4-phenoxybenzyl) aminocarbonyl]-3-(methoxycarboxymethoxycarbonyl)cyclobutane-4-carboxylic acid;

(1α,2β,3β,4α)-1,2-Di[N-propyl-N-(4-phenoxybenzyl) aminocarbonyl]-3,4-di(methoxycarboxymethoxycarbonyl))cyclobutane;

(1α,2β,3β,4α)-1,2-Di[N-propyl-N-(4-phenoxybenzyl) aminocarbonyl]-3-(propionyloxymethoxycarbonylmethyl)cyclobutane-4-acetic acid;

(1α,2β,3β,4α)-1,2-Di[N-propyl-N-(4-phenoxybenzyl) aminocarbonyl]-3,4-di(propionyloxymethoxycarbonylmethyl))cyclobutane;

(1α,2β,3β,4α)-1,2-Di[N-propyl-N-(4-phenoxybenzyl) aminocarbonyl]-3-(2-hydroxy-3,4-dioxocyclobut-1-enylamino)cyclobutane-4-carboxylic acid;

(1α,2β,3β,4α)-1,2-Di[N-propyl-N-(4-phenoxybenzyl) aminocarbonyl]-3-(5-oxo-4,5-dihydro-[1,3,4]oxadiazol-2-yl)cyclobutane-4-carboxylic acid;

(1α,2β,3β,4α)-1,2-Di[N-propyl-N-(4-phenoxybenzyl) aminocarbonyl]cyclobutane-3-(N-methanesulfonyl)carboxamido-4-carboxylic acid;

(1α,2β,3β,4α)-1,2-Di[N-propyl-N-(4-phenoxybenzyl) aminocarbonyl]cyclobutane-3-(4,6-dioxo-tetrahydropyran-2-yl)-4-carboxylic acid;

(1α,2β,3β,4α)-1,2-Di[(N-methyl-N-(R)-α-propyl-4-phenoxybenzyl)aminocarbonyl]cyclobutane-3,4-dicarboxylic acid;

(1α,2β,3β,4α)-1,2-Di[N-(S)-sec-butyl-N-(4-phenoxybenzyl)aminocarbonyl]cyclobutane-3,4-dicarboxylic acid;

(1α,2β,3β,4α)-1,2-Di[N-(R)-sec-butyl-N-(4-phenoxybenzyl)aminocarbonyl]cyclobutane-3,4-dicarboxylic acid;

(1α,2β,3β,4α)-1,2-Di[N-propyl-N-(4-phenoxybenzyl) aminocarbonyl]-3-(methoxyacetyl)cyclobutane-4-acetic acid;

(1α,2β,3β,4α)-1,2-Di[N-propyl-N-(4-phenoxybenzyl) aminocarbonyl]-3-(5-oxo-4,5-dihydro-[1,3,4]-oxadiazol-2-ylmethyl)cyclobutane-4-acetic acid;

(1α,2β,3β,4α)-1,2-Di[N-propyl-N-(4-phenoxybenzyl) aminocarbonyl]-3-(2-hydroxyethyl)cyclobutane-4-acetic acid;

(1α,2β,3β,4α)-1,2-Di[N-propyl-N-[4-phenoxybenzyl]-aminocarbonyl]-3-(2-oxo-ethyl)cyclobutane-4-acetic acid;

(1α,2β,3β,4α)-1,2-Di[N-propyl-N-[4-phenoxybenzyl] aminocarbonyl]-3-(5-tetrazolylmethyl)cyclobutane-4-acetic acid;

(1α,2β,3β,4α)-1,2-Di[N-propyl-N-(4-phenoxybenzyl) aminocarbonyl]-3-benzyloxycarbonylcyclobutane-4-carboxylic acid;

(1α,2β,3β,4α)-1,2-Di[N-propyl-N-(4-phenoxybenzyl) aminocarbonyl]-3-(N,N-diethylaminocarbonylmethoxycarbonyl)cyclobutane-4-carboxylic acid;

(1α,2β,3β,4α)-1,2-Di[N-propyl-N-(4-phenoxybenzyl) aminocarbonyl]-3-(indan-5-yloxycarbonyl)cyclobutane-4-carboxylic acid;

(+)-(1α,2β,3β,4α)-1,2-Di[N-propyl-N-(trans, trans-3,7-dimethyl-2,6-octadienyl)aminocarbonyl]cyclobutane-3,4-dicarboxylic acid;

(+)-(1α,2β,3β,4α)-1,2-Di[N-methyl-N-((1S)-1-(4-phenoxyphenyl)-1-ethyl)aminocarbonyl]cyclobutane-3,4-dicarboxylic acid;

(+)-(1α,2β,3β,4α)-1,2-Di[N-methyl-N-((1R)-1-(4-phenoxyphenyl)-1-butyl)aminocarbonyl]cyclobutane-3,4-dicarboxylic acid;

(+)-(1α,2β,3β,4α)-1,2-Di[N-methyl-N-((1S)-1-(4-phenoxyphenyl)-1-butyl)aminocarbonyl]cyclobutane-3,4-dicarboxylic acid;

(+)-(1α,2β,3β,4α)-1,2-Di[N-((1S)-1-(4-phenoxyphenyl)-1-butyl)aminocarbonyl]cyclobutane-3,4-dicarboxylic acid;

(+)-(1α,2β,3β,4α)-1,2-Di[N-propyl-N-((1S)-1-(4-phenoxyphenyl)-1-butyl)aminocarbonyl]cyclobutane-3,4-dicarboxylic acid;

(1α,2β,3β,4α)-1,2-Di[N-propyl-N-(4-phenoxybenzyl) aminocarbonylamino]cyclobutane-3,4-dicarboxylic acid;

(1α,2β,3β,4α)-1,2-Di[N-propyl-N-(4-phenoxybenzylcarbonyl)amino]cyclobutane-3,4-dicarboxylic acid;

(1α,2β,3β,4α)-1,2-Di[N-{(2S)-2-(4-phenoxyphenyl)pentanoylamino]cyclobutane-3,4-dicarboxylic acid;

(1α,2β,3β,4α)-1,2-Di[N-propyl-N-(4-phenoxybenzyl) aminocarbonyl]-4-(N-hydroxy-N-trifluoroacetylaminomethyl)cyclobutane-3-carboxylic acid;

(−)-(1α,2β,3β,4α)-1,2-Di[N-propyl-N-(4-phenoxybenzyl) aminocarbonyl]-3-(methoxycarbonyl)cyclobutane-4-carboxylic acid;

(1α,2β,3β,4α)-1,2-Di[N-propyl-N-(4-phenoxybenzyl) aminocarbonyl]-4-formylcyclobutane-3-carboxylic acid;

(−)-(1α,2β,3β,4α)-1,2-Di{N-propyl-N-[(4-phenoxy)benzyl]aminocarbonyl}cyclobutane-3,4-diacetic acid;

(−)-(1α,2β,3β,4α)-1,2-Di[N-propyl-N-(4-phenoxybenzyl) aminocarbonyl]-3-(5-oxo-4,5-dihydro-[1,3,4]-oxadiazol-2-ylmethyl)cyclobutane-4-acetic acid;

(−)-(1α,2β,3β,4α)-1,2-Di[N-propyl-N-(4-phenoxybenzyl) aminocarbonyl]-3,4-di(5-oxo-4,5-dihydro-[1,3,4]-oxadiazol-2-ylmethyl)cyclobutane;

(−)-(1α,2β,3β,4α)-1,2-Di{N-cyclopentyl-N-[(4-phenoxy)benzyl]aminocarbonyl}cyclobutane-3,4-diacetic acid;

(−)-(1α,2β,3β,4α)-1,2-Di[N-cyclopentyl-N-(4-phenoxybenzyl)aminocarbonyl]-3-(5-oxo-4,5-dihydro-[1,3,4]-oxadiazol-2-ylmethyl)cyclobutane-4-acetic acid;

(−)-(1α,2β,3β,4α)-1,2-Di[N-cyclopentyl-N-(4-phenoxybenzyl)aminocarbonyl]-3,4-diacetic acid 3-methyl ester;

(1α,2β,3β,4α)-1,2-Di[N-(R)-α-ethyl-(4-phenoxybenzyl)aminocarbonyl]cyclobutane-3,4-dicarboxylic acid;

(1α,2β,3β,4α)-1,2-Di[N-(S)-α-ethyl-(4-phenoxybenzyl)aminocarbonyl]cyclobutane-3,4-dicarboxylic acid;

(1α,2β,3β,4α)-1,2-Di[N-propyl-N-(R)-α-ethyl-N-(4-phenoxybenzyl)-aminocarbonyl]-cyclobutane-3,4-dicarboxylic acid;

(1α,2β,3β,4α)-1,2-Di[N-propyl-N-(S)-α-ethyl-N-(4-phenoxybenzyl)-aminocarbonyl]-cyclobutane-3,4-dicarboxylic acid;

(1α,2β,3β,4α)-1,2-Di[N-benzyl-N-(R)-α-ethyl-N-(4-phenoxybenzyl)-aminocarbonyl]-cyclobutane-3,4-dicarboxylic acid;

(1α,2β,3β,4α)-1,2-Di[N-benzyl-N-(S)-α-ethyl-N-(4-phenoxybenzyl)-aminocarbonyl]-cyclobutane-3,4-dicarboxylic acid;

(1α,2β,3β,4α)-1,2-Di[N-(cyclopropylmethyl)-N-(R)-α-ethyl-(4-phenoxybenzyl)-aminocarbonyl]cyclobutane-3,4-dicarboxylic acid;

(1α,2β,3β,4α)-1,2-Di[N-(cyclopropylmethyl)-N-(S)-α-ethyl-(4-phenoxybenzyl)-aminocarbonyl]cyclobutane-3,4-dicarboxylic acid;

(1α,2β,3β,4α)-1,2-Di[N-(R)-α-methyl-(4-phenoxybenzyl)aminocarbonyl]-cyclobutane-3,4-dicarboxylic acid;

(1α,2β,3β,4α)-1,2-Di[N-(S)-α-methyl-(4-phenoxybenzyl)aminocarbonyl]-cyclobutane-3,4-dicarboxylic acid;

(1α,2β,3β,4α)-1,2-Di[N-propyl-N-(R)-α-methyl-(4-phenoxybenzyl)-aminocarbonyl]-cyclobutane-3,4-dicarboxylic acid;

(1α,2β,3β,4α)-1,2-Di[N-propyl-N-(S)-α-methyl-(4-phenoxybenzyl)-aminocarbonyl]-cyclobutane-3,4-dicarboxylic acid;

(1α,2β,3β,4α)-1,2-Di[N-benzyl-N-(R)-α-methyl-(4-phenoxybenzyl)aminocarbonyl]-cyclobutane-3,4-dicarboxylic acid;

(1α,2β,3β,4α)-1,2-Di[N-benzyl-N-(S)-α-methyl-(4-phenoxybenzyl)-aminocarbonyl]-cyclobutane-3,4-dicarboxylic acid;

(1α,2β,3β,4α)-1,2-Di[N-(cyclopropylmethyl)-N-(R)-α-methyl-(4-phenoxybenzyl)-aminocarbonyl]cyclobutane-3,4-dicarboxylic acid;

(1α,2β,3β,4α)-1,2-Di[N-(cyclopropylmethyl)-N-(S)-α-methyl-(4-phenoxybenzyl)-aminocarbonyl]cyclobutane-3,4-dicarboxylic acid;

(1α,2β,2β,4α)-1,2-Di[N-(R)-α-(cyclopropylmethyl)-(4-phenoxybenzyl)amino-carbonyl]cyclobutane-3,4-dicarboxylic acid;

(1α,2β,3β,4α)-1,2-Di[N-(S)-α-(cyclopropylmethyl)-(4-phenoxybenzyl)amino-carbonyl]cyclobutane-3,4-dicarboxylic acid;

(1α,2β,3β,4α)-1,2-Di[N-propyl-N-(R)-α-(cyclopropylmethyl)-(4-phenoxybenzyl)-aminocarbonyl]cyclobutane-3,4-dicarboxylic acid;

(1α,2β,3β,4α)-1,2-Di[N-propyl-N-(S)-α-(cyclopropylmethyl)-(4-phenoxybenzyl)-aminocarbonyl]cyclobutane-3,4-dicarboxylic acid;

(1α,2β,3β,4α)-1,2-Di[N-benzyl-N-(R)-α-(cyclopropylmethyl)-(4-phenoxybenzyl)-aminocarbonyl]cyclobutane-3,4-dicarboxylic acid;

(1α,2β,3β,4α)-1,2-Di[N-benzyl-N-(S)-α-(cyclopropylmethyl)-(4-phenoxybenzyl)-aminocarbonyl]cyclobutane-3,4-dicarboxylic acid;

(1α,2β,3β,4α)-1,2-Di[N-(cyclopropylmethyl)-N-(R)-α-(cyclopropylmethyl)-(4-phenoxybenzyl)aminocarbonyl]cyclobutane-3,4-dicarboxylic acid; and (1α,2β,3β,4α)-1,2-Di[N-(cyclopropylmethyl)-N-(S)-α-(cyclopropylmethyl)-(4-phenoxybenzyl)aminocarbonyl]cyclobutane-3,4-dicarboxylic acid;

or a pharmaceutically acceptable salt thereof.

Preferred compounds are selected from the group consisting of (1α,2β,3β,4α)-1,2-Di[N-benzyl-N-(4-phenoxybenzyl)aminocarbonyl]cyclobutane-3,4-dicarboxylic acid;

(1α,2β,3β,4α)-1,2-Di[N-propyl-N-(4-phenoxybenzyl)aminocarbonyl]cyclobutane-3,4-dicarboxylic acid;

(−)-(1α,2β,3β,4α)-1,2-Di[N-propyl-N-(4-phenoxybenzyl)aminocarbonyl]cyclobutane-3,4-dicarboxylic acid;

(1α,2β,3β,4α)-1,2-Di[N-(2-ethylthioethyl)-N-(4-phenoxybenzyl)aminocarbonyl]cyclobutane-3,4-dicarboxylic acid;

(1α,2β,3β,4α)-1,2-Di[N-(cyclopropylmethyl)-N-(4-phenoxybenzyl)-aminocarbonyl]cyclobutane-3,4-dicarboxylic acid;

(1α,2β,3β,4α)-1-[N-Propyl-N-(4-phenoxybenzyl)aminocarbonyl]-2-[N-benzyl-N-(4-phenoxybenzyl)aminocarbonyl]cyclobutane-3,4-dicarboxylic acid;

(1α,2β,3β,4α)-1,2-Di[N-propyl-N-(4-phenylthiobenzyl)aminocarbonyl]cyclobutane-3,4-dicarboxylic acid;

(1α,2β,3β,4α)-1,2-Di[N-propyl-N-(4-phenoxybenzyl)aminocarbonyl-4-tetrazolylmethyl-cyclobutane-3-carboxylic acid;

(1α,2β,3β,4α)-1,2-Di[N-propyl-N-(4-phenoxybenzyl)aminocarbonyl]-4-(3-carboxypropionylamino)cyclobutane-3-carboxylic acid;

(1α,2β,3β,4α)-1,2-Di[N-propyl-N-(4-phenoxybenzyl)aminocarbonyl]-4-(1-carboxy-1-hydroxymethyl)cyclobutane-3-carboxylic acid;

(1α,2β,3β,4α)-1,2-Di[N-propyl-N-(4-phenoxybenzyl)aminocarbonyl]cyclobutane-3-[N-(5-tetrazolyl)]carboxamide-4-carboxylic acid;

(1α,2β,3β,4α)-4-(Carboxy)methyl)-1,2-di[N-propyl-N-(4-phenoxybenzyl)aminocarbonyl]cyclobutane-3-carboxylic acid;

(1α,2β,3β,4α)-1,2-Di[-N-propyl-N-(4-phenoxybenzyl)aminocarbonyl]cyclobutane-3,4-diacetic acid;

(1α,2β,3β,4α)-1,2-Di[N-propyl-N-(4-phenoxybenzyl)aminocarbonyl]-3-(2-hydroxy-3,4-dioxocyclobut-1-enylamino)cyclobutane-4-carboxylic acid;

(1α,2β,3β,4α)-1,2-Di[N-propyl-N-(4-phenoxybenzyl)aminocarbonyl]-3-(5-oxo-4,5-dihydro-[1,3,4]oxadiazol-2-yl)cyclobutane-4-carboxylic acid;

(1α,2β,3β,4α)-1,2-Di[N-propyl-N-(4-phenoxybenzyl)aminocarbonyl]-3-(5-oxo-4,5-dihydro-[1,3,4]-oxadiazol-2-ylmethyl)cyclobutane-4-acetic acid;

(1α,2β,3β,4α)-1,2-Di[N-propyl-N-(4-phenoxybenzyl)aminocarbonyl]-3-(5-tetrazolylmethyl)cyclobutane-4-acetic acid;

(−)-(1α,2β,3β,4α)-1,2-Di[N-propyl-N-(4-phenoxybenzyl)aminocarbonyl]-3-(methoxycarbonyl)cyclobutane-4-carboxylic acid;

(−)-(1α,2β,3β,4α)-1,2-Di{N-propyl-N-[(4-phenoxy)benzyl]aminocarbonyl}cyclobutane-3,4-diacetic acid;

(−)-(1α,2β,3β,4α)-1,2-Di[N-propyl-N-(4-phenoxybenzyl)aminocarbonyl]-3-(5-oxo-4,5-dihydro-[1,3,4]-oxadiazol-2-ylmethyl)cyclobutane-4-acetic acid;

(−)-(1α,2β,3β,4α)-1,2-Di{N-cyclopentyl-N-[(4-phenoxy)benzyl]aminocarbonyl}cyclobutane-3,4-diacetic acid; and (−)-(1α,2β,3β,4α)-1,2-Di[N-cyclopentyl-N-(4-phenoxybenzyl)aminocarbonyl]-3-(5-oxo-4,5-dihydro-[1,3,4]-oxadiazol-2-ylmethyl)cyclobutane-4-acetic acid;

or a pharmaceutically acceptable salt thereof.

Particularly preferred is the compound (−)-(1α,2β,3β,4α)-1,2-Di[N-propyl-N-(4-phenoxybenzyl)aminocarbonyl]-3-(methoxycarbonyl)cyclobutane-4-carboxylic acid, or a pharmaceutically acceptable salt thereof.

In general, the compounds of the invention can be prepared by the processes illustrated in Schemes I-XIX. According to reaction Scheme I, 1,2,3,4-cyclobutanetetracarboxylic dianhydride (where the two anhydrides are trans to one another) in an inert solvent such as dimethylformamide is treated with an appropriately substituted secondary amine ($HNR_1R_2$) in the presence of an aprotic base such as triethylamine to afford a mixture of the 1,2- and 1,3-diamides. (The isomeric diamides are separable by column chromatography.) The dicarboxylic acid (2) can be further elaborated, if desired, to its diester 4 (wherein $R_{10}$ is loweralkyl, benzyl, a carboxy protecting group or prodrug) by treatment with an alcohol such as methanol in the presence of concentrated sulfuric acid or with diazomethane.

Alternatively Scheme II illustrates the reaction of 1,2,3, 4-cyclobutanetetracarboxylic dianhydride (where the two anhydrides are trans to one another) with an alcohol such as methanol to give a mixture of the diesters 6 and 7 (wherein $R_{20}$ is loweralkyl or benzyl) following the procedure described in Angew. Chem. International Ed. 8: 208 (1969). (The isomeric diesters are separable by column chromatography or crystallization.) Compound 6 is activated as an acid halide (for example by treatment with thionyl chloride or phosphorus oxychloride) or activated ester including esters or anhydrides derived from formic acid, acetic acid and the like, alkoxycarbonyl halides, N-hydroxysuccinimide, N-hydroxyphthalimide, N-hydroxybenzotriazole, N-hydroxy-5-norbornene-2,3-dicarboxamide, 2,4,5-trichlorophenol and the like and then reacted with a secondary amine ($HNR_1R_2$) to give compound 8. Hydrolysis of the esters, for example, with sodium hydroxide in methanol-water or lithium hydroxide in THF) affords the dicarboxylic acid 2. Alternatively, the diacid is treated with diphenylphosphoryl azide and triethylamine followed by treatment with a secondary amine to give bisurea diester 9. Ester hydrolysis or catalytic hydrogenation of 9 affords the diacid 10.

The preparation of optically active compounds of the invention is shown in Scheme III. (In a preferred embodiment, $R_1$ is propyl and $R_2$ is 4-(phenoxy)benzyl.) The dicarboxylic acid 2 is esterified with a chiral alcohol (such as (+) or (−) sec-phenethyl alcohol or (+) or (−) menthol and the like) to give a mixture of phenethyl esters (11) which are separable by silica gel chromatography to give a single diastereomer 12. Catalytic hydrogenation or hydrolysis affords the optically active product 13.

The carboxy functionalities of compound 2 can be elaborated in a number of ways. Scheme IV shows the replacement of one of the carboxy groups with tetrazolyl. The dicarboxylic acid diamide 2, prepared in Scheme I, is converted to a mono-ester 14 where $R_{30}$ is loweralkyl (for example, making the diester and hydrolyzing one of the esters with a stoichiometric amount of lithium hydroxide). The remaining carboxylic acid moiety is reduced (for example, via a mixed anhydride with sodium borohydride or with $BH_3$ and the like) to give the hydroxymethyl compound 15. The hydroxymethyl compound is oxidized (for example, using tetrapropylammonium perruthenate (TPAP) or oxalyl chloride in DMSO and the like) to give the aldehyde 16. The aldehyde is reacted with hydroxylamine to give the oxime 17. Treatment of the oxime 17 with trifluoroacetic anhydride gives the cyano compound 18. The cyano compound is reacted by standard tetrazole forming methodology (for example, sodium azide and triethylamine hydrochloride in DMF) to give the tetrazolyl compound 19. Ester hydrolysis of 19 (for example, lithium hydroxide in THF) affords the tetrazolyl carboxylic acid 20.

Other modifications of the carboxy functionality are shown in Scheme V. To make the tetrazolylmethyl compound, the hydroxymethyl compound 15 where $R_{30}$ is loweralkyl, prepared in Scheme IV, is activated (for example, by reacting with methane sulfonyl chloride to give the methane sulfonate) and then reacted with potassium cyanide to give the cyanomethyl compound 21. The cyano compound is reacted by standard tetrazole forming methodology (for example, sodium azide and triethylamine hydrochloride in DMF) to give the tetrazolyl compound, which is hydrolyzed (for example, with lithium hydroxide in water and methanol) to give the carboxylic acid 22.

Starting from the carboxaldehyde 16 where $R_{30}$ is loweralkyl, prepared in Scheme IV, treatment with furan, n-butyl lithium and CuCN in an inert solvent such as THF, followed by acetylation with acetic anhydride affords the acetoxy furanyl methyl compound 23. Treatment of compound 23 with ruthenium oxide and sodium periodate converts the furan to a carboxylic acid; and then lithium hydroxide hydrolysis of the ester affords the dicarboxylic acid 24.

Starting from the mono-ester 14 where $R_{30}$ is loweralkyl, prepared in Scheme IV, the carboxylic acid is activated with isobutylchloroformate in the presence of 4-methylmorpholine and then reacted with diazomethane to give the diazoacetyl compound 25. Treatment of the diazoacetyl compound with silver benzoate in methanol affords the diester which is hydrolyzed to give the dicarboxylic acid 26.

Starting with the dicarboxylic acid 2, prepared in Scheme I, the carboxylic acids are activated with isobutylchloroformate in the presence of 4-methylmorpholine and then reacted with diazomethane to give the bis-diazoacetyl compound 27. Treatment of the diazoacetyl compound with silver benzoate in methanol affords the diester which is hydrolyzed to give the diacetic acid 28.

Starting with the mono-ester 14 (wherein $R_{30}$ is loweralkyl), prepared in Scheme IV, under standard peptide coupling conditions (for example, using 1-hydroxybenzotriazole and N-methylmorpholine in DMF) plus a carboxy-protected amino acid (for example, the methyl ester of norleucine, β-alanine, sarcosine, glycine, proline and the like) affords the carboxy-protected mono-amino acid derivative (where AA represents an amino acid), which is hydrolyzed to give the dicarboxylic acid 29. Di-, tri- and tetra-peptide derivatives can be similarly prepared, using the appropriate carboxy-protected di-, tri- or tetra-peptide.

Scheme VI illustrates further modifications of the carboxy moiety. The mono-ester 14 (wherein $R_{30}$ is loweralkyl), prepared in Scheme IV, is reacted with diphenylphosphorylazide in the presence of triethylamine followed by benzyl alcohol to give the benzyloxycarbonyl protected amine 43 (Z is benzyloxycarbonyl). Catalytic hydrogenation removes the Z protecting group to give the 4-amino compound 44. The amine 44 is reacted with $EtO_2C(CH_2)_rC(O)Cl$ (where r is 0 to 4) in the presence of 2,6-lutidine to give compound 45. Ester hydrolysis using lithium hydroxide in THF affords the dicarboxylic acid 46.

Aldehyde 16, prepared in Scheme IV, is reacted with methyl triphenylphoranylideneacetate to give compound 47 where E is $R_{30}$ where $R_{30}$ is lower alkyl. Lithium hydroxide hydrolysis of 47 in THF affords the diacid 48 where E is hydrogen.

Scheme VII illustrates the preparation of two other stereoisomers encompassed by the present invention. The (1α,2β, 3β,4α) isomer 2 results from the opening of 1,2,3,4-cyclobutanetetracarboxylic dianhydride 1 described in Scheme I. Another isomer is obtained by epimerization of one center on the cyclobutane ring. The mono-ester 14, prepared in Scheme IV, (wherein $R_{30}$ is loweralkyl) is dissolved in an inert solvent, such as THF or ether or dimethoxyethane and the like, cooled, and treated with a non-nucleophilic base (for example, with sodium hexamethyidisilazide or lithium diisopropylamide and the like). Quenching with a protic source such as acetic acid, followed by ester hydrolysis affords the (1α,2β,3α,4α)-isomer as the dicarboxylic acid 30.

Another isomer is obtained by taking the (1α,2β,3β,4α) isomer of diester 8, prepared in Scheme II, (wherein $R_{30}$ is loweralkyl) and epimerizing with sodium methoxide in methanol to give the (1α,2β,3α,4β) isomer 49 (wherein J is $R_{30}$ where $R_{30}$ is lower alkyl). Sodium hydroxide hydrolysis in methanol-water gives the dicarboxylic acid 50 (wherein J is hydrogen).

The preparation of other isomers is shown in Scheme VIII. Furan-2-acrylic acid 31 is photodimerized resulting in two isomers (the (1α,2α,3β,4α)-isomer 32 and the (1α,2α,3α,4α)-isomer 33) which are separable by column chromatography. These photoadducts are then coupled to the appropriate amine ($R_1R_2NH$) under standard peptide coupling conditions (for example, bis(2-oxo-3-oxazolidinyl) phosphinic chloride in DMF) to give the diamides 34 and 35. The furan groups can be converted to carboxylic acids using the procedure described by Danishefsky et al., J. Amer. Chem. Soc., 110 (12), 3929–3940 (1988) to give (1α,2α,3β,4β) 36 and (1α,2α,3α,4α) 37.

The preparation of yet another isomer is shown in Scheme IX. The (1α,2α,3β,4β)-isomer 36 is converted to the mono-ester 38 where $R_{30}$ is loweralkyl (for example, by converting to the dimethyl ester with diazomethane and then hydrolyzing one of the ester functionalities with a stoichiometric amount of lithium hydroxide). The mono-ester 38 is epimerized with a non-nucleophilic base (for example, with sodium hexamethyidisilazide or lithium diisopropylamide and the like) to give the (1α,2α,3α,4β)-isomer 39. The ester is then hydrolyzed to give the dicarboxylic acid 40.

The preparation of compounds where both amides are not the same is shown in Scheme X. Opening 1,2,3,4-cyclobutanetetra-carboxylic dianhydride with a stoichiometric amount of an amine ($R_1R_2NH$) gives the mono-amide tricarboxylic acid 41. Using typical peptide coupling conditions (for example, treating with dicyclohexylcarbodiimide in a mixture of DMF and methylene chloride) and an appropriate amine ($R_1*R_2*NH$) gives the desired diamide 42 having different amide substituents.

An alternate method for preparing the compounds of the invention is shown in Scheme XI. 1,2,3,4-Cyclobutanetetracarboxylic anhydride 1 is reacted with benzyl alcohol to give the 1,2-dibenzyl ester 51 as a solid obtained by crystallization, i.e. no chromatography is required to separate it from the 1,3-dibenzyl ester also obtained. Treatment of compound 51 with oxalyl chloride and the appropriate amine ($R_1R_2NH$) in the presence of Hunig's base affords the diamide 52. Catalytic hydrogenation (for example, using a palladium on carbon catalyst, hydrogen, and a methanol-ethyl acetate solvent system) to remove the benzyl protecting groups affords the desired diacid diamide 2.

A procedure for preparing reverse amides is shown in Scheme XII. A dicarboxylic acid where $R_{20}$ is loweralkyl or benzyl (for example, a diester 6 whose preparation was shown in Scheme II) is reacted with diphenylphosphoryl azide in an inert solvent (for example, in benzene or toluene and the like) in the presence of triethylamine followed by tert-butanol to give the bis(Boc-protected amine) 53. The protecting group is removed with trifluoroacetic acid to give the diamine 54 as its trifluoroacetate salt. This diamine is reacted with an acid ($R_2COOH$) 55 under amide coupling conditions (for example, 1-(3-dimethylaminopropyl)-3-ethylcarbodiimide HCl, 1-hydroxybenzotriazole hydrate, and triethylamine in THF) to give the diamide 56. Removal of the carboxy protecting groups (for example, hydrolysis of esters using sodium hydroxide in methanol-water or catalytic hydrogenation of benzyl esters) affords the diacid di-reverse amide 57.

A procedure for preparing N-substituted reverse amides is shown in Scheme XIII. The diamine 54 where $R_{20}$ is loweralkyl or benzyl, prepared in Scheme XII, is reacted with an acid chloride ($R_a*C(O)Cl$ wherein $R_a*$ is loweralkyl, cycloalkyl or cycloalkylalkyl) in the presence of triethylamine to give diamide 58. Reduction of the amide functionality (for example, using borane-tetrahydrofuran complex) affords the substituted amine compound 59. Treatment of 59 with the acid chloride of $R_2$—C(O)OH in the presence of triethylamine affords the diester diamide 60. Removal of the carboxy protecting groups (for example, hydrolysis of esters using sodium hydroxide in methanol-water or catalytic hydrogenation of benzyl esters) affords the diacid di-substituted reverse amide 61.

An alternate procedure for preparing N-substituted reverse amides is shown in Scheme XIV. The diacid 6 is converted to the N-protected diamine 65 (for example, by reaction with oxalyl chloride, followed by reaction with sodium azide, followed by reaction with t-BuOH and CuCl). Reaction of 65 with $R_a$-L ($R_a$ is loweralkyl, cycloalkyl or cycloalkylalkyl and L is a leaving group such as Cl, Br, I or a sulfonate) in the presence of a non-nucleophilic strong base (for example, NaH), followed by N-deprotection provides 66. Diamine 66 can be converted to 61 as described in Scheme XIII.

An alternative preparation of optically active compounds of the invention is shown in Scheme XV. The dibenzyl ester 51, prepared in Scheme XI, forms a salt with (−)-norephedrine in ethanol, and the desired optically active (−)-isomer crystallizes from solution. Separation of the salt of the (−)-isomer, followed by acidification affords the desired optically active dicarboxylic acid 62. Compound 62 is reacted with $R_1R_2NH$ to give the optically active diamide 63. Catalytic hydrogenation of compound 63 affords the optically active dicarboxylic acid 64.

The preparation of several carboxylic acid surrogates is shown in Scheme XVI. Amine 65 is prepared by the procedures outlined in the preceding schemes. Compound 66 is prepared from 3,4-dihydroxy-3-cyclobutene-1,2-dione and benzyl alcohol in toluene using a Dean-Stark trap and a catalytic amount of p-toluenesulfonic acid. Compound 65 is reacted with compound 66 in DMF with heating to give compound 67. Catalytic hydrogenation of compound 67 removes the protecting groups to give compound 68.

Mono-carboxylic acid 69 is prepared by the procedures described in the preceding schemes. The carboxylic acid group of compound 69 is activated (for example, using N-methylmorpholine and isobutyl chloroformate) and then reacted with tert-butyl carbazate to give the protected hydrazino carbonyl compound. Treatment with hydrogen chloride in dioxane affords the free hydrazino carbonyl compound 70. Compound 70 is reacted with phosgene in toluene to give cyclic compound 71. Debenzylation by catalytic hydrogenation affords the desired compound 72.

The preparation of other carboxylic acid surrogates is shown in Scheme XVII. Mono-carboxylic acid 69 is prepared by the procedures described in the preceding schemes. The carboxylic acid group of compound 69 is activated (for example, using carbonyldiimidazole) and then reacted with methanesulfonamide to give sulfonamido compound 73. Debenzylation by catalytic hydrogenation affords the desired compound 74.

Mono-carboxaldehyde 75 is prepared by the procedures described in the preceding schemes. 2,2,6-Trimethyl-4H-1, 3-dioxin-4-one is treated with a base such as lithium diisopropylamide and 1,3-dimethyl-3,4,5,6-tetrahydro-2(1H)-pyrimidone and then reacted with carboxaldehyde 75 to give compound 76. Treatment with potassium carbonate in methanol gives lactone 77. Debenzylation by catalytic hydrogenation affords the desired compound 78.

Several methods for preparing prodrugs are illustrated in Scheme XVIII. Diamide diacid (wherein $R_1$, $R_2$ and Q are as previously defined herein) 79 is mono-activated (for example, using carbonyldiimidazole) in an inert solvent such as methylene chloride and treated with an alcohol ($R_6OH$) to give compound 80. Alternatively, the diacid 79 is treated with a base (for example, sodium hydride) and sodium iodide in an inert solvent such as DMF and then reacted with a prodrug group (L—$R_6$) having a leaving group L (for example, a halide or a mesylate) to give compound 80.

Alternatively the diamide dibenzyl ester 81 is converted to the mono-carboxylic acid 82 using one equivalent of a base (for example, lithium hydroxide). The mono-carboxylic acid 82 is reacted with an alcohol ($R_6OH$) under coupling conditions (for example, 1-(3-dimethylaminopropyl)-3-ethylcarbodiimide hydrochloride and dimethylaminopyridine in DMF) to give the protected prodrug 83. Catalytic hydrogenation (for example, using a palladium on carbon catalyst) in solvent such as ethyl acetate effects debenzylation to afford compound 84.

The preparation of compounds having an optically active $R_2$ side chain is illustrated in Scheme XIX. The appropriate chiral oxazolidinone 85, (4S,5R) to give an (S)-side chain or (4R,5S) to give an (R)-side chain, is reacted with an activated (where T is an activating group, for example, a pivaloyloxy group or a halide) phenyl acetic acid 86 (where Z and $R_4$ are as previously defined herein) in the presence of an aprotic base such as triethylamine to give the N-acylated oxazolidinone 87. The oxazolidinone is alkylated by treatment with $NaN(Si(CH_3)_3)_2$ in THF followed by addition of the activated side chain (M—L where L is a leaving group such as halide or sulfonate) to give chiral compound 88. Oxazolidinone 88 is treated with 30% hydrogen peroxide followed by lithium hydroxide in THF and water to give the substituted phenyl acetic acid 89. The phenyl acetic acid 89 is reacted with diphenylphosphoryl azide in the presence of triethylamine followed by the addition of methanol to give carbamate 90. Compound 90 is reduced (for example, using lithium aluminum hydride) to give amine 91. The amine is coupled with the carboxylic acid functionalities of compound 92 (for example, using oxalyl chloride and a catalytic amount of DMF to give the acid chlorides) to give compound 93. Debenzylation by catalytic hydrogenation affords the diamide diacid 94.

SCHEME I

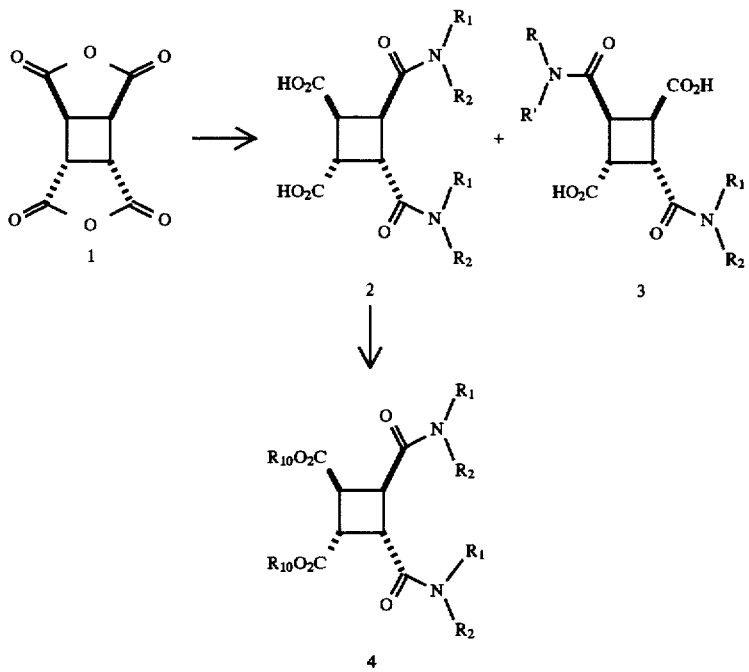

SCHEME II
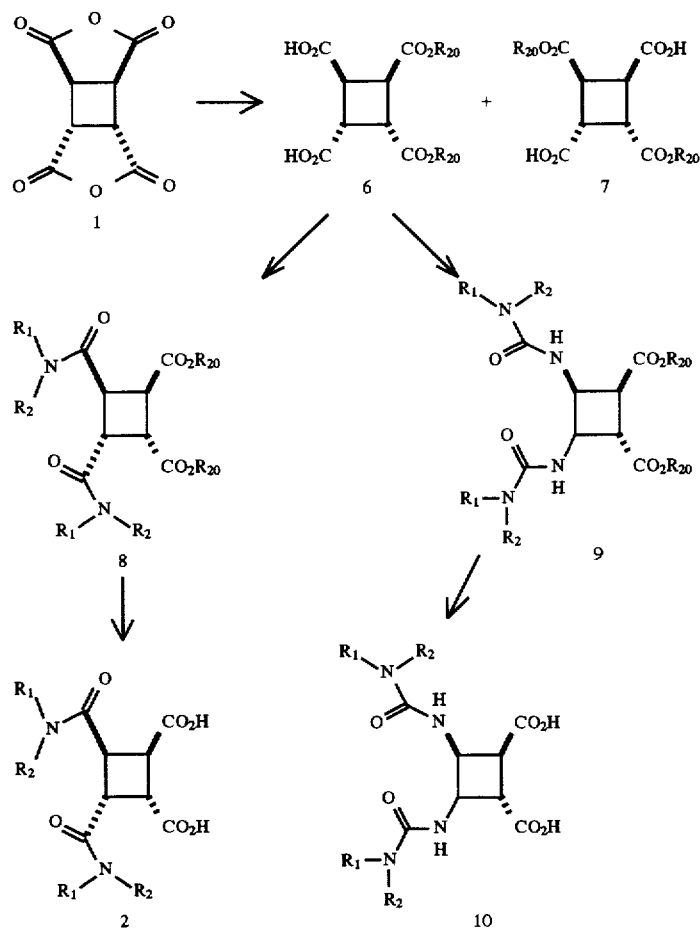
SCHEME III
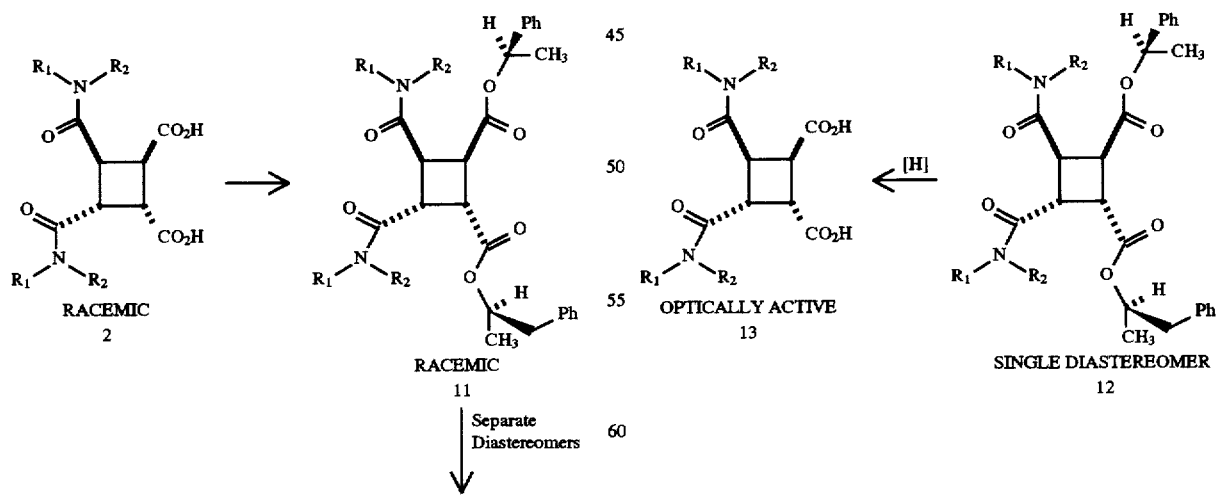

SCHEME IV
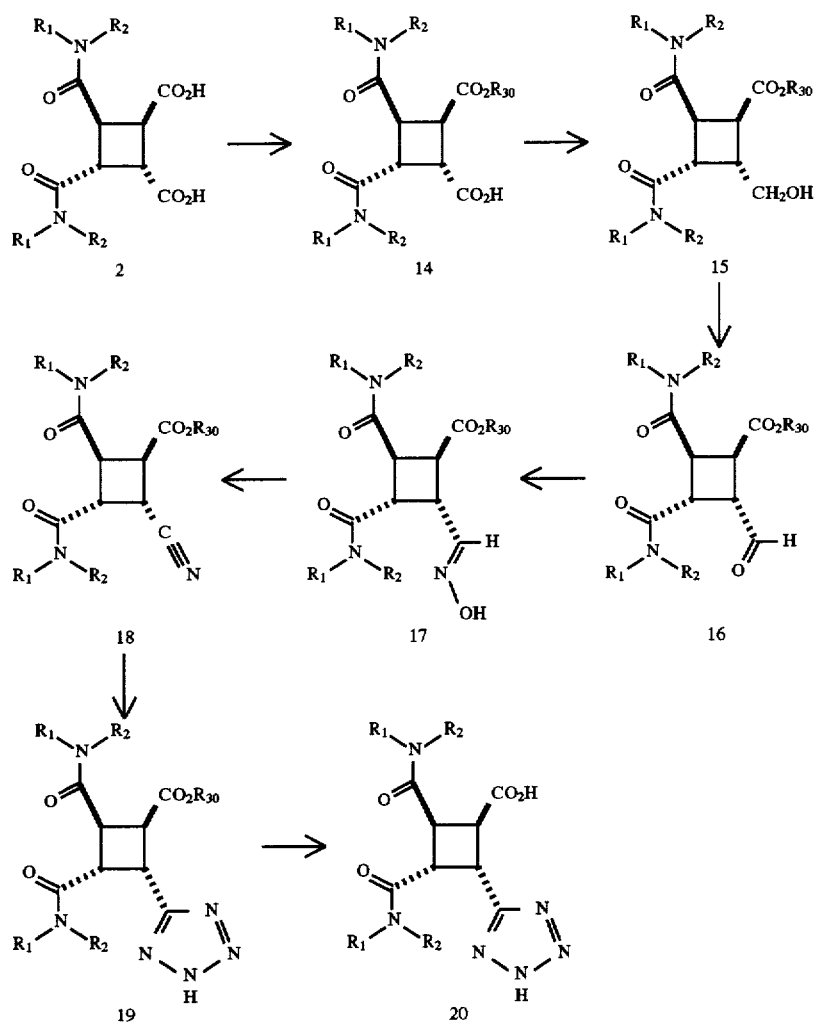
SCHEME V
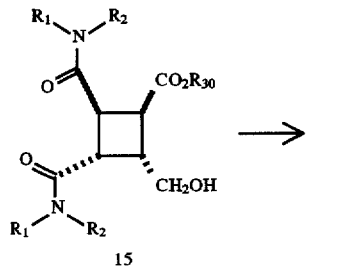
-continued
SCHEME V
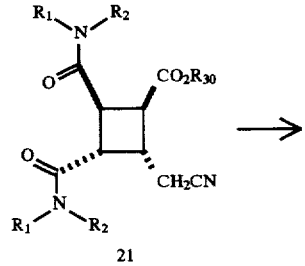

-continued
SCHEME V
-continued
SCHEME V
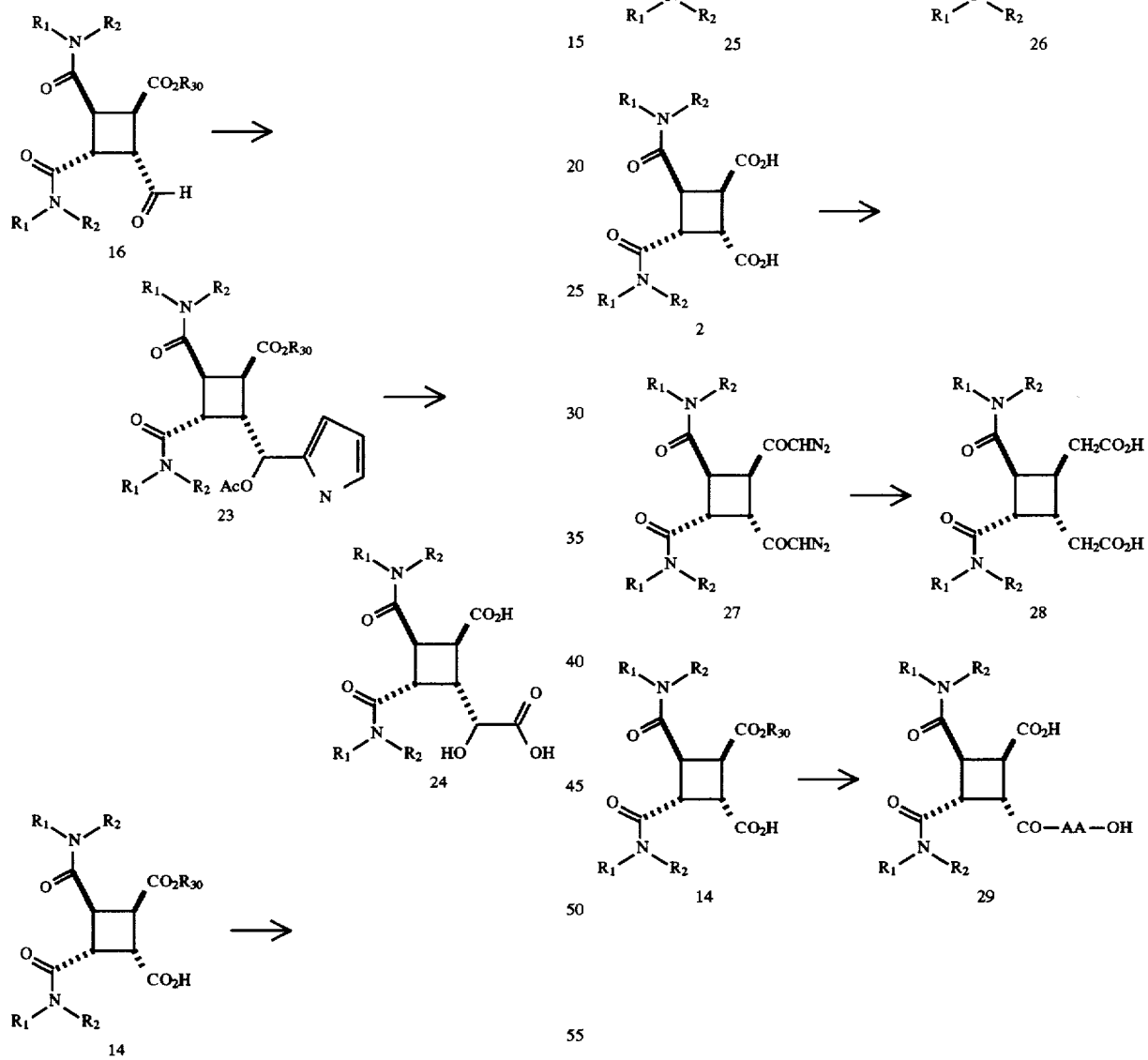

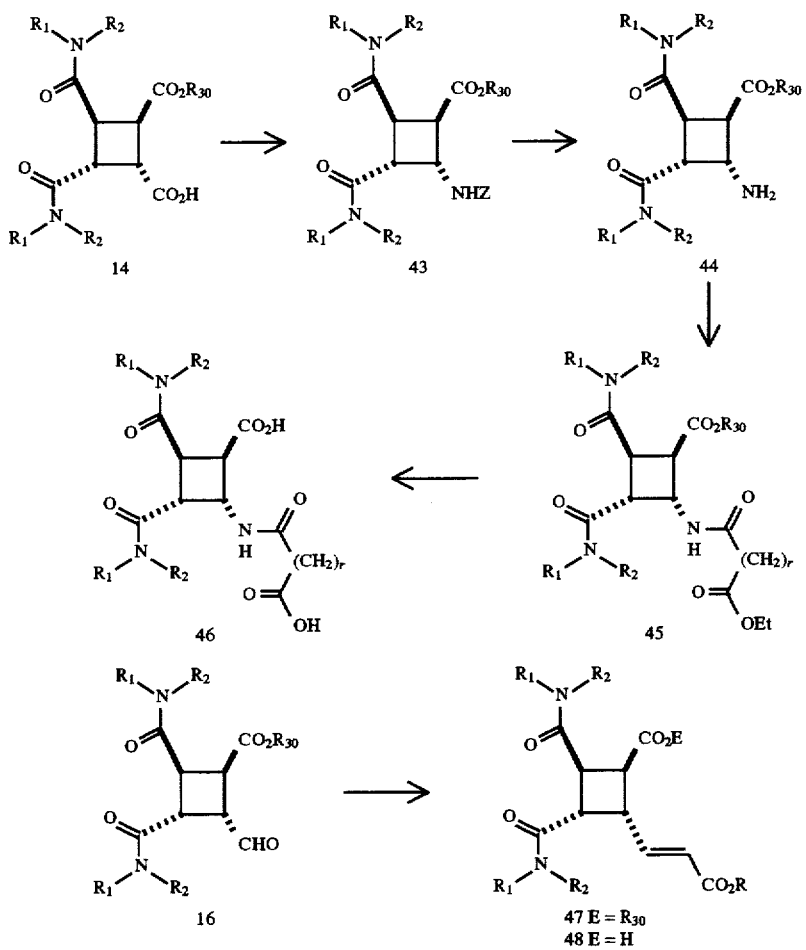
SCHEME VI
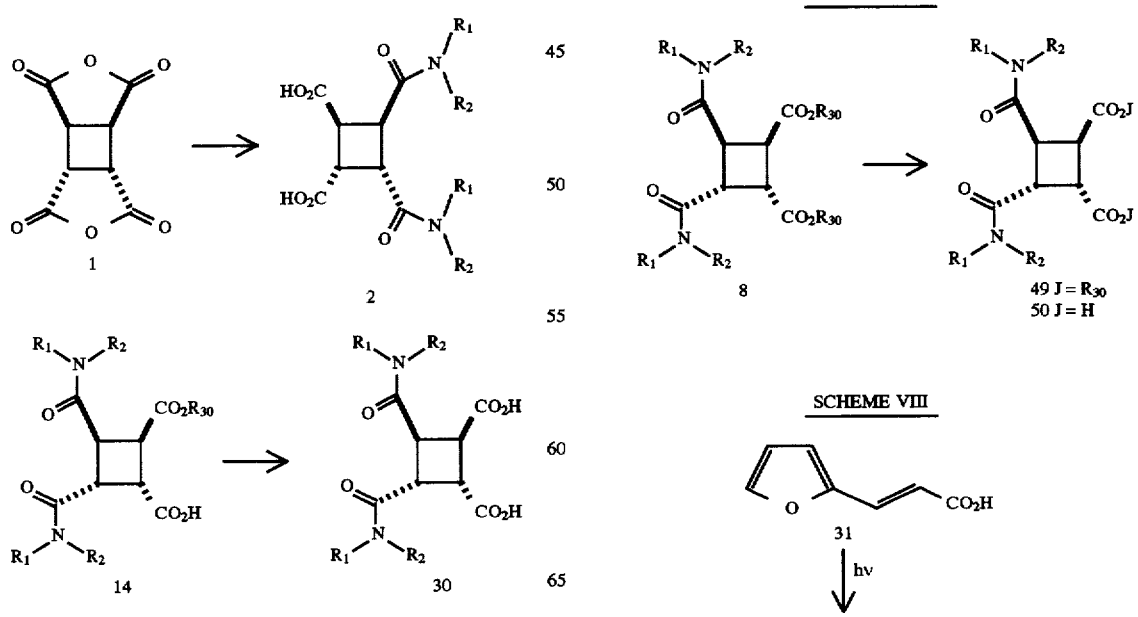
SCHEME VII
SCHEME VIII
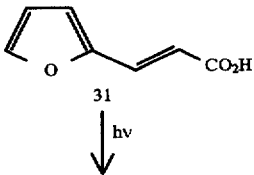

-continued
SCHEME VIII
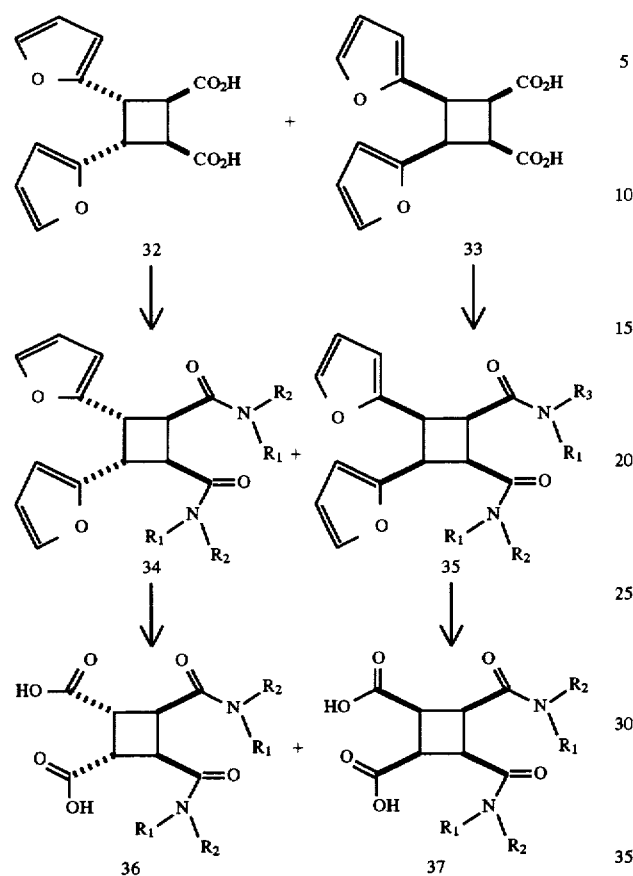
SCHEME X
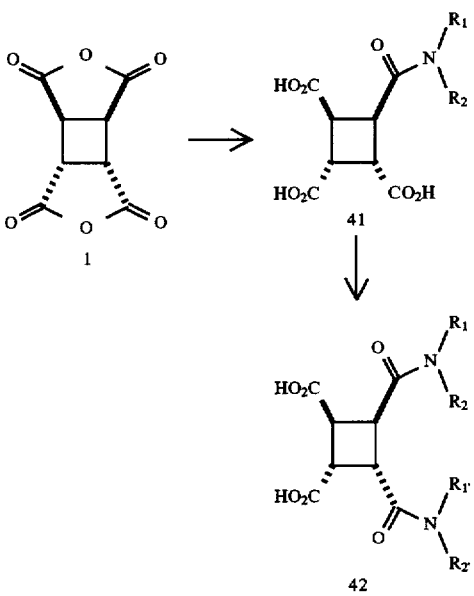
SCHEME IX
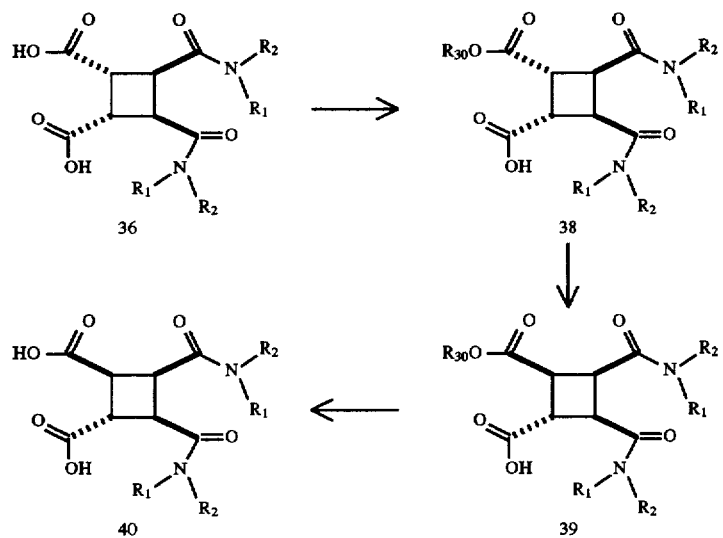

SCHEME XI
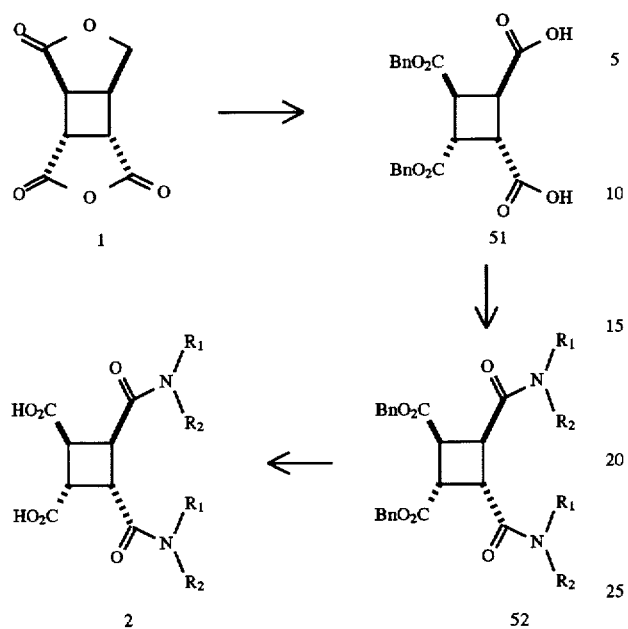
SCHEME XII
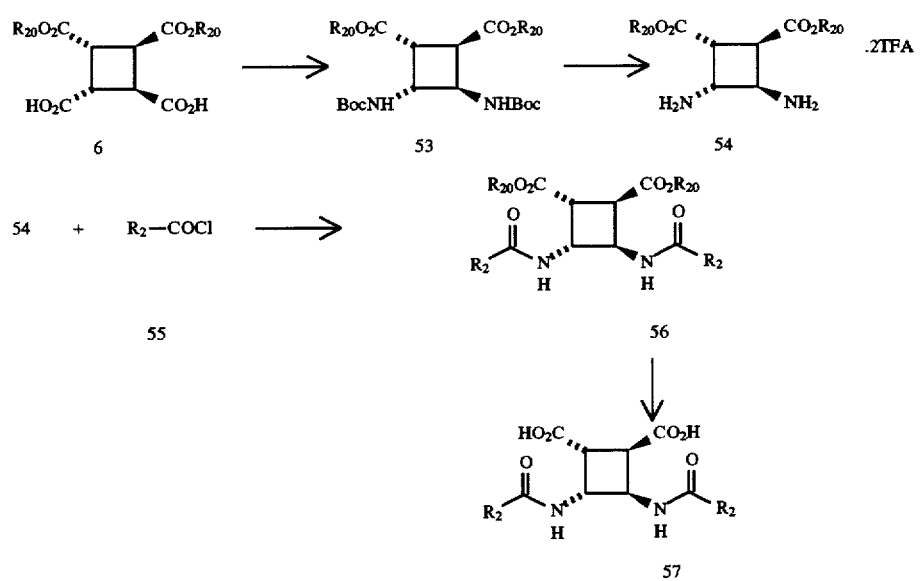

SCHEME XIII
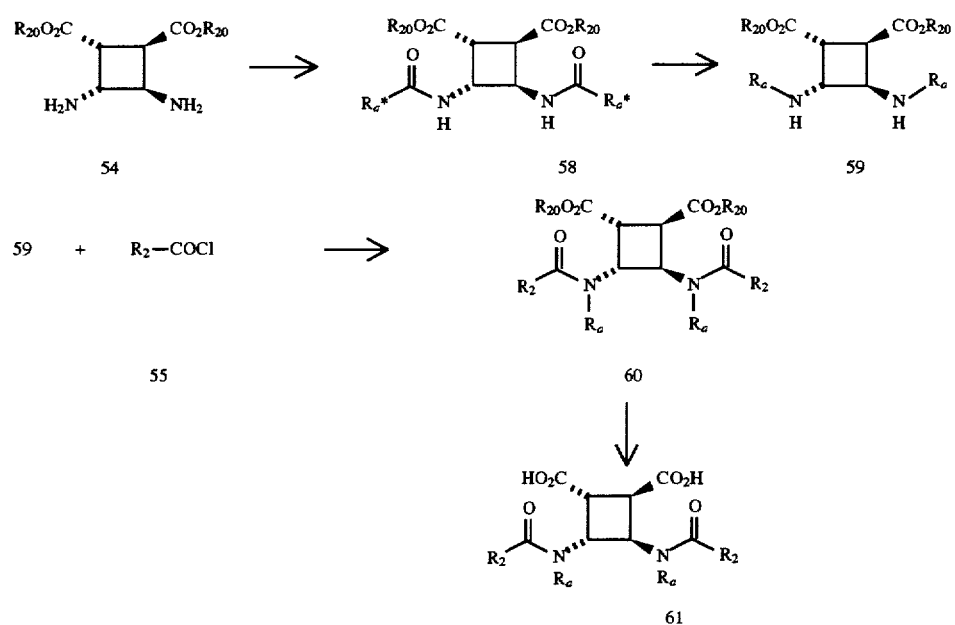
SCHEME XIV
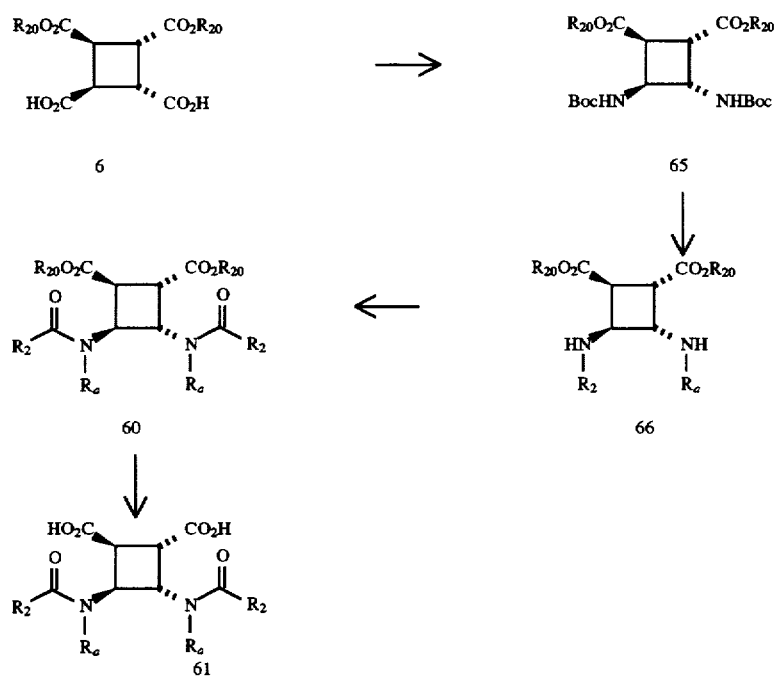

SCHEME XV
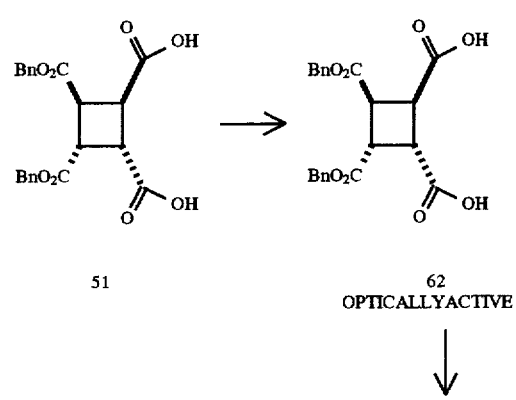
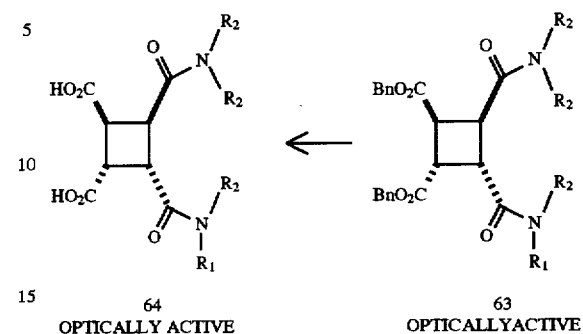
SCHEME XIV
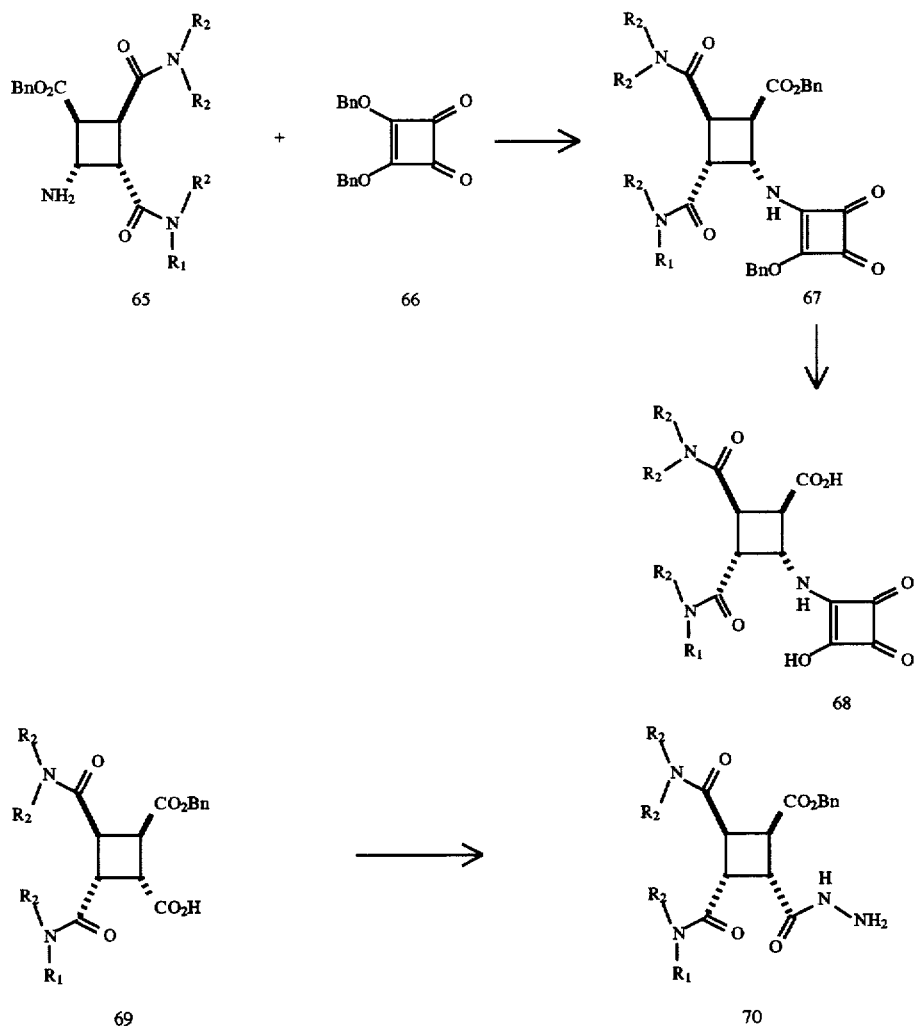

-continued
SCHEME XIV
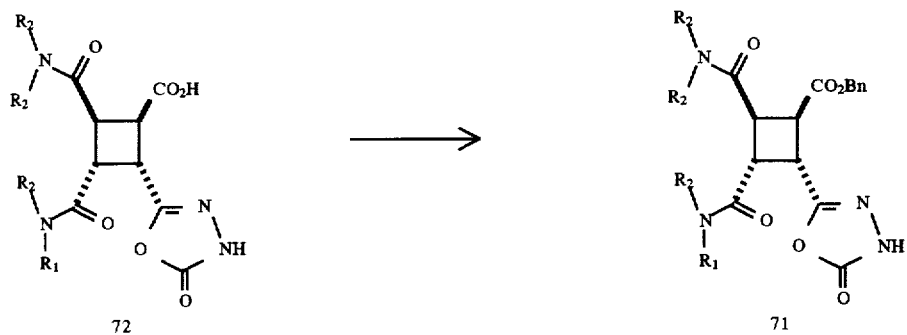
SCHEME XVII
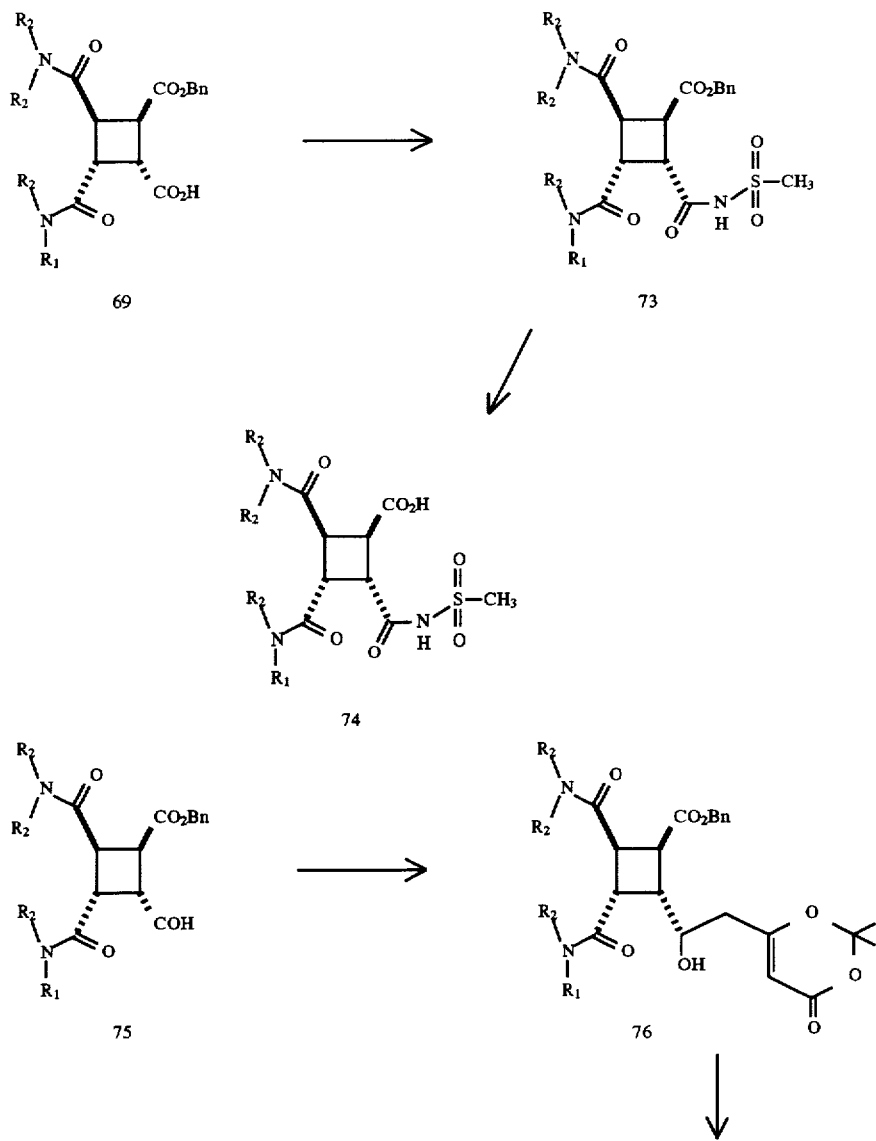

-continued
SCHEME XVII
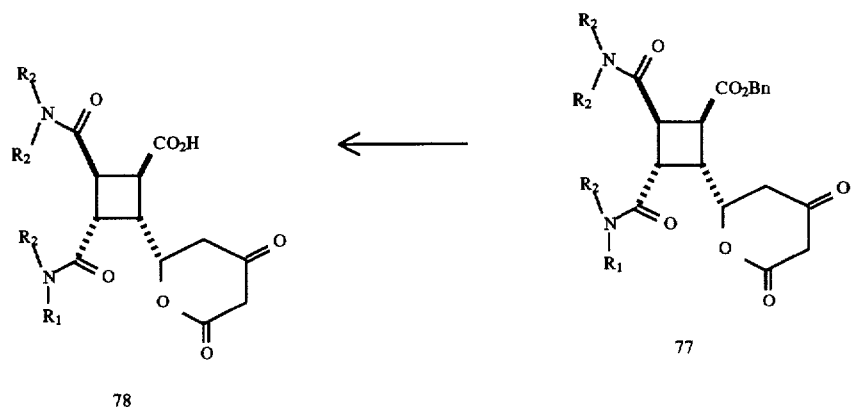
SCHEME XVIII
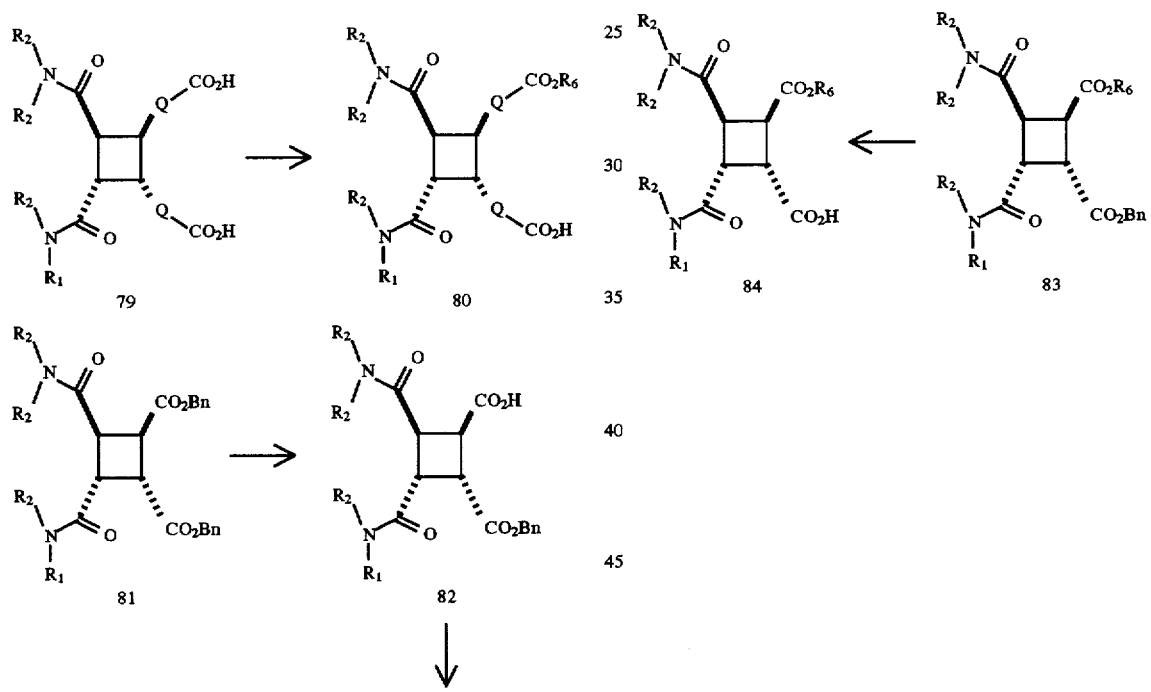
-continued
SCHEME XVIII SCHEME XIX
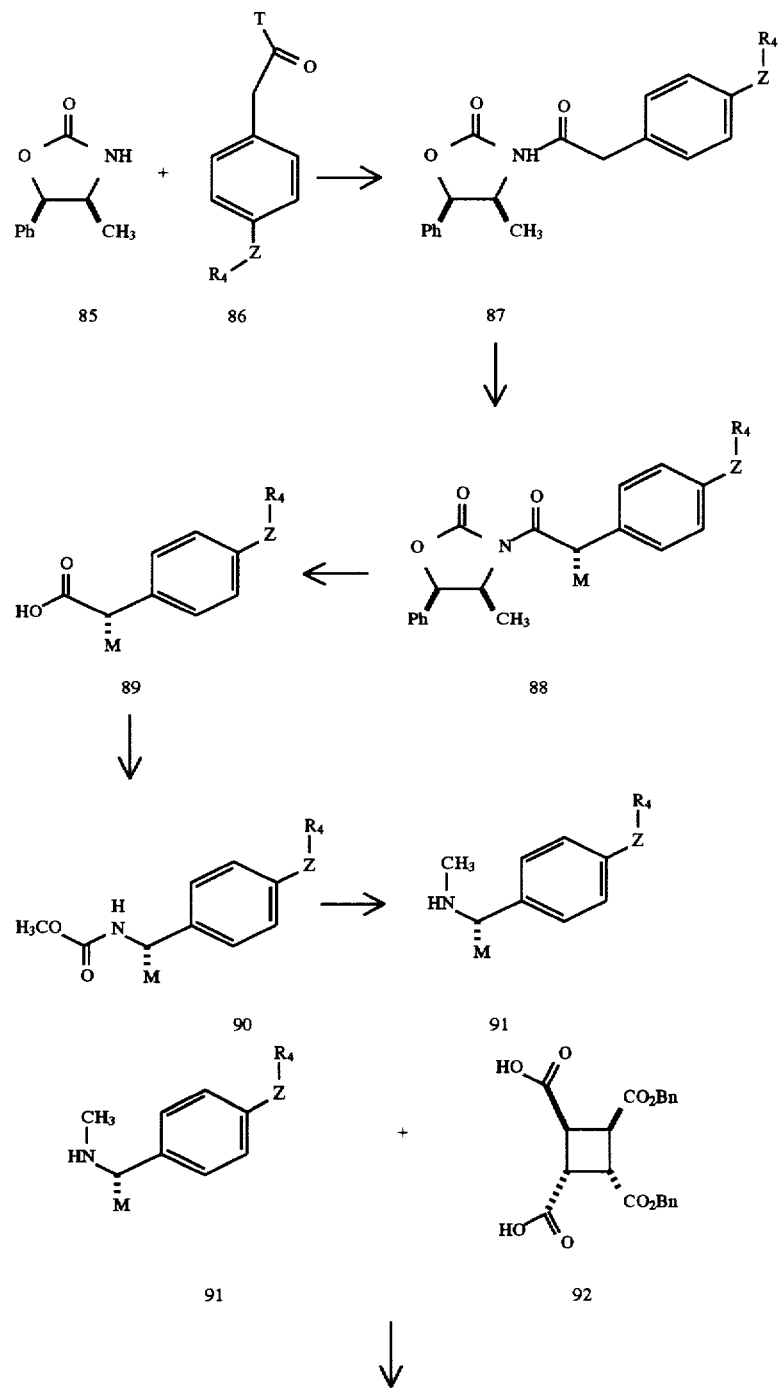

-continued
SCHEME XIX

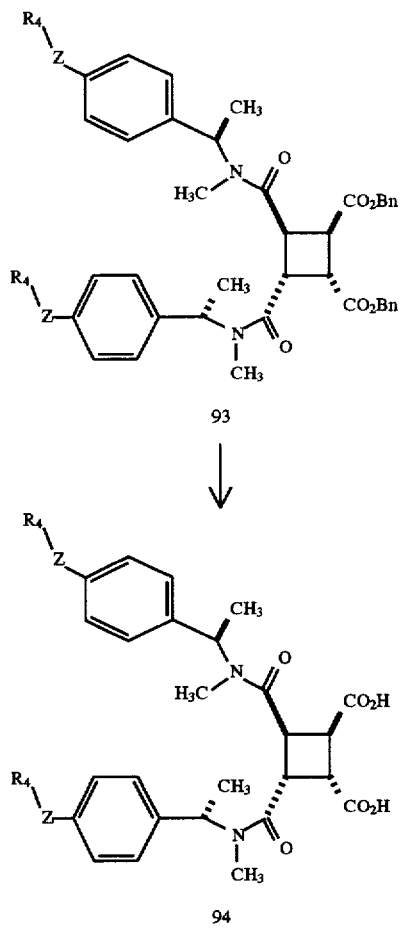

The foregoing may be better understood by reference to the following examples which are provided for illustration and not intended to limit the scope of the inventive concept.

The following abbreviations were used AgOBn for silver benzoate, BOP—Cl for bis(2-oxo-3-oxazolidinyl) phosphinic chloride, n-BuLi for n-butyl lithium, DIBAL for diisobutylaluminum hydride, DMAP for dimethylaminopyridine, DME for dimethoxyethane, DMF for dimethylformamide, DMSO for dimethylsulfoxide, EDCl for 1-(3-dimethylaminopropyl)-3-ethylcarbodiimide hydrochloride, Et$_3$N for triethylamine, Et$_2$O for diethyl ether, EtOAc for ethyl acetate, EtOH for ethanol, HOAc for acetic acid, HOBT for 1-hydroxybenzotriazole, LAH for lithium aluminum hydride, LDA for lithium diisopropylamide, MeOH for methanol, Pd/C for palladium on carbon, THF for tetrahydrofuran, and TPAP for tetrapropylammonium perruthenate.

EXAMPLE 1A

N-Methyl-N-(4-phenoxybenzyl)amine

4-Phenoxybenzaldehyde (10.0 g, 0.05 mol), excess methylamine and 1.5 g of 10% Pd/C in 200 mL of methanol were stirred under an atmosphere of hydrogen for 16 hours. After removal of the catalyst by filtration through a filter and (CELITE®), the filtrate was concentrated under reduced pressure to give the crude product as an oil. Chromatography on silica gel eluting with ethyl acetate gave the title compound in 80%.

EXAMPLE 1B

N-i-Butyl-N-(4-phenoxybenzyl)amine

4-Phenoxybenzaldehyde (10.0 g, 0.05 mol), excess isobutylamine and 1.0 g of 10% Pd/C in 200 mL of ethanol were stirred under an inert atmosphere for 16 hours followed by an atmosphere of hydrogen for 16 hours. After removal of the catalyst by filtration through a filter and (CELITE®), the filtrate was concentrated under reduced pressure to give the crude product as an oil. The oil was dissolved in ether and precipitated by treatment with anhydrous HCl. The solid was filtered, washed with ether, and partitioned between ethyl acetate and 1M NaOH. The ethyl acetate solution was washed with brine, dried over Na$_2$SO$_4$, and evaporated to give the title compound in 93% yield.

EXAMPLES 2–10

The following compounds were prepared by the procedures described in Examples 1A or 1B using the appropriate aldehydes and amines.

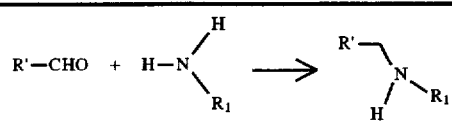

| Ex. No. | R'— | $R_1$— | Product |
|---|---|---|---|
| 2 | phenoxyphenyl | $CH_3CH_2$— | phenoxybenzyl-NH-ethyl |
| 3 | phenoxyphenyl | $CH_3CH_2CH_2$— | phenoxybenzyl-NH-propyl |
| 4 | 3-phenoxyphenyl | $CH_3$— | 3-phenoxybenzyl-NH-methyl |
| 5 | 4-benzyloxyphenyl | $CH_3$— | 4-benzyloxybenzyl-NH-methyl |
| 6 | 4-(4-fluorophenoxy)phenyl | $CH_3$— | 4-(4-fluorophenoxy)benzyl-NH-methyl |
| 7 | 3-(4-fluorophenoxy)phenyl | $CH_3$— | 3-(4-fluorophenoxy)benzyl-NH-methyl |
| 8 | 4-biphenyl | $CH_3$— | 4-biphenylmethyl-NH-methyl |
| 9 | phenoxyphenyl | Cyclopropyl | phenoxybenzyl-NH-cyclopropyl |

*The aldehyde was prepared from 4-fluorophenol and 4-bromobenzaldehyde.

EXAMPLE 10

N,N-Di(4-phenoxybenzyl)amine

4-Phenoxybenzaldehyde was reacted with ammonium acetate to give the title compound.

EXAMPLE 11

N-Propargyl-N-(4-phenoxybenzyl)amine

4-Phenoxybenzaldehyde (5.0 g, 25.2 mmol) and propargylamine (1.46 g, 26.5 mmol) were dissolved in 100 mL of 1% acetic acid in methanol under an atmosphere of dry nitrogen. Sodium cyanoborohydride (1.66 g, 26.5 mmol) was added, and stirring was continued for 18 hours at which time the solvent was removed under reduced pressure. The residue was suspended in ether, washed with 5% $NaHCO_3$ and brine, and dried over $Na_2SO_4$ to give 5.6 g (93%) of the title compound.

EXAMPLE 12

N-Benzyl-N-(4-phenoxybenzyl)amine

The title compound was prepared by the method described in Example 11 substituting benzylamine for propargylamine.

EXAMPLE 13

(1α,2β,3β,4α)-1,2-Di[N-methyl-N-(4-phenoxybenzyl)aminocarbonyl]cyclobutane-3,4-dicarboxylic acid To a solution cooled in an ice bath of 1,2,3,4-cyclobutanecarboxylic dianhydride (3.42 g, 17.4 mmol) in 30 mL of dimethylformamide was added triethylamine (3.51 g, 3.47 mmol). The mixture was then treated with N-methyl-(4-phenoxybenzyl)amine (10 g, 4.74 mmol) in 20 mL of dimethylformamide dropwise over 20 minutes. After stirring at ambient temperature overnight, the dimethylformamide was removed under reduced pressure to give a crude solid mixture. The crude solid was taken up in ethyl acetate, washed with dilute hydrochloric acid, water and saturated sodium chloride solution, dried over sodium sulfate, filtered and concentrated in vacuo. When solid began precipitating from solution, the mixture was cooled over an ice bath for 1 hour and then filtered. The combined filtrates were evaporated to give an oil product which was chromatographed on silica gel eluting with 94:5:1 chloroform-methanol-acetic acid to give 3 g (28%) of the title compound. m.p. 105°–108° C. $^1$H NMR (DMSO-$d_6$, 300 MHz) δ2.91 (s, 6H), 3.30 (d, 2H), 4.02 (d, 2H), 4.20 (d, 2H), 4.37 (d, 2H), 6.89–7.20 (m, 18H). MS m/e 623 $(M+H)^+$.

EXAMPLE 14

(1α,2β,3β,4α)-1,2-Di[N-methyl-N-(4-benzyloxybenzyl)aminocarbonyl]cyclobutane-3,4-dicarboxylic acid To a solution of 1,2,3,4-cyclobutanecarboxylic dianhydride (0.44 g, 2.29 mmol) and triethylamine (0.63 mL, 4.58 mmol) in dimethylformamide (20 mL) at 0° C. under nitrogen was added the compound resulting from Example 5 (1.3 g, 5.75 mmol). The reaction was stirred at 0° C. for 2 hours and then allowed to warm to ambient temperature overnight. The DMF was removed under reduced pressure, and the oily residue was partitioned between ethyl acetate and water. The organic phase was washed with 1N HCl, water and brine, dried over magnesium sulfate, filtered and evaporated under reduced pressure to give crude product. Flash silica gel chromatography eluting with 94:5:1 $CHCl_3$—MeOH—HOAc yielded 22% of the 1,2-di[N-methyl-N-(benzyloxybenzyl)aminocarbonyl]cyclobutane-3,4-dicarboxylic acid isomer. m.p. 210°–212° C. MS m/e 651 $(M+H)^+$.

EXAMPLE 15

(1α,2β,3β,4α)-1,2-Di[N-benzyl-N-(4-phenoxybenzyl)aminocarbonyl]cyclobutane-3,4-dicarboxylic acid To a solution of 1,2,3,4-cyclobutanetetracarboxylic dianhydride (0.5 g, 2.54 mmol) in THF (5 mL) was added N-benzyl-N-(4-phenoxybenzyl) amine (1.47 g, 5.08 mmol) in THF (5 mL) at 25° C. The initial slurry became homogeneous after stirring at 25° C. for 25 minutes. The solution was stirred one additional hour, then poured into 100 mL of ethyl acetate. The organic layer was washed successively with 50 mL 1N $H_3PO_4$, 50 mL 10% $NaHCO_3$ and 50 mL 10% NaCl, then dried over anhydrous sodium sulfate, filtered and solvent removed in vacuo to afford 2.2 g of a white foamy solid. The crude product containing both isomers was purified by silica gel chromatography eluting with 94:5:1 $CHCl_3$—MeOH—HOAc. The slower moving product was isolated in 6% yield and characterized as 1,2-Di[N-benzyl-N-(4-phenoxybenzyl)aminocarbonyl]cyclobutane-3,4-dicarboxylic acid. $^1$H NMR ($CDCl_3$+$CD_3OD$, 500 MHz) δ3.95–4.05 (m, 2H), 4.39–4.16 (m, 8H), 4.41–4.52 (m, 2H), 4.65–4.76 (m, 2H), 6.82–7.36 (m, 28H). MS ($DCl/NH_3$) m/e 775 $(M+H)^+$.

EXAMPLES 16–30

The following examples were prepared using the general procedures described in Example 13.

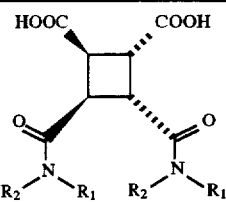

| Ex. No. | R₁ | R₂ | m.p. °C. |
|---|---|---|---|
| 16 | Ethyl | 4-ethylphenyl phenyl ether | 90–93 |
| 17 | Propyl | 4-ethylphenyl phenyl ether | * |
| 18 | Methyl | 3-ethylphenyl phenyl ether | 81–82.5 |
| 19 | 4-ethylphenyl phenyl ether | 4-ethylphenyl phenyl ether | 82–83 |
| 20 | Methyl | 4-ethylphenyl 4-fluorophenyl ether | 63–65 |
| 21 | Methyl | 3-ethylphenyl 4-fluorophenyl ether | 90–93 |
| 22 | Methyl | 4'-methylbiphenyl | 73–75 |
| 23 | i-Propyl | 4-ethylphenyl phenyl ether | 103–107 |
| 24 | i-Butyl | 4-ethylphenyl phenyl ether | * |
| 25 | n-Propyl | 4-ethylbenzyl phenyl | * |

-continued

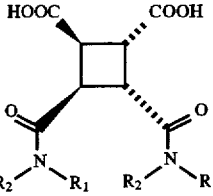

| Ex. No. | $R_1$ | $R_2$ | Yield |
|---|---|---|---|
| 26 | n-Butyl | 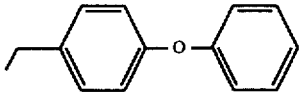 | * |
| 27 | —CH₂—C≡CH | 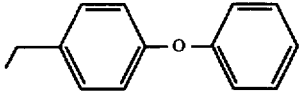 | * |
| 28 | N-Pentyl | 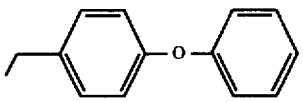 | * |
| 29 | —CH₂—CH=CH₂ | 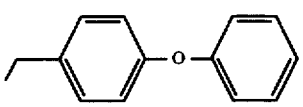 | * |
| 30 | Cyclopropyl | 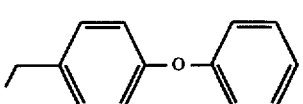 | 94–99 |

| Ex. No. | DATA |
|---|---|
| 17 | $^1$H NMR(DMSO-d₆, 300 MHz) δ 0.80(m, 6H), 1.46(m, 4H), 2.70–3.00(m, 4H), 3.60(m, 2H), 3.92(m, 2H), 4.27(m, 2H), 4.70(dd, 2H), 6.87–7.43(m, 18H) |
| 24 | $^1$H NMR(CDCl₃, 500 MHz) δ 0.85(m, 12H), 1.92(m, 2H), 3.02(m, 4H), 4.01(m, 4H), 4.39–4.62(m, 4H), 6.86–7.35(m, 18H) |
| 25 | $^1$H NMR(CDCl₃, 500 MHz) δ 0.80(m, 6H), 1.50(m, 4H), 3.15(m, 4H), 3.95(m, 8H), 4.10–4.62(m, 4H), 7.05–7.30(m, 18H) |
| 26 | $^1$H NMR(CD₃OD), 500 MHz) δ 0.90(m, 6H), 1.31(m, 4H), 1.4–1.6(m, 4H), 2.98(m, 1H), 3.12(m, 1H), 3.3–3.45(m, 1H) 3.5–3.62(m, 1H), 3.73–3.8(m, 3H), 4.08–4.16(m, 3H), 4.32–4.43(m, 3H), 4.62–4.82(m, 1H), 6.8–7.(m, 8H), 7.1(m, 2H), 7.19–7.35(m, 8H) |
| 27 | $^1$H NMR(CDCl₃, 500 MHz) δ 2.19(m, 2H), 3.86(m, 6H), 4.12(m, 2H), 4.25(m, 2H), 4.42(m, 2H), 4.59(m, 1H), 4.80(m, 1H), 6.83–7.40(m, 18H) |
| 28 | $^1$H NMR(CDCl₃, 500 MHz) δ 0.85(m, 6H), 1.24(m, 8H), 3.12(m, 2H), 3.24(m, 2H), 3.47(m, 2H), 3.96(m, 2H), 4.12(m, 2H), 4.53(m, 4H), 6.88–7.36(m, 18H), |
| 28 | $^1$H NMR(CDCl₃, 500 MHz) δ 3.73(m, 2H), 3.82(m, 4H), 4.11(m, 4H), 4.37(m, 2H), 4.55(m, 1H), 4.73(m, 1H), 5.13(m, 4H), 5.72(m, 2H), 6.90–7.35(m, 18H) |

EXAMPLE 31

(1α,2β,3β,4α)-1,2-Di[N-cyclohexylmethyl-N-phenoxybenzyl)aminocarbonyl]cyclobutane-3,4-dicarboxylic acid To a slurry of 1,2,3,4-cyclobutanetetracarboxylic dianhydride (0.3 g, 1.5 mmol) in CH₃CN (1 mL) was added N-cyclohexylmethyl-N-phenoxybenzylamine (0.95 g, 3.21 mmol) in CH₃CN (10 mL). The slurry was stirred for 5 minutes at 20° C. resulting in a homogeneous solution. The solution was stirred for 20 hours at 20° C. then concentrated in vacuo to a white foam. The foam was dissolved in 100 mL of ethyl acetate and washed successively with 50 mL 1N H₃PO₄ and 10% NaCl, then dried over anhydrous sodium sulfate, filtered and solvent removed in vacuo to afford 1.0 g of a white foamy solid. The crude product containing both isomers was purified by silica gel chromatography eluting with 94:5:1 CHCl₃—MeOH—HOAc. The slower moving product was isolated in 14% yield and characterized as 1,2-di[N-cyclohexylmethyl-N-phenoxybenzyl)aminocarbonyl]cyclobutane-3,4-dicarboxylic acid. $^1$H NMR (CDCl₃, 500 MHz) δ7.32–6.87 (m, 18H), 4.67–4.36 (m, 4H), 3.88–4.13 (m, 4H), 2.95–3.20 (m, 4H), 1.52–1.69 (m, 8H), 1.07–1.14 (m, 8H), 0.78–0.88 (m, 6H). MS (FAB⁺) m/e 787, (FAB⁻) 785.

EXAMPLE 32

(1α,2β,3β,4α)-1,2-Di[N-phenyl-N-phenoxybenzyl)aminocarbonyl]cyclobutane-3,4-dicarboxylic acid To a slurry of 1,2,3,4-cyclobutanetetracarboxylic dianhydride (0.5 g, 2.5 mmol) in DMF (5 mL) was added N-phenyl-N-phenoxybenzylamine HCl (1.6 g, 5.11 mmol), prepared by the procedures described in Example 11, in DMF (5 mL) followed by Et$_3$N (0.71 mL, 5.11 mmol). The slurry was stirred for 5 minutes at 20° C. resulting in a homogeneous solution. The solution was stirred 20 hours at 20° C., then concentrated in vacuo to a white foam. The foam was dissolved in 100 mL of ethyl acetate and washed successively with 50 mL 1N H$_3$PO$_4$ and 10% NaCl, then dried over anhydrous sodium sulfate, filtered and solvent removed in vacuo to afford 0.5 g of a clear oil. The crude product containing both isomers was purified by silica gel chromatography eluting with 94:5:1 CHCl$_3$—MeOH—HOAc. The slower moving product was isolated in 3% yield and characterized as 1,2-di[N-phenyl-N-phenoxybenzyl) aminocarbonyl]cyclobutane-3,4-dicarboxylic acid. $^1$H NMR (DMSO-d$_6$, 300 MHz) δ7.44–6.81 (m, 28H), 4.99–4.60 (m, 4H), 3.44–3.21 (m, 4H). MS (FAB$^+$) m/e 747, (FAB$^-$) 745.

EXAMPLE 33

(1α,2β,3β,4α)-1,2-Di[N-4-methoxybenzyl-N-4-phenoxybenzyl)aminocarbonyl]cyclobutane-3,4-dicarboxylic acid Following the procedures described in Example 31 and substituting N-4-methoxybenzyl-N-4-phenoxybenzylamine (1.02 g, 3.4 mmol), prepared by the procedures described in Example 11, for N-cyclohexylmethyl-N-phenoxybenzylamine afforded 1.2 g of crude product as a white foamy solid. The crude product containing both isomers was purified by silica gel chromatography eluting with 94:5:1 CHCl$_3$—MeOH—HOAc. The slower moving product was isolated in 27% yield and characterized as the title compound. $^1$H NMR (CDCl$_3$, 500 MHz) δ7.32–6.75 (m, 26H), 4.69–4.62 (m, 4H), 4.45–4.44 (m, 1H), 4.21–4.32 (m, 4H), 3.92–3.98 (m, 1H), 3.69–3.74 (m, 8H). MS (FAB$^+$) m/e 835, (FAB$^-$) 833.

EXAMPLE 34

(1α,2β,3β,4α)-1,2-Di[N-(S)-α-methylbenzyl-N-4-phenoxybenzyl)aminocarbonyl]cyclobutane-3,4-dicarboxylic acid To a slurry of 1,2,3,4-cyclobutanetetracarboxylic dianhydride (0.3 g, 1.5 mmol) in CH$_3$CN (6 mL) was added N-4-phenoxybenzyl-N-(S)-α-methylbenzylamine (1.02 g, 3.4 mmol), prepared by the procedures described in Example 11, in CH$_3$CN (3 mL) containing Et$_3$N (0.1 mL, 0.7 mmol). The slurry was stirred for 5 minutes at 20° C., resulting in a homogeneous solution which was stirred 20 hours at 20° C. The solution was diluted with 100 mL of ethyl acetate and washed successively with 50 mL 1N H$_3$PO$_4$ and 10% NaCl, then dried over anhydrous sodium sulfate, filtered and solvent removed in vacuo to afford 0.9 g of a white foamy solid. The crude product containing both isomers was purified by silica gel chromatography eluting with 94:5:1 CHCl$_3$—MeOH—HOAc. The slower moving product was isolated in 12% yield and characterized as the title compound. $^1$H NMR (DMSO-d$_6$, 300 MHz) δ1.28–2.05 (m, 6H), 3.58–3.98 (m, 4H), 4.01–4.16 (m, 1H), 4.19–4.41 (m, 1H), 4.71–4.76 (m, 1H), 4.91–5.18 (m, 1H), 6.02–6.06 (m, 2H), 6.72–7.38 (m, 28H), 10.12 (bs, 2H). MS (FAB$^+$) m/e 803, (FAB$^-$) 801.

EXAMPLE 35

(1α,2β,3β,4α)-1,2-Di[N-(R)-α-methylbenzyl-N-4-phenoxybenzyl)aminocarbonyl]cyclobutane-3,4-dicarboxylic acid Following the procedures described in Example 34 and substituting N-4-phenoxybenzyl-N-(R)-α-methylbenzylamine (1.02 g, 3.4 mmol), prepared by the procedures described in Example 11, for N-4-phenoxybenzyl-N-(S)-α-methylbenzylamine afforded 1.0 g of crude product as a white foamy solid. The crude product containing both isomers was purified by silica gel chromatography eluting with 94:5:1 CHCl$_3$—MeOH—HOAc. The slower moving product was isolated in 17% yield and characterized as the title compound. $^1$H NMR (CDCl$_3$, 500 MHz) δ1.38–1.54 (m, 6H), 3.60–3.82 (m, 4H), 4.01–4.05 (m, 1H), 4.15–4.18 (m, 1H), 4.27–4.30 (m, 1H), 4.44–4.48 (m, 1H), 5.96–5.97 (m, 2H), 6.69–7.46 (m, 28H), 10.12 (bs, 2H). MS (FAB$^+$) m/e 803, (FAB$^-$) 801.

EXAMPLE 36

(1α,2β,3β,4α)-1,2-Di[N-benzyl-N-(5-phenyl-2,4-pentadienyl)aminocarbonyl]cyclobutane-3,4-dicarboxylic acid Following the procedures described in Example 34 and substituting N-(5-phenyl-2,4-pentadienyl)-N-benzylamine (1.02 g, 3.4 mmol), prepared by the procedures described in Example 11, for N-4-phenoxybenzyl-N-(S)-α-methylbenzylamine afforded 0.9 g of crude product as a white foamy solid. The crude product containing both isomers was purified by silica gel chromatography eluting with 94:5:1 CHCl$_3$—MeOH—HOAc. The slower moving product was isolated in 11% yield and characterized as the title compound. $^1$H NMR (DMSO-d$_6$, 300 MHz) δ3.35–3.72 (m, 4H), 3.88–4.16 (m, 4H), 4.19–4.41 (m, 2H), 4.67–4.87 (m, 2H), 5.30–5.40 (m, 2H), 5.70–5.83 (m, 2H), 6.26–6.43 (m, 2H), 6.53–6.75 (m, 2H), 6.81–6.98 (m, 2H), 7.21–7.44 (m, 18H), 12.55 (bs, 2H). MS (FAB$^+$) m/e 695.

EXAMPLE 37

(−)-(1α,2β,3β,4α)-1,2-Di[N-propyl-N-(4-phenoxybenzyl)aminocarbonyl]cyclobutane-3,4-dicarboxylic acid

EXAMPLE 37A (R)-sec-Phenethyl (1α,2β,3β,4α)-1,2-di[N-propyl-N-(4-phenoxybenzyl)aminocarbonyl]cyclobutane-3,4-dicarboxylate A solution of 1,3-dicyclohexylcarbodiimide (1.26 g, 6.0 mmol), 4-dimethylaminopyridine (72 mg, 0.6 mmol), and 80 mL diethylether was added dropwise to a 0° C. solution of (±)-1,2-di[N-propyl-N-(phenoxybenzyl)aminocarbonyl] cyclobutane-3,4-dicarboxylic acid, the compound resulting from Example 17, (2.0 g, 2.9 mmol), R-(−)-sec-phenethyl alcohol (0.73 g, 6.0 mmol), and 20 mL diethylether. The reaction mixture was stirred for 0.25 hour at 0° C. and for 18 hours at room temperature, then was diluted with diethylether and filtered. The filtrate was washed with 0.5N HCl, H$_2$O, saturated aqueous NaHCO$_3$, and was dried over MgSO$_4$, filtered, and solvent evaporated under reduced pressure to afford 2.6 g of crude product as a white foam. The crude product was chromatagraphed on silica gel, eluting with 20% diethylether in hexanes to afford 0.22 g of the desired product as a single diastereomer. $^1$H NMR (CDCl$_3$, 300 MHz) δ0.70–0.81 (m, 6H), 1.20–1.31 (m, 2H), 1.35–1.46 (m, 2H), 1.50–1.65 (m, 6H), 2.75–2.95 (m, 2H), 3.10–3.25 (m, 2H), 3.82–4.18 (m, 6H), 4.31–4.48 (m, 2H), 5.72–5.83 (m, 1H), 5.85–5.96 (m, 1H), 6.84–7.02 (m, 10H), 7.02–7.15 (m, 4H), 7.22–7.40 (m, 14H). MS (FAB) m/e 925 (m+K)$^+$.

EXAMPLE 37B (−)-(1α,2β,3β,4α)-1,2-Di[N-propyl-N-(4-phenoxybenzyl)aminocarbonyl]cyclobutane-3,4-dicarboxylic acid The compound resulting from Example 37A (0.22 g, 0.2 mmol) was dissolved in 100 mL of EtOAc and hydrogenated at 4 atmospheres of hydrogen at room temperature over Pd/C (0.15 g, anhydrous) for 23 hours. The reaction mixture was filtered and solvent evaporated in vacuo to afford 0.14 g of crude product as a light yellow solid. The crude product was triturated with hexane/ether to afford 0.13 g as a colorless glass. The glass was lyophilized to afford 0.11 g of the title compound as a white powder. $^1$H NMR (CD$_3$OD, 300 MHz) δ0.82–0.97 (m, 6H), 1.48–1.68 (m, 4H), 2.88–3.00 (m, 1H), 3.02–3.20 (m, 1H), 3.29–3.34 (m, 3H), 3.45–3.68 (m, 1H), 3.72–3.85 (m, 2H), 4.08–4.22 (m, 2H), 4.31–4.44 (m, 2H), 4.65–4.81 (m, 2H), 6.86–7.00 (m, 8H), 7.05–7.14 (m, 2H), 7.18–7.38 (m, 8H). MS (FAB) m/e 701 (m+Na)$^+$. Anal calcd for C$_{40}$H$_{42}$N$_2$O$_8$·1.5 H$_2$O: C, 68.07; H, 6.43; N, 3.97. Found: C, 68.27; H, 6.01; N, 3.92. [α]$_D$=−77.4° (c=0.90, MeOH).

EXAMPLE 38

(1α,2β,3β,4α)-1,2-Di[N-propyl-N-(2-(4-phenoxyphenyl)ethyl)aminocarbonyl]cyclobutane-3,4-dicarboxylic acid

EXAMPLE 38A

4-Phenoxystyrene

To a suspension of methyltriphenylphosphonium bromide (7.85 g, 22 mmol) in THF (10 mL) was added potassium tert-butoxide (1.0M solution in THF, 22 mL). After 30 minutes, 4-phenoxybenzaldehyde (3.96 g, 20 mmol) was added to the above mixture. The reaction was diluted with equal volume of hexane after 20 minutes and filtered through silica gel (80 g). The residue was rinsed and washed with 20% ether in hexane. Concentration of the filtrate in vacuo gave the crude product as an off white solid which was used without further purification.

EXAMPLE 38B 2-(4-Phenoxyphenyl)ethyl alcohol

To the compound resulting from Example 38A in THF (40 mL) was added borane-methyl sulfide solution (10M, 1.6 mL, 16 mmol). After 3 hours, the reaction was cooled with an ice-water bath, and anhydrous ethanol (5 mL) was added carefully to destroy excess borane. Aqueous sodium hydroxide (15%, 4 mL) was added, followed by 30% hydrogen peroxide (4 mL). The resulting mixture was refluxed for 1 hour, cooled to room temperature, then extracted with ether (80 mL). The organic phase was then washed with water (20 mL×2), brine (20 mL), dried with anhydrous magnesium sulfate, filtered, and concentrated in vacuo. The residue was then purified by column chromatography eluting with 20% ethyl acetate in hexane, followed by 100% ether to give the title compound as the second fraction (2.32 g, 54%, 2 steps). $^1$H NMR (300 MHz, CDCl$_3$) δ7.37–6.94 (m, 9H), 3.87 (q, 2H), 2.86 (t, 2H), 1.37 (t, 1H).

EXAMPLE 38C 4-(2-Chloroethyl)phenyl phenyl ether

To a −78° C. solution of the compound resulting from Example 38B (3.64 g, 17.0 mmol) in anhydrous methylene chloride (40 mL) was slowly added phosphorus trichloride (2.61 g, 19.0 mmol). The cold bath was then removed, and the reaction was allowed to warm to room temperature over 1 hour. The reaction mixture was then slowly poured into an ice-cooled saturated sodium bicarbonate solution (50 mL), and extracted with ether (100 mL). The organic phase was washed with water (30 mL×2) and brine (20 mL), dried over anhydrous magnesium sulfate, filtered through silica gel, and concentrated in vacuo. The crude product was used without further purification for the next step. $^1$H NMR (300 MHz, CDCl$_3$) δ7.72–6.93 (m, 9H), 3.56 (t, 2H), 3.15 (t, 2H).

EXAMPLE 38D 2-(4-Phenoxyphenyl)ethylphthalimide

A solution of the product resulting from Example 38C and potassium phthalimide (3.78 g, 20.4 mmol) in THF (40 mL) was refluxed for 16 hours, then concentrated to near dryness. The residue was titraturated with 1:1 ether-hexane (5 mL), and the solid was filtered and air dried. The crude product was used directly for the next step. $^1$H NMR (300 MHz, CDCl$_3$) δ7.85 (m, 2H), 7.72 (m, 2H), 7.33–6.92 (m, 9H), 3.92 (t, 2H), 2.98 (t, 2H).

EXAMPLE 38E 2-(4-Phenoxyphenyl)ethylamine

A suspension of the crude compound resulting from Example 38D in ethanol (20 mL) was refluxed with hydrazine (0.65 mL, 20.4 mmol). The reaction mixture became homogeneous after about 10 minutes, and a white precipitate started to form in a short time. After 16 hours of refluxing, the reaction mixture was cooled to room temperature, filtered, and washed with ethanol (5 mL×3). The filtrate was diluted with ether (100 mL) and washed with 10% sodium carbonate (20 mL), water (30 mL) and brine (20 mL), dried over anhydrous potassium carbonate, filtered and concentrated in vacuo. The crude amine was used directly for the next step. $^1$H NMR (300 MHz, CDCl$_3$) δ7.35–6.94 (m, 9H), 2.98 (t, 2H), 2.72 9 t, 2H)

EXAMPLE 38F

N-(2-(4-Phenoxy)phenyl)ethylpropionamide

To the solution of crude amine resulting from Example 38E in methylene chloride (20 mL) and pyridine (5 mL) was added propionyl chloride (3.0 mL, 34 mmol). After 6 hours, the reaction was diluted with ethyl acetate (80 mL), washed with water (20 mL), 10% aqueous hydrochloric acid (20 mL), water (20 mL), saturated copper sulfate (20 mL), and brine (20 mL), dried over anhydrous magnesium sulfate, filtered, and concentrated in vacuo. The residue was purified by column chromatography eluting with 50% ethyl acetate in hexane to give the title compound (1.23 g, 27% for 4 steps). $^1$H NMR (300 MHz, CDCl$_3$): δ7.36–6.95 (m, 9H), 5.46 (bs, 1H), 3.51 (q, 2H), 2.80 (t, 2H), 2.19 (q, 2H), 1.15 (t, 3H).

EXAMPLE 38G

N-Ethyl-N-(2-(4-phenoxy)phenylethyl)amine

To a solution of the amide resulting from Example 38F (1.23 g, 4.57 mmol) in THF (10 mL) was slowly added lithium aluminum hydride (1.0M in THF, 4.6 mL). After the resulting mixture was refluxed for 3 hours, it was cooled to 0° C., and water (0.18 mL), 15% aqueous NaOH (0.18 mL), and water (0.54 mL) were carefully added. White precipitate formed, and the mixture was filtered through celite, washed with ether, and concentrated in vacuo to afford pure title compound (1.05 g, 88%). $^1$H NMR (300 MHz, CDCl$_3$) δ7.35–6.92 (m, 9H), 3.30 (bs, 1H), 2.83 (m, 2H), 2.60 (t, 2H), 2.37 (dd, 2H), 1.49 (m, 2H), 0.92 (t, 3H).

EXAMPLE 38H (1α,2β,3β,4α)-1,2-Di[N-propyl-N-(2-(4-phenoxyphenyl)ethyl)aminocarbonyl]cyclobutane-3,4-dicarboxylic acid A mixture of the amine resulting from Example 38G (0.942 g, 3.69 mmol), 1,2,3,4-cyclobutanetetracarboxylic dianhydride (0.290 g, 1.48 mmol), triethylamine (0.62 mL, 4.4 mmol) and DMAP (50 mg) in acetonitrile (10 mL) was stirred overnight. The reaction mixture was concentrated in vacuo and partitioned between 20% aqueous HCl and 3 portions of ethyl acetate. The combined organic extracts were washed with brine, dried over magnesium sulfate, filtered and concentrated in vacuo. The residue was purified by column eluting with 1:1 $CHCl_3$—EtOAc, followed by 50:50:2:1 $CHCl_3$—EtOAc—MeOH—AcOH to give 1,3-diamide-2,4-diacid as the first fraction (0.436 g, 42%) followed by the title compound (0.477 g, 46%). $^1$H NMR (500 MHz, DMSO) δ7.40–6.91 (m, 18H), 3.04 & 2.95 (2 m's, 8H), 2.81 & 2.39 (m, 4H), 2.93 & 2.82 (2 m's, 4H), 1.64 & 1.46 (2 m's, 4H), 0.91 & 0.82 (2 t's, 6H). MS (FAB$^-$) m/e 705 (M–H).

EXAMPLE 39

(1α,2β,3β,4α)-1,2-Di[N-propyl-N-(4-phenoxyphenyl)aminocarbonyl]cyclobutane-3,4-dicarboxylic acid

EXAMPLE 39A

N-(4-Phenoxy)phenylpropionamide

To a solution of 4-phenoxyaniline (4.62 g, 25 mmol) in methylene chloride (50 mL) and pyridine (10 mL) was added propionyl chloride (3.3 mL, 37.5 mmol). After 1 hour, the reaction mixture was diluted with ether (150 mL), washed with water (50 mL), 10% sodium carbonate (50 mL), 10% HCl (50 mL), saturated copper sulfate (50 mL), water (50 mL) and brine (30 mL), dried over anhydrous magnesium sulfate, filtered, and concentrated in vacuo. The title compound amide was used without further purification. $^1$H NMR (300 MHz, $CDCl_3$) δ7.49 9d, 2H), 7.31 (t, 2H), 7.11–6.95 (m, 5H), 2.40 (q, 2H), 1.25 (t, 3H).

EXAMPLE 39B

N-Propyl-(4-phenoxy)aniline

To a solution of the crude amide resulting from Example 39A in THF (30 mL) was added lithium aluminum hydride (1.0M in THF, 20 mL). After 14 hours, the reaction was cooled in an ice bath, and water (0.80 mL), 15% NaOH (0.80 mL) and water (2.4 mL) were added sequentially. The resulting mixture was filtered through celite, washed with ether, and concentrated in vacuo to give the title compound (5.16 g, 91% for 2 steps). $^1$H NMR (300 MHz, $CDCl_3$) δ7.28 (m, 2H), 6.99 9 t, 1H), 6.92 (m, 4H), 6.60 (d, 2H), 3.55 (bs, 1H), 3.06 (t, 2H), 1.65 (sextet, 2H), 1.01 (t, 3H).

EXAMPLE 39C (1α,2β,3β,4α)-1,2-Di[N-propyl-N-(4-phenoxyphenyl)aminocarbonyl]cyclobutane-3,4-dicarboxylic acid A mixture of the compound resulting from Example 39B (0.908 g, 4.0 mmol), 1,2,3,4-cyclobutanetetracarboxylic dianhydride (0.314 g, 1.6 mmol), triethylamine (0.69 mL, 4.8 mmol) and DMAP (20 mg) in acetonitrile (10 mL) were reacted, worked up and purified by the procedures described in Example 38H to give the 1,3-diamide-2,4-diacid as the first fraction (0.372 g, 36%) and the title compound as the second fraction (0.514 g, 49%). $^1$H NMR (500 MHz, $CDCl_3$) δ7.40–6.98 (m, 18H), 3.80–3.36 (m, 8H), 1.48 (m, 4H), 0.82 (t, 6H). MS (Cl) m/e 651 (M+H).

EXAMPLE 40

(1α,2β,3β,4α)-1,2-Di[N-(2-methoxyethyl)-N-(4-phenoxybenzyl)aminocarbonyl]cyclobutane-3,4-dicarboxylic acid

EXAMPLE 40A

N-(2-Methoxy)ethyl-N-(4-phenoxy)benzylamine

A mixture of 4-phenoxybenzaldehyde (1.98 g, 10 mmol) and 2-methoxyethylamine (0.751 g, 10 mmol) in ethanol (10 mL) was stirred for 1 hour. Acetic acid (1 mL) and sodium cyanoborohydride (10 mmol) were added, and the reaction was stirred an additional 14 hours. The reaction mixture was then partitioned between ether and 10% aqueous sodium hydroxide solution. The organic layer was further washed with water and brine, dried over anhydrous potassium carbonate, filtered and concentrated in vacuo to give the title compound (2.48 g, 97%). $^1$H NMR (300 MHz, $CDCl_3$) δ7.30 (m, 4H), 7.09 (t, 1H), 6.98 (m, 4H), 3.80 (s, 2H), 3.51 (t, 2H), 3.37 9 s, 3H), 2.51 (t, 2H).

EXAMPLE 40B (1α,2β,3β,4α)-1,2-Di[N-(2-methoxyethyl)-N-(4-phenoxybenzyl)aminocarbonyl]cyclobutane-3,4-dicarboxylic acid A mixture of the compound resulting from Example 40A (1.38 g, 5.36 mmol), 1,2,3,4-cyclobutanetetracarboxylic dianhydride (0.421 g, 2.15 mmol), triethylamine (0.90 mL, 6.5 mmol), and DMAP (50 mg) in acetonitrile (15 mL) were reacted, worked up and purified by the procedures described in Example 38H to give the 1,3-diamide-2,4-diacid as the first fraction (0.468 g, 31%) and the title compound as the second fraction (0.807 g, 53%). $^1$H NMR (500 MHz, DMSO) δ7.40–6.97 (m, 18H), 4.87–4.66 (m, 2H), 4.45–4.26 (m, 2H), 4.13–3.88(m, 2H), 3.67–3.48 (m, 4H), 3.47–3.30 (m, 4H), 3.19–3.13 (4 s's, 6H), 3.20–3.01 (m, 2H). MS (FAB$^+$) m/e 711 (M+H).

EXAMPLE 41

(1α,2β,3β,4α)-1,2-Di[N-(2-methylthioethyl)-N-(4-phenoxybenzyl)aminocarbonyl]cyclobutane-3,4-dicarboxylic acid

EXAMPLE 41A

N-(2-Methylthio)ethyl-N-(4-phenoxy)benzylamine

Following the procedures described in Example 40A, 4-phenoxybenzaldehyde (1.98 g, 10 mmol) and 2-(methylthio)ethylamine (0.912 g, 10 mmol) were combined to give the title compound (2.53 g, 93%). $^1$H NMR (300 MHz, $CDCl_3$) δ7.32 (m, 4H), 7.09 (t, 1H), 6.97 (m, 4H), 3.80 (s, 2H), 2.84 9 t, 2H), 2.68 (t, 2H), 2.10 (s, 3H).

EXAMPLE 41B (1α,2β,3β,4α)-1,2-Di[N-(2-methylthioethyl)-N-(4-phenoxybenzyl)aminocarbonyl]cyclobutane-3,4-dicarboxylic acid A mixture of the compound resulting from Example 41A (0.682 g, 2.5 mmol), 1,2,3,4-cyclobutanetetracarboxylic dianhydride (0.196 g, 1.0 mmol), triethylamine (0.42 mL, 3.0 mmol) and DMAP (12 mg) in acetonitrile (10 mL) were reacted, worked up and purified by the procedures described in Example 38H to give the 1,3-diamide-2,4-diacid as the first fraction (0.214 g, 29%) and the title compound as the second fraction (0.274 g, 37%). $^1$H NMR (500 MHz, CDCl$_3$) δ7.32–6.87 (m, 18H), 4.70–4.14 (m, 6H), 3.97–3.84 (m, 2H), 3.76–3.23 (m, 4H), 2.53 (m, 4H), 2.02 (4 s's, 6H). MS (FAB$^+$) m/e 743 (M+H).

EXAMPLE 42

(1α,2β,3β,4α)-1,2-Di[N-(2-ethylthioethyl)-N-(4-phenoxybenzyl)aminocarbonyl]cyclobutane-3,4-dicarboxylic acid Following the procedures described in Example 40A, 4-phenoxybenzaldehyde (1.98 g, 10 mmol), 2-(ethylthio) ethylamine hydrogen chloride (1.42 g, 10 mmol) and 20 mmol of sodium acetate were combined to give N-(2-ethylthio)ethyl-N-(4-phenoxy)benzylamine (2.72 g, 95%). $^1$H NMR (300 MHz, CDCl$_3$): δ7.33 (m, 4H), 7.09 (t, 1H), 6.98 (m, 4H), 3.78 (s, 2H), 2.84 (t, 2H), 2.71 (t, 2H), 2.54 (q, 2H), 1.26 (t, 3H).

A mixture of the amine prepared above (0.718 g, 2.5 mmol), 1,2,3,4-cyclobutanetetracarboxylic dianhydride (0.196 g, 1.0 mmol), triethylamine (0.42 mL, 3.0 mmol) and DMAP (24 mg) in acetonitrile (10 mL) were reacted, worked up and purified by the procedures described in Example 38H to give the 1,3-diamide-2,4-diacid as the first fraction (0.207 g, 27%) and the title compound as the second fraction (0.398 g, 52%). $^1$H NMR (500 MHz, CDCl$_3$) δ7.32–6.87 (m, 18H), 4.73–4.12 (m, 6H), 3.98–3.86 (m, 2H), 3.78–3.25 (m, 4H), 2.59 (m, 4H), 2.46 (m, 4H), 1.17 (m, 6H). MS (FAB$^+$) m/e 771 (M+H).

EXAMPLE 43

(1α,2β,3β,4α)-1,2-Di[N-(2-fluoroethyl)-N-(4-phenoxybenzyl)aminocarbonyl]cyclobutane-3,4-dicarboxylic acid Following the procedures described in Example 40A, 4-phenoxybenzaldehyde (1.98 g, 10 mmol), 2-fluoroethylamine hydrogen chloride (0.995 g, 10 mmol) and 20 mmol of sodium acetate were combined to give N-(2-fluoro)ethyl-N-(4-phenoxy)benzylamine (2.15 g, 88%). $^1$H NMR (300 MHz, CDCl$_3$) δ7.33 (m, 4H), 7.09 (t, 1H), 6.97 (m, 4H), 4.57 (dt, 2H), 3.73 (s, 2H), 2.94 (dt, 2H).

A mixture of the amine prepared above (0.613 g, 2.5 mmol), 1,2,3,4-cyclobutanetetracarboxylic dianhydride (0.196 g, 1.0 mmol), triethylamine (0.42 mL, 3.0 mmol) and DMAP (12 mg) in acetonitrile (10 mL) were reacted, worked up and purified by the procedures described in Example 38H to give the 1,3-diamide-2,4-diacid as the first fraction (0.195 g, 28%) and the title compound as the second fraction (0.377 g, 55%). $^1$H NMR (500 MHz, DMSO) δ7.39–6.90 (m, 18H), 4.88–4.73 (m, 2H), 4.65–4.15 (m, 6H), 4.06–3.90 (m, 2H), 3.85–3.61 (m, 4H), 3.25 (m, 2H). MS (FAB$^+$) m/e 687 (M+H).

EXAMPLE 44

(1α,2β,3β,4α)-1,2-Di[N-(furan-2-ylmethyl)-N-(4-phenoxybenzyl)aminocarbonyl]cyclobutane-3,4-dicarboxylic acid Following the procedures described in Example 40A, 4-phenoxybenzaldehyde (1.98 g, 10 mmol) and furfurylamine (0.971 g, 10 mmol) were combined to give N-(furan-2-yl)methyl-N-(4-phenoxy)benzylamine (2.43 g, 87%). $^1$H NMR (300 MHz, CDCl$_3$) δ7.30 (m, 5H), 7.09 (t, 1H), 6.98 (m, 4H), 6.34 (m, 1H), 6.19 (m, 1H), 3.80 (s, 2H), 3.77 (s, 2H).

A mixture of the amine prepared above (0.698 g, 2.5 mmol), 1,2,3,4-cyclobutanetetracarboxylic dianhydride (0.196 g, 1.0 mmol), triethylamine (0.42 mL, 3.0 mmol) and DMAP (12 mg) in acetonitrile (10 mL) were reacted, worked up and purified by the procedures described in Example 38H to give the 1,3-diamide-2,4-diacid as the first fraction (0.251g, 34%) and the title compound as the second fraction (0.438 g, 58%). $^1$H NMR (500 MHz, CDCl$_3$) δ7.39–6.90 (m, 20H), 6.27–6.13 (m, 4H), 4.89–3.92 (m, 12H). MS (DCl) m/e 755 (M+H).

EXAMPLE 45

(1α,2β,3β,4α)-1,2-Di[N-(thien-2-ylmethyl)-N-(4-phenoxybenzyl)aminocarbonyl]cyclobutane-3,4-dicarboxylic acid Following the procedures described in Example 40A, 4-phenoxybenzaldehyde (1.98 g, 10 mmol) and 2-thienylmethylamine (1.13 g, 10 mmol) were combined to give N-(thien-2-yl)methyl-N-(4-phenoxy)benzylamine (2.87 g, 97%). $^1$H NMR (300 MHz, CDCl$_3$) δ7.35–6.92 (m, 12H), 4.01 (s, 2H), 3.81 (s, 2H).

A mixture of the amine prepared above (0.738 g, 2.5 mmol), 1,2,3,4-cyclobutanetetracarboxylic dianhydride (0.196 g, 1.0 mmol), triethylamine (0.42 mL, 3.0 mmol) and DMAP (12 mg) in acetonitrile (10 mL) were reacted, worked up and purified by the procedures described in Example 38H to give the 1,3-diamide-2,4-diacid as the first fraction (0.193 g, 25%) and the title compound as the second fraction (0.382 g, 49%). $^1$H NMR (500 MHz, CDCl$_3$) δ7.37–6.82 (m, 24H), 4.89–3.97 (m, 12H). MS (DCl) m/e 787 (M+H).

EXAMPLE 46

(1α,2β,3β,4α)-1,2-Di[N-(2-ethylthioethyl)-N-(4-phenylthiobenzyl)aminocarbonyl]cyclobutane-3,4-dicarboxylic acid Following the procedures described in Example 40A, 4-phenylthiobenzaldehyde, 2-(ethylthio)ethylamine hydrochloride, sodium acetate and sodium cyanoborohydride are reacted to give N-(2-ethylthio)ethyl-N-(4-phenylthio)benzylamine.

A mixture of the amine prepared above, 1,2,3,4-cyclobutanetetracarboxylic dianhydride, triethylamine and DMAP in acetonitrile are reacted, worked up and purified by the procedures described in Example 38H to give the title compound.

EXAMPLE 47

(1α,2β,3β,4α)-1,2-Di[N-(cyclopropylmethyl)-N-(4-phenoxybenzyl)aminocarbonyl]cyclobutane-3,4-dicarboxylic acid

EXAMPLE 47A

N-(cyclopropylmethyl)-N-(4-phenoxybenzyl)amine

4-Phenoxybenzaldehyde (3.0 g, 15.1 mmol) and cyclopropylmethylamine (1.1 g, 15.1 mmol) were dissolved in methanol (85 mL) under nitrogen at room temperature. Sodium cyanoborohydride (0.95 g, 15.1 mmol) was added, and stirring was continued for 48 hours. The solvent was evaporated under reduced pressure, and the residue was suspended in ether, washed with brine, and dried over Na$_2$SO$_4$. The ether was evaporated, and the crude product was chromatographed on silica gel eluting with 3% methanol-methylene chloride to provide 3.0 g (78%) of the title compound as a colorless oil. $^1$H NMR (CDCl$_3$, 300 MHz) δ0.08–0.15 (m, 2H), 0.45–0.55 (m, 2H), 0.93–1.05 (m, 1H), 1.45 (br s, 1H), 2.50 (d, J=7.5 Hz, 2H), 3.78 (s, 2H), 6.95–7.03 (m, 4H), 7.05–7.13 (m, 1H), 7.25–7.38 (m, 4H). MS (DCI/NH$_3$) m/e 254 (M+H)$^+$.

EXAMPLE 47B (1α,2β,3β,4α)-1,2-Di[N-(cyclopropylmethyl)-N-(4-phenoxybenzyl)aminocarbonyl]cyclobutane-3,4-dicarboxylic acid A slurry of 1,2,3,4-cyclobutanetetracarboxylic dianhydride (1.0 g, 5.0 mmol) in acetonitrile (17 mL) under nitrogen at room temperature was treated with a solution of the compound resulting from Example 47A (2.5 g, 10.0 mmol) in acetonitrile (20 mL). The resulting suspension was refluxed for 15 hours, the solvent was evaporated, and the residue was chromatographed on silica gel eluting with 98:1:1 chloroform-methanol-acetic acid to provide a wet foam. The foam was dissolved in acetonitrile (7 mL), triturated with water, and lyophilized to provide 1.2 g (34%) of the title compound as a white powder. m.p. 89°–91° C. $^1$H NMR (DMSO-d$_6$, 300 MHz) δ0.01–1.25 (m, 4H), 0.27–0.52 (m, 4H), 0.80–0.96 (m, 2H), 2.68–2.92 (m, 2H), 3.20–3.55 (m, 2H), 3.56–3.68 (m, 2H), 3.89–4.98 (m, 1H), 4.00–4.10 (m, 1H), 4.28–4.58 (m, 2H), 4.65–4.89 (m, 2H), 6.85–7.04 (m, 8H), 7.08–7.30 (m, 6H), 7.33–7.43 (m, 4H), 12.11–12.20 (br s, 2H). MS (FAB) m/e 703 (M+H)$^+$.

EXAMPLE 48

(1α,2β,3β,4α)-1,2-Di[N-cyclobutyl-N-(4-phenoxybenzyl)aminocarbonyl]cyclobutane-3,4-dicarboxylic acid Following the procedures described in Example 47A and substituting cyclobutylamine (1.8 g, 25.0 mmol) for cyclopropylmethylamine afforded 5.63 g (89%) of N-cyclobutyl-N-(4-phenoxybenzyl)amine as a colorless oil. $^1$H NMR (CDCl$_3$, 300 MHz) δ1.56–1.80 (m, 5H), 2.15–2.30 (m, 2H), 3.25–3.39 (m, 1H), 3.68 (s, 2H), 6.94–7.04 (m, 4H), 7.05–7.15 (tt, J=7.5, 1.5 Hz, 1H), 7.25–7.38 (m, 4H). MS (DCI/NH$_3$) m/e 254 (M+H)$^+$.

Following the procedures described in Example 47B and using the amine prepared above (5.2 g, 20.0 mmol) provided the title compound as a wet foam after chromatography. The foam was dissolved in acetonitrile (15 mL), triturated with water, and lyophilized to provide 2.3 g (33%) of the title compound as a white powder. m.p. 110°–112° C. $^1$H NMR (DMSO-d$_6$, 300 MHz) δ1.44–1.64 (m, 4H), 1.80–2.19 (m, 10H), 3.48–3.57 (m, 1H), 3.60–3.80 (m, 2H), 3.90–4.50 (m, 1H), 4.20–4.75 (m, 4H), 6.84–7.02 (m, 8H), 7.04–7.28 (m, 6H), 7.30–7.44 (m, 4H) 12.20–12.31 (br s, 2H). MS (FAB) m/e 703 (M+H)$^+$.

EXAMPLE 49

(1α,2β,3β,4α)-1,2-Di[N-cyclopentyl-N-(4-phenoxybenzyl)aminocarbonyl]cyclobutane-3,4-dicarboxylic acid Following the procedures described in Example 47A and substituting cyclopentylamine (2.5 g, 25.0 mmol) for cyclopropylmethylamine afforded 5.5 g (83%) of N-cyclopentyl-N-(4-phenoxybenzyl)amine as a colorless oil. $^1$H NMR (CDCl$_3$, 300 MHz) δ1.31–1.45 (m, 2H), 1.49–1.65 (m, 2H), 1.65–1.80 (m, 3H), 1.81–1.95 (m, 2H), 3.15 (p, J=7.5 Hz, 1H), 3.75 (s, 2H), 6.94–7.04 (m, 4H, 7.05–7.14 (m, 1H), 7.25–7.40 (m, 4H). MS (DCI/NH$_3$) m/e 268 (M+H)$^+$.

Following the procedures described in Example 47B and using the amine prepared above (5.4 g, 20.0 mmol) provided the title compound as a wet foam after chromatography. The foam was dissolved in acetonitrile (15 mL), triturated with water, and lyophilized to provide 2.19 g (30%) of the title compound as a white powder. m.p. 115°–118° C. $^1$H NMR (DMSO-d$_6$, 300 MHz) δ1.35–1.85 (br m, 18H), 3.48–3.58 (m, 1H), 3.60–3.68 (m, 1H), 3.98–4.36 (m, 4H), 4.45–4.55 (m, 2H), 6.82–7.04 (m, 8H), 7.06–7.17 (m, 3H), 7.18–7.28 (m, 3H), 7.29–7.44 (m, 4H), 12.01–12.27 (br s, 2H). MS (FAB) m/e 731 (M+H)$^+$.

EXAMPLE 50

(1α,2β,3β,4α)-1,2-Di[N-cyclohexyl-N-(4-phenoxybenzyl)aminocarbonyl]cyclobutane-3,4-dicarboxylic acid Following the procedures described in Example 47A and substituting cyclohexylamine (2.5 g, 25.0 mmol) for cyclopropylmethylamine afforded 6.4 g (91%) of N-cyclohexyl-N-(4-phenoxybenzyl)amine as a colorless oil. $^1$H NMR (CDCl$_3$, 300 MHz) δ1.05–1.35 (m, 5H), 1.55–1.65 (m, 1H), 1.70–1.80 (m, 3H), 1.85–2.00 (m, 2H), 2.45–2.55 (m, 1H), 3.80 (s, 2H), 6.95–7.04 (m, 4H), 7.05 (tt, J=7.5, 1.5 Hz, 1H), 7.25–7.35 (m, 4H). MS (DCI/NH$_3$) m/e 282 (M+H)$^+$.

Following the procedures described in Example 47B and using the amine prepared above (5.6 g, 20.0 mmol) provided the title compound as a wet foam after chromatography. The foam was dissolved in acetonitrile (15 mL), triturated with water, and lyophilized to provide 2.9 g (38%) of the title compound as a white powder. m.p. 133°–135° C. $^1$H NMR (DMSO-d$_6$, 300 MHz) δ0.82–1.78 (br m, 22H), 3.48–3.69 (m, 2H), 3.64–3.73 (m, 1H), 3.84–3.94 (m, 1H), 4.10–4.64 (m, 4H), 6.80–7.05 (m, 8H), 7.07–7.18 (m, 3H), 7.19–7.44 (m, 7H), 12.15–12.29 (br s, 2H). MS (FAB) m/e 759 (M+H)$^+$.

EXAMPLE 51

(1α,2β,3β,4α)-1,2-Di[N-(cyclopentylmethyl)-N-(4-phenoxybenzyl)aminocarbonyl]cyclobutane-3,4-dicarboxylic acid

EXAMPLE 51A

N-(Cyclopentylmethyl)amine

A cooled (0° C.) solution of cylopentanecarbonitrile (5.0 g, 53 mmol) in THF (175 mL) was treated with 1M LAH in THF (53 mL). The solution was refluxed for 2 hours then cooled to 0° C. and quenched with Na$_2$SO$_4$.10H$_2$O. The suspension was diluted with THF and filtered through a pad of celite. Removal of the solvent in vacuo provided 4.9 g (95%) of the title compound as a pale green oil which was used without further purification. $^1$H NMR (CDCl$_3$, 300 MHz) δ1.10–2.10 (br m, 10H), 2.60 (d, J=7.5 Hz, 2H), 2.74–2.79 (m, 1H). MS (DCI/NH$_3$) m/e 100 (M+H)$^+$.

EXAMPLE 51B (1α,2β,3β,4α)-1,2-Di[N-(cyclopentylmethyl)-N-(4-phenoxybenzyl)aminocarbonyl]cyclobutane-3,4-dicarboxylic acid Following the procedures described in Example 47A and substituting the compound resulting from Example 51A (1.49 g, 15.1 mmol) for cyclopropylmethylamine afforded 3.4 g, 80% of N-(cyclopentylmethyl)-N-(4-phenoxybenzyl) amine as a colorless oil. $^1$H NMR (CDCl$_3$, 300 MHz) δ1.10–1.24 (m, 2H), 1.45–1.67 (m, 4H), 1.71–1.90 (m, 3H), 2.06 (p, J=7.5 Hz, 1H), 2.58 (d, J=7.5 Hz, 2H), 3.79 (s, 2H), 6.95–7.05 (m, 4H), 7.09 (tt, J=7.5, 1.5 Hz, 1H), 7.28–7.38 (m, 4H). MS (DCl) m/e 282 (M+H)$^+$.

Following the procedures described in Example 47B and using the amine prepared above (5.6 g, 20 mmol) provided the title compound as a wet foam after chromatography. The foam was dissolved in acetonitrile (15 mL), triturated with water, and lyophilized to provide 2.8 g (37%) of the the title compound as a white powder. m.p. 98°–99° C. $^1$H NMR (DMSO-d$_6$, 300 MHz) δ1.00–1.22 (m, 4H), 1.34–1.70 (m, 16H), 2.00–2.18 (m, 2H), 2.75–3.00 (m, 1H), 3.13–3.70 (m, 2H), 3.66–4.06 (m, 1H), 4.22–4.40 (m, 2H), 4.60–4.78 (m, 2H), 6.85–7.04 (m, 8H), 7.08–7.29 (m, 6H), 7.32–7.44 (m, 4H), 12.17–12.34 (br s, 2H). MS (FAB) m/e 759 (M+H)$^+$.

EXAMPLE 52

(1α,2β,3β,4α)-1,2-Di[N-(cyclobutylmethyl)-N-(4-phenoxybenzyl)aminocarbonyl]cyclobutane-3,4-dicarboxylic acid

EXAMPLE 52A

N-(4-phenoxybenzyl)cyclobutanecarboxamide

To a cooled (0° C.) solution of cyclobutanecarboxylic acid (0.26 g, 2.6 mmol), 4-phenoxybenzylamine hydrochloride (0.62 g, 2.6 mmol), HOBt, (0.71 g, 5.2 mmol) and triethylamine (1.1 mL, 7.83 mmol) in THF (9 mL) was added EDCl (0.55 g, 2.6 mmol). The mixture was stirred for 18 hours at room temperature. The solvent was removed, and the residue was suspended in ether and washed with 0.1N HCl, 5% NaHCO$_3$ and brine. The ether layer was dried (MgSO$_4$), filtered through a plug of silica gel and concentrated in vacuo to provide 0.70 g (96%) of the title compound as a white solid. m.p. 69°–71° C. $^1$H NMR (CDCl$_3$, 300 MHz) δ1.80–2.06 (m, 2H), 2.10–2.14 (m, 2H), 2.15–2.39 (m, 2H), 3.02 (pd, J=7.5, 1.2 Hz, 1H), 4.41 (d, J=6 Hz, 2H), 5.55 (br s, 1H), 6.94–7.04 (m, 4H), 7.08–7.15 (tt, J=7.5, 1.5 Hz, 1H), 7.20–7.28 (m, 2H), 7.30–7.38 (m, 2H). MS (DCl/NH$_3$) m/e 282 (M+H)$^+$.

EXAMPLE 52B

N-(Cyclobutylmethyl)-N-(4-phenoxybenzyl)amine

A cooled (0° C.) solution of the compound resulting from Example 52A (0.60 g, 2.1 mmol) in THF (7 mL) was treated with 1M LAH in THF (2.1 mL). The solution was refluxed for 2 hours then cooled to 0° C. and quenched with Na$_2$SO$_4$.H10H$_2$O. The suspension was diluted with THF and filtered through a pad of celite. Removal of the solvent provided 0.56 g (99%) of the title compound as a colorless oil. $^1$H NMR (CDCl$_3$, 500 MHz) δ1.15 (br s, 1H), 1.62–1.70 (m, 2H), 1.80–1.98 (m, 2H), 2.02–2.10 (m, 2H), 2.50 (p, J=7.5 Hz, 1H), 2.65 (d, J=7.5 Hz, 2H), 3.75 (s, 2H), 6.95–7.02 (m, 4H), 7.05–7.10 (tt, J=7.5, 1.2 Hz, 1H), 7.25–7.35 (m, 4H). MS (DCl/NH$_3$) m/e 268 (M+H)$^+$.

EXAMPLE 52C (1α,2β,3β,4α)-1,2-Di[N-(cyclobutylmethyl)-N-(4-phenoxybenzyl)aminocarbonyl]cyclobutane-3,4-dicarboxylic acid Following the procedures described in Example 47B and using the compound resulting from Example 52B (0.25 g, 0.94 mmol) provided the title compound as a wet foam after chromatography. The foam was dissolved in acetonitrile (2 mL), triturated with water, and lyophilized to provide 100 mg (29%) of the the title compound as a white powder. m.p. 94°–95° C. $^1$H NMR (DMSO-d$_6$, 300 MHz) δ1.55–2.00 (m, 12H), 2.90–3.01 (m, 1H), 3.04–3.15 (m, 1H), 3.35–3.46 (m, 3H), 3.51–3.68 (m, 3H), 3.82–3.97 (m, 1H), 4.00–4.14 (m, 1H), 4.18–4.35 (m, 2H), 4.60–4.83, (m, 2H), 6.89–7.05 (m, 8H), 7.09–7.17 (m, 2H), 7.18–7.28 (m, 4H), 7.34–7.44 (m, 4H), 12.00–12.27 (br s, 2H). MS (FAB) m/e 731 (M+H)$^+$.

EXAMPLE 53

(1α,2β,3β,4α)-1,2-Di[N-(4-fluorobenzyl)-N-(4-phenoxybenzyl)aminocarbonyl]cyclobutane-3,4-dicarboxylic acid

EXAMPLE 53A

N-(4-Fluorobenzyl)-N-(4-phenoxybenzyl)amine

4-Phenoxybenzaldehyde (1.0 g, 5.0 mmol) and 4-fluorobenzylamine (631 mg, 5.0 mmol) were dissolved in methanol (17 mL) under nitrogen at room temperature. Sodium cyanoborohydride (317 mg, 5.0 mmol) was added, and stirring was continued for 48 hours. The solvent was evaporated and the residue was suspended in ether, washed with brine, and dried over Na$_2$SO$_4$. The ether was evaporated, and the crude product was chromatographed on silica gel eluting with 3% methanol-methylene chloride to provide 1.5 g (97%) of the title compound as a colorless oil. $^1$H NMR (CDCl$_3$, 300 MHz) δ1.55 (s, 1H), 3.76 (s, 2H), 3.78 (s, 2H), 6.95–7.15 (m, 7H), 7.25–7.40 (m, 6H). MS (DCl/NH$_3$) m/e 308 (M+H)$^+$.

EXAMPLE 53B (1α,2β,3β,4α)-1,2-Di[N-(4-fluorobenzyl)-N-(4-phenoxybenzyl)aminocarbonyl]cyclobutane-3,4-dicarboxylic acid A slurry of 1,2,3,4-cyclobutanetetracarboxylic dianhydride (450 mg, 2.3 mmol) in acetonitrile (4 mL) under nitrogen at room temperature was treated with a solution of the compound resulting from Example 53A (1.4 g, 4.6 mmol) in acetonitrile (6 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile (5 mL), triturated with water, and lyophilized to provide 890 mg (48%) of the title compound as a white powder. m.p. 97°–99° C. $^1$H NMR (DMSO-d$_6$, 300 MHz) δ3.66–3.74 (m, 2H), 3.95–4.24 (m, 2H), 4.62–4.73 (m, 4H), 4.80–4.88 (m, 4H), 6.90–7.28 (m, 18H), 7.34–7.42 (m, 8H), 12.62–12.75 (br s, 2H). MS (FAB) m/e 811 (M+H)$^+$.

EXAMPLE 54

(1α,2β,3β,4α)-1,2-Di[N-(4-phenoxybenzyl)-N-(3-methoxyphenethyl) aminocarbonyl]cyclobutane-3,4-dicarboxylic acid

EXAMPLE 54A

N-(p-phenoxybenzyl)-N-(m-methoxyphenethyl) amine

A solution of 4-benzoxybenzaldehyde (2.5 g, 12.6 mmol), 3-methoxyphenethyl amine (1.9 g, 12.6 mmol), a catalytic amount of p-toluenesulfonic acid monohydrate in absolute ethanol (12 mL) was stirred at 80° C. for 1.5 hours. After cooling to room temperature, NaBH$_4$ (0.49 g, 13.0 mmol) was added in portions. The reaction mixture was stirred at 80° C. for 1 hour, then cooled to room temperature, and the ethanol was removed in vacuo. Water was added to the residue and the mixture was extracted with ethyl acetate. The combined extracts were washed with saturated NaCl, dried over MgSO$_4$, filtered, and solvent removed in vacuo to afford a colorless oil which was purified by silica gel chromatography eluting with 20% ethyl acetate in hexane saturated with NH$_3$ to afford the title compound (3.2 g, 76%) as a colorless oil. MS (DCI/NH$_3$) m/e 334 (M+H)$^+$. $^1$H NMR (CDCl$_3$, 300 MHz) δ2.82 (t, 2H), 2.92 (t, 2H), 3.77 (s, 2H), 3.80 (s, 3H), 6.80 (m, 3H), 6.98 (m, 3H), 6.08 (t, 1H), 7.22 (m, 3H), 7.32 (t, 2H).

EXAMPLE 54B (1α,2β,3β,4α)-1,2-Di[N-(4-phenoxybenzyl)-N-(3-methoxyphenethyl) aminocarbonyl]cyclobutane-3,4-dicarboxylic acid A solution of the product from Example 54A (1.26 g, 3.8 mmol), 1,2,3,4-cyclobutanetetracarboxylic dianhydride (0.38 g, 1.95 mmol), triethylamine (0.053 mL, 3.8 mmol), and CH$_3$CN (14 mL) was stirred at room temperature for 3 hours. The solvent was removed in vacuo, and the residue was dissolved in ethyl acetate, washed successively with 1N HCl and saturated NaCl, dried over MgSO$_4$, filtered, and evaporated to afford a white foam. The crude product (1.8 g) containing both isomers was purified by silica gel chromatography eluting with 97:2.5:0.5 CHCl$_3$—MeOH—HOAc. The slower running isomer was collected to afford 0.40 g (24%) of the desired product. $^1$H NMR (300 MHz, CDCl$_3$) δ2.71 (q, 4H), 3.21 (m, 2H), 3.40 (m, 3H), 3.70 (d,3H), 3.70 (m, 2H), 3.72 (d, 3H), 3.90 (m, 3H), 4.16 (m, 2H), 4.25 (m, 2H), 4.35 (m, 1H), 4.45 (d, 2H), 4.55 (d, 1H), 6.68 (m, 5H), 6.85 (m, 3H), 6.92 (m, 5H), 7.05 (m, 8H), 7.25, (m, 5H). MS (FAB) m/e 863 (M+H)$^+$.

EXAMPLE 55

(1α,2β,3β,4α)-1,2-Di[N-(4-phenoxybenzyl)-N-(3,4-dimethoxyphenethyl) aminocarbonyl]cyclobutane-3,4-dicarboxylic acid Using the procedures described in Example 54A, but substituting 3,4-dimethoxyphenethylamine for 3-methoxyphenethylamine, provided N-(4-phenoxybenzyl)-N-(3,4-dimethoxyphenethyl)amine. $^1$H NMR (300 MHz, CDCl$_3$) δ2.78 (t, 2H), 2.90 (t, 2H), 3.78 (s, 2H) 3.88 (s, 3H), 6.78 (m, 3H), 6.98 (t, 4H), 7.09 (t, 1H), 7.26 (t, 2H), 7.32 (t, 2H). MS (DCI/NH$_3$) m/e 364 (M+H)$^+$.

The amine prepared above was reacted by the procedures described in Example 54B to provide the title compound. $^1$H NMR (300 MHz, CDCl$_3$) δ2.70 (q, 4H), 3.10–3.50 (m, 4H), 3.78 (s, 12H), 3.92 (m, 2H), 4.02–4.32 (m, 4H), 4.55 (q, 2H), 6.59–6.75 (m, 6H), 6.85 (m, 3H), 6.94 (t, 4H), 7.09 (m, 6H), 7.28 (m, 5H). MS (FAB) m/e 923 (M+H)$^+$.

EXAMPLE 56

(1α,2β,3β,4α)-1,2-Di[N-(4-phenoxybenzyl)-N-phenethylaminocarbonyl]cyclobutane-3,4-dicarboxylic acid Using the procedures described in Example 54A, but substituting phenethylamine for 3-methoxyphenethylamine, provided N-(4-phenoxybenzyl)-N-phenethylamine. $^1$H NMR (300 MHz, CDCl$_3$) δ2.85 (t, 2H), 2.93 (t, 2H), 3.80 (s, 2H), 6.98 (m, 4H), 7.10 (t, 1H), 7.30 (m, 9H). MS (DCI/NH$_3$) m/e 304 (M+H)$^+$.

The amine prepared above was reacted by the procedures described in Example 54B to provide the title compound. $^1$H NMR (300 MHz, CDCl$_3$) δ2.78 (q, 4H), 3.19–3.30 (m, 1H), 3.30–3.50 (m, 2H), 3.60–3.80 (m, 2H), 3.90 (q, 2H), 4.11–4.29 (m, 2H), 4.34 (t, 1H), 4.45 (m, 2H), 6.85 (m, 3H), 6.91 (m, 4H), 7.09 (m, 10H), 7.18 (m, 5H), 7.25 (m, 6H). MS (FAB) m/e 841 (M+K)$^+$.

EXAMPLE 57

(1α,2β,3β,4α)-1,2-Di[N-(4-phenoxybenzyl)-N-(3-phenyl-1-propyl)aminocarbonyl]cyclobutane-3,4-dicarboxylic acid Using the procedures described in Example 54A, but substituting 3-phenyl-1-propyl amine for 3-methoxyphenethylamine, provided N-(4-phenoxybenzyl)-N-(3-phenyl-1-propyl)amine. $^1$H NMR (300 MHz, CDCl$_3$) δ1.85 (p, 2H), 2.70 (m, 4H), 3.75 (s, 2H), 7.00 (t, 3H), 7.10 (t, 1H), 7.20 (m, 3H), 7.30 (m, 7H). MS (DCI/NH$_3$) m/e 318 (M+H)$^+$.

The amine prepared above was reacted by the procedures described in Example 54B to provide the title compound. $^1$H NMR (300 MHz, CDCl$_3$) δ1.78 (m, 4H), 2.50 (q, 4H), 3.10 (m, 2H), 3.12 (m, 1H), 3.35–3.58 (m, 1H), 3.80–3.92 (m, 2H), 4.06 (t, 1H), 4.10–4.20 (m, 2H), 4.39–4.59 (m, 3H), 6.82 (dd,3H), 6.94 (m, 6H), 7.12 (t, 2H), 7.28 (m, 5H). MS (FAB) m/e 831 (M+H)$^+$.

EXAMPLE 58

(1α,2β,3β,4α)-1,2-Di[N-(4-phenoxybenzyl)-N-(4-phenyl-1-butyl)aminocarbonyl]cyclobutane-3,4-dicarboxylic acid Using the procedures described in Example 54A, but substituting N-(4-phenyl-1-butyl)amine for 3-methoxyphenethylamine, provided N-(4-phenoxybenzyl)-N-(4-phenyl-1-butyl)amine. $^1$H NMR (300 MHz, CDCl$_3$): δ1.50–1.72 (m, 4H), 2.65 (m, 4H), 3.25 (s, 2H), 6.98 (t, 4H), 7.09 (t, 1H), 7.19 (m, 3H), 7.30 (m, 6H). MS (DCI/NH$_3$) m/e 332 (M+H)$^+$.

The amine prepared above was reacted by the procedures described in Example 54B to provide the title compound. $^1$H NMR (300 MHz, CDCl$_3$) δ1.50 (br m, 8H), 2.52 (br dt, 4H), 3.02–3.28 (m, 3H), 3.35–3.58 (m, 1H), 3.81–3.95 (m, 2H), 4.00–4.20 (m, 2H), 4.21–4.65 (m, 4H), 6.90 (m, 7H), 7.05 (m, 10H), 7.25 (m, 7H). MS (FAB) m/e 859 (M+H)$^+$.

EXAMPLE 59

(1α,2β,3β,4α)-1,2-Di[N-(4-phenoxybenzyl)-N-(methoxycarbonylmethyl)aminocarbonyl]cyclobutane-3,4-dicarboxylic acid Following the procedures described in Examples 1A and 13, the title compound was prepared. $^1$H NMR (CDCl$_3$, 500 MHz) δ3.62–3.79 (m, 6H), 3.94–5.14 (m, 12H), 6.91–7.51 (m, 18H). MS m/e 739 (M+H)$^+$.

EXAMPLE 60

(1α,2β,3β,4α)-1,2-Di[N-(4-phenoxybenzyl)-N-(ethoxycarbonylethyl)aminocarbonyl]cyclobutane-3,4-dicarboxylic acid Following the procedures described in Examples 1A and 13, the title compound was prepared. $^1$H NMR (CDCl$_3$, 500

MHz) δ1.25 (t, 6H, J=7 Hz), 2.56 (m, 2H), 3.73 (q, 4H, J=7 Hz), 3.9–4.28 (m, 12H), 4.38 (m, 1H), 4.76 (m, 1H), 6.9–7.35 (m, 18H). MS m/e 795 (M+H)$^+$.

EXAMPLE 61

(1α,2β,3β,4α)-1,2-Di[N-propyl-N-(4-cyclohexyloxybenzyl)aminocarbonyl]cyclobutane-3,4-dicarboxylic acid

EXAMPLE 61A 4-(Cyclohex-2-enyloxy)benzaldehyde 4-(Cyclohex-2-enyloxy)benzoic acid (25 g, 115 mmol) was dissolved in 250 mL dry tetrahydrofuran and cooled to −10° C. under an atmosphere of dry nitrogen. N-Methylmorpholine (12.6 mL, 115 mmol) and isobutylchloroformate (15.9 mL, 115 mmol) were added. After 10 minutes at −10° C. the mixture was warmed to room temperature and filtered. The volume was reduced to 50 mL under reduced pressure before cooling to 0° C. and adding diisobutylaluminum hydride (1.5M in toluene, 160 mL) over 10 minutes. After 30 minutes, the reaction was warmed to ambient temperature for 2 hours. The mixture was cooled in an ice bath, diluted with ether, quenched with methanol, and poured into cold Rochelle's salt solution. The crude product was extracted with ether, dried over Na$_2$SO$_4$, and chromatographed eluting with 20% ethyl acetate in hexane to give 4.24 g (18%) of 4-(cyclohex-2-enyloxy)benzyl alcohol.

The alcohol prepared above (4.24 g, 20.7 mmol) was dissolved in 250 mL methylene chloride under an atmosphere of dry nitrogen. Pyridinium chlorochormate (5.62 g, 26.1 mmol) was added over 5 minutes. After stirring at ambient temperature for 72 hours, the mixture was filtered through Celite and concentrated in vacuo. Flash silica gel chromatography eluting with 10% ethyl acetate in hexane afforded 3.25 g (77%) of the title compound.

EXAMPLE 61B (1α,2β,3β,4α)-1,2-Di[N-propyl-N-(4-cyclohexyloxybenzyl)aminocarbonyl]cyclobutane-3,4-dicarboxylic acid N-propyl-N-(4-cyclohexyloxybenzyl)amine was prepared by the procedures described in Example 1A starting with the compound resulting from Example 61A.

The title compound was prepared using the amine prepared above and the procedures described in Example 13. $^1$H NMR (CDCl$_3$, 500 MHz) δ0.80 (m, 6H), 1.35 (m, 6H), 1.51 (m, 10H), 1.79 (m, 4H), 1.97 (m, 4H), 3.1 (m, 4H), 3.39 (m, 1H), 3.50 (m, 1H), 3.93–4.59 (m, 8H), 6.94 (m, 4H), 7.07–7.14 (m, 4H). MS m/e 691 (M+H)$^+$.

EXAMPLE 62

(1α,2β,3β,4α)-1-[N-Propyl-N-(4-phenoxybenzyl)aminocarbonyl]-2-[N-methyl-N-(homogeranyl)aminocarbonyl]cyclobutane-3,4-dicarboxylic acid

EXAMPLE 62A (1α,2β,3β,4α)-1-[N-Propyl-N-(4-phenoxybenzyl)aminocarbonyl]-cyclobutane-2,3,4-tricarboxylic acid To a solution of 1,2,3,4-cyclobutanetetracarboxylic dianhydride (1.0 g, 5.1 mmol) and triethylamine (0.7 mL, 5.1 mmol) in acetonitrile (50 mL) under an atmosphere of dry nitrogen was added N-propyl-4-phenoxybenzyl amine hydrochloride (1 equivalent). After stirring 18 hours, 1M HCl was added and stirring was continued for 18 hours. The mixture was diluted with ethyl acetate which was subsequently washed with 1M HCl and brine, dried over Na$_2$SO$_4$, and concentrated in vacuo to give 2.3 g of crude product.

A solution of crude triacid (1.1 g, 2.4 mmol) in methanol (25 mL) was treated with an excess of ethereal diazomethane. Evaporation and flash silica gel chromatography eluting with 50% ethyl acetate in hexane afforded the corresponding pure triester (0.8 g, 67%). The pure triester was dissolved in methanol (10 mL) and treated with 3M NaOH (5 mL) at 40° C. for 48 hours. The reaction mixture was diluted with water and washed with ethyl acetate. The aqueous solution was acidified to pH 2 with concentrated HCl. The product was extracted into ethyl acetate which was then washed with brine, dried over Na$_2$SO$_4$, and concentrated under reduced pressure to give 0.73 g (99%) of the pure triacid.

EXAMPLE 62B (1α,2β,3β,4α)-[N-Propyl-N-(4-phenoxybenzyl)aminocarbonyl]-2-[N-methyl-N-(homogeranyl)aminocarbonyl]cyclobutane-3,4-dicarboxylic acid To a solution of the compound resulting from Example 62A (0.43 g, 0.94 mmol) in dimethylformamide (1 mL) and methylene chloride (10 mL) at 0° C., was added dicyclohexylcarbodiimide (0.19 g, 0.94 mmol). After 1 hour, N-methyl-N-(homogeranyl)amine (0.94 mmol) and triethylamine (0.39 mL, 2.8 mmol) were added. The reaction was allowed to warm to ambient temperature and stirred for 18 hours. Ethyl acetate was added to the reaction mixture which was then washed with 1M HCl and brine, dried over Na$_2$SO$_4$, and concentrated under reduced pressure. The residue obtained was purified by flash silica gel chromatography eluting with 94:5:1 chloroform-methanol-acetic acid to give the title compound. $^1$H NMR (CDCl$_3$, 300 MHz) δ0.85 (m, 3H), 1.61 (m, 6H), 1.68 (m, 3H), 2.00 (m, 8H), 2.92 (m, 5H), 3.66 (m, 2H), 4.03 (m, 3H), 4.55 (m, 3H), 5.05 (m, 2H), 6.85–7.35 (m, 9H). MS m/e 619 (M+H)$^+$.

EXAMPLE 63

(1α,2β,3β,4α)-1-[N-Propyl-N-(4-phenoxybenzyl)aminocarbonyl]-2-[N-benzyl-N-(4-phenoxybenzyl)aminocarbonyl]cyclobutane-3,4-dicarboxylic acid The title compound was prepared using the procedures described in Example 62. $^1$H NMR (CDCl$_3$, 300 MHz) δ0.88 (m, 3H), 1.35 (m, 2H), 3.62–4.61 (m, 12H), 6.89–7.35 (m, 23H). MS m/e 727 (M+H)$^+$.

EXAMPLE 64

(1α,2β,3β,4α)-1-[N-Propyl-N-(4-phenoxybenzyl)aminocarbonyl]-2-[N-(4-phenoxybenzyl)aminocarbonyl]cyclobutane-3,4-dicarboxylic acid

EXAMPLE 64A

4-Phenoxybenzyl alcohol

A solution of 4-phenoxybenzaldehyde (10.0 g, 50 mmol) and 10 mL dry THF was added dropwise to a 0° C. suspension of lithium aluminum hydride (2.1 g, 55.3 mmol) and 100 mL dry THF. The reaction mixture was stirred for 1 hour at 0° C., then was quenched successively with 2.1 mL $H_2O$, 2.1 mL 10% NaOH, and 6.3 mL $H_2O$. The resultant slurry was stirred for 1.5 hours at room temperature, then was filtered through Celite and the filtrate was evaporated under reduced pressure to afford the title compound (9.9 g) as a white solid. $^1$H NMR (300 MHz, $CDCl_3$) δ1.68 (t, 1H), 4.68 (d, 2H), 7.00 (m, 4H), 7.10 (t, 1H), 7.35 (m, 4H). MS ($DCl/NH_3$) m/e 183 (M+1, $-H_2O)^+$.

EXAMPLE 64B

4-Phenoxybenzyl phthalimide

To the compound resulting from Example 64A (5.0 g, 25 mmol) was added to a solution of lithium bromide (4.4 g, 51 mmol), trimethylsilyl chloride (8.2 mL, 64 mmol), and 51 mL acetonitrile. The reaction mixture was stirred at reflux for 2 hours, then was cooled to room temperature. Water (25 mL) was added, the acetonitrile was removed under reduced pressure, and the aqueous layer was extracted with ether. The combined organic extracts were washed with saturated aqueous sodium bicarbonate and brine, dried ($MgSO_4$), filtered, and solvent evaporated in vacuo to afford 5.35 g clear oil. The crude bromide (20.3 mmol) was stirred at room temperature for 24 hours with potassium phthalimide (4.2 g, 22.1 mmol) and 45 mL DMF. Water was added and the mixture was extracted with methylene chloride. The combined organic extracts were washed with water (2×), 1N HCl and brine, dried ($MgSO_4$), filtered, and evaporated under reduced pressure to afford the title compound (7.9 g) as a white solid. $^1$H NMR (300 MHz, $CDCl_3$) δ4.83 (s, 2H), 6.95 (dd, 4H), 7.10 (t, 1H), 7.31 (t, 2H), 7.42 (d, 2H), 7.71 (m, 2H), 7.88 (m, 2H). MS ($DCl/NH_3$) m/e 347 (M+H+$NH_3)^+$.

EXAMPLE 64C

N-(4-Phenoxybenzyl)amine

The compound resulting from Example 64B (6.7 g, 20.4 mmol), hydrazine (2.1 mL, 35 wt. % in water) and 130 mL absolute ethanol were stirred at reflux for 4 hours. After cooling to room temperature, the solid present was filtered and air dried briefly. The solid was then partitioned between 1N KOH and methylene chloride. The layers were separated and the aqueous layer was extracted 2 more times with methylene chloride. The combined organic layers were washed with water and brine, dried ($MgSO_4$), filtered, and evaporated in vacuo to afford the title compound (2.7 g) as a clear oil. $^1$H NMR (300 MHz, $CDCl_3$) δ1.48 (s, 2H), 3.87 (s, 2H), 7.00 (m, 3H), 7.10 (t, 1H), 7.30 (m, 5H). MS ($DCl/NH_3$) m/e 200 $(M+H)^+$, 217 $(M+H+NH_3)^+$.

EXAMPLE 64D

(1α,2β,3β,4α)-1-[N-Propyl-N-(4-phenoxybenzyl)aminocarbonyl]-2-[N-(4-phenoxybenzyl)aminocarbonyl]cyclobutane-3,4-dicarboxylic acid The compound resulting from Example 62A was reacted with the compound resulting from Example 64C by the procedures described in Example 62B to give the title compound. $^1$H NMR ($CDCl_3$, 300 MHz) δ0.88 (m, 3H), 1.35 (m, 2H), 3.5–4.3 (m, 11H), 6.83–7.33 (m, 18H). MS m/e 635 $(M-H)^-$.

EXAMPLE 65

(1α,2β,3β,4α)-1,2-Di-(4-phenoxybenzyloxycarbonyl)-3,4-dicarboxylic acid

EXAMPLE 65A

4-Phenoxybenzyl alcohol

A solution of 4-phenoxybenzaldehyde (5.0 g, 25 mmol) in dry tetrahydrofuran (10 mL) at 0° C. was treated with borane (1M in tetrahydrofuran, 11.25 mL). After 45 minutes, the reaction was quenched with saturated $NH_4Cl$, diluted with ethyl acetate, and washed with 1M HCl, 5% $NaHCO_3$, and brine, and dried over $Na_2SO_4$, and concentrated under reduced pressure to give 4.7 g (92%) of 4-phenoxybenzyl alcohol.

EXAMPLE 65B

(1α,2β,3β,4α)-1,2-Di-(4-phenoxybenzyloxycarbonyl)-3,4-dicarboxylic acid

To a solution of the compound resulting from Example 65A (1.0 g, 5.0 mmol) in dry tetrahydrofuran (100 mL) at −78° C. under dry nitrogen was added n-butyl lithium (1.6M in hexane, 3.1 mL). After 15 minutes, a suspension of 1,2,3,4-cyclobutanetetracarboxylic dianhydride (0.49 g, 2.5 mmol) in tetrahydrofuran (5 mL) was added. The reaction was allowed to warm slowly to ambient temperature and stirred for 18 hours before quenching with saturated $NH_4Cl$. Solvents were removed under reduced pressure, and the residue was partitioned between ethyl acetate and 1M HCl. The organic layer was washed with 1M HCl and brine, dried over $Na_2SO_4$, and concentrated in vacuo. The residue obtained was purified by flash silica gel chromatography eluting with 94:5:1 chloroform-methanol-acetic acid to give 0.17 g (45%) of the title compound. $^1$H NMR ($CDCl_3$, 300 MHz) δ3.71 (m, 4H), 5.11 (s, 4H), 6.94–7.36 (m, 18H). MS m/e 595 $(M-H)^-$.

EXAMPLE 66

(1α,2β,3β,4α)-1,2-Di[N-propyl-N-(4-phenylaminophenyl)aminocarbonyl]cyclobutane-3,4-dicarboxylic acid

EXAMPLE 66A

N-Phenyl-N'-Propionyl-1,4-phenylenediamine

A stirred mixture of 1.84 g (10.0 mmol, 1 eq.) of commercial N-phenyl-1,4-phenylenediamine (a black solid) and 1.18 g (14.0 mmol, 1.4 eq.) of $NaHCO_3$ in 40 mL of $CH_2Cl_2$ was cooled to 0° C. To this suspension was added a solution of 0.96 mL (11.0 mmol, 1.1 eq.) of propionyl chloride in 10 mL of $CH_2Cl_2$ dropwise. The ice bath was removed and the mixture stirred for 1 hour and then poured into a seperatory funnel containing 50 mL of each $CH_2Cl_2$ and water. The organic phase was separated and extracted with 50 mL of saturated aqueous $NaHCO_3$, dried over $MgSO_4$, filtered and concentrated in vacuo. The residue was purified by flash column chromatography (100 g $SiO_2$, 1:1 ethyl acetate-hexanes) to give 1.79 g (75%) of product. $^1$H NMR (300 MHz, $CDCl_3$) δ7.41 (d, 2H), 7.21–7.43 (m, 2H), 7.14 9 (bs, 1H), 6.96–7.07 (m, 4H) 6.90 (t, 1H), 5.66 (bs, 1H), 2.38 (q, 2H), 1.25 (t, 3H). MS (DCl) m/e 258 $(M+NH_4)^+$, 241 $(M+H)^+$.

EXAMPLE 66B

N-Phenyl-N'-Propyl-4-phenylenediamine

A stirred solution of the compound resulting from Example 66A (1.5 g, 6.2 mmol, 1 eq.) in 10 mL of dry THF was cooled to 0° C. in an ice bath. To this solution was added 12.5 mL (12.5 mmol, 2 eq.) of a 1.0M solution of $LiAlH_4$ in THF dropwise. The ice bath was removed and the mixture was stirred at ambient temperature for 24 hours. The heterogeneous mixture was cooled to 0° C. and quenched by the careful addition of 0.5 mL of water in 5 mL of THF followed by the addition of 0.5 mL of 15% aqueous THF and then an additional 1.5 mL of water. The mixture was then vigorously stirred for 5 minutes. Hexanes (25 mL) and $Na_2SO_4$ (2 g) were added and vigorous stirring continued for 20 minutes. The mixture was filtered through celite and the pad washed well with ethyl acetate and the filtrate concentrated. The residue was purified by flash column chromatography on $SiO_2$ (50 g, 20% ethyl acetate/hexanes) to give 1.26 g (89%) of a brown oil. $^1H$ NMR (300 MHz ($CDCl_3$) δ7.18 (m (2H), 7.01 (m (2H), 6.82 (m (2H), 6.77 (m, 1H), 6.60 (m, 2H), 5.38 (bs, 1H), 3.53 (bs, 1H), 3.08 (t, 2H), 1.64 (hextet, 2H), 1.02 (t, 3H). MS (DCI) m/e 244 $(M+NH_4)^+$, 227 $(M+H)^+$.

EXAMPLE 66C (1α,2β,3β,4α)-1,2-Di[N-propyl-N-(4-phenylaminophenyl)aminocarbonyl]cyclobutane-3, 4-dicarboxylic acid To a suspension of 1,2,3,4-cyclobutanetetracarboxlic anhydride (0.48 g, 2.47 mmol, 1 eq) in acetonitrile at 0° C. was added a solution of the compound resulting from Example 66B (1.23 g, 5.43 mmol, 2.2 eq.) in acetonitrile. The cooling bath was removed and the mixture stirred overnight. The resulting suspension was concentrated and partitioned between 3N aqueous HCl and 3 portions of ethyl acetate. The combined organic phases were washed with brine, dried, filtered and concentrated in vacuo. The residue was purified by column chromatography on $SiO_2$ eluting with a $CHCl_3$—$CH_3OH$—HOAc solvent system to give 0.25 g (16%) of the 1,3-diacid and 0.77 g (48%) of the title compound. $^1H$ NMR (300 MHz (DMSO-$d_6$) δ12.35 (bs, 2H), 8.34 (s, 2H), 7.25 (t, 4H), 7.09 (m, 12H), 6.86 (t, 2H), 3.57 (m, 2H), 3.26–3.40 (m, 4H), 3.09 (m, 2H), 1.36 (m, 4H), 0.74 (t, 6H). MS (FAB$^+$) m/e 649 (MH). HRMS (FAB) calcd for $C_{38}H_{41}N_4O_6$ (M+H) 649.3026. Found: 649.3013. Anal calcd for $C_{38}H_{41}N_4O_6$: C, 70.35; H, 6.21; N, 8.63. Found: C, 69.05; H, 6.35; N, 8.05.

EXAMPLE 67

(1α,2β,3β,4α)-1,2-Di[N-propyl-N-(4-phenylaminobenzyl)aminocarbonyl]cyclobutane-3,4-dicarboxylic acid

EXAMPLE 67A

4-Phenylamino-N-propylbenzamide

To a stirred solution of 1.06 g (5.0 mmol, 1 eq.) of 4-phenylaminobenzoic acid (Portnaya, B. S., Turitsyna, N. F., Bobkova, T. P., and Levkeov, I. I., *Zhur. Obshchei. Khim.*, 30, 2693 (1960)), n-propylamine (0.82 mL, 10.0 mmol, 2 eq.), and 0.061 g (0.5 mmol, 0.1 eq.) of DMAP in THF at 0° C. was added 1.05 g (5.5 mmol, 1.1 eq.) of EDCl. The mixture was stirred overnight while the bath melted. The mixture was poured into 150 mL of ethyl acetate and washed with 50 mL each of water, 1N aqueous HCl, water and saturated aqueous $NaHCO_3$. The ethyl acetate layer was then dried over $Na_2SO_4$, filtered and concentrated in vacuo. The residue was purified by flash column chromatography (80 g $SiO_2$, 1:1 ethyl acetate-hexanes) to give 0.51 g (40%) of the title compound. $^1H$ NMR (300 MHz, $CDCl_3$) δ10.57 (bs, 2H), 7.21–7.41 (m, 9H), 3.96 (s, 2H), 2.75 (m, 2H), 1.64 (hextet, 2H), 0.92 (t, 3H). MS (DCI) m/e 255 $(M+H)^+$.

EXAMPLE 67B

N-Propyl-N-(4-phenylaminobenzyl) amine

To a stirred solution of the compound resulting from Example 67A 0.50 g (1.96 mmol, 1 eq.) in 10 mL of dry THF at 0° C. was added 3.9 mL (3.9 mmol, 2 eq.) of a 1.0M solution in THF of $LiAlH_4$. The ice bath was removed and stirring continued for 30 minutes. The solution was then heated at reflux for 20 hours and then cooled back to 0° C. The mixture was carefully quenched by the addition of 0.15 mL of water, 0.15 mL of 15% aqueous NaOH, and 0.45 mL of water and vigorously stirred for 10 minutes. Ethyl ether (20 mL) and $MgSO_4$ (2 g) were added and stirring continued for an additional 15 minutes. The heterogeneous mixture was filtered through a pad of $SiO_2$ and the pad was washed with 100 mL of ether and then 100 mL of 5% $CH_3OH$—$CHCl_3$. The filtrate was concentrated to give 0.398 g (85%) of a yellow oil that was used without further purification. $^1H$ NMR (300 MHz, $CDCl_3$) δ7.19–7.32 (m, 2H), 7.01–7.08 (m, 2H), 6.87–6.93 (m, 1H), 5.67 (bs, 1H), 3.72 (s, 2H), 2.61 (t, 2H), 1.53 (hextet, 2H), 1.39 (bs, 1H), 0.92 (t, 3H).

EXAMPLE 67C (1α,2β,3β,4α)-1,2-Di[N-propyl-N-(4-phenylaminobenzyl)aminocarbonyl]cyclobutane-3,4-dicarboxylic acid Following the procedures described in Example 66C, the compound resulting from Example 67B (0.378 g, 1.57 mmol, 2.2 eq.) and 1,2,3,4-cyclobutanetetracarboxylic dianhydride (0.140 g, 0.71 mmol, 1 eq.) were reacted to give 0.159 g (33%) of the title compound. $^1H$ NMR (300 MHz, $CDCl_3$) δ7.14–7.30 (m, 8H), 6.83–7.10 (m, 12H), 3.84–4.85 (m, 8H), 2.94–3.56 (m, 4H), 1.37–1.62 (m, 4H), 0.72–0.88 (m, 6H). MS (FAB$^+$) m/e 677 $(M+H)^+$. HRMS calcd for $C_{40}H_{45}N_4O_6$ (MH) 677.3339. Found: 677.3331. Anal calcd for $C_{40}H_{45}N_4O_6$: C, 70.99; H, 6.55; N, 8.28. Found: C, 69.46; H, 6.67; N, 7.89.

EXAMPLE 68

(1α,2β,3β,4α)-1,2-Di[N-propyl-N-(4-phenylthiobenzyl)aminocarbonyl]cyclobutane-3,4-dicarboxylic acid

EXAMPLE 68A

N-Propyl-N-(4-phenylthiobenzyl)amine

To a stirred solution of 2.14 g (10 mmol, 1.0 eq.) of 4-phenylthiobenzaldehyde (Portnaya, B. S., Turitsyna, N. F., Bobkova, T. P., and Levkeov, I. I., *Zhur. Obshchei. Khim.*, 30, 2693 (1960)) and 0.6 mL (10.0 mmol, 1.0 eq.) of acetic acid in 40 mL of $CH_3OH$ at 0° C. was added 1.6 mL (20.0 mmol, 2.0 eq.) of N-propylamine. After stirring 30 minutes at 0° C., $NaCNBH_3$ (0.69 g, 11 mmol, 1.1 eq.) was added and the mixture was stirred for an additional 2 hours whereupon an additional 0.69 g of $NaCNBH_3$ was added. The reaction mixture was stirred for an additional 14 hours and then poured into 200 mL of saturated $NaHCO_3$ and extracted with 3×50 mL of ethyl acetate. The combined organic phases were washed with brine, dried ($MgSO_4$), filtered and concentrated in vacuo. Purification of the residue by column chromatography (150 g $SiO_2$, 10% $CH_3OH$—$CHCl_3$, trace HOAc) gave 1.59 g (62%) of the title compound as a light yellow oil. Spectral analysis indicated the presence of ~1 eq. of AcOH. $^1H$ NMR (300 MHz, $CDCl_3$) δ7.54 (bs, 1H (AcOH)), 7.21–7.37 (m, 9H), 3.83 (s, 2H), 2.64 (t, 2H), 1.98 (s, 3H (AcOH)), 1.60 (hextet, 2H), 0.92 (t, 3H). MS (DCI) m/e 258 $(M+H)^+$.

EXAMPLE 68B (1α,2β,3β,4α)-1,2-Di[N-propyl-N-(4-phenylthiobenzyl)aminocarbonyl]cyclobutane-3,4-dicarboxylic acid Following the procedure described in Example 66C, the compound resulting from Example 68A (0.566 g, 2.2 mmol, 2.2 eq.) and 0.196 g (1.0 mmol, 1.0 eq.) of 1,2,3,4-cyclobutanetetracarboxylic dianhydride were reacted to give 0.284 g (40%) of the title compound as an off white foam. $^1$H NMR (300 MHz, CDCl$_3$) δ7.02–7.37 (m, 18H), 2.92–4.68 (m, 12H), 1.5 (m, 4H), 0.61 (m, 6H). MS (FAB$^+$) m/e 711 (M+H)$^+$. Anal calcd for C$_{40}$H$_{42}$N$_2$O$_6$S$_2$: C, 67.58; H, 5.95; N, 3.94. Found: C, 65.78; H, 5.86; N, 3.62.

EXAMPLE 69

(1α,2β,3β,4α)-1,2-Di[N-propyl-N-[4-phenoxymethylbenzyl]aminocarbonyl]cyclobutane-3,4-dicarboxylic acid

EXAMPLE 69A

Methyl-4-phenoxymethylbenzoate

To a stirred mixture of 5.72 g (25.0 mmol, 1.0 eq.) of methyl 4-bromomethylbenzoate (Aldrich) and 3.80 g (27.5 mmol, 1.1 eq.) of K$_2$CO$_3$ in 10 mL of DMF at ambient temperature was added a solution of 2.59 g (27.5 mmol, 1.1 eq.) of phenol in 10 mL of DMF dropwise and the mixture stirred overnight. The reaction mixture was poured into 100 mL of water and extracted with 3×100 mL portions of 25% CH$_2$Cl$_2$-hexanes. The combined organic phases were extracted with 3×100 mL portions of water, dried (MgSO$_4$), filtered and concentrated in vacuo. The solid residue was recrystallized from ~50 mL of hexanes to give 5.31 g (88%) of the title compound as a white, crystalline solid. $^1$H NMR (300 MHz, CDCl$_3$) δ8.05 (d, 2H), 7.51 (d, 2H), 7.26–7.33 (m, 2H), 6.95–7.02 (m, 3H), 5.13 (s, 2H), 3.92 (s, 3H). MS (DCI) m/e 260 (M+NH$_4$)$^+$.

EXAMPLE 69B

4-Phenoxymethylbenzoic acid

To a suspension of 2.42 g (10 mmol, 1.0 eq.) of the compound resulting from Example 69A in 20 mL of CH$_3$OH at 0° C. was added a solution of 0.97 g (15.0 mmol, 1.5 eq.) of KOH (87%) in 10 mL of CH$_3$OH. The suspension was allowed to reach ambient temperature overnight whereupon 5 mL of water was added. After stirring was continued for 3 additional hours, the mixture was poured into 200 mL of water and extracted with 3×50 mL of ethyl ether. The aqueous phase was acidified with 3N aqueous HCl and the resulting precipitate collected by filtration. Purification by recrystallization from acetone-CH$_3$OH gave 0.60 g (28%) of the title compound as a white crystalline solid. $^1$H NMR (300 MHz, CDCl$_3$) δ8.12 (d, 2H), 7.56 (d, 2H), 7.22–7.36 (m, 3H), 6.94–7.01 (m, 2H), 5.15 (s, 2H). MS (DCI) m/e 246 (M+NH$_4$)$^+$.

EXAMPLE 69C

N-Propyl-4-phenoxymethylbenzamide

To a stirred solution of 0.59 g (2.78 mmol, 1.0 eq.) of the compound resulting from Example 69B in 10 mL of THF at room temperature was added 0.495 g (3.05 mmol, 1.1 eq.) of 1,1'-carbonyldiimidazole. After the initial evolution of CO$_2$ was complete, the mixture was heated at reflux for 30 minutes and subsequently cooled to ambient temperature with a ice-water bath. The resulting nearly colorless solution was treated with 0.68 mL (8.33 mmol, 3.0 eq.) of N-propylamine and stirring was continued overnight. The reaction mixture was then partitioned between water (50 mL) and ethyl acetate (100 mL). The layers were separated and the aqueous phase was extracted with an additional 50 mL portion of ethyl acetate. The combined organic phases were then washed with 50 mL each of water, saturated NaHCO$_3$ and brine, dried (MgSO$_4$), filtered and concentrated in vacuo. The solid residue was purified by recrystallization form ethyl acetate to give 0.418 g (59%) of the title compound as a white solid. $^1$H NMR (300 MHz, CDCl$_3$) δ7.78 (m, 2H), 7.49 (d, 2H), 7.25–7.32 (m, 2H), 6.93–7.00 (m, 3H), 6.17 (bs, 1H), 5.11 (s, 2H), 3.42 (m, 2H), 1.62 (hextet, 2H), 0.98 (t, 3H). MS (DCl) m/e 287 (M+NH$_4$)$^+$.

EXAMPLE 69D

N-Propyl-N-(4-phenoxymethylbenzyl)amine hydrochloride

To a stirred solution of 0.400 g (1.58 mmol, 1.0 eq.) of the compound resulting from Example 69C in 2 mL of dry THF at 0° C. was added 3.16 mL (3.16 mmol, 2 eq.) of a 1.0M solution of LiAlH$_4$ in THF dropwise. The ice bath was removed and the mixture heated at reflux for 18 hours. After cooling to 0° C., the excess hydride was carefully quenched by the sequential addition of 0.12 mL of water in 1 mL of THF, 0.12 mL of 15% aqueous NaOH and 0.36 mL of water. The resulting suspension was vigorously stirred for 10 minutes followed by the addition of ether (15 mL) and MgSO$_4$ (2 g) and the vigorous stirring continued for an additional 15 minutes. The reaction mixture was filtered through a pad of SiO$_2$ (pre-wetted with ether) and the pad was washed well with ethyl acetate. The filtrate was concentrated to dryness and the residue dissolved in THF and treated with a slight excess of aqueous HCl. The solution was concentrated to dryness again (using toluene to remove the excess water). The solid residue was purified by recrystallization from methanol-acetone to give 0.314 g (72%) of the title compound as a white crystalline solid. $^1$H NMR (300 MHz, CD$_3$OD) δ7.52 (q 4H), 7.25 (m, 2H), 6.89–7.00 (m, 3H), 5.13 (s, 2H), 4.20 (s, 2H), 3.01 (m, 2H), 1.72 (m, 2H), 1.02 (t, 3H).

EXAMPLE 69E (1α,2β,3β,4α)-1,2-Di[N-propyl-N-[4-phenoxymethylbenzyl]aminocarbonyl]cyclobutane-3,4-dicarboxylic acid To a stirred suspension of 0.098 g (0.5 mmol, 1.0 eq.) of 1,2,3,4-cyclobutanetetracarboxylic acid dianhydride in 3 mL of acetonitrile at 0° C. was added 0.15 mL (1.05 mmol, 2.1 eq.) of Et$_3$N. After 15 minutes the compound resulting from Example 69D (0.276 g, 1.0 mmol, 2.0 eq.) was added and the mixture allowed to reach room temperature and stirring continued for 66 hours. The reaction mixture was poured into 20 mL of 4N aqueous H$_2$SO$_4$ and extracted with 3×20 mL of ethyl acetate. The combined organic phases were then washed with water and brine, dried (MgSO$_4$), filtered and concentrated in vacuo. The residue was purified by column chromatography on SiO$_2$ (35 g) eluting with 94:5:1 CHCl$_3$—CH$_3$OH-acetic acid to give the 1,3-diacid (0.100 g, 28%) followed by the title compound (0.093 g, 26%) as a white foam. $^1$H NMR (CDCl$_3$) δ7.11–7.40 (m, 12H), 6.88–6.99 (m, 6H), 4.99 (m, 4H), 4.31–4.70 (m, 4H), 3.87–4.18 (m, 4H), 2.59–3.63 (m, 4H), 1.49 (m, 4H), 0.82 (m, 6H). HRMS (FAB) calcd for C$_{42}$H$_{46}$N$_2$O$_8$: 707.3332. Found: 707.3323. Anal calcd for C$_{42}$H$_{46}$N$_2$O$_8$: C, 71.37; H, 6.56; N, 3.96. Found: C, 70.70; H, 6.56; N, 3.85.

EXAMPLE 70

(1α,2β,3β,4α)-1,2-Di[N-propyl-N-(4-phenoxybenzyl)aminocarbonyl]-4-hydroxymethyl-cyclobutane-3-carboxylic acid

EXAMPLE 70A

Methyl (1α,2β,3β,4α)-1,2-Di[N-propyl-N-[4-phenoxybenzyl]aminocarbonyl]-4-hydroxymethyl-cyclobutane-3-carboxylate To a stirred solution of (1α,2β,3β,4α)-1,2-di[N-propyl-N-[4-phenoxybenzyl]aminocarbonyl]cyclobutane-3,4-dicarboxylic acid mono methyl ester, the compound resulting from Example 95, (0.562 g, 0.81 mmol, 1.0 eq.) in 12 mL of dry THF at −20° C. was added 0.098 mL (0.89 mmol, 1.1 eq.) of N-methylmorpholine followed by 0.115 mL (0.89 mmol, 1.1 eq.) of isobutylchloroformate. After stirring for 30 minutes, a cold (−20° C.) suspension of 0.184 g (4.86 mmol, 3 eq.) of $NaBH_4$ in 1 mL of $CH_3OH$ was carefully added (a vigorous reaction occurs) and the mixture stirred for 30 minutes more. The reaction was quenched by the careful addition of 2 mL of 3N aqueous HCl and the poured into 50 mL of cold 3N aqueous HCl and extracted with 3×50 mL of ethyl acetate. The combined organic extracts were washed with 50 mL of saturated aqueous $NaHCO_3$, dried ($MgSO_4$), filtered and concentrated in vacuo. The residue was purified by flash column chromatography on $SiO_2$ (40 g, 1:1 ethyl acetate-hexanes) to give 0.507 g (92%) of the title compound as a colorless foam. $^1H$ NMR ($CDCl_3$) δ6.84–7.35 (m, 18H, 2.68–5.02 (m, 18H), 1.41–1.72 (m, 4H), 0.73–0.97 (m, 6H). MS (DCI) m/e 679 (M+H)$^+$.

EXAMPLE 70B (1α,2β,3β,4α)-1,2-Di[N-propyl-N-(4-phenoxybenzyl)aminocarbonyl]-4-hydroxymethyl-cyclobutane- 3-carboxylic acid To a stirred solution of the compound resulting from Example 70A (68 mg, 0.1 mmol, 1.0 eq.) in 1 mL of 3:1 THF-water at 0° C. was added 8 mg (0.2 mmol, 2.0 eq.) of $LiOH \cdot H_2O$ and stirring was continued at 0° C. for 4 hours and at room temperature for 30 minutes. The reaction was then quenched by the addition of 2 mL of 3N aqueous HCl and then concentrated to dryness. Purification of the residue by column chromatography on $SiO_2$ (9 g, 94:4:1 $CHCl_3$—$CH_3OH$—HOAc) gave the title compound 0.047 g (71%) as a white foam. $^1H$ NMR (DMSO d$_6$) δ12.26 (bs, 1H), 7.38, m, 3H), 7.17–7.31 (m, 4H), 7.12 (m, 1H), 7.00 (m, 4H), 6.91 (m, 2H), 4.58–4.84 (m, 3H), 4.09–4.32 (m, 3H), 3.78–4.07 (m, 3H), 3.17–3.60 (m, 6H), 3.12 (m, 1H), 2.98 (m, 1H), 2.86 (m, 1H), 2.69 (m, 1H), 1.31–1.62 (m, 4H), 0.70–0.89 (m, 6H). MS (FAB$^+$) m/e 665 (M+H), 687 (M+Na), 703 (M+K). HRMS calcd for $C_{40}H_{45}N_2O_7$ (MH) 665.3227. Found: 665.3217. Anal calcd for $C_{40}H_{45}N_2O_7$: C, 72.27; H, 6.67; N, 4.21. Found: C, 71.45; H, 6.79; N, 4.21.

EXAMPLE 71

(1α,2β,3β,4α)-1,2-Di[N-propyl-N-[4-phenoxybenzyl]aminocarbonyl]-4-[(hydroxyimino) methyl]-cyclobutane-3-carboxylic acid

EXAMPLE 71A

Methyl (1α,2β,3β,4α)-1,2-Di[N-propyl-N-(4-phenoxybenzyl)aminocarbonyl]-4-carboxaldehyde-cyclobutane-3-carboxylate To a stirred solution of 0.339 g (0.5 mmol, 1.0 eq.) of the compound resulting from Example 70B in 5 mL of 10% acetonitrile-$CH_2Cl_2$ at room temperature was added 0.088 g (0.75 mmol, 1.5 eq.) of N-methylmorpholine-N-oxide followed by 0.50 g of powdered, activated 4 Å molecular sieves. After stirring 15 minutes at room temperature, TPAP (0.009 g, 0.025 mmol, 0.05 eq) was added and the resulting black mixture was stirred for an additional 30 minutes. The reaction mixture was treated with ~1 g of celite and then diluted with 5 mL of ether. After 10 minutes further stirring, the mixture was filtered through a pad of $SiO_2$ (pre-wetted with ether). The pad was washed well with ether (~200 mL) and the filtrate concentrated. The green residue was purified by column chromatography on $SiO_2$ (25 g, 1:1 ethyl acetate-hexanes) to give 0.269 g (80%) of the title compound as a thick syrup. $^1H$ NMR ($CDCl_3$) δ9.69–9.76 (m, 1H), 6.89–7.38 (m, 18H), 4.09–4.87 (m, 5H), 3.48–4.03 (m, 6H), 2.41–3.47 (m, 4H), 1.42–1.67) (m, 4H), 0.76–0.98 (m, 6H). MS (DCI) m/e 677 (M+H)$^+$.

EXAMPLE 71B

Methyl (1α,2β,3β,4α)-1,2-Di[N-propyl-N-(4-phenoxybenzyl)aminocarbonyl]-4-[(hydroxyimino) methyl]-cyclobutane-3-carboxylate To a stirred solution of 0.054 g (0.78 mmol, 1.5 eq.) of $NH_2OH \cdot HCl$ in 1 mL of $CH_3OH$ at room temperature was added 0.064 g (0.78 mmol, 1.5 eq.) of NaOAc. The resulting solution was treated with a solution of the compound resulting from Example 71A (355 mg, 0.52 mmol, 1.0 eq.) in 2 mL of $CH_3OH$ and stirring was continued for 1 hour. The mixture was partitioned between ethyl acetate (20 mL) and water (20 mL) and the layers were separated. The aqueous layer was extracted with 2 additional 20 mL portions of ethyl acetate and the combined organic phases were dried ($Na_2SO_4$), filtered and concentrated in vacuo. The residue was purified by column chromatography on $SiO_2$ (30 g, 40% ethyl acetate-hexanes) to give 0.273 g (76%) of the title compound (as a mixture of cis and trans oximes) as a colorless syrup.

EXAMPLE 71C (1α,2β,3β,4α)-1,2-Di[N-propyl-N-(4-phenoxybenzyl)aminocarbonyl]-4-[(hydroxyimino) methyl]-cyclobutane-3-carboxylic acid To a solution of 0.035 g (0.05 mmol, 1.0 eq.) of the compound resulting from Example 71B in 0.5 mL of THF at 0° C. was added a solution of 0.011 g (0.25 mmol, 5 eq.) of $LiOH \cdot H_2O$ in 0.2 mL of water. The resulting cloudy mixture was stirred for 3 hours and quenched by the addition of 1 mL of 0.5M $H_3PO_4$. The mixture was extracted with 3×2 mL of ethyl acetate and the combined organic phases were washed with 5 mL of brine, dried ($MgSO_4$), filtered and concentrated in vacuo. The residue was purified by column chromatography on $SiO_2$ (10 g, 94:5:1 $CHCl_3$—$CH_3OH$—AcOH) to give a colorless oil. This mixture was dissolved in 2 mL of acetonitrile and water was added until cloudy. The mixture was then lyophilized to give 0.024 g (70%) of the title compound as a fluffy, white lyophilate. $^1H$ NMR (DMSO d$_6$) δ12.46 (bs, 1H), 10.76–10 90 (m, 1H), 7.38 (m, 4H), 7.09–7.30 (m, 6H), 6.86–7.0 (m, 8H), 4.55–4.88 (m, 2H), 3.87–4.29 (m, 4H), 3.16–3.67 (m, 5H), 2.94 (m, 1H), 2.71 (m, 1H), 1.52–1.61 (m, 4H), 0.73–0.86 (m, 6H. MS (FAB$^+$) m/e 678 (M+H)$^+$. HRMS (FAB) calcd for $C_{40}H_{44}N_3O_7$ (MH) 678.3179. Found: 678.3190. Anal calc for $C_{40}H_{44}N_3O_7$: C, 70.88; H, 6.39; N, 6.20. Found: C, 70.80; H, 6.32; N, 6.03.

EXAMPLE 72

(1α,2β,3β,4α)-1,2-Di[N-propyl-N-(4-phenoxybenzyl)aminocarbonyl]-4-tetrazolyl-cyclobutane-3-carboxylic acid

EXAMPLE 72A

Methyl (1α,2β,3β,4α)-1,2-Di[N-propyl-N-(4-phenoxybenzyl)aminocarbonyl]-4-cyano-cyclobutane-3-carboxylate To a stirred solution of 0.173 g (0.25 mmol, 1.0 eq.) of the compound resulting from Example 71C in 2 mL of dry acetonitrile at 0° C. was added 0.11 mL (0.75 mmol, 3.0 eq.) of Et$_3$N followed by the dropwise addition of 0.040 mL (0.28 mmol, 1.1 eq.) of trifluoroacetic anhydride. The cooling bath was removed and the mixture stirred for 3 hours and poured into 10 mL of saturated aqueous NaHCO$_3$. The aqueous mixture was extracted with 3×10 mL of ethyl acetate and the combined organic phases were dried (MgSO$_4$), filtered and concentrated in vacuo. Flash column chromatography of the residue on SiO$_2$ (40 g, 40% ethyl acetate-hexanes) gave 0.116 g (69%) of the title compound as a cloudy syrup. $^1$H NMR (CDCl$_3$) δ6.91–7.43 (m, 18H), 3.93–4.94 (m, 6H), 3.56–3.90 (m, 5H), 2.93–3.55 (m, 4H), 1.43–1.72 (m, 4H), 0.80–0.97 (m, 6H). MS (DCI) m/e 691 (M+18)$^+$, 674 (M+H)$^+$.

EXAMPLE 72B

Methyl (1α,2β, 3β,4α)-1,2-Di[N-propyl-N-(4-phenoxybenzyl)aminocarbonyl]-4-tetrazolyl-cyclobutane-3-carboxylate A mixture of the compound resulting from Example 72A (0.116 g, 0.17 mmol, 1 eq.), NaN$_3$ (0.034 g, 0.52 mmol, 3.0 eq.) and Et$_3$N.HCl (0.072 g, 0.52 mmol, 3.0 eq.) in 1 mL of DMF were heated to 60° C. for 14 hours. The bath temperature was increased to 100° C. for 4 hours whereupon an additional 3.0 eq. each of NaN$_3$ ad Et$_3$N.HCl were added. After an additional 70 hours at 100° C., the mixture was cooled to room temperature and partitioned between water (20 mL) and ethyl acetate (20 mL). The aqueous phase was extracted with 2×10 mL of ethyl acetate and the combined organic phases were washed with 3×10 mL of water and brine, dried (Na$_2$SO$_4$), filtered and concentrated in vacuo to give 0.115 g of the title compound which was used without purification. Analysis of this crude material showed by $^1$H NMR showed that it contained ~2 eq. of DMF.

EXAMPLE 72C (1α,2β,3β,4α)-1,2-Di[N-propyl-N-(4-phenoxybenzyl)aminocarbonyl]-4-tetrazolyl-cyclobutane-3-carboxylic acid To a stirred solution of 0.030 g (0.042 mmol, 1.0 eq.) of the compound resulting from Example 72B in 0.75 mL of THF at 0° C. was added 0.25 mL of H$_2$O followed by 0.011 g (0.25 mmol, 6.0 eq.) of LiOH.H$_2$O. After stirring 2 hours at 0° C. and 2 hours at room temperature, the mixture was poured into 10 mL of 3N aqueous HCl and extracted with 3×10 mL of ethyl acetate. The combined organic extracts were dried (MgSO$_4$), filtered and concentrated in vacuo. The residue was purified by column chromatography on SiO$_2$ (20 g, 94:5:1 CHCl$_3$—CH$_3$OH—AcOH) to give a thick oil. This oil was dissolved in acetonitrile and treated with water until turbid and then freeze-dried to give 0.021 g (70%) of the title compound as a fluffy, white lyophilate. $^1$H NMR (DMSO d$_6$) δ6.56–7.41 (m, 18H), 4.62–4.83 (m, 3H), 4.25–4.49 (m, 4H), 3.73–0.17 (m, 4H), 3.06 (m, 1H), 2.76 (m, 1H), 2.41 (m, 1H), 1.50 (m, 4H), 0.44–0.92 m, 6H). MS (FAB$^+$) m/e 703 (M+H)$^+$, (FAB$^-$) m/e 701 (M–H)$^+$. HRMS calcd for C$_{40}$H$_{43}$N$_6$O$_6$: 703.3244. Found: 703.3229. Anal calcd for C$_{40}$H$_{43}$N$_6$O$_6$: C, 68.36; H, 6.02; N, 11.96. Found: C, 65.94; H, 6.11; N, 11.14.

EXAMPLE 73

(1α,2β,3β,4α)-1,2-Di[N-propyl-N-(4-phenoxybenzyl)aminocarbonyl-4-tetrazolylmethyl-cyclobutane-3-carboxylic acid

EXAMPLE 73A

Methyl (1α,2β,3β,4α)-1,2-Di[N-propyl-N-(4-phenoxybenzyl)aminocarbonyl]-4-cyanomethyl-cyclobutane-3-carboxylate To a solution of the compound resulting from Example 70A (0.260 g, 0.38 mmol, 1.0 eq.) in 4 mL of 1:1 CH$_2$Cl$_2$-2,6-lutidine at –10° C. was added 0.060 mL (0.76 mmol, 2.0 eq.) of methanesulfonyl chloride. The mixture was then placed in a refrigerator overnight. The resulting yellow solution was diluted with CH$_2$Cl$_2$ and extracted with 3N aqueous HCl, dried (MgSO$_4$), filtered and concentrated in vacuo to give 0.284 g (99%) of the mesylate that was used directly. The mesylate (0.284 g, 0.38 mmol, 1.0 eq.) was dissolved in 1.5 mL of DMSO and treated with 0.073 g (1.12 mmol, 3.0 eq.) of KCN. This suspension was stirred vigorously overnight at room temperature and then at 50°–60° C. for 2 hours. This mixture was cooled to room temperature and poured into 25 mL of water and extracted with 3×10 mL of ethyl acetate. The combined organic phases were then extracted with 2×20 mL of water and 2×10 mL of brine, dried (Na$_2$SO$_4$), filtered and concentrated in vacuo. The residue was purified by column chromatography on SiO$_2$ (20 g, 40% ethyl acetate-hexanes) to give 0.178 g (68%) of the title compound as a thick oil. $^1$H NMR (CDCl$_3$) δ6.88–7.37 (m, 18H), 4.55–4.87 (m, 2H), 3.91–4.46, (m, 4H), 2.91–3.83 (m, 9H), 2.41–2.69 (m, 2H), 1.40–1.69 (m, 4H), 0.78–0.97 (m, 6H). MS (DCI) m/e 688 (M+H)$^+$.

EXAMPLE 73B (1α,2β,3β,4α)-1,2-Di[N-propyl-N-(4-phenoxybenzyl)aminocarbonyl-4-tetrazolylmethyl-cyclobutane-3-carboxylic acid To a solution of the compound resulting from Example 73A (0.170 g, 0.25 mmol, 1.0 eq.) in 1.5 mL of DMF was added 0.081 g (1.15 mmol, 5.0 eq.) of NaN$_3$ followed by 0.172 g (1.25 mmol, 5.0 eq.) of Et$_3$N.HCl. The resulting suspension was heated at 100° C. overnight whereupon an additional 5 eq. each of NaN$_3$ and Et$_3$N.HCl were added. After further heating at 100° C. for 24 hours, the mixture was cooled to room temperature and poured into 20 mL of dilute H$_2$SO$_4$ and extracted with 3×20 mL of ethyl acetate. The combined organic phases were extracted with 2×20 mL of water and 1×10 mL of brine, dried (MgSO$_4$), filtered and concentrated in vacuo to give 0.166 g (91%) of the tetrazole as a yellow syrup that was used directly. The crude tetrazole was dissolved in 1 mL of THF and cooled to 0° C. To this solution was added a solution of 0.034 g (0.88 mmol, 4 eq.) of LiOH.H$_2$O in 0.3 mL of water. Methanol (20 drops) was added to obtain a homogeneous solution and the mixture stirred overnight while the bath was allowed to melt. The reaction mixture was poured into 20 mL of 4N $H_2SO_4$ and extracted with 3×10 mL of ethyl acetate and the combined organic phases were washed with water and brine, dried ($MgSO_4$), filtered and concentrated in vacuo. The residue was purified by column chromatography on $SiO_2$ (30 g, 94:5:1 $CHCl_3$—$CH_3OH$—AcOH) to give an oil. The product was then lyophilized ($CH_3CN/H_2O$) to give 0.064 g (40%) of the title compound as a fluffy, off white solid. $^1H$ NMR ($CDCl_3$) δ6.76–7.38 (m, 18H), 4.20–4.75, (m, 5H), 2.91–4.09 (m, 9H), 1.36–1.64 (m, 4H), 0.65–0.92 (m, 4H). MS ($FAB^+$) m/e 717 $(M+H)^+$, ($FAB^-$) 715 $(M-H)^+$. Anal calcd for $C_{41}H_{44}N_6O_6$: C, 68.70; H, 6.19; N, 11.72. Found: C, 66.74; H, 6.18; N, 11.21.

EXAMPLE 74

(1α,2β,3β,4α)-1,2-Di[N-propyl-N-(4-phenoxybenzyl)aminocarbonyl]-4-(carboxycarbonylamino)cyclobutane-3-carboxylic acid

EXAMPLE 74A

Methyl (1α,2β,3β,4α)-1,2-Di[N-propyl-N-(4-phenoxybenzyl)aminocarbonyl]-4-(benzyloxycarbonyl)amino-cyclobutane-3-carboxylate To a stirred solution of 0.346 g (0.5 mmol, 1.0 eq.) of the compound resulting from Example 95, (1α,2β,3β,4α)-1,2-di[N-propyl-N-(4-phenoxybenzyl)aminocarbonyl] cyclobutane-3,4-dicarboxylic acid mono methyl ester, in 5 mL of dry toluene at room temperature was added 0.077 mL (0.55 mmol, 1.1 eq.) of triethylamine followed by 0.13 mL (0.60 mmol, 1.2 eq.) of diphenylphosphorylazide. The yellow solution was heated at 65–70° C. for 3 hours. To this solution was added 0.52 mL (5 mmol, 10 eq.) of benzyl alcohol and the oil bath temperature was increased to 90° C. and stirring continued at this temperature overnight. After cooling to room temperature, the mixture was diluted with 50 mL of $CH_2Cl_2$ and extracted with 3N aqueous HCl and saturated $NaHCO_3$, dried ($MgSO_4$), filtered, and concentrated in vacuo. The residue was purified by column chromatography on $SiO_2$ (40 g, 5–10% ethyl acetate-$CH_2Cl_2$) to give 0.235 g (59%) of the title compound as a thick syrup. $^1H$ NMR ($CDCl_3$) δ6.81–7.39 (m, 23H), 5.62 (m, 1H), 4.94–5.18 (m, 3H), 4.05–4.87 (m, 5H), 2.86–4.05 (m, 9H), 1.34–1.65 (m, 4H), 0.76–0.94 (m, 6H). MS (DCI) m/e 798 $(M)^+$.

EXAMPLE 74B

Methyl (1α,2β,3β,4α)-1,2-Di[N-propyl-N-(4-phenoxybenzyl)aminocarbonyl]-4-amino-cyclobutane-3-carboxylate A stirred mixture of 0.233 g (0.29 mmol) of the compound resulting from Example 74A and 0.050 g of 10% Pd/C in 5 mL of ethyl acetate were hydrogenated 8 hours. The mixture was filtered through celite and the celite pad washed well with ethyl acetate. The filtrate was concentrated to give 0.191 g of the title compound as a light yellow oil. $^1H$ NMR ($CDCl_3$) δ6.89–7.38 (m, 18H), 4.46–4.90 (m, 2H), 4.24–4.42 (m, 3H), 3.78–4.07 (m, 2H), 3.50–3.73 (m, 3H), 2.91–3.41 (m, 5H), 1.39–1.68 (m, 4H), 1.39 (bs, 2H), 0.79–0.98 (m, 6H). MS (DCI) m/e 664 $(M+H)^+$.

EXAMPLE 74C

Methyl (1α,2β,3β,4α)-1,2-Di[N-propyl-N-(4-phenoxybenzyl)aminocarbonyl]-4-(ethoxylcarbonylcarbonyl)amino-cyclobutane-3-carboxylate To a solution of 0.033 g (0.05 mmol, 1.0 eq.) of the compound resulting from Example 74B in 1 mL of $CH_2Cl_2$ at −10° C. was added 0.012 mL (0.10 mmol, 2 eq.) of 2,6-lutidine followed by 0.009 mL (0.075 mmol, 1.5 eq.) of ethyl oxalyl chloride. After stirring for 30 minutes at this temperature, the mixture was diluted with 10 mL of $CH_2Cl_2$ and extracted with 10 mL of saturated $NaHCO_3$, dried ($MgSO_4$), filtered and concentrated in vacuo. The residue was purified by column chromatography on $SiO_2$ (15 g, 1:1 ethyl acetate-hexanes) to give 0.029 g (76%) of the title compound as a light yellow syrup. $^1H$ NMR ($CDCl_3$) δ7.84–8.04 (m, 1H), 6.83–7.37 (m, 18H), 5.16–5.37 (m, 1H), 4.48–4.94 (m, 2H), 3.92–4.39 (m, 6H), 3.54–3.76 (m, 4H), 2.87–3.46 (m, 4H), 1.43–1.64 (m, 4H), 1.24–1.43 (m, 3H), 0.78–0.93 (m, 6H). MS (CCI) m/e 764 $(M+H)^+$.

EXAMPLE 74D (1α,2β,3β,4α)-1,2-Di[N-propyl-N-(4-phenoxybenzyl)aminocarbonyl]-4-(carboxycarbonylamino)cyclobutane-3-carboxylic acid To a stirred solution of 0.027 g (0.035 mmol, 1.0 eq.) of the compound resulting from Example 74C in 1 mL of THF at 0° C. was added 0.007 g (0.18 mmol, 5 eq.) of $LiOH.H_2O$ in 0.3 mL of water. The cold bath was removed and the mixture was stirred for 2 hours and poured into 10 mL of 3N aqueous HCl. The aqueous phase was extracted with 3×15 mL of ethyl acetate and the combined organic phases were extracted with brine, dried ($MgSO_4$), filtered and concentrated in vacuo to give an oil. This material was then lyophilized ($CH_3CN/H_2O$) to give 0.026 g (100%) of the title compound as a fluffy white solid. $^1H$ NMR ($CDCl_3$) δ12.45 (bs, 2H), 6.81–7.40 (m, 18H), 4.58–5.00 (m, 3H), 3.57–4.31 (m, 9H), 2.58–3.01 (m, 3H), 1.32–1.56 (m, 4H), 0.65–0.84 (m, 6H). MS ($FAB^+$) m/e 744 (M+Na), 722 (M+H)+; ($FAB^-$) m/e 720 $(M-H)^+$. HRMS calcd for $C_{41}H_{44}N_3O_9$ (MH): 722.3078. Found: 722.3081.

EXAMPLE 75

(1α,2β,3β,4α)-1,2-Di[N-propyl-N-(4-phenoxybenzyl)aminocarbonyl]-4-(3-carboxypropionylamino)cyclobutane-3-carboxylic acid

EXAMPLE 75A

Methyl (1α,2β,3β,4α)-1,2-Di[N-propyl-N-(4-phenoxybenzyl)aminocarbonyl]-4-(3-carboxypropionylamino)cyclobutane-3-carboxylate To a stirred solution of 0.024 g (0.036 mmol, 1 eq.) of the compound resulting from Example 74B in 1 mL of dry $CH_3CN$ at 0° C. was added 0.010 mL (0.072 mmol, 2 eq.) of $Et_3N$ followed by 0.004 g (0.038 mmol, 1.1 eq) of succinic anhydride. The mixture was then stirred overnight (during which time the ice bath melted) and partitioned between 2 mL of 3N aqueous HCl and 3×2 mL of ethyl acetate. The combined organic phases were washed with 2 mL each water and brine, dried ($Na_2SO_4$), filtered and concentrated to give 0.028 g (100%) of the title compound as a colorless syrup. $^1H$ NMR ($CDCl_3$) δ6.88–7.39 (m, 18H), 5.06–5.29 (m, 1H), 3.92–4.88 (m, 7H), 3.41–3.73 (m, 5H), 2.84–3.32 (m, 4H), 2.04–2.74 (m, 6H), 1.39–1.65 (m, 4H), 1.47 (m, 1H), 0.78–0.97 (m, 6H). MS (DCI) m/e 764 $(M+H)^+$.

EXAMPLE 75B (1α,2β,3β,4α)-1,2-Di[N-propyl-N-(4-phenoxybenzyl)aminocarbonyl]-4-(3-carboxypropionylamino)cyclobutane-3-carboxylic acid To a solution of 0.026 g (0.034 mmol, 1 eq.) of the compound resulting from Example 75A in 1 mL of THF at 0° C. was added a solution of 7 mg (0.17 mmol, 5 eq) of LiOH.H$_2$O in 0.3 mL of water. The ice bath was removed and the mixture stirred for 6 hours and poured into 10 mL of 3N aqueous HCl and extracted with 3×10 mL of ethyl acetate. The combined organic phases were washed with 10 mL each of water and brine, dried (MgSO$_4$), filtered and concentrated to give a nearly colorless syrup. This material was lyophilized (CH$_3$CN—H$_2$O) to give 0.021 g (84%) of the title compound as a fluffy, off white solid. $^1$H NMR (CDCl$_3$) δ6.87–7.37 (m, 18H), 5.02–5.25 (m, 1H), 4.13–4.74 (m, 5H), 3.51–4.09 (m, 5H), 2.92–3.35 (m, 3H), 2.23–2.79 (m, 4H), 1.40–1.62 (m, 4H), 1.27 (bs, 1H), 0.76–0.92 (m, 6H). MS (FAB$^+$) m/e 750 (M+H)$^+$. HRMS calcd for C$_{43}$H$_{48}$N$_3$O$_9$ (MH): 750.3391. Found: 750.3375.

EXAMPLE 76

(1α,2β,3β,4α)-1,2-Di[N-propyl-N-(4-phenoxybenzyl)aminocarbonyl-4-(E-2-carboxyethenyl-cyclobutane-3-carboxylic acid

EXAMPLE 76A

Methyl (1α,2β,3β,4α)-1,2-Di[N-propyl-N-(4-phenoxybenzyl)aminocarbonyl-4-(E-2-carbomethoxyethenyl-cyclobutane-3-carboxylate To a stirred solution of 0.068 g (0.10 mmol, 1.0 eq.) of the compound resulting from Example 71A in 1 mL of CH$_2$Cl$_2$ at 0° C. was added 0.040 g (0.12 mmol, 1.2 eq.) of methyl triphenylphoranylidene-acetate. The resulting solution was stirred for 3 hours and then applied directly to a column of SiO$_2$ (15 g) and eluted with 1:1 ethyl acetate-hexanes to give 0.062 g of the title compound as a thick syrup. Analysis of the $^1$H NMR spectrum indicated a >95:5 ratio of olefin isomers. $^1$H NMR (DMSO-d$_6$) δ6.77–7.42 (m, 18H), 5.96–6.07 (m, 1H), 4.56–4.99 (m, 2H), 4.18–4.24 (m, 2H), 3.68–4.07 (m, 3H), 3.17–4.66 (m, 9H), 2.92–3.05 (m, 1H), 2.53–2.86 (m, 2H), 1.25–1.60 (m, 4H), 0.69–0.88 (m, 6H). MS (DCI) m/e 733 (M+H)$^+$.

EXAMPLE 76B (1α,2β,3β,4α)-1,2-Di[N-propyl-N-(4-phenoxybenzyl)aminocarbonyl-4-(E-2-carboxyethenyl-cyclobutane-3-carboxylic acid To a stirred solution of the compound resulting from Example 76A (25 mg, 0.034 mmol, 1.0 eq.) in 1 mL of THF at 0° C. was added 9 mg (0.204 mmol, 6 eq.) of LiOH.H$_2$O in 0.3 mL of water. After stirring for 1 hour at 0° C. and 2 hours at room temperature, the mixture was poured into 10 mL of 3N aqueous HCl and extracted with 2×10 mL of ethyl acetate. The organic phases were then washed with brine, dried (MgSO$_4$), filtered and concentrated to give 0.025 g of product. This material was then lyophilized (CH$_3$CN—H$_2$O) to give 0.019 g (79%) of the title compound as a white lyophilate. $^1$H NMR (DMSO-d$_6$) δ6.80–7.41 (m, 18H), 6.86–6.95 (m, 1H), 4.10–5.02 (m, 5H), 3.16–4.08 (m, 9H), 2.44–2.98 (m, 3H), 1.30–1.44 (m, 4H), 0.66–0.91 (m, 6H). MS (FAB$^+$) m/e 727 (M+Na), 705 (M+H)$^+$.

EXAMPLE 77

(1α,2β,3β,4α)-1,2-Di[N-propyl-N-(4-phenoxybenzyl)aminocarbonyl-4-(2-carboxyethyl)-cyclobutane-3-carboxylic acid

EXAMPLE 77A

Methyl (1α,2β,3β,4α)-1,2-Di[N-propyl-N-(4-phenoxybenzyl)aminocarbonyl-4-(2-carboxyethyl)-cyclobutane-3-carboxylate A stirred mixture of the compound resulting from Example 76A (32 mg, 0.044 mmol, 1.0 eq.), triethylsilane (0.011 mL, 0.066 mmol, 1.5 eq.) and Wilkinson's catalyst (4 mg, 0.004 mmol, 0.01 eq.) in 1 mL of dry toluene was heated to 80°–90° C. After 1 hour, additional triethylsilane (0.050 mL) and Wilkinson's (4 mg) were added and heating continued for an additional 2 hours. After the mixture had cooled to room temperature, 2 mL of CH$_3$OH was added and the mixture stirred for 15 minutes and filtered through a short plug of SiO$_2$. The filtrate was concentrated and purified by column chromatography on SiO$_2$ (10 g, 1:1 ethyl acetate-hexanes) to give 0.029 g (91%) of the title compound as a thick oil. $^1$H NMR (CDCl$_3$) δ6.88–7.41 (m, 18H), 4.48–5.04 (m, 3H), 3.93–4.38 (m, 4H), 3.49–3.75 (m, 6H), 2.76–3.33 (m, 5H), 2.12–2.35 (m, 2H), 1.41–1.88 (m, 6H), 0.77–1.02 (m, 6H). MS (DCI) m/e 735 (M)$^+$.

EXAMPLE 77B (1α,2β,3β,4α)-1,2-Di[N-propyl-N-(4-phenoxybenzyl)aminocarbonyl-4-(2-carboxyethyl)-cyclobutane-3-carboxylic acid To a stirred solution of the compound resulting from Example 77A (27 mg, 0.037 mmol, 1.0 eq.) in 1 mL of THF at 0° C. was added a solution of 8 mg (0.184 mmol, 5 eq.) of LiOH.H$_2$O in 0.3 mL of water. The cooling bath was removed and the mixture stirred for 6 hours and then poured into 10 mL of 3N aqueous HCl. The aqueous phases was extracted with ethyl acetate (3×10 mL) and the combined organic phases were washed with saturated aqueous NaCl, dried (Na$_2$SO$_4$), filtered and concentrated. The residue was purified by column chromatography on SiO$_2$ (10 g, 94:5:1 CHCl$_3$—CH$_3$OH—AcOH) to give an oily residue. Lyophilization of this residue gave the title compound (0.019 g, 73%) as a fluffy, white lyophilate. $^1$H NMR (CDCl$_3$) δ6.84–7.37 (m, 18H), 4.55–4.98 (m, 2H), 4.13–4.48 (m, 2H), 3.45–3.96 (m, 2H), 2.81–3.37 (m, 6H), 2.25–2.43 (m, 2H), 1.39–1.82 (m, 6H), 0.74–0.94 (m, 6H). MS (FAB$^+$) m/e 783 (M+2K—H)$^{30}$, 745 (M+K)$^+$, 707 (M+H)$^+$.

EXAMPLE 78

(1α,2β,3β,4α)-1,2-Di[N-propyl-N-(4-phenoxybenzyl)aminocarbonyl]-4-(1-carboxy-1-hydroxymethyl)cyclobutane-3-carboxylic acid

EXAMPLE 78A

Methyl (1α,2β,3β,4α)-1,2-Di[N-propyl-N-(4-phenoxybenzyl)aminocarbonyl]-4-(1-acetoxy-1-(2-furanyl)-methyl)cyclobutane-3-carboxylate To a solution of 0.029 mL (0.40 mmol, 4.0 eq.) of furan in 0.8 mL of dry THF at 0° C. was added 0.25 mL (0.4 mmol, 4.0 eq.) of a 1.6M solution of n-BuLi in hexanes dropwise. The solution was briefly warmed to room temperature and then cooled to 0° C. The yellow solution was then added via cannula to a suspension of 18 mg (0.2 mmol, 2.0 eq.) of CuCN in 0.6 mL of THF at −20° C. and this mixture stirred 5 minutes at 0° C. To the resulting solution (yellow) was added a solution of 68 mg (0.1 mmol, 1.0 eq.) of the compound resulting from Example 71A in 0.5 mL of dry THF. The mixture was stirred for 1.5 hours at −20°–0° C. and then quenched by the addition of 1 mL of 95:5 saturated aqueous NH$_4$Cl-conc aqueous NH$_4$OH. The cooling bath was removed, 5 mL of ether was added, and the biphasic solution was stirred vigorously for 15 minutes. The mixture was then poured into 10 mL of the above NH$_4$Cl/NH$_4$OH solution and extracted with 2×10 mL of ethyl acetate. The combined organic phases were washed with the NH$_4$Cl/

NH₄OH mixture (10 mL), dried (MgSO₄), filtered and concentrated. The residue was dissolved in 0.5 mL of CH₂Cl₂ and cooled to 0° C. The mixture was then treated with excess 2,6-lutidine, DMAP (0.005 g) and acetic anhydride (0.017 mL). After stirring for 30 minutes at room temperature, the mixture was diluted with 25 mL of ethyl acetate and washed with water, 3N aqueous HCl and saturated aqueous NaHCO₃ (10 mL each), dried (MgSO₄), filtered and concentrated. The residue was purified by column chromatography on SiO₂ (15 g, 40% ethyl acetate-hexanes) to give 0.031 g (39%) of the title compound as a colorless oil. $^1$H NMR (CDCl₃) δ6.89–7.38 (m, 18H), 5.93–6.42 (m, 3H), 4.92 (m, 1H), 3.92–4.68 (m, 5H), 3.37–3.81 (m, 5H), 2.75–3.37 (m, 3H), 1.71–2.29 (m, 3H), 1.20–1.67 (m, 4H), 0.73–0.98 (m, 6H). MS (DCI) m/e 787 (M+H)⁺.

EXAMPLE 78B (1α,2β,3β,4α)-1,2-Di[N-propyl-N-(4-phenoxybenzyl)aminocarbonyl]-4-(1-carboxy-1-hydroxymethyl)cyclobutane-3-carboxylic acid To a vigorously stirred solution 1 mg (0.007 mmol, 0.2 eq.) of RuO₂·H₂O in 0.5 mL of 3:2:3 CH₃CN/CCl₄/H₂O at room temperature was added 62 mg (0.29 mmol, 8.0 eq.) of NaIO₄. After 15 minutes, NaHCO₃ (150 mg) was added followed by the addition of the compound resulting from Example 78A (28 mg, 0.036 mmol, 1.0 eq.) in 0.3 mL CH₃CN. The yellow solution immediately turned black. Excess NaIO₄ was added followed by 5 mL of ethyl acetate. The mixture was poured into water and acidified by the addition of 4N aqueous H₂SO₄ and the phases were separated. The aqueous phase was extracted with 2×10 mL of ethyl acetate and the combined organic phases were washed with 3×10 mL of 10% aqueous NaHSO₃, dried (MgSO₄) filtered and concentrated to give 0.024 g (86%) of the title compound as a colorless syrup which was used directly.

To a solution of 0.024 g (0.031 mmol, 1.0 eq.) of the above acid-ester in 0.5 mL of THF at 0° C. was added a solution of 13 mg (0.31 mmol, 10 eq.) of LiOH·H₂O in 0.2 mL of water. The ice bath was removed and the mixture was stirred for 2 hours at room temperature and then poured into 10 mL of 3N aqueous HCl. The aqueous phase was extracted with 3×10 mL of ethyl acetate and the combined organic phases were washed with brine, dried (Na₂SO₄), filtered and concentrated to give a light yellow oil. This oil was then lyophilized (CH₃CN—H₂O) to give 0.020 g (91%) of the title compound as an off white, fluffy lyophilate. $^1$H NMR (CD₃OD) δ6.86–7.37 (m, 18H), 4.69–4.78 (m, 1H), 4.23–4.47 (m, 3H), 2.84–3.67 (m, 12H), 1.46–1.71 (m, 4H), 0.81–0.97 (m, 6H). MS (FAB+) m/e 747 (M+K)⁺, 731 (M+Na)⁺, 709 (M+H)⁺, (FAB⁻) m/e 707 (M–H)⁺.

EXAMPLE 79

(1α,2β,3β,4α)-1,2-Di[N-propyl-N-(4-phenoxybenzyl)aminocarbonyl]-3,4-di [(hydroxyimino)methyl]-cyclobutane

EXAMPLE 79A (1α,2β,3β,4α)-1,2-Di[N-propyl-N-(4-phenoxybenzyl)aminocarbonyl]-cyclobutane-3,4-di (O-benzyloxime)

A solution of the compound resulting from Example 64B (200 mg (0.29 mmol) in dry tetrahydrofuran (10 mL) was cooled to –15° C. under dry nitrogen. N-Methylmorpholine (60 mg, 0.59 mmol) and isobutylchloroformate (81 mg, 0.59 mmol) were added followed by a solution of O-benzylhydroxylamine hydrochloride (94 mg, 0.59 mmol) and N-methylmorpholine (60 mg, 0.59 mmol) in dimethylformamide (2 mL). After stirring at –15° C. for 15 minutes, the mixture was stirred at ambient temperature for 3 hours. The reaction mixture was concentrated under reduced pressure, dissolved in ethyl acetate, washed with 1M HCl, 5% NaHCO₃, and brine, dried over Na₂SO₄, and concentrated in vacuo. The residue obtained was purified by flash silica gel chromatography eluting with 5% methanol in chloroform to give 100 mg (38%) of the benzyl protected oximes.

EXAMPLE 79B (1α,2β,3β,4α)-1,2-Di[N-propyl-N-(4-phenoxybenzyl)aminocarbonyl]-3,4-di [(hydroxyimino)methyl]-cyclobutane A solution of the compound resulting from Example 79A (50 mg (56 μmol) in methanol (15 mL) with 10% palladium on carbon (5 mg) was stirred under an atmosphere of hydrogen for 5 hours. Filtration through Celite and evaporation provided 20.5 mg (51%) of the title compound. $^1$H NMR (CDCl₃, 300 MHz) δ0.88 (m (6H) (1.45 (m (4H) (2.95 (m (4H) (3.62 (m (4H) (4.18 (m (4H) (6.85–7.37 (m (18H). MS m/e 709 (M+H)⁺.

EXAMPLE 80

(1α,2β,3β,4α)-1,2-Di[N-methyl-N-(4-phenoxybenzyl)aminocarbonyl]cyclobutane-3,4-dicarboxylic acid dimethyl ester To the dicarboxylic acid resulting from Example 13 (1.00 g, 1.60 mmol) dissolved in 20 mL of anhydrous methanol was added 5 drops of concentrated sulfuric acid. The clear mixture was stirred at ambient temperature overnight. The solvents were removed under reduced pressure to give a residue which was dissolved in ethyl acetate, washed with sodium bicarbonate solution, water and saturated sodium chloride solution, dried, filtered and concentrated in vacuo. The residue obtained was chromatographed on silica gel eluting with 4:1 ethyl acetate-hexane to give the title compound in 70% yield. $^1$H NMR (DMSO-d₆, 300 MHz) δ2.89 (s (6H) (3/59 (s (6H) (3.76 (d (J=9.6 Hz (2H) (4.14 (d (2H) (4.40 (d (2H) (4.56 (d (2H) (6.95–7.40 (m (18H). MS m/e 651 (M+H)⁺.

EXAMPLE 81

(1α,2β,3β,4α)-1,2-Di[N-propyl-N-(3-phenoxybenzyl)aminocarbonyl]-cyclobutane-3,4-dicarboxylic acid

EXAMPLE 81A

N-Propyl-N-(3-phenoxybenzyl)amine

3-Phenoxybenzaldehyde (2.00 mL, 2.29 g, 11.6 mmol), n-propylamine (0.95 mL, 0.68g, 11.5mmol), and p-toluenesulfonic acid monohydrate (15 mg, 0.08 mmol) were dissolved in absolute ethanol (15 mL), then heated to 80° C. in a sealed tube for 2.5 hours. The reaction was cooled to room temperature, transferred to a round-bottom flask, then sodium borohydride (440 mg, 11.6 mmol) was added, followed by heating under reflux for 2.5 hours. The reaction was concentrated, the residue was partitioned between water and EtOAc, and the EtOAc layer was washed with water and brine. After drying with $Na_2SO_4$, filtration, and concentration, the residue was purified by chromatography on silica gel using 4:6 followed by 3:7 hexane-EtOAc to give 1.59 g (57%) light yellow oil. $^1$H NMR ($CDCl_3$) δ7.30 (m, 3H), 7.08 (m, 2H), 7.00 (m, 3H), 6.88 (dd, 1H), 3.77 (s, 2H), 2.60 (t, 2H), 1.53 (m, 2H), 0.92 (t, 3H). MS ($DCI/NH_3$) m/e 242 $(M+H)^+$.

EXAMPLE 81B (1α,2β,3β,4α)-1,2-Di[N-propyl-N-(3-phenoxybenzyl)aminocarbonyl-cyclobutane-3,4-dicarboxylic acid To 1,2,3,4-cyclobutanetetracarboxylic dianhydride (313 mg, 1.60 mmol) slurried in $CH_3CN$ (4.0 mL) was added the compound resulting from Example 81A (803 mg, 3.30 mmol). The reaction was stirred at room temperature under $N_2$ overnight, then diluted with EtOAc, washed with 2×1M $H_3PO_4$ and brine, dried over $Na_2SO_4$ and concentrated in vacuo. Chromatography of the residue obtained using 98.5:1.5:0.5 followed by 97:3:1 $CHCl_3$—MeOH—$CH_3CO_2H$ gave a glass which was dissolved in $CH_3CN$ (10 mL). Water (10 mL) was added to the $CH_3CN$ solution, then the solution was frozen and lyophilized to give 390 mg (36%) of the title compound as a white solid. $^1$H NMR (DMSO-$d_6$) δ7.39, 7.28, 7.13, 7.00, 6.93, 6.85 (all m, total 18H), 4.60, 4.45, 4.30 (all m, total 4H), 3.90, 3.60 (both m, total 4H), 3.45, 3.25, 3.00, 2.80 (all m, total 4H), 1.40 (m, 4H), 0.78 (m, 6H). MS ($FAB^+$) m/e 679 $(M+H)^+$. Anal. calcd for $C_{40}H_{42}N_2O_8 \cdot 0.25H_2O$: C, 70.32; H, 6.27; N, 4.10. Found: C, 70.20; H, 6.51; N, 4.04.

EXAMPLE 82

(1α,2β,3β,4α)-1,2-Di[N-propyl-N-(5-phenoxyfurfuryl)aminocarbonyl}cyclobutane-3,4-dicarboxylic acid

EXAMPLE 82A

5-Phenoxy-2-furaldehyde

Phenol (3.80 g, 40.4 mmol) in DMSO (25 mL) was added dropwise to a suspension of NaH (60%, 1.63 g, 40.4 mmol) in DMSO (25 mL) over a period of 15 minutes. After another 15 minutes, a solution of 5-nitro-2-furaldehyde (4.85 g, 34.4 mmol) in DMSO (20 mL) was added. The reaction was stirred at room temperature for 4.5 hours, then the reaction was partitioned between ice-water, brine and $Et_2O$. The aqueous layer was extracted with $Et_2O$, and the combined $Et_2O$ extracts were washed with 7% KOH, dried over $Na_2SO_4$ and concentrated in vacuo to afford a brown oil. Vacuum distillation (2.8 mm Hg, 137°–8° C.) gave 3.3 g (51%) yellow oil. $^1$H NMR ($CDCl_3$) δ9.42 (s, 1H), 7.42 (m, 2H), 7.28 (m, 1H), 7.20 (m, 3H), 5.55 (d, 1H). MS (DCI/$NH_3$) m/e 189 $(M+H)^+$, 206 $(M+H+NH_3)^+$.

EXAMPLE 82B (1α,2β,3β,4α)-1,2-Di[N-propyl-N-(5-phenoxyfurfuryl)aminocarbonyl}cyclobutane-3,4-dicarboxylic acid Using the compound resulting from Example 82A, N-propyl-N-(5-phenoxyfurfuryl)amine was prepared by the method of Example 81A. $^1$H NMR ($CDCl_3$) δ7.32 (m, 2H), 7.10, (m, 1H), 7.04 (m, 2H), 6.12 (d, 1H), 5.51 (d, 1H), 3.70 (s, 2H), 2.59 (t, 2H), 1.54 (m, 2H), 0.92 (t, 3H). MS ($DCI/NH_3$) $(M+H)^+$ 232.

Using the amine prepared above, the title compound was prepared using the method of Example 81B. $^1$H NMR (DMSO-$d_6$) δ7.38 (m, 4H), 7.15 (m, 2H), 7.07 (m, 2H), 7.02 (m, 2H), 6.34, 6.32, 6.29, 6.25 (all d, total 2H), 5.70, 5.67 (d, m, total 2H), 4.52, 4.35, 4.17 (all m, total 4H), 3.90, 3.65, 3.60, 3.55 (all m, total 4H), 3.40–3.20, 3.00 (envelope, m, total 4H), 1.40 (m, 4H), 0.75 (m, 6H). MS ($FAB^-$) m/e 657 $(M-H)^-$. Anal calcd for $C_{36}H_{38}N_2O_{10} \cdot 0.5 H_2O$: C, 64.76; H, 5.89; N, 4.20. Found: C, 64.80; H, 5.79; N, 4.02.

EXAMPLE 83

(1α,2β,3β,4α)-1,2-Di[N-propyl-N-(5-phenoxythien-2-ylmethyl)aminocarbonyl]cyclobutane-3,4-dicarboxylic acid

EXAMPLE 83A

N-Propyl-N-(5-phenoxythiophene-2-methyl)amine

Using 5-nitrothiophene-2-carboxaldehyde, 5-phenoxythiophene-2-carboxaldehyde was prepared by the method of Example 82A, except chromatography using 9:1 hexane-EtOAc was used for purification. $^1$H NMR ($CDCl_3$) δ9.72 (s, 1H), 7.54 (d, 1H), 7.42 (m, 2H), 7.25 (m, 1H), 7.20 (m, 2H), 6.51 (d, 1H). MS ($DCI/NH_3$) m/e 205 $(M+H)^+$, 222 $(M+H+NH_3)^+$.

EXAMPLE 83B (1α,2β,3β,4α)-1,2-Di[N-propyl-N-(5-phenoxythien-2-ylmethyl)aminocarbonyl]cyclobutane-3,4-dicarboxylic acid Using the compound resulting from Example 83A, N-propyl-N-(5-phenoxythiophene-2-methyl)amine was prepared by the method of Example 81A. $^1$H NMR ($CDCl_3$) δ7.32 (m, 2H), 7.10, (m, 3H), 6.52 (dt, 1H), 6.38 (d, 1H), 3.88 (d, 2H), 2.63 (t, 2H), 1.54 (m, 2H), 0.92 (t, 3H); MS ($DCI/NH_3$) $(M+H)^+$ 248.

Using the amine prepared above, the title compound was prepared by the method of Example 81B. $^1$H NMR (DMSO-$d_6$) δ7.37 (m, 4H), 7.13, 7.05 (both m, total 6H), 6.98, 6.94 (both m, total 2H), 6.52, 6.46, 6.45, 6.40 (all d, total 2H), 4.65, 4.40 (both m, total 4H), 3.95–3.50 (envelope, total 4H), 3.43, 3.20, 3.03, 2.88 (all m, total 4H), 1.43 (m, total 4H), 0.80, 0.70 (both m, total 6H). MS ($FAB^-$) m/e 689 $(M-H)^-$. Anal calcd for $C_{36}H_{38}N_2O_8S_2 \cdot 0.25 H_2O$: C, 62.19; H, 5.58; N, 4.03. Found: C, 62.08; H, 5.51; N, 3.92.

EXAMPLE 84

(1α,2β,3β,4α)-1,2-Di[N-propyl-N-(4-(furan-2-yloxybenzyl)aminocarbonyl]cyclobutane-3,4-dicarboxylic acid

EXAMPLE 84A 5-(4-Ethoxycarbonylphenoxy)-2-furaldehyde

Using ethyl-4-hydroxybenzoate, the title compound was prepared by the method of Example 82A, except chromatography using 3:1 hexane-EtOAc was used for purification. $^1$H NMR ($CDCl_3$) δ9.45 (s, 1H), 8.10 (m, 2H), 7.25 (d, 1H), 7.19 (m, 2H), 5.75 (d, 1H), 4.40 (q, 2H), 1.41 (t, 3H). MS ($DCI/NH_3$) m/e 261 $(M+H)^+$, 278 $(M+H+NH_3)^+$.

EXAMPLE 84B 5-(4-Ethoxycarbonylphenoxy)-2-furoic acid

A solution of potassium dihydrogen phosphate (10.8 g, 79.0 mmol) and sodium chlorite (80%, 12.0 g, 106 mmol) in water (95 mL) was added to a solution of the compound resulting from Example 84A (3.00 g, 11.5 mmol) in t-butanol (240 mL) and 2-methyl-2-butene (57 mL). The two-phase reaction mixture was mechanically stirred at room temperature for 2 hours, then the aqueous layer was removed, and the organic layer concentrated. The aqueous layer and the organic residue were combined, the pH was adjusted to 2 with 1.1N $NaHSO_4$, then extracted with $Et_2O$. The $Et_2O$ layer was washed with 5% sodium bisulfite, then extracted with saturated $NaHCO_3$. The saturated $NaHCO_3$ layer was washed with 3×$Et_2O$, then the pH was adjusted to 1 with 1.1N $NaHSO_4$, and extracted with 3×$Et_2O$. After drying over $Na_2SO_4$ and concentrating under reduced pressure 1.10 g (34%) of the title compound as a light yellow solid was obtained. $^1H$ NMR ($CD_3OD$) δ8.08 (m, 2H), 7.27 (d, 1H), 7.21 (m, 2H), 5.90 (d, 1H), 4.36 (q, 2H), 1.39 (t, 3H). MS ($DCI/NH_3$) m/e 294 $(M+H+NH_3)^+$.

EXAMPLE 84C

Ethyl 4-(furan-2-yloxy)benzoate

To the compound resulting from Example 84B (1.05 g, 3.80 mmol) slurried in quinoline (1.7 mL) was added copper powder (70 mg). The reaction was heated to 200° C. for 1 hour, cooled to room temperature, and partioned between $Et_2O$ and 1M $H_3PO_4$. The $Et_2O$ layer was washed with 3×1M $H_3PO_4$, 3×saturated $NaHCO_3$ and brine, dried over $Na_2SO_4$ and concentrated in vacuo. Chromatography of the residue using 2% EtOAc in hexanes gave 550 mg of the title compound as a yellow oil (62%). $^1H$ NMR ($CDCl_3$) δ8.04 (m, 2H), 7.10 (dd, 1H), 7.03 (m, 2H), 6.40 (dd, 1H), 5.70 (dd, 1H), 4.36 (q, 2H), 1.39 (t, 3H). MS ($DCI/NH_3$) m/e 233 $(M+H)^+$, 250 $(M+H+NH_3)^+$.

EXAMPLE 84D 4-(Furan-2-yloxy)benzyl alcohol

A solution of the compound resulting from Example 84C (535 mg, 2.30 mmol) in THF (4 mL) was added to a solution of LAH in THF (4 mL of 1.0M LAH). The reaction mixture was stirred at room temperature for 1 hour and then cooled to 5° C. Water (0.13 mL), 15% NaOH (0.13 mL), and water (0.35 mL) were added sequentially, and the mixture was stirred for 15 minutes. After the addition of $Et_2O$ and $MgSO_4$, the mixture was filtered through a small plug of silica gel and the filtrate concentrated under reduced pressure to afford 435 mg (100%) of the title compound as a yellow oil. $^1H$ NMR ($CDCl_3$) δ7.35 (m, 2H), 7.05 (dd, 1H), 7.03 (m, 2H), 6.44 (dd, 1H), 5.60 (dd, 1H), 4.66 (d, 2H), 1.63 (t, 1H); MS ($DCI/NH_3$) m/e 191 $(M+H)^+$.

EXAMPLE 84E 4-(Furan-2-yloxy)benzaldehyde

To the compound resulting from Example 84D (430 mg, 2.30 mmol) dissolved in 9:1 $CH_2Cl_2$—$CH_3CN$ (22 mL) was added N-morpholine-N-oxide (400 mg, 3.40 mmol) and powdered activated molecular sieves (2.10 g). After stirring for 10 minutes, tetrapropyl-ammonium perruthenate (40 mg, 0.11 mmol) was added, the reaction was stirred at room temperature for 30 minutes, and then celite and $Et_2O$ were added. The mixture was filtered through a small plug of silica gel, and the filtrate concentrated to give 350 mg (81%) of the title compound as a brown oil. $^1H$ NMR ($CDCl_3$) δ9.95 (s, 1H), 7.88 (m, 2H), 7.12 (m, 3H), 6.42 (dd, 1H), 5.76 (dd, 1H). MS ($DCI/NH_3$) m/e 189 $(M+H)^+$, 206 $(M+H+NH_3)^+$.

EXAMPLE 84F

N-Propyl-N-4-(furan-2-yloxy)benzylamine

Using the compound resulting from Example 84E, the title compound was prepared by the method of Example 81A. $^1H$ NMR ($CDCl_3$) δ7.28 (m, 2H), 7.05 (dd, 1H), 6.99 (m, 2H), 6.33 (dd, 1H), 5.56 (dd, 1H), 3.77 (s, 2H), 2.60 (t, 2H), 1.55 (m, 2H), 0.93 (t, 3H). MS ($DCI/NH_3$) m/e 232 $(M+H)^+$.

EXAMPLE 84G (1α,2β,3β,4α)-1,2-Di[N-propyl-N-(4-(furan-2-yloxybenzyl)aminocarbonyl]cyclobutane-3,4-dicarboxylic acid Using the compound resulting from Example 84F, the title compound was prepared by the method of Example 81B. $^1H$ NMR (DMSO-$d_6$) δ7.32, 7.25 (both m, total 6H), 7.02, 6.95 (both m, total 4H), 6.48 (m, 2H), 5.78 (m, 2H), 4.70, 4.25 (both m, total 4H), 3.90, 3.60 (both m, total 4H), 3.55–3.15, 2.93, 2.78 (envelope, m, m, total 4H), 1.48 (m, 4H), 0.80 (m, 6H). MS (FAB–) m/e 657 $(M-H)^-$. Anal cald for $C_{36}H_{38}N_2O_{10}$·0.5 $H_2O$: C, 64.76; H, 5.89; N, 4.20. Found: C, 64.82; H, 5.81; N, 3.99.

EXAMPLE 85

(1α,2β,3β,4α)-1,2-Di[N-propyl-N-(4-(thiazol-2-yloxybenzyl)aminocarbonyl]cyclobutane-3,4-dicarboxylic acid Using ethyl-4-hydroxybenzoate and 2-bromothiazole, ethyl 4-(thiazol-2-yloxy)benzoate was prepared by the method of Example 82A, except the reaction was heated to 120° C. overnight, and chromatography using 9:1 hexane-EtOAc was used for the purification. $^1H$ NMR ($CDCl_3$) δ8.10 (m, 2H), 7.35 (m, 2H), 7.28 (d, 1H), 6.90 (d, 1H), 4.38 (q, 2H), 1.39 (t, 3H). MS ($DCI/NH_3$) $(M+H)^+$250 and $(M+H+NH_3)^+$267.

Using the ester prepared above and the procedures described in Example 84D provided 4-(thiazol-2-yloxy)benzyl alcohol. $^1H$ NMR ($CDCl_3$) δ7.43 (m, 2H), 7.28 (m, 2H), 7.23 (d, 1H), 6.82 (d, 1H), 4.70 (d, 2H), 1.88 (t, 1H). MS ($DCI/NH_3$) $(M+H)^+$208.

Using the alcohol prepared above and the procedures described in Example 84E, except chromatography using 4:1 hexane-EtOAc was used for purification, provided 4-(thiazol-2-yloxy)benzaldehyde. $^1H$ NMR ($CDCl_3$) δ10.00 (s, 1H), 7.95 (m, 2H), 7.46 (m, 2H), 7.30 (d, 1H), 6.95 (d, 1H). MS ($DCI/NH_3$) $(M+H)^+$206 and $(M+H+NH_3)^+$223.

Using the aldehyde prepared above and the procedures described in Example 81A, except 3–5% MeOH in $CHCl_3$ was used for the chromatography, provided N-propyl-N-(4-(thiazoly-2-yloxy)benzyl)amine. $^1H$ NMR ($CDCl_3$) δ7.39 (m, 2H), 7.23 (d, 1H), 7.23 (m, 2H), 6.80 (d, 1H), 5.56 (dd, 1H), 3.80 (s, 2H), 2.63 (t, 2H), 1.55 (m, 2H), 0.96 (t, 3H). MS ($DCI/NH_3$) $(M+H)^+$249.

Using the amine prepared above, the title compound was prepared by the method of Example 81B, except additional purification by preparative HPLC was required (Rainin Dynamax-60A C18 column, using a gradient of 20–100% $CH_3CN$ vs 0.1% TFA in water). $^1H$ NMR (DMSO-$d_6$) δ7.40–7.20 (envelope, 12H), 4.75, 4.30 (both m, total 4H), 4.00, 3.89, 3.65 (all m, total 4H), 3.55–3.20, 2.96, 2.78 (envelope, m, m, total 4H), 1.50 (m, 4H), 0.80 (m, 6H). MS (FAB+) m/e 693 $(M+H)^+$. Anal cald for $C_{34}H_{36}N_4O_8S_2$·0.33 TFA: C, 56.99; H, 5.01; N, 7.67. Found: C, 57.02; H, 5.11; N, 7.64.

EXAMPLE 86

(1α,2β,3β,4α)-1,2-Di[N-propyl-N-(4-(pyrrol-1-ylmethyl)benzyl)aminocarbonyl]cyclobutane-3,4-dicarboxylic acid

EXAMPLE 86A

N-(4-(Pyrrol-1-ylmethyl)benzyl)amine

Using pyrrole and 4-(bromomethyl)benzonitrile and the method of Example 83A, except using DMF as the solvent, provided N-(4-cyanobenzyl)pyrrole. $^1$H NMR (CDCl$_3$) δ7.62 (m, 2H), 7.14 (m, 2H), 6.69 (m, 2H), 6.24 (m, 2H), 5.15 (s, 2H). MS (DCI/NH$_3$) (M+H)$^+$183 and (M+H+NH$_3$)$^+$200.

Using the nitrile prepared above and the method of Example 84D, except after 1 hour at room temperature the reaction was heated under reflux for 75 minutes, provided the title compound. $^1$H NMR (CDCl$_3$) δ7.28 (m, 2H), 7.10 (m, 2H), 6.69 (m, 2H), 6.19 (m, 2H), 5.05 (s, 2H) 3.85 (s, 2H). MS (DCI/NH$_3$) (M+H)$^+$187 and (M+H+NH$_3$)$^+$204.

EXAMPLE 86B

N-[4-(Pyrrol-1-ylmethyl)benzyl]propylamide

To the compound resulting from Example 86A (1.00 g, 5.38 mmol) and triethylamine (0.60 g, 0.82 mL, 5.93 mmol) in CH$_2$Cl$_2$ (8 mL) cooled to 0° C. was added propionyl chloride (0.50 g, 0.47 mL, 5.41 mmol) in CH$_2$Cl$_2$ (5.5 mL) dropwise. The bath was removed and the reaction mixture stirred for 10 minutes, then diluted with EtOAc. The resulting solution was washed with 3×1M H$_3$PO$_4$, 3×saturated NaHCO$_3$ and brine, dried over Na$_2$SO$_4$ and concentrated under reduced pressure to afford 1.25 g (96%) white solid. $^1$H NMR (CDCl$_3$) δ7.24 (d, 2H), 7.08 (d, 2H), 6.69 (m, 2H), 6.19 (m, 2H), 5.75 (br s, 1H), 5.05 (s, 2H) 4.40 (d, 2H), 2.23 (q, 2H), 1.18 (t, 3H). MS (DCI/NH$_3$) (M+H)$^+$243 and (M+H+NH$_3$)$^+$260.

EXAMPLE 86C

N-Propyl-N-(4-(pyrrol-1-ylmethyl)benzyl)amine

A solution of the compound resulting from Example 86B (1.20 g, 4.96 mmol) in THF (8 mL) was added to a solution of LAH in THF (9.9 mL of 1.0M LAH), heated under reflux 3 hours, then cooled to 5° C. Then water (0.50 mL), 15% NaOH (0.50 mL), and water (1.50 mL) were added and the mixture stirred for 15 minutes. After the addition of Et$_2$O and MgSO$_4$, the mixture was filtered through a small plug of silica gel, which was rinsed with CH$_2$Cl$_2$. The filtrate was concentrated under reduced pressure and purified by chromatography using 97:3 CHCl$_3$—MeOH to give a yellow oil (880 mg, 78%). $^1$H NMR (CDCl$_3$) δ7.28 (d, 2H), 7.08 (d, 2H), 6.69 (m, 2H), 6.19 (m, 2H), 5.05 (s, 2H) 3.77 (s, 2H), 2.59 (t, 2H), 1.55 (m, 2H), 0.93 (t, 3H). MS (DCI/NH$_3$) (M+H)$^+$229.

EXAMPLE 86D (1α,2β,3β,4α)-1,2-Di[N-propyl-N-(4-(pyrrol-1-ylmethyl)benzyl)aminocarbonyl]cyclobutane-3,4-dicarboxylic acid Using the compound resulting from Example 86C, the title compound was prepared by the method of Example 81B. $^1$H NMR (DMSO-d$_6$) δ7.20–7.00 (envelope, 8H), 6.80 (m, 4H), 6.02 (m, 4H) 5.78 (m, 2H), 5.10, 5.08 (both s, total 4H), 4.70, 4.25 (both m, total 4H), 3.92, 3.80, 3.60 (all m, total 4H), 3.55–3.10, 2.90, 2.75 (envelope, m, m, total 4H), 1.45 (m, 4H), 0.78 (m, 6H). MS (FAB+) m/e 653 (M+H)$^+$. Anal cald for C$_{38}$H$_{44}$N$_4$O$_6$·0.25 H$_2$O: C, 69.44; H, 6.82; N, 8.52. Found: C, 69.47; H, 6.70; N, 8.35.

EXAMPLE 87

(1α,2β,3β,4α)-1,2-Di[N-propyl-N-(3-methyl-4-phenoxybenzyl)aminocarbonyl]cyclobutane-3,4-dicarboxylic acid

EXAMPLE 87A

3-Methyl-4-phenoxybenzaldehyde

Phenol (2.58 g, 24.0 mmol) in DMSO (5 mL) was added dropwise to a suspension of NaH (60%, 1.63 g, 40.4 mmol) in DMSO (10 mL) over a period of 15 minutes. After another 15 minutes, a solution of 4-fluoro-3-methylbenzaldehyde (2.54 g, 20.5 mmol) in DMSO (5 mL) was added. The reaction was heated at 125° C. for 3 hours, then cooled to room temperature and partitioned between 1N HCl and Et$_2$O. The Et$_2$O layer was washed with 15% NaOH and brine, dried over Na$_2$SO$_4$. Vacuum distillation (3.4 mm Hg, 154–8° C.) gave 2.35 g oil which was purified by chromatography using 9:1 hexane-Et$_2$O to afford 1.98 g (46%) of a colorless oil. $^1$H NMR (CDCl$_3$) δ9.92 (s, 1H), 7.85 (m, 2H), 7.30 (m, 1H), 7.05 (m, 3H), 6.90 (m, 2H), 2.38 (s, 3H). MS (DCI/NH$_3$) (M+H)$^+$213 and (M+H+NH$_3$)$^+$230.

EXAMPLE 87B (1α,2β,3β,4α)-1,2-Di{N-propyl-[4-(3'-methyl)phenoxybenzyl]aminocarbonyl}cyclobutane-3,4-dicarboxylic acid Using the compound resulting from Example 87A and the procedures described in Example 81A provided N-propyl-N-(3-methyl-4-phenoxybenzyl)amine. $^1$H NMR (CDCl$_3$) δ7.28 (m, 2H), 7.30 (m, 1H), 6.95 (m, 2H), 6.90 (m, 1H), 6.80 (m, 2H), 3.77 (s, 2H), 2.33 (s, 3H), 2.62 (t, 2), 1.55 (m, 2H), 0.93 (t, 3H). MS (DCI/NH$_3$) (M+H)$^+$256.

Using the amine prepared above and the procedures described in Example 81B provided the title compound. $^1$H NMR (DMSO-d$_6$) δ7.30–7.10 (envelope, 6H), 7.00–6.75 (envelope, 10H), 4.70, 4.25 (both m, total 4H), 3.95, 3.63 (both m, total 4H), 3.55–3.15, 2.95, 2.80 (envelope, m, m, total 4H), 2.27 (m, 6H), 1.50 (m, 4H), 0.80 (m, 6H). MS (FAB$^+$) (M+H)$^+$707. Anal cald for C$_{42}$H$_{46}$N$_2$O$_8$: C, 71.37; H, 6.56; N, 3.96. Found: C, 71.12; H, 6.49; N, 3.82.

EXAMPLE 88

(1α,2β,3β,4α)-1,2-Di[N-propyl-N-(4-naphth-2-yloxybenzyl)aminocarbonyl]cyclobutane-3,4-dicarboxylic acid Using 2-naphthol and the method of Example 87A, except the vacuum distillation was omitted, afforded 4-(naphth-2-yloxy)benzaldehyde. $^1$H NMR (CDCl$_3$) δ9.94 (s, 1H), 7.90 (m, 4H), 7.78 (m, 1H), 7.50 (m, 3H), 7.28 (dd, 1H), 7.12 (m, 2H). MS (DCI/NH$_3$) (M+H)$^+$249 and (M+H+NH$_3$)$^+$266.

Using the aldehyde prepared above and the procedures described in Example 81A afforded N-propyl-N-(4-(naphth-2-yloxybenzyl)amine. $^1$H NMR (CDCl$_3$) δ7.82 (m, 2H), 7.70 (m, 1H), 7.42 (m, 2H), 7.32 (m, 1H), 7.27 (m, 3H), 7.04 (m, 2H), 3.79 (s, 2H), 2.62 (t, 2H), 1.55 (m, 2H), 0.93 (t, 3H). MS (DCI/NH$_3$) (M+H)$^+$292.

Using the amine prepared above and the procedures described in Example 81B afforded the title compound. $^1$H NMR (DMSO-$d_6$) δ7.90 (m, 4H), 7.78 (m, 2H), 7.44 (m, 6H), 7.25 (m, 6H), 7.00 (m, 4H), 4.70, 4.30 (both m, total 4H), 3.95, 3.63 (both m, total 4H), 3.55–3.15, 3.00, 2.80 (envelope, m, m, total 4H), 1.50 (m, 4H), 0.80 (m, 6H). MS (FAB+) (M+H)$^+$779. Anal cald for $C_{48}H_{46}N_2O_8$: C, 74.02; H, 5.95; N, 3.60. Found: C, 73.70; H, 6.10; N, 3.54.

EXAMPLE 89

(1α,2β,3β,4α)-1,2-Di[N-propyl-N-(4-(3-methyl-1-phenoxy)benzyl)aminocarbonyl]cyclobutane-3,4-dicarboxylic acid

EXAMPLE 89A 4-(3-Methyl-1-phenoxy)benzonitrile

Using phenol and 2-fluoro-5-nitrotoluene and the procedures described in Example 82A, except the reaction was heated to 60° C. overnight and vacuum distilled at 4.5 mm Hg, 174°–5° C., provided 4-(3-methyl-1-phenoxy) nitrobenzene. $^1$H NMR (CDCl$_3$) δ8.16 (dd, 1H), 8.00 (dd, 1H), 7.42 (m, 2H), 7.23 (m, 1H), 7.05 (m, 2H), 6.78 (d, 1H), 2.42 (s, 3H). MS (DCI/NH$_3$) (M+H)$^+$247.

The nitro compound prepared above was reduced under H$_2$ using 10% Pd/C catalyst in MeOH to give 4-(3-methyl-1-phenoxy)aniline. $^1$H NMR (CDCl$_3$) δ7.27 (m, 2H), 6.97 (m, 1H), 6.83 (m, 2H), 6.80 (d, 1H), 6.60 (d, 1H), 6.52 (m, 1H), 3.53 (br s, 2H), 2.11 (s, 3H). MS (DCI/NH$_3$) (M+H)$^+$ 200 and (M+H+NH$_3$)$^+$217.

The amine prepared above (2.75 g, 13.8 mmol) was added to 2N HCl (20 mL), then cooled to 5° C., giving a thick purple slurry. A solution of sodium nitrite (0.84 g, 14.2 mmol) in water (2 mL) was added dropwise, keeping the reaction temperature ~5° C. Addition of another small portion of sodium nitrite to the reaction resulted in a positive HONO test with a KI-starch strip, so the pH was adjusted to 7–8 using solid Na$_2$CO$_3$. This solution was added in portions to a vigorously stirred mixture of toluene (10 mL) and a solution of sodium cyanide (1.65 g, 33.6 mmol) and copper (I) cyanide (1.45 g, 16.2 mmol) in water (15 mL), keeping the reaction temperature ~5° C. The very thick, brown reaction mixture was diluted with more toluene, stirred at 5° C. for 15 minutes, then at room temperature for 2 hours. The reaction mixture was added to EtOAc and 2N HCl; the organic layer was dried with Na$_2$SO$_4$ and concentrated in vacuo. The residue obtained was chromatographed eluting with 95:5 hexane-Et$_2$O to give the title compound as an orange-red oil (500 mg, 17%). $^1$H NMR (CDCl$_3$) δ7.55 (d, 1H), 7.40 (m, 3H), 7.20 (m, 1H), 7.00 (m, 2H), 6.79 (d, 1H), 2.35 (s, 3H). MS (DCI/NH$_3$) (M+H+NH$_3$)$^+$227.

EXAMPLE 89B 4-(3-Methyl-1-phenoxy)benzaldehyde

To the compound resulting from Example 89A (490 mg, 2.34 mmol) dissolved in toluene (12 mL) and cooled to 0° C. was added 5 mL of 1.5M DIBAL in toluene. The reaction mixture was stirred at 0°–10° C. for 2.5 hours, then EtOAc and 1N HCl were added. The organic layer was washed with water and brine, dried over Na$_2$SO$_4$ and concentrated under reduced pressure. Chromatography of the residue using 95:5 hexane-EtOAc gave the title compound as an orange oil (330 mg, 66%). $^1$H NMR (CDCl$_3$) δ9.90 (s, 1H), 7.80 (d, 1H), 7.63 (dd, 1H), 7.40 (m, 2H), 7.19 (m, 1H), 7.03 (m, 2H), 6.85 (d, 1H), 2.40 (s, 3H). MS (DCI/NH$_3$) (M+H)$^+$213 and (M+H+NH$_3$)$^+$230.

EXAMPLE 89C (1α,2β,3β,4α)-1,2-Di{N-propyl-[3-methyl-4-phenoxybenzyl]aminocarbonyl}cyclobutane-3,4-dicarboxylic acid Using the compound resulting from Example 89B and the procedures described in Example 81A afforded N-propyl-N-(4-(3-methyl-1-phenoxy)benzyl)amine. $^1$H NMR (CDCl$_3$) δ7.30 (m, 2H), 7.22 (d, 1H), 7.10 (dd, 1H), 7.03 (m, 1H), 6.88 (m, 3H), 3.76 (s, 2H), 2.64 (t, 2H), 2.22 (s, 3H), 1.58 (m, 2H), 0.95 (t, 3H). MS (DCI/NH$_3$) (M+H)$^+$256.

Using the amine prepared above and the procedures described in Example 81B, the title compound was prepared. $^1$H NMR (DMSO-$d_6$) δ7.35 (m, 4H), 7.19 (m, 2H), 7.07 (m, 4H), 6.84 (m, 6H), 4.65, 4.30 (both m, total 4H), 3.95, 3.63 (both m, total 4H), 3.55–3.10, 3.00, 2.80 (envelope, m, m, total 4H), 2.18, 2.15, 2.13, 2.10 (all s, total 3H), 1.50 (m, 4H), 0.80 (m, 6H). MS (FAB+) (M+H)$^+$707. Anal cald for $C_{42}H_{46}N_2O_8$: C, 71.37; H, 6.56; N, 3.96. Found: C, 70.96; H, 6.39; N, 3.84.

EXAMPLE 90

(1α,2β,3β,4α)-1,2-Di[N-propyl-N-(4-(4-methyl-1-phenoxy)benzyl)aminocarbonyl]cyclobutane-3,4-dicarboxylic acid Using p-cresol and the procedures described in Example 87A, except the vacuum distillation was omitted, afforded 4-(4-methyl-1-phenoxy)benzaldehyde. $^1$H NMR (CDCl$_3$) δ9.92 (s, 1H), 7.82 (m, 2H), 7.21 (m, 2H), 7.04 (m, 2H), 6.98 (m, 2H), 2.38 (s, 3H). MS (DCI/NH$_3$) (M+H)$^+$213 and (M+H+NH$_3$)$^+$230.

Using the aldehyde prepared above and the procedures described in Example 81A afforded N-propyl-N-(4-(4-methyl-1-phenoxy)benzyl)amine. $^1$H NMR (CDCl$_3$) δ7.28 (m, 2H), 7.13 (m, 2H), 6.95 (m, 2H), 6.90 (m, 2H), 3.77 (s, 2H), 2.62 (t, 2H), 2.32 (s, 3H), 1.55 (m, 2H), 0.93 (t, 3H). MS (DCI/NH$_3$) (M+H)$^+$256.

Using the amine prepared above and the procedures described in Example 81B afforded the title compound. $^1$H NMR (DMSO-$d_6$) δ7.20 (m, 8H), 6.96–6.82 (envelope, 8H), 4.70, 4.25 (both m, total 4H), 3.90, 3.60 (both m, total 4H), 3.55–3.15, 2.95, 2.78 (envelope, m, m, total 4H), 2.27 (m, 6H), 1.50 (m, 4H), 0.80 (m, 6H). MS (FAB+) (M+H)$^+$707. Anal cald for $C_{42}H_{46}N_2O_8 \cdot 0.25 H_2O$: C, 70.92; H, 6.59; N, 3.94. Found: C, 70.80; H, 6.69; N, 3.83.

EXAMPLE 91

(1α,2β,3β,4α)-1,2-Di[N-propyl-N-(4-naphth-1-yloxybenzyl)aminocarbonyl]cyclobutane-3,4-dicarboxylic acid Using 1-naphthol and the procedures described in Example 87A, except the vacuum distillation was omitted, afforded 4-(naphth-1-yloxy)benzaldehyde. $^1$H NMR (CDCl$_3$) δ9.93 (s, 1H), 8.00 (dd, 1H), 7.93 (d, 1H), 7.85 (m, 2H), 7.76 (d, 1H), 7.55 (m, 1H), 7.49 (m, 2H), 7.17 (dd, 1H), 7.08 (m, 2H). MS (DCI/NH$_3$) (M+H)$^+$249 and (M+H+NH$_3$)$^+$266.

Using the aldehyde prepared above and the procedures described in Example 81A afforded N-propyl-N-(4-(naphth-1-yloxy)benzyl)amine. $^1$H NMR (CDCl$_3$) δ8.21 (m, 1H), 7.87 (m, 1H), 7.60 (d, 1H) 7.50 (m, 2H), 7.37 (dd, 1H), 7.30 (m, 2H), 7.02 (m, 2H), 6.93 (dd, 1H), 3.79 (s, 2H), 2.62 (t, 2H), 1.55 (m, 2H), 0.93 (t, 3H). MS (DCI/NH$_3$) (M+H)$^+$292.

Using the amine prepared above and the procedures described in Example 81B, the title compound was prepared. $^1$H NMR (DMSO-d$_6$) δ8.05 (m, 2H), 7.97 (m, 2H), 7.73 (m, 2H), 7.60–7.40 (envelope, 6H), 7.25, 7.18 (both m, total 4H), 6.95 (m, 6H), 4.70, 4.27 (both m, total 4H), 3.90, 3.63 (both m, total 4H), 3.55–3.15, 2.95, 2.78 (envelope, m, m, total 4H), 1.50 (m, 4H), 0.80 (m, 6H). MS (FAB+) (M+H)$^+$779. Anal cal'd for C$_{48}$H$_{46}$N$_2$O$_8$·0.25 H$_2$O: 73.59 C, 5.98H, 3.58N. Found: C, 73.46; H, 5.94; N, 3.48.

EXAMPLE 92

(1α,2β,3β,4α)-1,2-Di[N-propyl-N-(4-phenoxybenzyl)aminocarbonyl]cyclobutane-3-[N-(5-tetrazolyl)]carboxamide-4-carboxylic acid

EXAMPLE 92A

Methyl (1α,2β,3β,4α)-1,2-Di[N-propyl-N-(4-phenoxybenzyl)aminocarbonyl]cyclobutane-3-[N-(5-tetrazolyl)]carboxamide-4-carboxylate To the compound resulting from Example 95 (118 mg, 0.17 mmol) dissolved in THF (0.8 mL) was added carbonyl diimidazole (28 mg, 0.17 mmol). The reaction was heated under reflux for 1.5 hours, and then anhydrous 5-aminotetrazole (22 mg, 0.26 mmol) was added, and the reflux was continued for another 2.5 hours. After cooling to room temperature, ice and 3N HCl were added, followed by extraction with EtOAc. The combined organic extracts were washed with brine, dried over Na$_2$SO$_4$, and concentrated under reduced pressure. The residue obtained was purified by chromatography eluting with 98.75:1.25:0.5 CHCl$_3$—MeOH—CH$_3$CO$_2$H to afford 50 mg (38%) of the title compound as a glass. MS (FAB+) m/e 760 (M+H)$^+$.

EXAMPLE 92B (1α,2β,3β,4α)-1,2-Di[N-propyl-N-(4-phenoxybenzyl)aminocarbonyl]cyclobutane-3-[N-(5-tetrazolyl)]carboxamide-4-carboxylic acid To the compound resulting from Example 92A (47 mg, 0.062 mmol) dissolved in MeOH (1.2 mL) and cooled to 0° C. was added a solution of lithium hydroxide monohydrate (11 mg, 0.26 mmol) in water (0.3 mL). The reaction was stirred at 0°–10° C. under N$_2$ for 1.5 hours, then warmed at room temperature for 3 hours. The reaction mixture was partitioned between EtOAc and 1M H$_3$PO$_4$, and the organic phase was washed with brine, dried over Na$_2$SO$_4$, and concentrated under reduced pressure. The residue obtained was purified by chromatography eluting with 97.5:2.5:0.5 CHCl$_3$—MeOH—CH$_3$CO$_2$H to afford a glass that was treated as in Example 81B to give 20 mg (44%) of the title compound as a white solid. $^1$H NMR (DMSO-d$_6$) δ7.39, 7.28, 7.13, 7.00 (all m, total 18H), 6.63 (m, 1H), 4.75, 4.33 (both m, total 4H), 4.00, 3.75 (both m, total 4H), 3.60–2.60 (envelope, total 4H), 1.50, 1.15 (both m, total 4H), 0.83, 0.55 (both m, total 6H). MS (FAB+) (M+H)$^+$746. Anal cald for C$_{41}$H$_{43}$N$_7$O$_7$·1.0 H$_2$O: C, 64.47; H, 5.94; N, 12.84. Found: C, 64.59; H, 6.00; N, 12.60.

EXAMPLE 93

(1α,2β,3β,4α)-1,2-Di[N-propyl-N-(4-phenoxybenzyl)aminocarbonyl]cyclobutane-3-(N-(5-tetrazolyl)aminocarbonylamino)-4-carboxylic acid

EXAMPLE 93A

Methyl (1α,2β,3β,4α)-1,2-Di[N-propyl-N-(4-phenoxybenzyl)aminocarbonyl]cyclobutane-3-(N-(5-tetrazolyl)aminocarbonylamino)-4-carboxylate To the compound resulting from Example 95 (212 mg, 0.30 mmol) dissolved in toluene (3 mL) was added triethylamine (0.42 mL, 31 mg, 0.30 mmol) and diphenylphosphorylazide (0.72 mL, 92 mg, 0.33 mmol). After stirring at 65° C. under N$_2$ for 2.25 hours, anhydrous 5-aminotetrazole (255 mg, 3.00 mmol) was added and stirring was continued at 90° C. under N$_2$ overnight. The reaction was diluted with EtOAc, washed with 1M H$_3$PO$_4$ and brine, then dried over Na$_2$SO$_4$. After filtration and evaporation, the residue was purified by chromatography using 98.75:1.25:0.5 CHCl$_3$—MeOH—CH$_3$CO$_2$H to afford 50 mg (21%) of the title compound as a glass. MS (FAB+) (M+H)$^+$775.

EXAMPLE 93B (1α,2β,3β,4α)-1,2-Di[N-propyl-N-(4-phenoxybenzyl)aminocarbonyl]cyclobutane-3-(N-(5-tetrazolyl)aminocarbonylamino)-4-carboxylic acid Using the compound resulting from Example 93A and the procedures described in Example 82B, except the reaction was run at room temperature overnight and the chromatography used 97:3:1 CHCl$_3$—MeOH—CH$_3$CO$_2$H, afforded the title compound. $^1$H NMR (DMSO-d$_6$) was consistent with expected structure. MS (FAB$^+$) (M+H)$^+$761. Anal cald for C$_{41}$H$_{44}$N$_8$O$_7$·1.25 H$_2$O: C, 62.87; H, 5.98; N, 14.30. Found: C, 62.61; H, 5.80; N, 14.06.

EXAMPLE 94

(1α,2β,3β,4α)-1,2-Di[N-propyl-N-(4-phenoxybenzyl)aminocarbonyl]cyclobutane-3,4-dicarboxylic acid Dimethyl Ester The resultant acid from Example 17 (268 mg, 0.395 mmol) in dichloromethane (5 mL) was treated with an excess of an ether solution of diazomethane. Evaporation of the solvent afforded 283 mg (100%) of the title compound as an oil. $^1$H NMR (CDCl$_3$, 300 MHz) δ7.40–6.87 (m, 18H), 4.83, 4.81, 4.64, 4.57, 4.34, 4.22 (6 d, total 4H), 4.20–4.08, 3.97–3.81 (2 m, total 4H), 3.72, 3.69, 3.53, 3.52 (4 s, total 6H), 3.63–3.43, 3.35–3.17, 3.17–3.01, 3.01–2.86 (4 m, total 4H), 1.68–1.48 (m, 4H), 0.97–0.78 (m, 6H).

EXAMPLE 95

(1α,2β,3β,4α)-1,2-Di[N-propyl-N-(4-phenoxybenzyl)aminocarbonyl]-3-(methoxycarbonyl)cyclobutane-4-carboxylic Acid The resultant acid from Example 17 (10.97 g, 16.16 mmol) in dichloromethane was treated with an excess of an ether solution of diazomethane. The solvent was evaporated, and the residue was dissolved in a mixture of tetrahydrofuran (135 mL) and methanol (20 mL) and cooled to −10° C. A cold solution of LiOH monohydrate (680 mg, 16.2 mmol) in water (45 mL) was added, and the reaction was stirred at −10° to 0° C. for 3 hours and then was placed in a −20° C. freezer overnight. The reaction was quenched with 2M HCl and concentrated. The residue was dissolved in ethyl acetate, washed with brine, dried over Na$_2$SO$_4$ and evaporated. Chromatography of the residue on silica gel with 2–4% methanol in chloroform afforded 5.56 g (50%) of the title compound as a foam. $^1$H NMR (CDCl$_3$, 300 MHz) δ7.40–6.83 (m, 18H), 4.88–3.80 (envelope, 8H), 3.71, 3.68, 3.52, 3.51 (4 s, total 6H), 1.65–1.38 (m, 4H), 0.94–0.75 (m, 6H). Anal calcd for C$_{41}$H$_{44}$N$_2$O$_8$·0.5 H$_2$O: C, 70.17; H, 6.46; N, 3.99. Found: C, 69.82; H, 6.28; N, 4.01.

EXAMPLE 96

(1α,2β,3α,4α)-1,2-Di[N-propyl-N-(4-phenoxybenzyl)aminocarbonyl]cyclobutane-3,4-dicarboxylic Acid

EXAMPLE 96A (1α,2β,3α,4α)-1,2-Di[N-propyl-N-(4-phenoxybenzyl)aminocarbonyl]-3-(methoxycarbonyl)cyclobutane-4-carboxylic Acid To diisopropylamine (36 μL, 0.26 mmol) in tetrahydrofuran (1 mL) at −78° C. was added n-BuLi (110 μL, 0.237 mmol, 2.15M in hexane). After 10 minutes the resultant compound from Example 95 (70.1 mg, 0.101 mmol) in tetrahydrofuran (1 mL) was added. After 20 minutes at −78° C., acetic acid (60 μL) in tetrahydrofuran (1 mL) was added, the solvent was evaporated, and the residue was partitioned between chloroform and a 2:1 mixture of brine and 2M HCl. The mixture was extracted with chloroform which was dried over $Na_2SO_4$ and evaporated to afford 71.2 mg of a mixture of the title compound and the starting monoester. $^1H$ NMR $\delta(CDCl_3$, 300 MHz) 3.655, 3.650, 3.595, 3.590 (title compound) and 3.71, 3.68, 3.52, 3.51 (starting monoacid) (8 s, total 6H).

EXAMPLE 96B (1α,2β,3α,4α)-1,2-Di[N-propyl-N-(4-phenoxybenzyl)aminocarbonyl]cyclobutane-3,4-dicarboxylic Acid To the resultant compound mixture from Example 96A (64.3 mg, 0.093 mmol) in tetrahydrofuran (1.5 mL) at 0° C. was added LiOH monohydrate (14 mg, 0.33 mmol) in water (0.5 mL). After 2 hours at 0° C. and 1 hour at ambient temperature the reaction was quenched with a 1:1 mixture of brine and 2M HCl. The mixture was extracted with chloroform which was dried over $Na_2SO_4$ and evaporated to afford 59.4 mg of a mixture of the title compound and the resultant compound from Example 17. Separation by reverse-phase HPLC (60% $CH_3CN$/40% $H_2O$/0.1% trifluoroacetic acid mobile eluent) afforded 23.9 mg of the title compound. $^1H$ NMR $\delta(D_6$-DMSO, 300 MHz) 7.40–7.30, 7.20–7.06, 7.02–6.91, 6.91–6.82 (4 m, total 18H), 5.15–4.98, 4.78–4.53, 4.45–4.30, 4.27–4.08 (4 m, total 4H).

EXAMPLE 97

(1α,2β,3α,4β)-1,2-Di[N-propyl-N-(4-phenoxybenzyl)aminocarbonyl]cyclobutane-3,4-dicarboxylic Acid Sodium methoxide in methanol (2 mL of 27.4 mg Na in 10 mL methanol) was added to the resultant compound from Example 94 (70.3 mg, 0.099 mmol), and the mixture was heated at reflux for 18 hours. The mixture was diluted with ethyl acetate, washed with 2M HCl and brine, and then was dried over $Na_2SO_4$ and evaporated to afford 60.9 mg (87%) of an oil. This material was dissolved in methanol (2 mL) and treated with 1M NaOH (0.5 mL). After 5 hours at ambient temperature, the solvent was evaporated, and the residue was partitioned between chloroform and a 2:1 mixture of brine and 2M HCl. The mixture was extracted with chloroform which was dried over $Na_2SO_4$ and evaporated. Recrystallization of the residue from a mixture of ethyl acetate and hexane afforded 42.3 mg (63%) of the title compound as a white solid. $^1H$ NMR ($D_6$-DMSO, 150° C., 300 MHz) δ7.40–6.90 (envelope, 18H), 4.55 (d, 2H), 4.44 (d, 2H), 3.76 (d, 2H), 3.36 (d, 2H), 3.21 (t, 4H), 1.53–1.40 (m, 4H), 0.80 (t, 6H). Anal calcd for $C_{40}H_{42}N_2O_8$: C, 70.78; H, 6.24; N, 4.13. Found: C, 70.66; H, 6.20; N, 4.07.

EXAMPLE 98

(1α,2β,3β,4α)-1,2-Di[N-propyl-N-(4-phenoxybenzyl)aminocarbonyl]-3-[(hydroxyamino)carbonyl]cyclobutane-4-carboxylic acid

EXAMPLE 98A (1α,2β,3β,4α)-3-(Benzyloxyamino)carbonyl-1,2-di[N-propyl-N-(4-phenoxybenzyl)aminocarbonyl]-4-(methoxycarbonyl)cyclobutane To the resultant compound from Example 95 (72.5 mg, 0.105 mmol) in dichloromethane (2 mL) at −10° C. was added 4-methylmorpholine (28 μL, 0.26 mmol) followed by isobutylchloroformate (15 μL, 0.11 mmol). After 3 minutes, (O-benzyl)hydroxylamine hydrochloride (20 mg, 0.13 mmol) was added. The reaction was stirred at −10° to 0° C. for 15 minutes and then at ambient temperature for 2 hours. The mixture was diluted with ethyl acetate and washed sequentially with 2M HCl, saturated $NaHCO_3$ solution and brine, dried over $Na_2SO_4$ and evaporated. Chromatography of the residue on silica gel with 50% ethyl acetate in hexane afforded 67.1 mg (80%) of the title compound. $^1H$ NMR ($CDCl_3$, 300 MHz) δ7.45–6.85 (m, 23H), 5.43–4.70 (m, 2H), 3.67, 3.62, 3.53, 3.51 (4 s, total 3H).

EXAMPLE 98B (1α,2β,3β,4α)-1,2-Di[N-propyl-N-(4-phenoxybenzyl)aminocarbonyl]-3-(hydroxyamino)carbonyl-4-(methoxycarbonyl)cyclobutane The resultant compound from Example 98A (65.0 mg, 0.081 mmol) and 10% Pd/C (51 mg) in ethyl acetate (2 mL) were stirred under a hydrogen atmosphere for 4 hours. The mixture was filtered and evaporated to afford 51.7 mg (90%) of the title compound as a foam. $^1H$ NMR ($CDCl_3$, 300 MHz) δ7.40–6.77 (m, 19H), 4.85–4.22 (m, 4H), 4.22–3.70 (m, 4H), 3.69, 3.66, 3.55, 3.53 (4 s, total 3H), 3.60–2.90 (envelope, 4H), 1.65–1.30 (m, 4H), 0.93–0.75 (m, 6H).

EXAMPLE 98C (1α,2β,3β,4α)-1,2-Di[N-propyl-N-(4-phenoxybenzyl)aminocarbonyl]-3-[(hydroxyamino)carbonyl]cyclobutane-4-carboxylic Acid To the resultant compound mixture from Example 98B (48.9 mg, 0.069 mmol) in tetrahydrofuran (1.5 mL) at 0° C. was added LiOH monohydrate (11.0 mg, 0.26 mmol) in water (0.5 mL). After 1 hour at 0° C. the reaction was quenched with 2M HCl and concentrated. The residue was dissolved in ethyl acetate, washed with a 1:1 mixture of brine and 2M HCl and then brine, dried over $Na_2SO_4$ and evaporated. The residue was dissolved in dichloromethane which was made turbid with hexane and evaporated to afford 45.8 mg (96%) of the title product as a foam. $^1H$ NMR ($CDCl_3$, 300 MHz) δ7.45–6.75 (m, 19H), 4.85–2.65 (envelope, 12H), 1.60–1.25 (m, 4H), 0.90–0.65 (m, 6H). Anal calcd for $C_{40}H_{43}N_3O_8$: C, 69.25; H, 6.25; N, 6.06. Found: C, 69.25; H, 6.47; N, 5.79.

EXAMPLE 99

(1α,2β,3β,4α)-3-(Amino)carbonyl-1,2-di[N-propyl-N-(4-phenoxybenzyl)aminocarbonyl]cyclobutane-4-carboxylic acid

EXAMPLE 99A (1α,2β,3β,4α)-3-(Amino)carbonyl-1,2-di[N-propyl-N-(4-phenoxybenzyl)aminocarbonyl]-4-(methoxycarbonyl)cyclobutane Using the procedure of Example 98A but replacing (O-benzyl)hydroxylamine hydrochloride with concentrated aqueous $NH_4OH$ gave, after chromatography on silica gel with 80% ethyl acetate in hexane, the title compound in 89% yield as a foam. $^1H$ NMR ($CDCl_3$, 300 MHz) δ7.25–6.72 (m, 18H), 6.32–6.05, 5.29–5.08 (2 br, total 2H), 4.80, 4.75, 4.65, 4.58, 4.45, 4.38, 4.35–4.25 (6 d, 1 m, total 4H), 4.16–3.92 (m, 4H), 3.75, 3.73, 3.62 (3 s, total 3H), 3.75–2.90 (envelope, total 4H), 1.70–1.35 (m, 4H), 0.95–0.75 (m, 6H).

EXAMPLE 99B (1α,2β,3β,4α)-3-(Amino)carbonyl-1,2-di[N-propyl-N-(4-phenoxybenzyl)aminocarbonyl]cyclobutane-4-carboxylic Acid Using the procedure of Example 98C with the resultant compound from Example 99A afforded the title compound in 100% yield as a foam. $^1$H NMR (CDCl$_3$, 300 MHz) δ7.40–6.85 (m, 18H), 6.50–6.20, 5.60–5.40 (2 br, total 2H), 4.82–4.15 (envelope, total 4H), 4.15–3.90 (m, 4H), 3.75–2.90 (envelope, total 4H), 1.70–1.35 (m, 4H), 0.95–0.72 (m, 6H). Anal calcd for C$_{40}$H$_{43}$N$_3$O$_7$.0.4 hexane: C, 71.52; H, 6.89; N, 5.89. Found: C, 71.26; H, 6.91; N, 5.57.

EXAMPLE 100

(1α,2β,3β,4α)-1,2-Di[N-propyl-N-(4-phenoxybenzyl)aminocarbonyl]-3-(trifluoromethanesulfonylamino)cyclobutane-4-carboxylic acid

EXAMPLE 100A (1α,2β,3β,4α)-3-(tert-Butyloxycarbonylamino)-1,2-di[N-propyl-N-(4-phenoxybenzyl)aminocarbonyl]-4-(methoxycarbonyl)cyclobutane The resultant compound from Example 95 (147.5 mg, 0.213 mmol) in toluene (2 mL) was treated with triethylamine (30 μL, 0.21 mmol) and diphenylphosphoryl azide (50 μL, 0.23 mmol) and then was heated to 65°–70° C. for 2 hours. tert-Butanol (200 μL, 2.1 mmol) was added, and the reaction was stirred at 90° C. for 90 hours. The mixture was diluted with ethyl acetate, washed sequentially with 2M HCl, saturated NaHCO$_3$ solution and brine, dried over Na$_2$SO$_4$ and evaporated. Chromatography of the residue on silica gel with 25–30% ethyl acetate in hexane afforded 64.0 mg (39%) of the title compound as a foam. $^1$H NMR (CDCl$_3$, 300 MHz) δ7.47–6.87 (m, 18H), 5.40–2.90 (envelope, total 13H), 3.71, 3.69, 3.56 (3 s, total 3H), 1.63–1.30 (m, 4H), 1.54, 1.53, 1.45 (3 s, total 9H), 0.95–0.77 (m, 6H).

EXAMPLE 100B (1α,2β,3β,4α)-1,2-Di[N-propyl-N-(4-phenoxybenzyl)aminocarbonyl]-4-methoxycarbonyl-3-[(trifluoromethanesulfonyl)amino]cyclobutane The resultant compound from Example 100A (62.0 mg, 0.081 mmol) was stirred for 1 hour in 4M HCl in dioxane and evaporated. The residue was dissolved in dichloromethane, treated with triethylamine (25 μL) and applied directly to the top of a silica gel column which was eluted with ethyl acetate to afford 44.5 mg (83%) of the primary amine as a foam. To this compound (44.5 mg, 0.067 mmol) in dichloromethane (2 mL) at −78° C. was added triethylamine (10 μL, 0.071 mmol) and trifluoromethanesulfonic anhydride (12 μL, 0.071 mmol). After 1 hour, the reaction was warmed to ambient temperature and applied directly to the top of a silica gel column which was eluted with 25% ethyl acetate in hexane to afford 39.0 mg (73%) of the title compound as a foam. $^1$H NMR (CDCl$_3$, 300 MHz) δ7.45–6.85 (m, 18H), 5.00–2.87 (envelope, total 12H), 3.75, 3.72, 3.56, 3.54 (4 s, total 3H), 1.70–1.37 (m, 4H), 0.95–0.75 (m, 6H).

EXAMPLE 100C (1α,2β,3β,4α)-1,2-Di[N-propyl-N-(4-phenoxybenzyl)aminocarbonyl]-3-[(trifluoromethanesulfonyl)amino]cyclobutane-4-carboxylic Acid Using the hydrolysis procedure of Example 97 with the resultant compound from Example 100B afforded the title compound in 100% yield as a glass. $^1$H NMR (CDCl$_3$, 300 MHz) δ7.40–6.80 (m, 18H), 5.02–2.90 (envelope, total 12H), 1.70–1.35 (m, 4H), 0.95–0.75 (m, 6H). Anal calcd for C$_{40}$H$_{42}$N$_3$O$_8$F$_3$S.0.25 H$_2$O: C, 61.10; H, 5.45; N, 5.34. Found: C, 60.991; H, 5.13; N, 5.13.

EXAMPLE 101

(1α,2β,3β,4α)-4-(Carboxy)methyl)-1,2-di[N-propyl-N-(4-phenoxybenzyl)aminocarbonyl]cyclobutane-3-carboxylic acid

EXAMPLE 101A (1α,2β,3β,4α)-1,2-Di[N-propyl-N-(4-phenoxybenzyl)aminocarbonyl]-3-diazoacetyl-4-(methoxycarbonyl)cyclobutane To the resultant compound from Example 95 (259 mg, 0.374 mmol) in dichloromethane (3 mL) at −10° C. was added 4-methylmorpholine (50 μL, 0.46 mmol) followed by isobutylchloroformate (54 μL, 0.41 mmol). After 3 minutes, an excess of an ether solution of diazomethane was added. The reaction was warmed from −10° to 10° C. over 3 hours. The mixture was washed with saturated NaHCO$_3$ solution and brine, dried over Na$_2$SO$_4$ and evaporated. Chromatography of the residue on silica gel with 40% ethyl acetate in hexane afforded 213 mg (80%) of the title compound as a pale yellow foam. $^1$H NMR (CDCl$_3$, 300 MHz) δ7.39–6.87 (m, 18H), 5.47, 5.43, 5.33, 5.29 (4 s, total 1H), 4.98–2.90 (envelope, total 12H), 3.72, 3.71, 3.562, 3.560 (4 s, total 3H), 1.67–1.40 (m, 4H), 0.95–0.76 (m, 6H).

EXAMPLE 101B (1α,2β,3β,4α)-1,2-Di[N-propyl-N-(4-phenoxybenzyl)aminocarbonyl]-3-methoxycarbonyl-4-(methoxycarbonylmethyl)cyclobutane The resultant compound from Example 101A (210 mg, 0.293 mmol) in methanol (2 mL) was treated with a solution of silver benzoate in triethylamine (50 μL of 50 mg AgOBn in 1.0 mL triethylamine). After 1 hour, the solvent was evaporated, and the residue was chromatographed on silica gel with 25% ethyl acetate in hexane to afford 174 mg (82%) of the title compound as an oil. $^1$H NMR (CDCl$_3$, 300 MHz) δ7.40–6.87 (m, 18H), 4.98–4.05 (envelope, total 8H), 3.71, 3.68, 3.65, 3.64, 3.542, 3.540, 3.52, 3.51 (8 s, total 6H), 3.60–2.75 (envelope, total 4H), 2.62–2.38 (m, 2H), 1.69–1.39 (m, 4H), 0.97–0.78 (m, 6H).

EXAMPLE 101C (1α,2β,3β,4α)-4-(Carboxy)methyl)1,2-di[N-propyl-N-(4-phenoxybenzyl)aminocarbonyl]cyclobutane-3-carboxylic Acid Using the procedure of Example 98C with the resultant compound from Example 101B afforded the title compound in 100% yield as a foam. $^1$H NMR (CDCl$_3$, 300 MHz) δ7.47–6.82 (m, 18H), 4.88–2.78 (envelope, total 12H), 2.68–2.25 (m, 2H), 1.65–1.35 (m, 4H), 0.95–0.72 (m, 6H). Anal calcd for C$_{41}$H$_{44}$N$_2$O$_8$: C, 71.08; H, 6.40; N, 4.04. Found: C, 71.31; H, 6.55; N, 3.73.

EXAMPLE 102

(1α,2β,3β,4α)-3,4-Bis(diazoacetyl)-1,2-di[N-propyl-N-(4-phenoxybenzyl)aminocarbonyl]cyclobutane To the resultant compound from Example 17 (202 mg, 0.298 mmol) in dichloromethane (2 mL) at −10° C. was added 4-methylmorpholine (75 μL, 0.68 mmol) followed by isobutylchloroformate (85 μL, 0.65 mmol). After 4 minutes, an excess of an ether solution of diazomethane was added. The reaction was warmed from $-10°$ to $10°$ C. over 3 hours. The mixture was washed with saturated $NaHCO_3$ solution and brine, dried over $Na_2SO_4$ and evaporated. Chromatography of the residue on silica gel with 50% ethyl acetate in hexane afforded 130 mg (60%) of the title compound as a yellow foam. $^1$H NMR ($CDCl_3$, 300 MHz) $\delta$7.38–6.88 (m, 18H), 5.28, 5.23, 5.15, 5.12 (4 s, total 2H), 4.98–3.84 (envelope, total 8H), 3.65–2.97 (envelope, total 4H), 1.68–1.45 (m, 4H), 0.97–0.79 (m, 6H).

EXAMPLE 103

(1α,2β,3β,4α)-1,2-Di[-N-propyl-N-(4-phenoxybenzyl)aminocarbonyl]cyclobutane-3,4-diacetic acid

EXAMPLE 103A (1α,2β,3β,4α)-1,2-di[N-propyl-N-(4-phenoxybenzyl)aminocarbonyl]-cyclobutane-3,4-diacetic acid dimethyl ester The resultant compound from Example 102 (120 mg, 0.165 mmol) in methanol (2 mL) was treated with a solution of silver benzoate in triethylamine (50 μL of 50 mg AgOBn in 1.0 mL triethylamine). After 2 hours, the solvent was evaporated, and the residue was chromatographed on silica gel with 25% ethyl acetate in hexane to afford 90.6 mg (75%) of the title compound as an oil. $^1$H NMR ($CDCl_3$, 300 MHz) $\delta$7.40–6.87 (m, 18H), 4.97–4.87, 4.73–4.62, 4.25–4.05 (3 m, total 8H), 3.66, 3.64, 3.55 (3 s, total 6H), 3.73–3.54, 3.32–3.15, 3.08–2.95, 2.85–2.35 (4 m, total 8H), 1.72–1.42 (m, 4H), 0.98–0.78 (m, 6H).

EXAMPLE 103B (1α,2β,3β,4α)-1,2-Di[-N-propyl-N-(4-phenoxybenzyl)aminocarbonyl]cyclobutane-3,4-diacetic acid To the resultant compound from Example 103A (87.8 mg, 0.119 mmol) in methanol (1.5 mL) and tetrahydrofuran was added 1M NaOH (0.5 mL). After 15 hours the reaction was quenched with 2M HCl and concentrated. The residue was dissolved in ethyl acetate and washed with a 1:1 mixture of brine and 2M HCl and then brine, dried over $Na_2SO_4$ and evaporated to afford 88 mg (100%) of the final product as a foam. $^1$H NMR ($CDCl_3$, 300 MHz) $\delta$7.37–6.90 (m, 18H), 4.97–4.89, 4.62–4.54, 4.35–4.23, 4.20–4.10, 3.68–3.58, 3.21–3.04, 2.96–2.51, 2.32–2.22, 2.19–2.08 (multiplets, total 16H), 1.76–1.46 (m, 4H), 0.98–0.82 (m, 6H). Anal calcd for $C_{42}H_{46}N_2O_8$: C, 71.37; H, 6.56; N, 3.96. Found: C, 71.09; H, 6.83; N, 3.70.

EXAMPLES 104A and 104B (1α,2β,3β,4α)-1,2-Di[N-propyl-N-(4-phenoxybenzyl)aminocarbonyl]cyclobutane-3,4-dicarboxylic acid Mono-Norleucine Amide The resultant compound from Example 95 (100 mg, 0.144 mmol), d,l-Norleucine-OMe hydrochloride (35.0 mg, 0.193 mmol), 1-hydroxybenzotriazole (53.0 mg, 0.392 mmol) and 4-methylmorpholine (35 μL, 0.32 mmol) in dimethylformamide (1.5 mL) at $-10°$ C. were treated with 1-(3-dimethylaminopropyl)-3-ethylcarbodiimide hydrochloride (40 mg, 0.21 mmol). After 2 hours the cooling bath was removed, and the reaction was stirred at ambient temperature for 14 hours. The mixture was poured into saturated $NaHCO_3$ solution and extracted into ethyl acetate which was washed with water and brine, dried over $Na_2SO_4$ and evaporated. Chromatography of the residue on silica gel with 30–35% ethyl acetate in hexane afforded two monoesters, diastereomeric at the leucine α-carbon, in 89% total yield. Each was hydrolyzed according to the procedure of Example 98C to afford the title compounds. Anal calcd for 104A $C_{46}H_{53}N_3O_9$: C, 69.76; H, 6.75; N, 5.31. Found: C, 69.73; H, 6.69; N, 5.10. Anal calcd for 104B $C_{46}H_{53}N_3O_9 \cdot 0.3\ H_2O$: C, 69.29; H, 6.76; N, 5.27. Found: C, 68.90; H, 6.85; N, 5.04.

EXAMPLE 105–113

The following compounds were prepared according to the method of Example 104.

EXAMPLE 105A (1α,2β,3β,4α)-1,2-Di[N-propyl-N-(4-phenoxybenzyl)aminocarbonyl]cyclobutane-3-phenoxycarbonyl-4-carboxylic acid Anal calcd for $C_{49}H_{51}N_3O_9$: C, 71.26; H, 6.22; N, 5.09. Found: C, 70.99; H, 6.32; N, 4.86.

EXAMPLE 105B (1α,2β,3β,4α)-1,2-Di[N-propyl-N-(4-phenoxybenzyl)aminocarbonyl]cyclobutane-3-phenoxycarbonyl-4-carboxylic acid Anal calcd for $C_{49}H_{51}N_3O_9 \cdot 0.5\ H_2O$: C, 70.49; H, 6.28; N, 5.03. Found: C, 70.33; H, 6.33; N, 4.85.

EXAMPLE 106

(1α,2β,3β,4α)-1,2-Di[N-propyl-N-(4-phenoxybenzyl)aminocarbonyl]cyclobutane-3,4-dicarboxylic acid mono-Glycine amide Anal calcd for $C_{42}H_{45}N_3O_9 \cdot 0.25\ H_2O$: C, 68.14; H, 6.19; N, 5.66. Found: C, 68.28; H, 6.16; N, 5.28.

EXAMPLE 107

(1α,2β,3β,4α)-1,2-Di[N-propyl-N-(4-phenoxybenzyl)aminocarbonyl]cyclobutane-3,4-dicarboxylic acid mono-d,l-Proline amide

EXAMPLE 108

(1α,2β,3β,4α)-1,2-Di[N-propyl-N-(4-phenoxybenzyl)aminocarbonyl]cyclobutane-3,4-dicarboxylic acid mono-Sarcosine amide Anal calcd for $C_{43}H_{47}N_3O_9 \cdot 0.25\ H_2O$: C, 68.47; H, 6.35; N, 5.57. Found: C, 68.27; H, 6.19; N, 5.39.

EXAMPLE 109

(1α,2β,3β,4α)-1,2-Di[N-propyl-N-(4-phenoxybenzyl)aminocarbonyl]cyclobutane-3,4-dicarboxylic acid mono-d,l-Aspartic acid amide Anal calcd for $C_{44}H_{47}N_3O_{11} \cdot 0.5\ H_2O$: C, 65.82; H, 6.03; N, 5.23. Found: C, 65.66; H, 6.00; N, 4.94.

EXAMPLE 110A (1α,2β,3β,4α)-1,2-Di[N-propyl-N-(4-phenoxybenzyl)aminocarbonyl]cyclobutane-3,4-dicarboxylic acid mono-Serine amide Anal calcd for $C_{43}H_{47}N_3O_{10} \cdot 0.75\ H_2O$: C, 66.27; H, 6.27; N, 5.39. Found: C, 66.00; H, 6.20; N, 5.13.

EXAMPLE 110B (1α,2β,3β,4α)-1,2-Di[N-propyl-N-(4-phenoxybenzyl)aminocarbonyl]cyclobutane-3,4-dicarboxylic acid mono-Serine amide Anal calcd for $C_{43}H_{47}N_3O_{10} \cdot 0.75\ H_2O$: C, 66.27; H, 6.27; N, 5.39. Found: C, 66.25; H, 6.36; N, 5.16.

EXAMPLE 111

(1α,2β,3β,4α)-1,2-Di[N-propyl-N-(4-phenoxybenzyl)aminocarbonyl]cyclobutane-3,4-dicarboxylic acid mono-β-Alanine amide Anal calcd for $C_{43}H_{47}N_3O_9$: C, 68.88; H, 6.32; N, 5.60. Found: C, 68.49; H, 6.66; N, 5.47.

EXAMPLE 112

(1α,2β,3β,4α)-1,2-Di[N-propyl-N-(4-phenoxybenzyl)aminocarbonyl]cyclobutane-3,4-dicarboxylic acid mono-d-Norleucine amide The title compound was obtained as a single enantiomer. Anal calcd for $C_{52}H_{64}N_4O_{10} \cdot H_2O$: C, 67.65; H, 7.20; N, 6.07. Found: C, 67.60; H, 7.00; N, 5.93.

EXAMPLE 113

(1α,2β,3β,4α)-1,2-Di[N-propyl-N-(4-phenoxybenzyl)aminocarbonyl]cyclobutane-3,4-dicarboxylic acid mono-l-Norleucine amide The title compound was obtained as a single enantiomer. Anal calcd for $C_{52}H_{64}N_4O_{10}$:

EXAMPLE 114

(1α,2β,3β,4α)-1,2-Di[N-(4-pyridyl)methyl-N-(phenoxybenzyl)aminocarbonyl]cyclobutane-3,4-dicarboxylic acid To a slurry of 1,2,3,4-cyclobutanetetracarboxylic dianhydride (0.3 g, 1.5 mmol) in $CH_3CN$ (5 mL) was added N-pyridylmethyl-N-phenoxybenzylamine (0.93 g, 3.21 mmol), prepared by the procedures described in Example 11, in $CH_3CN$ (10 ml). The slurry was stirred for 5 minutes at 20° C. resulting in a homogeneous solution. The solution was stirred 20 hours at 20° C., then concentrated in vacuo to a white foam. The foam was dissolved in 100 mL of ethyl acetate and washed successively with 50 mL 1N $H_3PO_4$ and 10% NaCl, then dried over anhydrous sodium sulfate, filtered and solvent removed in vacuo to afford 1.0 g of a white foamy solid. The crude product containing both isomers was purified by silica gel chromatography eluting with 94:5:1 $CHCl_3$—MeOH—HOAc. The slower moving product was isolated and characterized as the title compound. $^1H$ NMR (DMSO-$d_6$, 500 MHz) δ8.51–8.61 (m, 4H), 7.38–6.87 (m, 24H), 4.65–4.76 (m, 2H), 4.52–4.41(m, 2H), 4.39–4.13 (m, 8H), 3.95–4.05 (m, 2H).

EXAMPLE 115

(1α,2α,3β,4β)-1,2-Di[N-propyl-N-(phenoxybenzyl)aminocarbonyl]cyclobutane-3,4-dicarboxylic acid

EXAMPLE 115A (1α,2α,3β,4β)-1,2-Di-(2-furyl)cyclobutane-3,4-dicarboxylic acid and (1α,2α,3α,4α)-1,2-Di-(2-furyl)cyclobutane-3,4-dicarboxylic acid Furan-2-acrylic acid (2 g, 0.014 mol), freshly recrystallized from ethanol/water, was dissolved in 60 mL $CH_3CN$.

Benzophenone (0.001 mol) was added and the resulting clear solution was bubbled with nitrogen for 30 minutes and during irradiation for 7 hours with a high pressure 450 W Hg lamp. The mixture was cooled to room temperature, and the solvent was evaporated in vacuo leaving a clear yellow oil. The oil was dissolved in 40 mL ethyl ether and washed twice with 50 mL portions of saturated sodium bicarbonate solution. The combined bicarbonate washes were re-acidified to pH 2 and extracted with two 50 mL portions ethyl acetate. The combined organic extracts were washed with 50 mL 10% NaCl solution, dried over anhydrous sodium sulfate, filtered and solvent removed in vacuo leaving 1.5 g yellow oil. The resulting crude yellow oil was dissolved in $CHCl_3$ and purified by silica gel chromatography eluting with 1% MeOH in $CHCl_3$. Two products were isolated and characterized by NMR spectroscopy. The faster moving product obtained in 30% yield was found to be (1α,2α,3β,4β)-1,2-di-(2-furyl)cyclobutane-3,4-dicarboxylic acid. NMR ($CDCl_3$, 300 MHz) δ7.35 (m, 1H), 6.38 (m, 1H), 6.17 (m, 1H), 3.82 (m, 1H, J=10 Hz), 3.58 (m, 1H, J=10 Hz). MS ($DCI/NH_4$) m/e 276. The slower moving product, obtained in 15% yield eluted from the column with 8% MeOH in $CHCl_3$. This product was characterized as (1α,2α,3α,4α)-1,2-di-(2-furyl)cyclobutane-3,4-dicarboxylic acid. NMR ($CDCl_3$, 300 MHz) δ7.48 (m, 1H), 7.20 (m, 1H), 5.94 (m, 1H), 4.24 (m, 1H, J=7 Hz), 3.93 (m, 1H, J=7 Hz). MS ($DCI/NH_4$) m/e 276.

EXAMPLE 115B (1α,2α,3β,4β)-1,2-Di[N-propyl-N-(phenoxybenzyl)aminocarbonyl]cyclobutane-3,4-dicarboxylic acid The (1α,2α,3β,4β)-compound resulting from Example 115A (2 g, 7.2 mmol) was dissolved in 20 mL of DMF and cooled to 0°–5° C. in an ice bath. To this solution was added 4.2 g (15 mmol) of N-propyl-N-4-phenoxybenzylamine hydrochloride in 5 mL DMF, and the salt was neutralized with 2.1 mL (15 mmol) triethylamine. The mixture was stirred 5 minutes then 3.8 g BOP—Cl (15 mmol) was added followed by an additional 2.1 mL of triethylamine. The mixture was stirred 2 hours at 0°–5° C. then warmed to room temperature and stirred another 20 hours at room temperature. When the reaction was deemed complete by TLC analysis, the mixture was diluted with 200 mL ethyl acetate and washed with 2×50 mL 1N $H_3PO_4$, 2×50 mL saturated $NaHCO_3$, and 2×50 mL 10% NaCl. The organic layer was dried over anhydrous $Na_2SO_4$, filtered and concentrated in vacuo leaving 2.8 g (54%) of crude product. The crude product was purified by silica gel chromatography eluting with 3:1 hexane-ethyl acetate yielding (1α,2α,3β,4β)-1,2-di[N-propyl-N-(phenoxybenzyl)aminocarbonyl]-3,4-di(2-furyl)cyclobutane (1.5 g) as a light yellow oil. $^1$NMR ($CDCl_3$, 300 MHz) δ7.37–6.86 (m, 18H), 6.29–6.06 (m, 6H), 4.50–4.61 (m, 4H), 3.81–4.24 (m, 4H), 2.88–3.39 (m , 4H), 1.28–1.73 (m, 0.71–0.87 (m, 6H). MS (FAB$^+$): 723.

The furan groups were converted to carboxylic acids using the procedure described by Danishefsky et al., J. Amer. Chem. Soc., 110 (12), 3929–3940 (1988). The crude product was purified by silica gel chromatography eluting with 94:5:1 $CHCl_3$—MeOH—HOAc to give the title compound (12 mg, 13%). $^1H$ NMR ($CDCl_3$, 500 MHz) δ0.80–0.95 (m, 6H), 1.25–1.70 (m, 4H), 3.08–3.40 (m, 4H), 3.50–3.65 (m, 2H), 3.88–4.05 (m, 2H), 4.20 4.27 (dd, 2H), 4.40–4.65 (m, 2H), 6.87–7.39 (m, 18H). MS (FAB$^+$) m/e 679, (FAB$^-$) m/e 677.

EXAMPLE 116

(1α,2α,3α,4α)-1,2-Di[N-propyl-N-(phenoxybenzyl)aminocarbonyl]cyclobutane-3,4-dicarboxylic acid The (1α,2α,3α,4α)-1,2-di-(2-furyl)cyclobutane-3,4-dicarboxylic acid prepared in Example 115A was coupled with N-propyl-N-4-phenoxybenzylamine and the furan groups converted to carboxylic acids by the procedures described in Example 115B. The crude product was purified by silica gel chromatography eluting with 94:5:1 CHCl$_3$—MeOH—HOAc to give the title compound (10 mg, 7%). $^1$H NMR (DMSO-d$_6$, 500 MHz) δ0.67–0.80 (m, 6H), 1.24–1.45 (m, 4H), 2.90–2.93 (m, 2H), 3.11–3.14 (m, 2H), 3.50–3.59 (m, 2H), 3.74–3.83 (m, 2H), 4.20–4.26 (m, 2H), 4.58–4.63 (m, 2H), 6.84–7.38 (m, 18H). MS (FAB$^+$) m/e 679, (FAB$^-$) m/e 677.

EXAMPLE 117

(1α,2α,3α,4β)-1,2-Di[N-propyl-N-(4-phenoxybenzyl)aminocarbonyl]cyclobutane-3,4-dicarboxylic acid The compound resulting from Example 116 was converted to the mono-ester by the procedure described in Example 95. Equilibration of the mono-ester was carried out by the procedures described in Example 96A substituting LDA for n-BuLi at −78° C. to afford 8 mg (10%) of the title compound. $^1$H NMR (DMSO-d$_6$, 500 MHz) δ0.67–0.80 (m, 6H), 1.24–1.45 (m, 4H),2.90–2.93 (m, 2H), 3.11–3.14 (m, 2H), 3.50–3.59 (m, 2H), 3.83–3.94 (m, 2H), 4.20–4.26 (m, 2H), 4.58–4.63 (m, 2H), 6.84–7.38 (m, 18H). MS (FAB$^+$) m/e 679, (FAB$^-$) m/e 677.

EXAMPLE 118

(1α,2β,3β,4α)-1,2-Di[N-propyl-N-(4-benzoylbenzyl)aminocarbonyl]cyclobutane-3,4-carboxylic acid

EXAMPLE 118A

N-Propyl-N-(4-benzoylbenzyl)amine

A solution of α-bromo-p-benzoyl toluene (2.75 g, 0.01 mol) in benzene (100 mL) was added dropwise over 30–40 minutes to a stirred solution of n-propylamine (10 mL, 0.12 mol) in benzene (50 mL) under a nitrogen atmosphere. After stirring for 4–5 hours at ambient temperature, most of the solvent was removed under reduced pressure. The residue obtained was triturated with ice-water and ether, and basified with dilute aqueous sodium hydroxide. The ether layer was separated, and the aqueous layer was extracted with additional ether. The combined ether extracts were washed with saturated sodium chloride, dried over sodium sulfate, filtered and concentrated in vacuo to give 2.5 g of a yellow liquid. The liquid was taken up in ether, filtered from undissolved impurities, and acidified with HCl in isopropanol. The solid obtained was filtered and recrystallized from methanol-ethyl acetate to give 1.9 g (58%) of the title compound as colorless crystalline flakes. m.p. 193.5°–194.5° C. $^1$H NMR (CDCl$_3$, 300 MHz) δ0.98 (t, 3H), 1.9 (q, 2H), 2.8 (s, 2H), 4.15 (s, 2H), 7.4–7.8 (m, 9H), 10.09 (s, 2H). MS (DCI/NH$_3$) m/e 254 (M+H)$^+$.

EXAMPLE 118B (1α,2β,3β,4α)-1,2-Di[N-propyl-N-(4-benzoylbenzyl)aminocarbonyl]cyclobutane-3,4-carboxylic acid A suspension of the compound resulting from Example 118A (1.45 g, 5 mmol) in acetonitrile (20 mL) containing triethylamine (0.7 mL) was added all at once to a stirred suspension of 1,2,3,4-cyclobutane-tetracarboxylic dianhydride in acetonitrile (20 mL) at 0° C. under nitrogen. The mixture was stirred, and the temperature was slowly allowed to rise to ambient temperature. Stirring was continued for 60 hours, and then the clear reaction mixture was poured onto ice-water containing HCl and extracted with ether. The combined ether extracts were washed with ice-water and saturated aqueous sodium chloride solution, dried over sodium sulfate, filtered and concentrated under reduced pressure to give 1.2 g of a mixture of 1,2- and 1,3-isomers as a solid foam. The foam was purified by chromatography on silica gel eluting with 97:2.5:0.5 chloroform-methanol-acetic acid to give 0.22 g (13%) of the title compound. m.p. 100°–107° C. $^1$H NMR (DMSO-d$_6$, 500 MHz) δ0.8 (m, 6H), 1.5 (m, 4H), 2.85 (m, 1H), 2.35 (s, 4H), 2.7 (m, 2H), 3.1 (m, 1H), 3.8 (d, 1H), 4.0 (d, 1H), 4.4 (m, 2H), 4.9 (m, 2H), 7.3–7.7 (m, 18H). MS (DCI/NH$_3$) m/e 703 (M+H)$^+$.

EXAMPLE 119

(1α,2β,3β,4α)-1,2-Di[N-propyl-N-(4-(3,4-methylenedioxyphenoxy)benzyl)aminocarbonyl]cyclobutane-3,4-carboxylic acid

EXAMPLE 119A 4-(3,4-Methylenedioxyphenoxy)benzaldehyde

A solution of 3,4-methylenedioxy phenol (7.0 g, 50.7 mmol) in anhydrous DMSO was added dropwise over 30 minutes to a stirred suspension of 60% oil dispersion NaH (2.02 g, 50 mmol) in anhydrous DMSO (40 mL) under nitrogen. Following the addition, a solution of p-fluorobenzaldehyde (6.2 g, 0.05 mol) in DMSO (10 mL) was added, and the temperature was slowly raised to 150° C. The temperature was maintained between 130°–160° C. for 1 hour and then allowed to cool to ambient temperature. After 12 hours at ambient temperature, the reaction mixture was poured onto crushed ice-water and made barely acidic with concentrated HCl and extracted with ether. The combined ether extracts were washed successively with cold dilute aqueous sodium hydroxide solution, cold dilute HCl solution, cold water and saturated aqueous sodium chloride solution, dried over sodium sulfate, filtered and evaporated to give a red liquid which solidified. The solid was triturated with boiling n-pentane, filtered and washed with boiling pentane to give 8.2 g (67%) of the title compound. m.p. 67°–70° C. $^1$H NMR (CDCl$_3$, 300 MHz) δ6.0 (s, 2H), 6.6 (m, 2H), 6.8 (d, 1H), 7.04 (m, 2H), 7.84 (m, 2H), 9.92 (s, 1H). MS (DCI/NH$_3$) m/e 243 (M+H)$^+$.

EXAMPLE 119B

N-Propyl-N-[4-(3,4-methylenedioxyphenoxy)benzyl]amine hydrochloride

A mixture of the compound resulting from Example 119A (6.0 g, 24 mmol) and 0.6 g of 10% Pd/C and n-propylamine (9.3 mL) in ethanol (200 mL) was shaken, first for 24 hours at ambient temperature, and then for 48 hours with hydrogen at atmospheric pressure. The reaction mixture was filtered and the filtrate evaporated. The resulting residue was taken up in ether, converted to the hydrochloride salt, which was then decolorized with norite and recrystallized from methanol-ethyl acetate to give 6.2 g (88%) of the title compound as a colorless crystalline solid. m.p. 185°–186° C. $^1$H NMR (CDCl$_3$, 300 MHz) δ0.95 (t, 3H), 1.86 (q, 2H), 2.75 (t, 2H), 3.98 (s, 2H), 5.98 (s, 2H), 6.45 (q, 1H), 6.52 (d, 1H), 6.75 (d, 1H), 6.95 (m, 1H), 7.26 (s, 1H), 7.5 (d, 2H), 9.85 (s, 2H). MS (DCI/NH$_3$) m/e 286 (M+H)$^+$.

EXAMPLE 119C (1α,2β,3β,4α)-1,2-Di[N-propyl-N-(4-(3,4-methylenedioxyphenoxy)benzyl)aminocarbonyl] cyclobutane-3,4-carboxylic acid To a suspension of 1,2,3,4-cyclobutanetetracarboxylic dianhydride (0.98 g, 5 mmol) in acetonitrile (10 mL) was added 1.6 mL (11 mmol) of triethylamine at 0°–5° C. After several minutes, a suspension of the compound resulting from Example 119B (3.23 g, 10 mmol) in acetonitrile (30 mL) and triethylamine (1.6 mL, 11 mmol) was added to the above stirred mixture. The reaction mixture was stirred for 24 hours at ambient temperature and then poured into cold dilute HCl. The acidic solution was extracted with ether, and the combined ether extracts were washed with saturated sodium chloride solution, dried over sodium sulfate and evaporated. The residue obtained was taken up in methylene chloride, filtered and evaporated to give 2.6 g of a mixture of the 1,2- and 1,3-isomers as a solid foam. The foam was chromatographed on silica gel eluting with 97:2.5:0.5 chloroform-methanol-acetic acid to give 0.8 g (21%) of the title compound. m.p. 95°–110° C. $^1$H NMR (DMSO-d$_6$, 500 MHz) δ0.8 (m, 6H), 1.5 (m, 4H), 2.5 (s, 1H), 2.8 (m, 1H), 3.3 (s, 8H), 3.6 (m, 1H), 3.9 (m, 1H), 4.3 (m, 1H), 4.7 (m, 1H), 5.6 (s, 4H), 6.5–7.2 (m, 14H). MS (DCI/NH$_3$) m/e 267 (M+H)$^+$.

EXAMPLE 120

(1α,2β,3β,4α)-1,2-Di[N-methyl-N-(4-phenoxybenzyl)aminocarbonylamino]cyclobutane-3,4-dicarboxylic acid A mixture of 1,2-di[methoxycarbonyl]cyclobutane-3,4-dicarboxylic acid (400 mg, 1.54 mmol), prepared by the procedure described in Angew. Chem. International Ed. vol 8: 208 (1969), diphenylphosphoryl azide (DPPA) (936 mg, 3.4 mmol) and triethylamine (344 mg, 3.4 mmol) in 20 mL of toluene was heated at 80° C. for 3 hours. The mixture was allowed to cool to ambient temperature, and then the compound resulting from Example 1 (700 mg, 3.4 mmol) was added. After stirring at ambient temperature for 16 hours, the mixture was taken up in ethyl acetate and washed with dilute hydrochloric acid, water, saturated sodium bicarbonate solution and saturated sodium chloride solution, dried and filtered. The filtrate was evaporated under reduced pressure to an oily residue which was chromatographed on silica gel eluting with 4:1 ethyl acetate-hexane to give 100 mg (19.2%) of the diester.

To the diester (40 mg, 0.058 mmol) dissolved in 30 mL of methanol was added KOH (33 mg, 0.58 mmol) in 1 mL of water. The clear solution was stirred at ambient temperature for 3 hours and left standing overnight. The methanol was removed under reduced pressure, and the aqueous solution was acidified with sodium hydrogen sulfate. The precipitate formed was filtered, washed with water and dried to give 27 mg of the title compound. m.p. 192°–195° C. (dec). $^1$H NMR δ(DMSO-d$_6$, 300 MHz) δ2.72 (s, 6H), 4.30–4.50 (dd, 4H), 6.90–7.40 (m, 18H).

EXAMPLE 121

(1α,2β,3β,4α)-1,2-Di[N,N-dibenzylaminocarbonyl] cyclobutane-3,4-dicarboxylic acid To a slurry of 1,2,3,4-cyclobutanetetracarboxylic dianhydride (2.7 g, 13.8 mmol) in THF (30 mL) was added N,N-dibenzylamine (5.72 g, 28.9 mmol) in THF (10 mL). The slurry was stirred for 5 minutes at 20° C., whereupon, a homogeneous solution resulted. The resulting solution was stirred for 20 hours at 20° C., then concentrated in vacuo to a white foam. The foam was dissolved in 100 mL of ethyl acetate and washed successively with 50 mL 1N H$_3$PO$_4$ and 10% NaCl, then dried over anhydrous sodium sulfate, filtered and concentrated in vacuo to afford 4.4 g of a white foamy solid. The crude product (2.1 g) containing both isomers was purified by silica gel chromatography eluting with 94:5:1 CHCl$_3$—MeOH—HOAc. The slower moving product was isolated in 22% yield and characterized as the title compound. $^1$H NMR δ(CDCl$_3$, 500 MHz) δ3.98–4.00 (d, 2H), 4.22–4.31 (m, 6H), 4.46–4.49 (d, 2H), 4.73–4.76 (d, 2H), 7.11–7.31 (m, 20H). MS (FAB) m/e 591 (M+H)$^+$.

EXAMPLE 122

(1α,2β,3β,4α)-1,2-Di[N-benzyl-N-(4-chlorobenzyl) aminocarbonyl]cyclobutane-3,4-dicarboxylic acid

EXAMPLE 122A

N-Benzyl-N-(4-chlorobenzyl)amine Hydrochloride

To 4-chlorobenzaldehyde (1.5 g, 10.7 mmol) dissolved in 40 mL CH$_2$Cl$_2$ was added benzylamine (1.15g, 10.7 mmol) followed by 1 mL of 6N HCl. The resulting cloudy solution was stirred overnight at room temperature and then concentrated in vacuo to give a white solid. The solid was immediately dissolved in 50 mL of MeOH and the pH of the solution was adjusted to 6 with glacial acetic acid. To this solution was added NaCNBH$_3$ (0.67 g, 10.7 mol), and the resulting clear solution was stirred three hours at room temperature. The mixture was acidified to pH 2 with 6M HCl whereupon a thick white slurry developed. The solid was stirred for 30 minutes and filtered, yielding the title compound as a white solid. $^1$H NMR δ(DMSO-d$_6$, 300 MHz) δ4.1–4.2 (broad multiplet, 4H), 7.4–7.6 (m, 9H). MS (DCI/NH$_3$) m/e 232 (M+H)$^+$.

EXAMPLE 122B (1α,2β,3β,4α)-1,2-Di[N-benzyl-N-(4-chlorobenzyl) aminocarbonyl]cyclobutane-3,4-dicarboxylic acid To a slurry of 1,2,3,4-cyclobutanetetracarboxylic dianhydride (0.5 g, 2.5 mmol) in DMF (6 mL) was added the compound resulting from Example 122A (1.36 g, 5.1 mmol) in DMF (3 mL) containing Et$_3$N (0.71 mL, 5.1 mmol). The slurry was stirred for 5 minutes at 20° C., whereupon, a homogeneous solution resulted. The resulting solution was stirred 20 hours at 20° C. The solution was diluted with 100 mL of ethyl acetate and washed successively with 50 mL 1N H$_3$PO$_4$ and 10% NaCl, then dried over anhydrous sodium sulfate, filtered and concentrated in vacuo to afford 1.1 g of a white foamy solid. The crude product containing both isomers was purified by silica gel chromatography eluting with 94:5:1 CHCl$_3$—MeOH—HOAc. The slower moving product was isolated in 21% yield and characterized as the title compound. $^1$H NMR δ(DMSO-d$_6$, 300 MHz) δ3.68–3.71 (m, 2H), 3.92–4.06 (m, 4H), 4.13–4.21 (m, 2H), 4.65–4.72 (m, 2H), 4.82–4.92 (m, 2H), 7.14–7.42 (m, 18H), 12.55 (bs, 2H). MS (FAB) m/e 659 (M+H)$^+$.

EXAMPLE 123

Alternate Preparation of (1α,2β,3β,4α)-1,2-Di[N-propyl-N-(4-phenoxybenzyl)aminocarbonyl] cyclobutane-3,4-dicarboxylic acid

EXAMPLE 123A (1α,2β,3β,4α)-1,2-Di(benzyloxycarbonyl) cyclobutane-3,4-dicarboxylic acid To a solution of 1,2,3,4-cyclobutanetetracarboxylic anhydride (21 g, 107.1 mmol) in acetonitrile (530 mL) at −7.5°

C. was added benzyl alcohol (70 mL, 680 mmol) all at once. Triethylamine (30 mL, 210 mmol) was added dropwise over 3–5 minutes and the temperature rose to 2.8° C. Dimethylaminopyridine (1.3 g, 10.6 mmol) was added and the temperature returned to −5° C. The reaction mixture was stirred for 18 hours at which time the internal temperature was 9.2° C. and then concentrated in vacuo. The residue was dissolved in ethyl acetate (1 L) and washed with 2M HCl (2×375 mL). The product was then extracted into saturated NaHCO$_3$ solution (2×375 mL). The aqueous solution was allowed to stand at ambient temperature and then was cooled in a refrigerator overnight. The solid was collected and washed with cold saturated NaHCO$_3$ solution (200 mL) and then was dissolved in water (500 mL), acidified with 2M HCl (375 mL) and extracted into ethyl acetate (2×375 mL). The combined organic extracts were washed with brine, dried over sodium sulfate and concentrated in vacuo to afford the title compound (25.65 g, 58%) as a white solid. m.p. 164.5°–165.5° C.

EXAMPLE 123B (1α,2β,3β,4α)-1,2-Di[N-propyl-N-(4-phenoxybenzyl)aminocarbonyl]cyclobutane-3,4-dicarboxylate dibenzyl ester To the compound resulting from Example 123A (66 mg, 0.15 mmol) slurried in methylene chloride (0.5 mL) was added oxalyl chloride (28 μL, 0.32 mmol) followed by 1 drop DMF. To this solution was added N-propyl-N-(4-phenoxybenzyl)amine (81 mg, 0.34 mmol) and Hunig's base (115 μL, 0.66 mmol) in methylene chloride (0.2 mL). The reaction mixture was stirred at ambient temperature for 1 hour and then diluted with ethyl acetate. The solution was washed 3 times with 1M H$_3$PO$_4$, 3 times with saturated NaHCO$_3$ solution and brine, dried over sodium sulfate and concentrated under reduced pressure. The residue obtained was dissolved in methylene chloride and applied to the top of a silica gel plug which was eluted with 7:3 hexane-ethyl acetate to give the title compound (114 mg, 88%) as an oil.

EXAMPLE 123C (1α,2β,3β,4α)-1,2-Di[N-propyl-N-(4-phenoxybenzyl)aminocarbonyl]cyclobutane-3,4-dicarboxylic acid The compound resulting from Example 123B (100 mg, 0.12 mmol) was dissolved in 1.5 mL 1:1 methanol-ethyl acetate, treated with 9 mg of 10% Pd/C and then hydrogenolyzed under a H2 balloon for 1.5 hours. The catalyst was removed by filtration through Celite and the filtrate concentrated in vacuo to afford the title compound. $^1$H NMR (DMSO-d$_6$, 300 MHz) δ0.80 (m, 6H), 1.46 (m, 4H), 2.70–3.00 (m, 4H), 3.60 (m, 2H), 3.92 (m, 2H), 4.27 (m, 2H), 4.70 (dd, 2H), 6.87–7.43 (m, 18H). MS (FAB) m/e 679 (M+H)$^+$, 701 (M+Na)$^+$.

EXAMPLE 124

(1α,2β,3β,4α)-1,2-Di[(4-phenoxybenzyl)carbonylamino]cyclobutane-3,4-dicarboxylic acid

EXAMPLE 124A

Methyl 1,2-diaminocyclobutane-3,4-dicarboxylate

A mixture of 1,2-di[methoxycarbonyl]cyclobutane-3,4-dicarboxylic acid (500 mg, 1.92 mmol), prepared by the procedure described in Angew. Chem. International Ed. vol 8: 208 (1969), in 20 mL of toluene was treated with 407 mg (4.03 mmol) of triethylamine and 1.11g (4.03 mmol) of diphenylphosphoryl azide. The mixture was warmed to 80° C. under a nitrogen atmosphere for 3 hours. Volatiles were removed under reduced pressure to afford a viscous oil. The oil was dissolved in 20 mL of 2-methyl-2-propanol and stirred for 18 hours. Volatiles were removed under reduced pressure to afford an oil. Purification by flash column chromatography on silica gel eluting with 2:1 hexane-ethyl acetate afforded methyl 1,2-di(Boc-amino)cyclobutane-3,4-dicarboxylate as a white powder (123 mg, 16%. $^1$H NMR (CDCl$_3$) δ1.43 (s, 18H), 3.45–3.52 (m, 1H), 3.75 (s, 6H), 4.52–4.63 (m, 1H), 5.55–5.65 (m, 1H).

A solution of 70 mg (0.17 mmol) of protected diamine prepared above in 3 mL of trifluoroacetic acid was stirred for 3 hours. A 50 mL portion of ethyl ether was added, causing the product to precipitate as a white solid. The solid was collected by filtration and dried, affording 56 mg of the title compound which was used without further purification.

EXAMPLE 124B

Methyl (1α,2β,3β,4α)-1,2-Di[(4-phenoxybenzyl)carbonylamino]cyclobutane-3,4-dicarboxylate A mixture of the compound resulting from Example 124A (56 mg, 0.13 mmol), 4-phenoxyphenylacetic acid (61 mg, 0.27 mmol), 1-(3-dimethylaminopropyl)-3-ethylcarbodiimide. HCl (54 mg, 0.28 mmol), 1-hydroxybenzotriazole hydrate (38 mg, 0.28 mmol), and 59 mg (0.59 mmol) of triethylamine in 5 mL of dry tetrahydrofuran was stirred under an atmosphere of nitrogen for 3 days. A 50 mL portion of water was added, and the mixture was extracted with three 50 mL portions of ethyl acetate. The combined extracts were dried (MgSO$_4$), and all volatiles were removed under reduced pressure to afford an oil. Purification of the oil by flash column chromatography on silica gel eluting with 2:1 hexane-ethyl acetate afforded 60 mg (75%) of the title compound as a clear colorless oil that solidified on standing. MS (FAB) m/e 623 (M+H)$^+$.

EXAMPLE 124C (1α,2β,3β,4α)-1,2-Di[(4-phenoxybenzyl)carbonylamino]cyclobutane-3,4-dicarboxylic acid A mixture of 60 mg (0.097 mmol) of the compound resulting from Example 124B in 3 mL of methanol was treated with 0.5 mL of a 50% aqueous solution of sodium hydroxide. After 3 hours the mixture was treated with concentrated HCl until the mixture was acidic. All volatiles were removed under reduced pressure to afford a solid. The solid was washed with water and dried, affording 25 mg (42%) of the title compound as a white powder. MS (FAB) m/e 595 (M+H)$^+$.

EXAMPLE 125

(1α,2β,3β,4α)-1,2-Di[(N-propyl-N-(4-phenoxybenzyl)carbonylamino]cyclobutane-3,4-dicarboxylic acid The compound resulting from Example 124A is reacted with propionyl chloride in the presence of triethylamine to give methyl 1,2-di(propionylamino)cyclobutane- 3,4-dicarboxylate. Reduction of the diamide with borane-tetrahydrofuran complex at 0° C. affords methyl 1,2-di(n-propylamino)cyclobutane-3,4-dicarboxylate. Treatment of this secondary amine with the acid chloride of 4-phenoxyphenylacetic acid in the presence of triethylamine yields methyl1,2-di[(N-propyl-N-(4-phenoxybenzyl) carbonylamino]cyclobutane-3,4-dicarboxylate. Hydrolysis of the methyl esters with aqueous sodium hydroxide affords the title compound.

EXAMPLE 126

(1α,2β,3β,4α)-1,2-Di-[N-propyl-N-(4-phenoxybenzyl)aminocarbonyl]-3,4-bis (tetrazolylmethyl)cyclobutane

EXAMPLE 126A (1α,2β,3β,4α)-1,2-Di-(benzyloxycarbonyl)-3,4-bis (hydroxymethyl)cyclobutane To the compound resulting from Example 123A (2.06 g, 5 mmol) dissolved in THF (3 mL) at −10° C. was added $BH_3$ (1.0M in THF, 11 mL, 11 mmol) at such a rate so as to maintain the internal temperature below 0° C. The mixture was then stirred for 5 hours during which time the bath melted. The colorless solution was quenched by the careful addition of 1:1 acetic acid-water (0.3 mL) and poured into 50 mL of saturated $NaHCO_3$ and extracted with 2×75 mL portions of ethyl acetate. The combined organic phases were extracted with water (50 mL) and brine (50 mL), dried over $MgSO_4$, filtered and concentrated. The residue was purified by column chromatography on $SiO_2$ (120 g) using ethyl acetate as the eluent to give 1.42 g (74%) as a white solid. $^1H$ NMR (300 MHz, $CDCl_3$) δ7.24–7.48 (m, 12H), 5.16 (m, 4H), 3.72 (m, 4H), 3.61 (m, 2H), 2.67 (m, 2H), 2.19 (t, 2H). MS (DCI) m/e 402 (4%); 294 (6%); 203 (52%); 186 (100%); 143 (22%); 126 (50%).

EXAMPLE 126B (1α,2β,3β,4α)-1,2-Di-(benzyloxycarbonyl)-3,4-bis (methanesulfonyloxymethyl)cyclobutane To a solution of the compound resulting from Example 126A (577 mg, 1.5 mmol) in 10 mL of $CH_2Cl_2$ at −10° C. was added triethylamine (0.63 mL, 4.5 mmol), followed by the dropwise addition of methanesulfonyl chloride (0.29 mL, 3.75 mmol). The solution was warmed to 0° C. and stirred for 1.5 hours. The mixture was diluted with 40 mL of $CH_2Cl_2$ and washed with 25 mL each water and dilute aqueous HCl. The organic fraction was dried over $MgSO_4$, filtered and concentrated to give 767 mg (95%) of the desired compound as an off white solid. This material was used without further purification. $^1H$ NMR (300 MHz, $CDCl_3$) δ7.38 (s, 12H), 5.15 (AB quartet, 4H), 4.32 (m, 4H), 3.77 (d, 2H), 2.95 (m, 2H), 2.88 (s, 6H). MS (DCI) m/e 558 (28%); 372 (35%); 204 (40%); 186 (100%).

EXAMPLE 126C (1α,2β,3β,4α)-1,2-Di-(benzyloxycarbonyl)-3,4-bis (cyanomethyl)cyclobutane A mixture of the compound resulting from Example 126B (270 mg, 0.5 mmol) and KCN (195 mg, 3 mmol) in 5 mL of DMSO was heated with stirring at 65° C. for 3 hours. The mixture was cooled to room temperature and partitioned between 50 mL of water and 2×50 mL of ethyl acetate. The combined organic fractions were washed with 2×25 mL of water and 25 mL of brine, dried over $MgSO_4$, filtered and concentrated. The residue was purified by column chromatography on $SiO_2$ (20 g) eluting with 1:1 ethyl acetate-hexanes to give 182 mg (76%) of the title compound as a thick oil. $^1H$ NMR (300 MHz, $CDCl_3$) δ7.26–7.42 (m, 12H), 5.17 (s, 4H), 3.18 (m, 2H), 2.57–2.78 (m, 6H). MS (DCI) m/e 420 (100%); 393 (10%); 344 (8%); 286 (22%); 221 (25%); 219 (100%); 125 (23%).

EXAMPLE 126D (1α,2β,3β,4α)-1,2-Di[N-propyl-N-(4-phenoxybenzyl)aminocarbonyl]-3,4-bis (cyanomethyl)cyclobutane A solution of the compound resulting from Example 126C (175 mg, 0.43 mmol) in 3 mL of 10% $CH_2Cl_2$-ethyl acetate was treated with 100 mg of 10% Pd/C and stirred under a balloon of $H_2$ for 3 hours. The black mixture was filtered through celite, the celite pad was washed well with methanol and the resulting filtrate was concentrated. The residue was suspended in $CH_2Cl_2$ (4 mL) and treated with oxalyl chloride (0.092 mL, 1.05 mmol) and 1 drop of DMF. The mixture was stirred for 1 hour and then treated with 2 mL of acetonitrile (to try to dissolve the unreacted acid). After stirring for 1 hour more, the mixture was concentrated. The residue was concentrated twice with 2 mL of toluene (to remove HCl and unreacted oxalyl chloride) and then dissolved in 2 mL of $CH_2Cl_2$. In a separate flask was added the amine from Example 3 (302 mg, 1.26 mmol), $CH_2Cl_2$ (5 mL) and saturated aqueous $NaHCO_3$ (5 mL). This mixture was cooled to 0° C. and then treated with the acid chloride solution dropwise. The mixture was stirred for 1 hour and then poured into a separatory funnel. The layers were separated and the organic phase was washed with dilute aqueous HCl, dried over $MgSO_4$, filtered and concentrated. The residue was purified by column chromatography on $SiO_2$ (30 g) eluting with 1:1 ethyl acetate-hexanes to give 149 mg (53%) of the title compound as a colorless oil. $^1H$ NMR (300 MHz, $CDCl_3$) δ6.87–7.40 (m, 18H), 4.18–4.75 (m, 4H), 2.11–3.63 (m, 10H), 2.38 (m, 2H), 1.42–1.62 (m, 4H), 0.78–0.97 (m, 6H). MS (DCl) m/e 686 (8%); 669 (4%); 240 (100%).

EXAMPLE 126E (1α,2β,3β,4α)-1,2-Di-[N-propyl-N-(4-phenoxybenzyl)aminocarbonyl]-3,4-bis (tetrazolylmethyl)cyclobutane To a solution of the above dinitrile (136 mg, 0.20 mmol) in 2 mL of DMF was added $NaN_3$ (198 mg, 3.04 mmol) and triethylamine hydrochloride (418 mg, 304 mmol). The mixture was then heated to 100°–110° C. for 20 hours and cooled to room temperature. The yellow mixture was partitioned between dilute aqueous HCl (25 mL) and ethyl acetate (3×20 mL). The combined organic fractions were washed with water (3×10 mL) and brine (10 mL), dried over $MgSO_4$, filtered and concentrated. The resulting off white solid was recrystallized from ethyl acetate to give 111 mg (in two crops) of the title compound as a white solid. $^1H$ NMR (300 MHz, $CDCl_3$) δ6.83–7.34 (m, 18H), 4.30–4.77 (m, 4H), 2.79–3.76 (m, 12H), 1.34–1.63 (m, 4H), 0.75–0.90 (m, MS ($FAB^+$) m/e 755 (75%); 240 (18%); 183 (100%). Anal calcd for $C_{42}H_{46}N_{10}O_4$: C, 66.83; H, 6.14; N, 18.55. Found: C, 66.54; H, 6.05; N, 18.94.

EXAMPLE 127

(1α,2β,3β,4α)-1,2-Di-[N-propyl-N-(4-phenoxybenzyl)aminocarbonylmethyl]-cyclobutane-3,4-dicarboxylic acid

EXAMPLE 127A (1α,2β,3β,4α)-1,2-Di-[benzyloxycarbonyl]-cyclobutane-3,4-diacetic acid To (1α,2β,3β,4α)-1,2-Di-[benzyloxycarbonyl]-3,4-bis (diazoacetyl)cyclobutane (50 mg, 0.109 mmol), the compound resulting from Example 128A, in THF (2 mL) and water (1 mL) was added silver benzoate in triethylamine (35 μL of a 50 mg/1 mL solution). After stirring at room temperature for 2 hours, the reaction mixture was poured into a saturated sodium bicarbonate solution. The mixture was washed two time with ethyl acetate, acidified with 2M HCl, and extracted into ethyl acetate. The combined organic extracts were washed with brine, dried over sodium sulfate and concentrated in vacuo to afford 28 mg (58%) of the title compound as an off white powder.

EXAMPLE 127B (1α,2β,3β,4α)-1,2-Di-[N-propyl-N-(4-phenoxybenzyl)aminocarbonylmethyl]-cyclobutane-3,4-dicarboxylic acid dibenzyl ester To the compound resulting from Example 127A (45 mg, 0.02 mmol) in methylene chloride (1 mL) was added oxalyl chloride (19 μL, 0.23 mmol) and DMF (0.5 μL). After stirring at room temperature approximately 3 hours, the reaction mixture was cooled to 0° C. and treated with N-propyl-N-(4-phenoxybenzyl)amine hydrochloride (51 mg, 0.229 mmol) and 1 mL of saturated sodium bicarbonate solution. The cooling bath was removed, and the reaction mixture was stirred 14 hours at room temperature and diluted with methylene chloride. The solution was washed with saturated sodium bicarbonate solution, dried over sodium sulfate and concentrated in vacuo to afford 85 mg of crude material. Purification by chromatography on silica gel eluting with 30% ethyl acetate in hexane afforded 72.5 mg (80%) of the title compound as a colorless oil.

EXAMPLE 127C (1α,2β,3β,4α)-1,2-Di-[N-propyl-N-(4-phenoxybenzyl)aminocarbonylmethyl]-cyclobutane-3,4-dicarboxylic acid The compound resulting from Example 127B (69.4 mg, 0.078 mmol) and 10% palladium on carbon (70 mg) in 1:1 methanol-ethyl acetate (2 mL) were stirred under hydrogen for 2 hours. The catalyst was removed by filtration and the filtrate concentrated in vacuo to afford the title compound (51.6 mg, 93%) as a slightly gray powder. $^1$H NMR (CDCl$_3$, 300 MHz) δ6.87–7.40 (m, 18H), 4.39–4.68 (m, 3H), 3.89 (m, 2H), 3.07–3.52 (m, 3H), 2.20–2.90 (m, 5H), 1.55 (m, 6H), 1.27 (m, 1H), 0.88 (m, 6H).

EXAMPLE 128

(1α,2β,3β,4α)-1,2-Di{N-benzyl-N-[(4-phenoxy)benzyl]aminocarbonyl}cyclobutane-3,4-diacetic acid

EXAMPLE 128A (1α,2β,3β,4α)-1,2-Di(benzyloxycarbonyl)-3,4-bis(diazoacetyl)cyclobutane The compound resulting from Example 123A was converted to the bis(acid chloride) by the method described in the first sentence of Example 123B. A solution of the bis(acid chloride) (25.6 g, 62.0 mmol) in CH$_2$Cl$_2$ (250 mL) at 0° C. was treated with ~850 mL of an ether solution of diazomethane, prepared by adding 1-methyl-3-nitro-1-nitrosoguanidine (63.0 g, 428 mmol) to ether (1 L) over 40% aqueous KOH (220 mL), previously cooled to 5° C. The resultant slurry was periodically shaken while maintaining the temperature at 5° C. for 30 minutes, then nitrogen was vigorously bubbled through the slurry for 40 minutes. The solids were filtered and recrystallized from EtOAc/hexane, to give the title compound as a light yellow solid (13.0 g). The mother liquor from this recrystallization was combined with the initial filtrate, concentrated under reduced pressure, and the residue was purified by chromatography eluting with 6:4 hexane-EtOAc to give an additional 4.2 g, for a total of 17. 2 g (60%). $^1$H NMR (CDCl$_3$) δ7.35 (m, 10H), 5.18 (s, 2H), 5.12 (dd, 4H), 3.86 (d, 2H), 3.70 (br d, 2H). MS (FAB$^+$) m/e 461 (M+H)$^+$.

EXAMPLE 128B

Alternative Preparation of (1α,2β,3β,4α)-1,2-Di(benzyloxycarbonyl)-3,4-bis(diazoacetyl)cyclobutane The bis(acid chloride) described in Example 128A in CH$_3$CN (0.4M) was added to a 0° C. 1:2 mixture of trimethylsilyldiazomethane (2M in hexane) in CH$_3$CN, (4.4 moles TMSCHN$_2$ per mole bis(acid chloride)). The reaction was stirred at 0°–17° C. over 4 hours then concentrated. The residue was partitioned between saturated aqueous NaHCO$_3$ and EtOAc, and the EtOAc layer was washed with brine and dried over Na$_2$SO$_4$, and concentrated in vacuo. The crude solids were recrystallized by dissolving in hot EtOAc (80–100 mg/mL), then adding five volumes of hexane to the hot solution and allowing the mixture to cool at room temperature overnight.

EXAMPLE 128C (1α,2β,3β,4α)-1,2-Di(benzyloxycarbonyl)cyclobutane-3,4-diacetic acid dimethyl ester Using the compound resulting from Example 128A or B, the title compound was prepared by the method of Example 103A. $^1$H NMR (CDCl$_3$) δ7.35 (m, 10H), 5.10 (dd, 4H), 3.70 (br d, 2H), 3.55 (s, 6H), 2.92 (m, 2H), 2.49 (m, 4H). MS (DCI/NH$_3$) m/e 469 (M+H)$^+$, 486 (M+H+NH$_3$)$^+$.

EXAMPLE 128D (1α,2β,3β,4α)-1,2-Di(carboxy)cyclobutane-3,4-diacetic acid dimethyl ester Using the compound resulting from Example 128C, the title compound was prepared by the method of Example 123C. $^1$H NMR (CD$_3$OD) δ3.65 (s, 6H), 3.51 (m, 2H), 2.82 (m, 2H), 2.57 (m, 4H). MS (FAB$^+$) m/e 289 (M+H)$^+$.

EXAMPLE 128E (1α,2β,3β,4α)-1,2-Di{N-benzyl-N-[(4-phenoxy)benzyl]aminocarbonyl}cyclobutane-3,4-diacetic acid dimethyl ester Using the compound resulting from Example 128D and the amine described in Example 12, the title compound was prepared by the method of Example 123B. $^1$H NMR (CDCl$_3$) δ7–40–6.90 (envelope, 28H), 5.14 (dd, 2H), 4.65 (m, 2H), 4.32 (m, 2H), 4.13 (dd, 2H), 3.80 (m, 2H) 3.56–3.51 (4 s, total 6H), 2.75–2.40 (envelope, 6H). MS (DCI/NH$_3$) m/e 831 (M+H)$^+$.

EXAMPLE 128F (1α,2β,3β,4α)-1,2-Di{N-benzyl-N-[(4-phenoxy)benzyl]aminocarbonyl}cyclobutane-3,4-diacetic acid Using the compound resulting from Example 128E, the title compound was prepared by the method of Example 103B. $^1$H NMR (DMSO-d$_6$) δ7.42–7.10 (envelop, 20H), 6.95 (m, 6H), 6.90 (d, 2H), 4.80, 4.70 (d, dd, total 4H), 4.20 (m, 2H), 4.05 (m, 4H), 2.67 (br m, 2H), 2.40 (br m, 4H). MS (FAB$^+$) m/e 803 (M+H)$^+$ and 801 (FAB$^-$) (M–H)$^-$. Anal calcd for C$_{50}$H$_{46}$N$_2$O$_8$·0.5 H$_2$O: C, 73.97; H, 5.83; N, 3.45. Found: C, 73.66; H, 5.75; N, 3.20.

EXAMPLE 129

(−)-(1α,2β,3β,4α)-1,2-Di[N-cyclopropylmethyl-N-(4-phenoxybenzyl)aminocarbonyl]cyclobutane-3,4-dicarboxylic acid

EXAMPLE 129A (−)-(1α,2β,3β,4α)-1,2-Di[benzyloxycarbonyl]cyclobutane-3,4-dicarboxylic acid To the compound resulting from Example 123A (1.0 g, 2.4 mmol) dissolved in absolute EtOH (45 mL) was added a solution of (−)-norephedrine (0.74 g, 4.9 mmol) in absolute EtOH (5 mL). The solution allowed to sit at room temperature overnight. The resultant crystals were collected and recrystallized twice from hot absolute EtOH (4.5 mg/mL), then partitioned between 1M H$_3$PO$_4$ and Et$_2$O. The Et$_2$O layer was washed with brine, dried over Na$_2$SO$_4$, filtered and concentrated to give the title compound. [α]$_D$=+17.3° (c=0.92, MeOH).

EXAMPLE 129B (−)-(1α,2β,3β,4α)-1,2-Di[N-cyclopropylmethyl-N-(4-phenoxybenzyl)aminocarbonyl]cyclobutane-3,4-dicarboxylic acid The compound resulting from Example 129A and the amine resulting from Example 47A were reacted by the methods of Examples 123B and 123C to give the title compound which was obtained by lyophilization. $^1$H NMR (DMSO-d$_6$), δ0.01–1.25 (m, 4H), 0.27–0.52 (m, 4H), 0.80–0.96 (m, 2H), 2.68–2.92 (m, 2H), 3.20–3.55 (m, 2H), 3.56–3.68 (m, 2H), 3.89–4.98 (m, 1H), 4.00–4.10 (m, 1H), 4.28–4.58 (m, 2H), 4.65–4.89 (m, 2H), 6.85–7.04 (m, 8H), 7.08–7.30 m, 6H), 7.33–7.43 (m, 4H). MS (FAB$^-$) m/e 701 (M–H)$^-$. Anal calcd for C$_{42}$H$_{42}$N$_2$O$_8$·0.5 H$_2$O: C, 70.87; H, 6.09; N, 3.94. Found: C, 70.68; H, 5.91; N, 3.85. [α]$_D$=−80.60° (c=0.625, MeOH).

EXAMPLE 130

(1α,2β,3β,4α)-1,2-Di[N-propyl-N-(4-phenoxybenzyl)aminothiocarbonyl]cyclobutane-3,4-dicarboxylic acid

EXAMPLE 130A (1α,2β,3β,4α)-1,2-Di[N-propyl-N-(4-phenoxybenzyl)aminothiocarbonyl]cyclobutane-3,4-dicarboxylic acid dibenzyl ester A solution of the compound resulting from Example 123B (500 mg, 0.6 mmol) in benzene (4 mL) was treated with Lawesson's reagent (235 mg, 0.6 mmol). The resulting suspension was refluxed for 96 hours. The solvent was evaporated, and the residue was dissolved in ethyl acetate (20 mL), washed with 1M Na$_3$PO$_4$ (20 mL), and dried over MgSO$_4$. The solvent was evaporated, and the residue was dissolved in methylene chloride, treated with silica gel, and concentrated to dryness. The silica gel was poured onto a prepacked column and eluted with 10% ethyl acetate/hexane to provide 205 mg (39%) of the title compound as a colorless oil. $^1$H NMR (CDCl$_3$, 300 MHz) δ0.65–0.9 (m, 6H), 1.4–1.6 (m, 1H), 1.65–1.75 (m, 1H), 3.39–3.52 (m, 2H), 3.53–3.8 (m, 2H), 3.84–3.90 (m, 2H) 4.5 (dd, J=16.5, 4.5Hz, 1H), 4.78–4.99 (m, 2H), 5.0–5.3 (m, 9H), 6.85–7.14 (m, 10H), 7.15–7.4 (m, 18H). MS (DCl) m/e 891 (M+H)$^+$.

EXAMPLE 130B (1α,2β,3β,4α)-1,2-Di[N-propyl-N-(4-phenoxybenzyl)aminothiocarbonyl]cyclobutane-3,4-dicarboxylic acid The compound resulting from Example 129A (71 mg, 0.08 mmol) in 3:1 THF/H$_2$O (2 mL) at 0° C. was treated with 1M LiOH (800 μL). The solution was stirred at 0° C. for 8 hours then at room temperature for 18 hours. The solution was acidified with 1N HCl (1 mL) and concentrated to dryness. The residue was chromatographed eluting with 98:1:1 CHCl$_3$—MeOH—HOAc to provide 10 mg (18%) of the title compound as a colorless oil which was dissolved in CH$_3$CN and H$_2$O and lyophilized to provide a white solid. m.p. 92°–93° C. MS DCl) m/e 710 (M+H)$^+$.

EXAMPLE 131

(1α,2β,3β,4α)-1,2-Di[N-(S)-α-(cyclopropylmethyl)benzyl-N-(4-phenoxybenzyl)aminocarbonyl]cyclobutane-3,4-dicarboxylic acid

EXAMPLE 131A (4S,5R)-3-(2-Phenyl)acetyl-4-methyl-5-phenyl-1,3-oxazolidin-2-one A mechanically stirred solution of phenylacetic acid at −78° C. is treated with one part pivaloyl chloride then one part triethylamine. The mixture is stirred at −78° C. for 15 minutes, at 0° C. for 45 minutes, then recooled to −78° C. In a separate flask, one part 2.5M nBuLi is added to a solution of (4S,5R)-(−)-4-methyl-5-phenyl-2-oxazolidinone in THF at −78° C. The solution is stirred for 15 minutes then transferred to the flask containing pivalic anhydride via cannula. The mixture is stirred for 15 minutes at −78° C. and 9 hours at room temperature. The mixture is quenched with 2M KHSO$_4$ and, after evaporation of the THF, is extracted 3 times with ethyl acetate. The combined ethyl acetate extracts are dried over MgSO$_4$, filtered and concentrated to provide the crude title compound which is purified by column chromatography eluting with ethyl acetate-hexane.

EXAMPLE 131B (4S,5R,2'S)-3-(2-Propenyl-2-phenyl)acetyl-4-methyl-5-phenyl-1,3-oxazolidin-2-one A solution of one equivalent of the compound resulting from Example 131A in THF at −78° C. is transferred via cannula to a solution of one equivalent 1M sodium bis(trimethylsilyl)amide in THF at −78° C. The cold enolate solution is stirred for 15 minutes at −78° C. then treated via cannula with 2 parts allyl iodide in THF at −78° C. The solution is stirred for 6 hours at −78° C. then warmed to 0° C. and quenched with saturated ammonium chloride. The THF is removed, and the water layer is extracted 2 times with ethyl acetate. The combined washings are dried over MgSO$_4$, filtered and concentrated to provide the crude title compound which is purified by column chromatography eluting with ethyl acetate-hexane.

EXAMPLE 131C (4S,5R,2'S)-3-[2-(Cyclopropylmethyl)-2-phenyl]
acetyl-4-methyl-5-phenyl-1,3-oxazolidin-2-one One equivalent of the compound resulting from Example 131B in $CH_2Cl_2$ at $-23°$ C. is treated with 5 equivalents of 1M diethyl zinc and 10 equivalents of diiodomethane. The solution is stirred at $-23°$ C. to $0°$ C. over 12 hours, quenched with saturated $NH_4Cl$, and extracted with ether. The organic layer is washed with 10% $NaHCO_3$ and brine, dried over $MgSO_4$, filtered, concentrated and chromatographed eluting with ethyl acetate-hexane to provide the title compound.

EXAMPLE 131D (S)-α-(Cyclopropylmethyl)phenylacetic acid

To a solution of one equivalent of the compound resulting from Example 131C in 3:1 THF-$H_2O$ at $0°$ C. is added 8 equivalents of 30% $H_2O_2$ in $H_2O$ followed by 2 equivalents of 1M LiOH. After stirring 2 hours at $0°$ C., the THF is removed, and the aqueous solution is extracted 3 times with $CH_2Cl_2$. The aqueous solution is acidified to pH 1 with 1N HCl and extracted three times with ethyl acetate. The combined organic extracts are dried over $MgSO_4$, filtered and concentrated to provide the title compound.

EXAMPLE 131E

N-t-Butyloxycarbonyl-(S)-α-(cyclopropylmethyl)
benzylamine

A solution of one equivalent of the compound resulting from Example 131D in toluene is treated with one equivalent of diphenylphosphoryl azide and warmed at $70°$ C. for 2 hours. The toluene is removed, and the residue is treated with 50 equivalents of 2-methyl-2-propanol and refluxed for 24 hours. The solvent is removed, and the residue is dissolved in ethyl acetate and washed with brine. The organic layer is dried over $MgSO_4$, filtered, concentrated, and chromatographed eluting with ethyl acetate-hexane to provide the title compound.

EXAMPLE 131F (S)-N-α-(Cyclopropylmethyl)benzylamine

One equivalent of the compound resulting from Example 131E in $CH_2Cl_2$ at $0°$ C. is treated with 10 equivalents of trifluoroacetic acid. The solution is stirred at room temperature for 18 hours, and all volatiles are removed in vacuo. The residue is dissolved in methanol and treated with 10 parts of Amberlite® IRA-400(OH) ion exchange resin. After 3 hours, the solution is filtered and concentrated to provide the title compound.

EXAMPLE 131G (1α,2β,3β,4α)-1,2-Di[N-(S)-α-(cyclopropylmethyl)
benzyl-N-(4-phenoxybenzyl)aminocarbonyl]
cyclobutane-3,4-dicarboxylic acid The compound resulting from Example 131F is reacted with 4-phenoxybenzaldehyde by the procedures described in Example 11. The resulting N-(S)-α-(cyclopropylmethyl)benzyl-N-(4-phenoxybenzyl)-amine is reacted with 1,2,3,4-cyclobutanetetracarboxylic dianhydride by the procedures described in Example 15 to afford the title compound.

EXAMPLE 132

(1α,2β,3β,4α)-1,2-Di[N-(R)-α-(cyclopropylmethyl)
benzyl-N-(4-phenoxybenzyl)aminocarbonyl]
cyclobutane-3,4-dicarboxylic acid The title compound is prepared by the procedures described in Example 131 substituting (4R,5S)-(+)-4-methyl-5-phenyl-2-oxazolidinone for (4S,5R)-(−)-4-methyl-5-phenyl-2-oxazolidinone in Example 131A.

EXAMPLE 133

(1α,2β,3β,4α)-1,2-Di[N-propyl-N-(S)-α-
(cyclopropylmethyl)-(4-phenoxybenzyl)-
aminocarbonyl]cyclobutane-3,4-dicarboxylic acid

EXAMPLE 133A (4S,5R)-3-(2-(4-(Phenoxyphenyl)acetyl)-4-methyl-
5-phenyl-1,3-oxazolidin-2-one A mechanically stirred solution of 4-phenoxyphenylacetic acid at $-78°$ C. is treated with one equivalent pivaloyl chloride then one equivalent triethylamine. The mixture is stirred at $-78°$ C. for 15 minutes, at $0°$ C. for 45 minutes, then recooled to $-78°$ C. In a separate flask, one part 2.5M nBuLi is added to a solution of (4S,5R)-(−)-4-methyl-5-phenyl-2-oxazolidinone in THF at $-78°$ C. The solution is stirred for 15 minutes then transferred to the flask containing pivalic anhydride via cannula. The mixture is stirred for 15 minutes at $-78°$ C. and 9 hours at room temperature. The mixture is quenched with 2M $KHSO_4$ and, after evaporation of the THF, is extracted 3 times with ethyl acetate. The combined ethyl acetate extracts are dried over $MgSO_4$, filtered and concentrated to provide the crude title compound which is purified by column chromatography eluting with ethyl acetate-hexane.

EXAMPLE 133B (4S, 5R,2'S)-3-[2-(2-Propenyl)-2-(4-phenoxyphenyl)
]acetyl-4-methyl-5-phenyl-1,3-oxazolidin-2-one A solution of one equivalent of the compound resulting from Example 133A in THF at $-78°$ C. is transferred via cannula to a solution of one equivalent of 1M sodium bis(trimethylsilyl)amide in THF at $-78°$ C. The cold enolate solution is stirred for 15 minutes at $-78°$ C. then treated via cannula with 2 equivalents of allyl iodide in THF at $-78°$ C. The solution is stirred for 6 hours at $-78°$ C. then warmed to $0°$ C. and quenched with saturated ammonium chloride. The THF is removed, and the water layer is extracted 2 times with ethyl acetate. The combined washings are dried over $MgSO_4$, filtered and concentrated to provide the crude title compound which is purified by column chromatography eluting with ethyl acetate-hexane.

EXAMPLE 133C (4S,5R,2'S)-3-[2-(Cyclopropylmethyl)-2-(4-
phenoxyphenyl)]acetyl-4-methyl-5-phenyl-1,3-
oxazolidin-2-one One equivalent of the compound resulting from Example 133B in $CH_2Cl_2$ at $-23°$ C. is treated with 5 equivalents of 1M diethyl zinc and 10 equivalents of diiodomethane. The solution is stirred at $-23°$ C. to $0°$ C. over 12 hours, quenched with saturated $NH_4Cl$, and extracted with ether. The organic layer is washed with 10% $NaHCO_3$ and brine, dried over MgSO$_4$, filtered, concentrated and chromatographed with ethyl acetate-hexane to provide the title compound.

EXAMPLE 133D (S)-α-(Cyclopropylmethyl)-4-phenoxyphenylacetic acid

To a solution of one equivalent of the compound resulting from Example 133C in 3:1 THF-H$_2$O at 0° C. is added 8 equivalents of 30% H$_2$O$_2$ in H$_2$O followed by 2 equivalents of 1M LiOH. After stirring 2 hours at 0° C., the THF is removed, and the aqueous solution is extracted 3 times with CH$_2$Cl$_2$. The aqueous solution is acidified to pH 1 with 1N HCl and extracted three times with ethyl acetate. The combined organic extracts are dried over MgSO$_4$, filtered and concentrated to provide the title compound.

EXAMPLE 133E

N-t-Butyloxycarbonyl-(S)-α-(cyclopropylmethyl)-4-phenoxybenzylamine

A solution of one equivalent of the compound resulting from Example 133D in toluene is treated with one equivalent of diphenylphosphoryl azide and warmed at 70° C. for 2 hours. The toluene is removed, and the residue is treated with 50 equivalents of 2-methyl-2-propanol and refluxed for 24 hours. The solvent is removed, and the residue is dissolved in ethyl acetate and washed with brine. The organic layer is dried over MgSO$_4$, filtered, concentrated, and chromatographed eluting with ethyl acetate-hexane to provide the title compound.

EXAMPLE 133F (S)-N-α-(Cyclopropylmethyl)-4-phenoxybenzylamine

One equivalent of the compound resulting from Example 133E in CH$_2$Cl$_2$ at 0° C. is treated with 10 equivalents of trifluoroacetic acid. The solution is stirred at room temperature for 18 hours, and all volatiles are removed in vacuo. The residue is dissolved in methanol and treated with 10 parts Amberlite® IRA-400(OH) ion exchange resin. After 3 hours, the solution is filtered and concentrated to provide the title compound.

EXAMPLE 133G (1α,2β,3β,4α)-1,2-Di[N-propyl-N-(S)-α-(cyclopropylmethyl)-(4-phenoxybenzyl)aminocarbonyl]cyclobutane-3,4-dicarboxylic acid The compound resulting from Example 131F is reacted with propionaldehyde in analogy to the procedures described in Examples 1 and 2. The resulting N-propyl-N-(S)-α-(cyclopropylmethyl)-(4-phenoxybenzyl)-amine is reacted with 1,2,3,4-cyclobutanetetracarboxylic dianhydride by the procedures described in Example 13 to afford the title compound.

EXAMPLE 134

(1α,2β,3β,4α)-1,2-Di[N-propyl-N-(R)-α-(cyclopropylmethyl)-(4-phenoxybenzyl)aminocarbonyl]cyclobutane-3,4-dicarboxylic acid The title compound is prepared by the procedures described in Example 133 substituting (4R,5S)-(+)-4-methyl-5-phenyl-2-oxazolidinone is substituted for (4S,5R)-(−)-4-methyl-5-phenyl-2-oxazolidinone in Example 133A.

EXAMPLE 135

Alternate Preparation of (1α,2β,3β,4α)-1,2-Di[N-propyl-N-(4-phenoxybenzyl)aminocarbonyl]cyclobutane-3,4-dicarboxylic acid A mixture of 507 mg (1.23 mmol) of the compound resulting from Example 123A in 10 mL of toluene was reacted with 5 mL of oxalyl chloride. The mixture was heated to reflux for 0.5 hour. All volatiles were removed under reduced pressure affording a pale yellow oil. The oil was dissolved in 5 mL of acetone and reacted with 168 mg (2.58 mmol) of sodium azide dissolved in 1 mL of water. After 2 hours the mixture was filtered and the volatiles were removed under reduced pressure while keeping the flask cool. The oil was dissolved in 30 mL of toluene and the solution was heated at 70° C. for 2 hours. Half of the solvent was removed under reduced pressure and 1.0 mL of 2-methyl-2-propanol and 20 mg of copper (I) chloride was added. The mixture was heated at 70° C. for 6 hours. All volatiles were removed under reduced pressure to afford a white solid. Purification by flash column chromatography on silica gel eluting with 2:1 hexane-ethyl acetate afforded 250 mg (36.7%) of white powder.

A 200 mg (0.361 mmol) sample of this powder was dissolved in 4 mL of dry DMF and was reacted sequentially with 127 mg (0.758 mmol) of allyl iodide and 30 mg (0.76 mmol) of a 60% dispersion of sodium hydride in mineral oil. After 18 hours water was added and the mixture was extracted with ethyl acetate. All volatiles were removed under reduced pressure affording an oil. Purification by flash column chromatography on silica gel eluting with 2:1 hexane-ethyl acetate afforded 110 mg (48%) of a clear oil. This oil was dissolved in 10 mL of methylene chloride and cooled to 0° C. under nitrogen, whereupon 1 mL of trifluoroacetic acid was added. After 2 hours all volatiles were removed under reduced pressure, affording 75.5 mg of crude product. This product was dissolved in 10 mL of dry tetrahydrofuran and was treated with 87.3 mg (0.382 mmol) of 4-phenoxyphenylacetic acid, 80.8 mg (0.421 mmol) of 1-(3-dimethylaminopropyl)-3-ethylcarbodiimide hydrochloride, 56.8 mg (0.421 mmol) of 1-hydroxybenzotriazole hydrate, and 128 mg (1.26 mmol) of triethylamine. After 3 days 50 mL of ethyl acetate was added and the mixture was washed with brine and dilute hydrochloric acid. All volatiles are removed under reduced pressure affording an oil. The oil was dissolved in 20 mL of ethyl acetate with 40 mg of 10% palladium on charcoal and was stirred under an atmosphere of hydrogen for two days. The mixture was filtered and purified by flash column chromatography on silica gel eluting with 40:1:1 ethyl acetate-formic acid-water to yield 6 mg of the title compound. MS (FAB) m/e 678.

EXAMPLE 136

(1α,2β,3β,4α)-1,2-Di[N-propyl-N-(4-phenoxybenzyl)aminocarbonyl]-3-(ethoxycarbonyl)cyclobutane-4-carboxylic acid To the compound resulting from Example 17 (0.44 mmol) dissolved in 5 mL of CH$_2$Cl$_2$ was added 1,1-carbonyldiimidazole (0.40 mmol). The resulting solution was stirred 5 minutes at room temperature and then treated with ethanol (0.40 mmol) in one portion. The mixture was allowed to react 18 hours at room temperature, diluted with 50 mL of CH$_2$Cl$_2$, washed with 25 mL of 1N H$_3$PO$_4$ and 25 mL of 10% NaCl, dried over anhydrous MgSO$_4$, filtered and concentrated in vacuo to afford a foamy solid. The solid was dissolved in 5 mL of 98:1.5:0.5 CHCl$_3$—MeOH—HOAc, applied to a column containing silica gel and eluted to afford the title compound as a white amorphous solid. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.71–3.80 (m, 2H), 3.68–3.45 (m, 1H), 3.34–3.29 (m, 3H), 3.20–3.02 (m, 1H), 3.02–2.88 (m, 1H), 1.48–1.68 (m, 4H), 0.82–0.97 (m, 9H). MS (FAB+) m/e 707 (M+H)$^+$. MS (FAB–) m/e 705 (M–H)$^+$.

EXAMPLE 137

(1α,2β,3β,4α)-1,2-Di[N-propyl-N-(4-phenoxybenzyl)aminocarbonyl]-3-(propoxycarbonyl)cyclobutane-4-carboxylic acid The title compound was prepared by the methods described in Example 136. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.71–3.80 (m, 2H), 3.68–3.45 (m, 1H), 3.34–3.29 (m, 3H), 3.20–3.02 (m, 1H), 3.02–2.88 (m, 1H), 1.48–1.68 (m, 4H), 0.82–0.97 (m, 9H). MS (FAB+) m/e 721 (M+H)$^+$. MS (FAB–) m/e 719 (M–H)$^+$.

EXAMPLE 138

(1α,2β,3β,4α)-1,2-Di[N-propyl-N-(4-phenoxybenzyl)aminocarbonyl]-3-(butoxycarbonyl)cyclobutane-4-carboxylic acid The title compound was prepared by the methods described in Example 136. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.71–3.80 (m, 2H), 3.68–3.45 (m, 1H), 3.34–3.29 (m, 3H), 3.20–3.02 (m, 1H), 3.02–2.88 (m, 1H), 2.85–2.75 (m, 2H), 1.48–1.68 (m, 4H), 0.82–0.97 (m, 9H). MS (FAB+) m/e 735 (M+H)$^+$. MS (FAB–) m/e 733 (M–H)$^+$.

EXAMPLE 139

(1α,2β,3β,4α)-1,2-Di[N-propyl-N-(4-phenoxybenzyl)aminocarbonyl]-3-(isobutoxycarbonyl)cyclobutane-4-carboxylic acid The title compound was prepared by the methods described in Example 136. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.71–3.80 (m, 2H), 3.68–3.45 (m, 1H), 3.34–3.29 (m, 3H), 3.20–3.02 (m, 1H), 3.02–2.88 (m, 1H), 1.75–1.99 (m, 2H), 1.48–1.68 (m, 4H), 0.82–0.97 (m, 12H). MS (FAB+) m/e 735 (M+H)$^+$. MS (FAB–) m/e 733 (M–H)$^+$.

EXAMPLE 140

(1α,2β,3β,4α)-1,2-Di[N-propyl-N-(4-phenoxybenzyl)aminocarbonyl]-3-(pentoxycarbonyl)cyclobutane-4-carboxylic acid The title compound was prepared by the methods described in Example 136. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.71–3.80 (m, 2H), 3.68–3.45 (m, 1H), 3.34–3.29 (m, 3H), 3.20–3.02 (m, 1H), 3.02–2.88 (m, 1H), 1.48–1.68 (m, 4H),1.20–1.38 (m, 4H), 0.82–0.97 (m, 9H). MS (FAB+) m/e 749 (M+H)$^+$. MS (FAB–) m/e 747 (M–H)$^+$.

EXAMPLE 141

(1α,2β,3β,4α)-1,2-Di[N-propyl-N-(4-phenoxybenzyl)aminocarbonyl]-3-(1-methylpropoxycarbonyl)cyclobutane-4-carboxylic acid The title compound was prepared by the methods described in Example 136. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.71–3.80 (m, 1H), 3.68–3.45 (m, 1H), 3.34–3.29 (m, 3H), 3.20–3.02 (m, 1H), 3.02–2.88 (m, 1H), 1.48–1.68 (m, 4H), 1.10–1.30 (m, 2H), 0.82–0.97 (m, 12H). MS (FAB+) m/e 735 (M+H)$^+$. MS (FAB–) m/e 733 (M–H)$^+$.

EXAMPLE 142

(1α,2β,3β,4α)-1,2-Di[N-propyl-N-(4-phenoxybenzyl)aminocarbonyl]-3-(tert-butyloxycarbonyl)cyclobutane-4-carboxylic acid The title compound was prepared by the methods described in Example 136. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.68–3.45 (m, 1H), 3.34–3.29 (m, 3H), 3.20–3.02 (m, 1H), 3.02–2.88 (m, 1H), 1.48–1.68 (m, 13H), 0.82–0.97 (m, 6H). MS (FAB+) m/e 735 (M+H)$^+$. MS (FAB–) m/e 733 (M–H)$^+$.

EXAMPLE 143

(1α,2β,3β,4α)-1,2-Di[N-propyl-N-(4-phenoxybenzyl)aminocarbonyl]-3-(isopropoxycarbonyl)cyclobutane-4-carboxylic acid The title compound was prepared by the methods described in Example 136. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.71–3.80 (m, 2H), 3.68–3.45 (m, 1H), 3.34–3.29 (m, 3H), 3.20–3.02 (m, 1H), 3.02–2.88 (m, 1H), 1.48–1.68 (m, 4H), 1.10–1.30 (m, 6H), 0.82–0.97 (m, 6H). MS (FAB+) m/e 721 (M+H)$^+$. MS (FAB–) m/e 719 (M–H)$^+$.

EXAMPLE 144

(1α,2β,3β,4α)-1,2-Di[N-propyl-N-(4-phenoxybenzyl)aminocarbonyl]-3-(isoamyloxycarbonyl)cyclobutane-4-carboxylic acid The title compound was prepared by the methods described in Example 136. $^1$H NMR (CDCl$_3$) δ7.38–7.18 (m, 8H), 7.14–7.05 (m, 2H), 6.86–7.00 (m, 8H), 4.81–4.65 (m, 2H), 4.44–4.31 (m, 2H), 4.22–4.08 (m, 2H), 3.85–3.72 (m, 2H), 3.71–3.80 (m, 2H), 3.68–3.45 (m, 1H), 3.34–3.29 (m, 3H), 3.20–3.02 (m, 1H), 3.02–2.88 (m, 1H), 1.48–1.68 (m, 4H),1.1–1.4 (m, 3H), 0.82–0.97 (m, 12H). MS (FAB+) m/e 749 (M+H)$^+$. MS (FAB–) m/e 747 (M–H)$^+$.

EXAMPLE 145

(1α,2β,3β,4α)-1,2-Di[N-propyl-N-(4-phenoxybenzyl)aminocarbonyl]-3-((1S)-1-methoxycarbonyl-1-ethoxycarbonyl)cyclobutane-4-carboxylic acid The title compound was prepared by the methods described in Example 136. $^1$H NMR (CDCl$_3$) δ7.38–7.18

(m, 8H), 7.14–7.05 (m, 2H), 6.86–7.00 (m, 8H),4.99–5.09 (m, 1H), 4.81–4.65 (m, 2H), 4.44–4.31 (m, 2H), 4.22–4.08 (m, 2H), 3.85–3.72 (m, 2H), 3.71–3.80 (s, 3H total ), 3.68–3.45 (m, 1H), 3.34–3.29 (m, 3H), 3.20–3.02 (m, 1H), 3.02–2.88 (m, 1H), 1.48–1.68 (m, 4H), 1.2–1.3 (d, 3H), 0.82–0.97 (m, 6H). MS (FAB+) m/e 765 (M+H)$^+$. MS (FAB−) m/e 763 (M−H)$^+$.

EXAMPLE 146

(1α,2β,3β,4α)-1,2-Di[N-propyl-N-(4-phenoxybenzyl)aminocarbonyl]-3-(butoxycarbonylmethyl)cyclobutane-4-acetic acid To the compound resulting from Example 103 (0.44 mmol) dissolved in 5 mL of CH$_2$Cl$_2$ was added 1,1-carbonyldiimidazole (0.40 mmol). The resulting solution was stirred 5 minutes at room temperature, then n-butanol (0.40 mmol) was added in one portion. The mixture was stirred for 18 hours at room temperature and then diluted with 50 mL of CH$_2$Cl$_2$ and washed with 25 mL of 1N H$_3$PO$_4$ and 25 mL of 10% NaCl, dried over anhydrous MgSO$_4$, filtered and concentrated in vacuo to give a foamy solid. The solid was dissolved in 5 mL of 98:1.5:0.5 CHCl$_3$—MeOH—HOAc, applied to a column containing silica gel and eluted to give the title compound as a white amorphous solid. $^1$H NMR (CDCl$_3$) δ7.37–6.90 (m, 18H), 4.97–4.89, 4.62–4.54, 4.35–4.23, 4.20–4.10, 3.68–3.58, 3.21–3.04, 2.96–2.51, 2.32–2.22, 2.19–2.08 (complex multiplets, total 18H), 1.76–1.46 (m, 6H), 1.22–1.38 (m, 2H), 0.98–0.82 (m, 9H). MS (FAB+) m/e 763 (M+H)$^+$. MS (FAB−) m/e 761 (M−H)$^+$.

EXAMPLE 147

(1α,2β,3β,4α)-1,2-Di[N-propyl-N-(4-phenoxybenzyl)aminocarbonyl]-3-((1S)-1-methoxycarbonyl-1-ethoxycarbonylmethyl) cyclobutane-4-acetic acid The title compound was prepared by the procedures described in Example 146. $^1$H NMR (CDCl$_3$) δ7.37–6.90 (m, 18H), 5.11–4.99 (m, 1H), 4.97–4.89, 4.62–4.54, 4.35–4.23, 4.20–4.10, 3.71–3.75 (m, 3H), 3.68–3.58, 3.21–3.04, 2.96–2.51, 2.32–2.22, 2.19–2.08 (complex multiplets, total 16H), 1.76–1.46 (m, 6H), 0.98–0.82 (m, 9H). MS (FAB+) m/e 793 (M+H)$^+$. MS (FAB−) m/e 791 (M−H)$^+$.

EXAMPLE 148

(1α,2β,3β,4α)-1,2-Di[N-propyl-N-(4-phenoxybenzyl)aminocarbonyl]-3-(N,N-diethylacetamidocarbonylmethyl)cyclobutane-4-acetic acid The title compound was prepared by the procedures described in Example 146. $^1$H NMR (CDCl$_3$) 7.37–6.90 (m, 18H), 4.97–4.89, 4.62–4.54, 4.35–4.23, 4.20–4.10, 3.68–3.58, 3.21–3.04, 2.96–2.51, 2.32–2.22, 2.19–2.08 (complex multiplets, total 18H)1.76–1.46 (m, 6H);1.22–1.38 (m, 4H) 0.98–0.82 (m, 12H). MS (FAB+K) m/e 858 (M+H)$^+$.

EXAMPLE 149A (1α,2β,3β,4α)-1,2-Di[N-propyl-N-(4-phenoxybenzyl)aminocarbonyl]-3-(acetoxymethoxycarbonyl)cyclobutane-4-carboxylic acid and

EXAMPLE 149B (1α,2β,3β,4α)-1,2-Di[N-propyl-N-(4-phenoxybenzyl)aminocarbonyl]-3,4-di (acetoxymethoxycarbonyl)cyclobutane A mixture of 100 mg (0.148 mmol) of the compound resulting from Example 17, 22.6 mg (0.148 mmol) of bromomethyl acetate, 9.0 mg (0.054 mmol) of potassium iodide, and 6.5 mg (0.148 mmol) of a 60% dispersion of sodium hydride in mineral oil in 5.0 mL of anhydrous dimethyl formamide was heated to between 80° C. and 120° C. for 6 hours. The reaction mixture was poured into water, and the mixture was extracted with ethyl acetate. The combined extracts were dried over magnesium sulfate, filtered, and concentrated under reduced pressure to give an oil containing a mixture of isomers. The oil was purified by flash column chromatography on silica gel, first eluting with 5:1 hexane-ethyl acetate, then with 2:1 hexane-ethyl acetate, and, lastly with 1800:1:1 ethyl acetate-formic acid-water (1800:1:1) to give the title compounds. Example 149A: $^1$H NMR (CDCl$_3$, 300 MHz) δ0.8–1.0 (m, 6H), 1.4–1.6 (m, 4H), 2.0–2.1 (m, 3H), 2.9–3.3 (m, 4H), 3.8–4.2 (m, 4H), 4.3–4.7 (m, 4H), 5.4–5.8 (m, 2H), 6.8–7.4 (m, 18H). MS (FAB$^+$) m/e 751 (M+H)$^+$. Example 149B: $^1$H NMR (CDCl$_3$, 300 MHz) δ0.8–1.0 (m, 6H), 1.4–1.6 (m, 4H), 2.0–2.1 (m, 6H), 2.9–3.3 (m, 4H), 3.8–4.2 (m, 4H), 4.3–4.7 (m, 4H), 5.4–5.8 (m, 4H), 6.8–7.4 (m, 18H). MS (FAB$^+$) m/e 823 (M+H)$^+$.

EXAMPLE 150A (1α,2β,3β,4α)-1,2-Di[N-propyl-N-(4-phenoxybenzyl)aminocarbonyl]-3-(propionyloxymethoxycarbonyl)cyclobutane-4-carboxylic acid and

EXAMPLE 150B (1α,2β,3β,4α)-1,2-Di[N-propyl-N-(4-phenoxybenzyl)aminocarbonyl]-3,4-di (propionyloxymethoxycarbonyl)cyclobutane The title compounds were prepared by the procedures described in Example 149 substituting chloromethyl propionate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 150A: $^1$H NMR (CDCl$_3$, 300 MHz) δ0.8–1.0 (m, 6H), 1.1–1.2 (m, 3H), 1.4–1.6 (m, 4H), 2.2–2.4 (m, 2H), 2.9–3.3 (m, 4H), 3.8–4.2 (m, 4H), 4.3–4.7 (m, 4H), 5.4–5.8 (m, 2H), 6.8–7.4 (m, 18H). MS (FAB+) m/e 765 (M+H)$^+$. Example 150B: $^1$H NMR (CDCl$_3$, 300 MHz) δ0.8–1.0 (m, 6H), 1.1–1.2 (m, 6H), 1.4–1.6 (m, 4H), 2.2–2.4 (m, 4H), 2.9–3.3 (m, 4H), 3.8–4.2 (m, 4H), 4.3–4.7 (m, 4H), 5.4–5.8 (m, 2H), 6.8–7.4 (m, 18H). MS (FAB$^+$) m/e 851 (M+H)$^+$.

EXAMPLE 151A (1α,2β,3β,4α)-1,2-Di[N-propyl-N-(4-phenoxybenzyl)aminocarbonyl]-3-(butyryloxymethoxycarbonyl)cyclobutane-4-carboxylic acid and

EXAMPLE 151B (1α,2β,3β,4α)-1,2-Di[N-propyl-N-(4-phenoxybenzyl)aminocarbonyl]-3,4-di (butyryloxymethoxycarbonyl)cyclobutane The title compounds were prepared by the procedures described in Example 149 substituting chloromethyl butyrate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 151A: $^1$H NMR (CDCl$_3$, 300 MHz)

δ0.8–1.0 (m, 9H), 1.4–1.7 (m, 6H), 2.2–2.4 (m, 2H), 3.0–3.4 (m, 4H), 3.8–4.1 (m, 4H), 4.3–4.6 (m, 4H), 5.4–5.8 (m, 2H), 6.8–7.4 (m, 18H). MS (FAB⁺) m/e 779 (M+H)⁺. Example 152B: ¹H NMR (CDCl₃, 300 MHz) δ0.8–1.0 (m, 12H), 1.4–1.7 (m, 8H), 2.2–2.4 (m, 4H), 3.0–3.4 (m, 4H), 3.8–4.1 (m, 4H), 4.3–4.6 (m, 4H), 5.4–5.8 (m, 4H), 6.8–7.4 (m, 18H). MS (FAB⁺) m/e 879 (M+H)⁺.

EXAMPLE 152A (1α,2β,3β,4α)-1,2-Di[N-propyl-N-(4-phenoxybenzyl)aminocarbonyl]-3-(isobutyryloxymethoxycarbonyl)cyclobutane-4-carboxylic acid and

EXAMPLE 152B (1α,2β,3β,4α)-1,2-Di[N-propyl-N-(4-phenoxybenzyl)aminocarbonyl]-3,4-di(isobutyryloxymethoxycarbonyl)cyclobutane The title compounds were prepared by the procedures described in Example 149 substituting chloromethyl isobutyrate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 152A: ¹H NMR (CDCl₃, 300 MHz) δ0.8–1.0 (m, 6H), 1.1–1.3 (m, 6H) 1.4–1.7 (m, 4H), 2.4–2.7 (m, 1H), 3.0–3.4 (m, 4H), 3.8–4.1 (m, 4H), 4.3–4.6 (m, 4H), 5.4–5.8 (m, 2H), 6.8–7.4 (m, 18H). MS (FAB⁺) m/e 779 (M+H)⁺. Example 152B: ¹H NMR (CDCl₃, 300 MHz) δ0.8–1.0 (m, 6H), 1.1–1.3 (m, 12H) 1.4–1.7 (m, 4H), 2.4–2.7 (m, 2H), 3.0–3.4 (m, 4H), 3.8–4.1 (m, 4H), 4.3–4.6 (m, 4H), 5.4–5.8 (m, 4H), 6.8–7.4 (m, 18H). MS (FAB⁺) m/e 879 (M+H)⁺.

EXAMPLE 153A (1α,2β,3β,4α)-1,2-Di[N-propyl-N-(4-phenoxybenzyl)aminocarbonyl]-3-(pivaloyloxymethoxycarbonyl)cyclobutane-4-carboxylic acid and

EXAMPLE 153B (1α,2β,3β,4α)-1,2-Di[N-propyl-N-(4-phenoxybenzyl)aminocarbonyl]-3,4-di(pivaloyloxymethoxycarbonyl)cyclobutane The title compounds were prepared by the procedures described in Example 149 substituting chloromethyl pivalate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 153A: ¹H NMR (CDCl₃, 300 MHz) δ0.8–1.0 (m, 6H), 0.8–1.0 (m, 6H), 1.2–1.4 (m, 9H), 1.4–1.6 (m, 4H), 3.0–3.5 (m, 4H), 3.8–4.2 (m, 4H), 4.3–4.7 (m, 4H), 5.4–5.8 (m, 2H), 6.8–7.4 (m, 18H). MS (FAB⁺) m/e 793 (M+H)⁺. Example 153B: ¹H NMR (CDCl₃, 300 MHz) δ8–1.0 (m, 6H), 1.2–1.4 (m, 18H), 1.4–1.6 (m, 4H), 3.0–3.5 (m, 4H), 3.8–4.2 (m, 4H), 4.3–4.7 (m, 4H), 5.4–5.8 (m, 4H), 6.8–7.4 (m, 18H). MS (FAB⁺) m/e 907 (M+H)⁺.

EXAMPLE 154

(1α,2β,3β,4α)-1,2-Di[N-propyl-N-(4-phenoxybenzyl)aminocarbonyl]-3,4-di(cyclopropylcarboxymethoxycarbonyl)cyclobutane The title compound was prepared by the procedures described in Example 149 substituting chloromethyl cyclopropylcarboxylate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. ¹H NMR (CDCl₃, 300 MHz) δ0.8–1.0 (m, 14H), 1.4–1.6 (m, 6H), 2.0–2.1 (m, 6H), 2.9–3.3 (m, 4H), 3.8–4.2 (m, 4H), 4.3–4.7 (m, 4H), 5.4–5.8 (m, 4H), 6.8–7.4 (m, 18H). MS (FAB⁺) m/e 875 (M+H)⁺.

EXAMPLE 155A (1α,2β,3β,4α)-1,2-Di[N-propyl-N-(4-phenoxybenzyl)aminocarbonyl]-3-(cyclobutylcarboxymethoxycarbonyl)cyclobutane-4-carboxylic acid and

EXAMPLE 155B (1α,2β,3β,4α)-1,2-Di[N-propyl-N-(4-phenoxybenzyl)aminocarbonyl]-3,4-di(cyclobutylcarboxymethoxycarbonyl)cyclobutane The title compounds were prepared by the procedures described in Example 149 substituting chloromethyl cyclobutylcarboxylate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 155A: ¹H NMR (CDCl₃, 300 MHz) δ0.8–1.0 (m, 6H), 1.4–1.7 (m, 4H), 1.8–2.1 (m, 2H), 2.1–2.4 (m, 4H), 3.0–3.5 (m, 5H), 3.8–4.2 (m, 4H), 4.3–4.7 (m, 4H), 5.4–5.8 (m, 2H), 6.8–7.4 (m, 18H). MS (FAB⁺) m/e 791 (M+H)⁺. Example 155B: ¹H NMR (CDCl₃, 300 MHz) δ0.8–1.0 (m, 6H), 1.4–1.6 (m, 4H), 1.8–2.1 m, 4H), 2.1–2.4 (m, 8H), 3.0–3.5 (m, 6H), 3.8–4.2 (m, 4H), 4.3–4.7 (m, 4H), 5.4–5.8 (m, 4H), 6.8–7.4 (m, 18H). MS (FAB⁺) m/e 903 (M+H)⁺.

EXAMPLE 156A (1α,2β,3β,4α)-1,2-Di[N-propyl-N-(4-phenoxybenzyl)aminocarbonyl]-3-(cyclopentylcarboxymethoxycarbonyl)cyclobutane-4-carboxylic acid and

EXAMPLE 156B (1α,2β,3β,4α)-1,2-Di[N-propyl-N-(4-phenoxybenzyl)aminocarbonyl]-3,4-di(cyclopentylcarboxymethoxycarbonyl)cyclobutane The title compounds were prepared by the procedures described in Example 149 substituting chloromethyl cyclopentylcarboxylate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 156A: ¹H NMR (CDCl₃, 300 MHz) δ0.8–1.0 (m, 6H), 1.4–2.0 (m, 12H), 2.6–2.9 (m, 1H), 3.0–3.5 (m, 4H), 3.8–4.2 (m, 4H), 4.3–4.7 (m, 4H), 5.4–5.8 (m, 2H), 6.8–7.4 (m, 18H). MS (FAB⁺) m/e 805 (M+H)⁺. Example 156B: ¹H NMR (CDCl₃, 300 MHz) δ0.8–1.0 (m, 6H), 1.4–2.0 (m, 20H), 2.6–2.9 (m, 2H), 3.0–3.5 (m, 4H), 3.8–4.2 (m, 4H), 4.3–4.7 (m, 4H), 5.4–5.8 (m, 4H), 6.8–7.4 (m, 18H). MS (FAB⁺) m/e 931 (M+H)⁺.

EXAMPLE 157A (1α,2β,3β,4α)-1,2-Di[N-propyl-N-(4-phenoxybenzyl)aminocarbonyl]-3-(cyclohexylcarboxymethoxycarbonyl)cyclobutane-4-carboxylic acid and

EXAMPLE 157B (1α,2β,3β,4α)-1,2-Di[N-propyl-N-(4-phenoxybenzyl)aminocarbonyl]-3,4-di(cyclohexylcarboxymethoxycarbonyl)cyclobutane The title compounds were prepared by the procedures described in Example 149 substituting chloromethyl cyclohexylcarboxylate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 157A: $^1$H NMR (CDCl$_3$, 300 MHz) δ0.8–1.0 (m, 6H), 1.2–2.0 (m, 14H), 2.2–2.4 (m, 1H), 3.0–3.5 (m, 4H), 3.8–4.2 (m, 4H), 4.3–4.7 (m, 4H), 5.4–5.8 (m, 2H), 6.8–7.4 (m, 18H). MS (FAB$^+$) m/e 819 (M+H)$^+$. Example 157B: $^1$H NMR (CDCl$_3$, 300 MHz) δ0.8–1.0 (m, 6H), 1.2–2.0 (m, 24H), 2.2–2.4 (m, 2H), 3.0–3.5 (m, 4H), 3.8–4.2 (m, 4H), 4.3–4.7 (m, 4H), 5.4–5.8 (m, 4H), 6.8–7.4 (m, 18H). MS (FAB$^+$) m/e 959 (M+H)$^+$.

EXAMPLE 158A (1α,2β,3β,4α)-1,2-Di[N-propyl-N-(4-phenoxybenzyl)aminocarbonyl]-3-(cyclohexylcarboxymethoxycarbonyl)cyclobutane-4-carboxylic acid and

EXAMPLE 158B (1α,2β,3β,4α)-1,2-Di[N-propyl-N-(4-phenoxybenzyl)aminocarbonyl]-3,4-di(cyclohexylcarboxymethoxycarbonyl)cyclobutane The title compounds were prepared by the procedures described in Example 149 substituting chloromethyl benzoate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 158A: $^1$H NMR (CDCl$_3$, 300 MHz) δ0.6–1.0 (m, 6H), 1.2–1.7 (m, 4H), 2.9–3.3 (m, 4H), 3.8–4.2 (m, 4H), 4.3–4.7 (m, 4H), 5.7–6.0 (m, 2H), 6.8–7.6 (m, 23H), 8.0–8.1 (m, 1H). MS (FAB$^+$) m/e 813 (M+H)$^+$. Example 157B: $^1$H NMR (CDCl$_3$, 300 MHz) δ0.6–1.0 (m, 6H), 1.2–1.7 (m, 4H), 2.9–3,3 (m, 4H), 3.8–4.2 (m, 4H), 4.3–4.7 (m, 4H), 5.7–6.0 (m, 2H), 6.8–7.6 (m, 27H), 8.0–8.1 (m, 2H). MS (FAB$^+$) m/e 947 (M+H)$^+$.

EXAMPLE 159

(1α,2β,3β,4α)-1,2-Di[N-propyl-N-(4-phenoxybenzyl)aminocarbonyl]-3-(1-propionyloxyethoxycarbonyl)cyclobutane-4-carboxylic acid The title compound was prepared by the procedures described in Example 149 substituting chloroethyl propionate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. $^1$H NMR (CDCl$_3$, 300 MHz) δ0.7–0.9 (m, 6H), 1.0–1.1 (m, 3H), 1.3–1.6 (m, 4H), 2.2–2.4 (m, 2H), 2.9–3.4 (m, 4H), 3.8–4.2 (m, 4H), 4.3–4.7 (m, 4H), 6.8–7.6 (m, 19H). MS (FAB$^+$) m/e 779 (M+H)$^+$.

EXAMPLE 160A (1α,2β,3β,4α)-1,2-Di[N-propyl-N-(4-phenoxybenzyl)aminocarbonyl]-3-(1-pivaloyloxyethoxycarbonyl)cyclobutane-4-carboxylic acid and

EXAMPLE 160B (1α,2β,3β,4α)-1,2-Di[N-propyl-N-(4-phenoxybenzyl)aminocarbonyl]-3,4-di(1-pivaloyloxyethoxycarbonyl))cyclobutane The title compounds were prepared by the procedures described in Example 149 substituting chloroethyl pivalate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 160A: $^1$H NMR (CDCl$_3$, 300 MHz) δ0.6–1.0 (m, 6H), 1.1–1.2 (m, 9H),1.2–1.7 (m, 7H), 2.9–3.5 (m, 4H), 3.8–4.2 (m, 4H), 4.3–4.7 (m, 4H), 6.8–7.6 (m, 19H). MS (FAB$^+$) m/e 845 (M+H)$^+$. Example 160B: $^1$H NMR (CDCl$_3$, 300 MHz) δ0.6–1.0 (m, 6H), 1.1–1.2 (m, 18H),1.2–1.7 (m, 10H), 2.9–3.5 (m, 4H), 3.8–4.2 (m, 4H), 4.3–4.7 (m, 4H), 6.8–7.6 (m, 20H). MS (FAB$^+$) m/e 973 (M+H)$^+$.

EXAMPLE 161

(1α,2β,3β,4α)-1,2-Di[N-propyl-N-(4-phenoxybenzyl)aminocarbonyl]-3-(1-methyl-1-propionyloxyethoxycarbonyl)cyclobutane-4-carboxylic acid The title compound was prepared by the procedures described in Example 149 substituting 2-chloropropyl propionate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. $^1$H NMR (CDCl$_3$, 300 MHz) δ0.7–0.9 (m, 6H), 1.0–1.1 (m, 3H), 1.3–1.6 (m, 4H), 2.2–2.4 (m, 2H), 2.9–3.4 (m, 4H), 3.5 (s, 6H) 3.8–4.2 (m, 4H), 4.3–4.7 (m, 4H), 6.8–7.6 (m, 18H). MS (FAB$^+$) m/e 793 (M+H)$^+$.

EXAMPLE 162A (1α,2β,3β,4α)-1,2-Di[N-propyl-N-(4-phenoxybenzyl)aminocarbonyl]-3-(methoxycarboxymethoxycarbonyl)cyclobutane-4-carboxylic acid and

EXAMPLE 162B (1α,2β,3β,4α)-1,2-Di[N-propyl-N-(4-phenoxybenzyl)aminocarbonyl]-3,4-di(methoxycarboxymethoxycarbonyl))cyclobutane The title compounds were prepared by the procedures described in Example 149 substituting chloromethyl methyl carbonate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 162A: $^1$H NMR (CDCl$_3$, 300 MHz) δ0.7–1.0 (m, 6H), 1.4–1.7 (m, 4H), 3.0–3.4 (m, 4H), 3.7–3.8 (m, 3H), 3.8–4.2 (m, 4H), 4.3–4.7 (m, 4H), 5.4–5.8 (m, 2H), 6.9–7.4 (m, 18H). MS (FAB$^+$) m/e 767 (M+H)$^+$. Example 162B: $^1$H NMR (CDCl$_3$, 300 MHz) δ0.7–1.0 (m, 6H), 1.4–1.7 (m, 4H), 3.0–3.4 (m, 4H), 3.7–3.8 (m, 6H), 3.8–4.2 (m, 4H), 4.3–4.7 (m, 4H), 5.4–5.8 (m, 4H), 6.9–7.4 (m, 18H). MS (FAB$^+$) m/e 855 (M+H)$^+$.

EXAMPLE 163A (1α,2β,3β,4α)-1,2-Di[N-propyl-N-(4-phenoxybenzyl)aminocarbonyl]-3-(propionyloxymethoxycarbonylmethyl)cyclobutane-4-acetic acid and

EXAMPLE 163B (1α,2β,3β,4α)-1,2-Di[N-propyl-N-(4-phenoxybenzyl)aminocarbonyl]-3,4-di(propionyloxymethoxycarbonylmethyl))cyclobutane The title compounds were prepared by the procedures described in Example 149 substituting the compound resulting from Example 103 for the compound resulting from Example 17 and chloromethyl propionate, prepared by the method of Neuenschwander, M., Bigler, P., Christen, K., Iseli, R., Kyburz, R., Muhle, H., Helv. Chim. Acta 61: 2047–2058 (1978), for bromomethyl acetate. Example 162A: $^1$H NMR (CDCl$_3$, 300 MHz) δ0.8–1.0 (m, 6H), 1.1–1.2 (m, 3H), 1.4–1.8 (m, 4H), 2.3–2.5 (m, 2H), 2.5–2.9 (m, 7H), 3.0–3.4 (m, 2H), 3.5–3.7 (m, 1H), 4.1–4.3 (m, 4H), 4.6–4.8 (m, 1H), 4.8–4.9 (m, 1H), 5.6–5.8 (m, 2H), 6.8–7.4 (m, 18H). MS (FAB$^+$) m/e 793 (M+H)$^+$. Example 162B: $^1$H NMR (CDCl$_3$, 300 MHz) δ0.8–1.0 (m, 6H), 1.1–1.2 (m, 6H), 1.4–1.8 (m, 4H), 2.3–2.5 (m, 4H), 2.5–2.9 (m, 7H), 3.0–3.4 (m, 2H), 3.5–3.7 (m, 1H), 4.1–4.3 (m, 4H), 4.6–4.8 (m, 1H), 4.8–4.9 (m, 1H), 5.6–5.8 (m, 4H), 6.8–7.4 (m, 18H). MS (FAB$^+$) m/e 879 (M+H)$^+$.

EXAMPLE 164

(1α,2β,3β,4α)-1,2-Di[N-propyl-N-(4-phenoxybenzyl)aminocarbonyl]-3-(2-hydroxy-3,4-dioxocyclobut-1-enylamino)cyclobutane-4-carboxylic acid

EXAMPLE 164A

Benzyl (1α,2β,3β,4α)-1,2-Di[N-propyl-N-(4-phenoxybenzyl)aminocarbonyl]-3-aminocyclobutane-4-carboxylate The compound resulting from Example 123B was hydrolyzed by the method of Example 95 to give the corresponding monoacid. MS (FAB+) m/e 769 (M+H)$^+$.

The above monoacid was treated by the method of Example 93A using allyl alcohol instead of 5-aminotetrazole, and using 2:1 hexane-EtOAc as the eluant for the chromatography to give the allyl carbamate. MS (FAB+) m/e 824 (M+H)$^+$.

To the above carbamate (90 mg, 0.11 mmol) dissolved in CH$_2$Cl$_2$ (0.5 mL), was added triphenylphosphine (2 mg, 0.007 mmol), tetrakis(triphenylphosphine)- palladium(O) (3.5 mg 0.003 mmol) and pyrrolidine (0.01 9 mL, 16 mg, 0.23 mmol). After stirring at room temperature for 1 hour, the reaction mixture was filtered through a small plug of silica gel eluting with EtOAc to give the title compound (82 mg, 100%). MS (FAB+) m/e 740 (M+H)$^+$.

EXAMPLE 164B 3,4-Dibenzyloxy-3-cyclobutene-1,2-dione 3,4-Dihydroxy-3-cyclobutene-1,2-dione (2.0 g, 17 mmol), benzyl alcohol (5.0 mL, 5.2 g, 48 mmol), and p-toluenesulfonic acid monohydrate (170 mg, 0.9 mmol) were slurried in toluene (20 mL), and heated under reflux with a Dean-Stark trap for 3 days. The insoluble material was filtered off, and the filtrate was diluted with ether (100 mL), washed with 2× with saturated aqueous NaHCO$_3$ solution and brine, dried over Na$_2$SO$_4$, filtered and concentrated to a crude residue. The crude product was purified by chromatography eluting with 4:1 hexane-EtOAc to give the title compound (1.5 g, 29%) as an oil which slowly solidified on standing. MS (FAB+) m/e 312 (M+NH$_3$+H)$^+$.

EXAMPLE 164C

Benzyl (1α,2β,3β,4α)-1,2-Di[N-propyl-N-(4-phenoxybenzyl)aminocarbonyl]-3-(2-hydroxy-3,4-dioxocyclobut-1-enylamino)cyclo butane-4-carboxylate The compounds resulting from Examples 164A (80 mg, 0.11 mmol) and 164B (46 mg, 0.16 mmol) were dissolved in DMF (0.33 mL), and stirred at 75° C. overnight. The reaction was cooled to room temperature, diluted with EtOAc, washed with 2× with water and brine, dried over Na$_2$SO$_4$, filtered and concentrated. The crude residue was purified by chromatography eluting with 6:4 hexane-EtOAc to give the title compound (53 mg, 53%). MS (FAB+) m/e 926 (M+H)$^+$.

EXAMPLE 164D (1α,2β,3β,4α)-1,2-Di[N-propyl-N-(4-phenoxybenzyl)aminocarbonyl]-3-(2-hydroxy-3,4-dioxocyclobut-1-enylamino)cyclobutane-4-carboxylic acid The compound resulting from Example 164C was hydrogenolyzed by the method of Example 74B, with the residue resulting from concentration of the filtrate being treated as in Example 81B to give the title compound. $^1$H NMR (DMSO-d$_6$) δ7.39, 7.28, 7.15, 6.97, 6.86 (all m, total 18H), 5.05, 4.70 (both m, total 4H), 4.40–3.35 (envelope, 6H), 3.25 (m, 1H), 3.05–2.65 (envelope, 1H), 1.47 (m, 4H), 0.80 (m, 6H). MS (FAB−) m/e 744 (M−H)$^-$. Anal cald for C$_{43}$H$_{43}$N$_3$O$_9$.0.5 H$_2$O: C, 68.42; H, 5.88; N, 5.57. Found: C, 68.45; H, 5.84; N, 5.38.

EXAMPLE 165

(1α,2β,3β,4α)-1,2-Di[N-propyl-N-(4-phenoxybenzyl)aminocarbonyl]-3-(5-oxo-4,5-dihydro-[1,3,4]oxadiazol-2-yl)cyclobutane-4-carboxylic acid

EXAMPLE 165A

Benzyl (1α,2β,3β,4α)-1,2-Di[N-propyl-N-(4-phenoxybenzyl)aminocarbonyl]cyclobutane-3-hydrazinocarbonyl-4-carboxylate To the monoacid resulting from the first part of Example 164A (450 mg, 0.58 mmol) dissolved in THF (5 mL) and cooled to −15° C. were added N-methylmorpholine (0.070 mL, 64 mg, 0.64 mmol) and isobutyl chloroformate (0.079 mL, 83 mg, 0.61 mmol). After 20 minutes, t-butyl carbazate (85 mg, 0.64 mmol) was added, and the reaction allowed to warm to room temperature overnight. The reaction was diluted with EtOAc, washed with 3× with 1M H$_3$PO$_4$ and brine, dried over Na$_2$SO$_4$, filtered and concentrated. The resulting crude residue was purified by chromatography eluting with 2:1 hexane-EtOAc to give the protected hydrazide (450 mg, 88%).

The protected hydrazide was dissolved in 4N HCl in dioxane (7 mL), stirred at room temperature for 1 hour, concentrated, and partitioned between saturated aqueous NaHCO$_3$ and EtOAc. The organic layer was washed with water and brine, dried over Na$_2$SO$_4$, filtered and concentrated to give the title compound (415 mg). MS (FAB+) m/e 783 (M+H)$^+$.

EXAMPLE 165B

Benzyl (1α,2β,3β,4α)-1,2-Di[N-propyl-N-(4-phenoxybenzyl)aminocarbonyl]-3-(5-oxo-4,5-dihydro-[1,3,4]oxadiazol-2-yl)cyclobutane-4-carboxylate To toluene (0.5 mL) cooled to 0° C. was added a 1.93M solution of phosgene in toluene (0.087 mL, 0.17 mmol) followed by a solution of the compound resulting from Example 165A (125 mg, 0.16 mmol) in toluene (1 mL) added dropwise. After 1 hour, the bath was removed, and the reaction was heated under reflux for 5 hours. The reaction was then cooled to room temperature, concentrated, and purified by chromatography eluting with 65:35 hexane-EtOAc to give the title compound (70 mg, 54%). MS (FAB+) m/e 809 (M+H)$^+$.

EXAMPLE 165C (1α,2β,3β,4α)-1,2-Di[N-propyl-N-(4-phenoxybenzyl)aminocarbonyl]-3-(5-oxo-4,5-dihydro-[1,3,4]oxadiazol-2-yl)cyclobutane-4-carboxylic acid Using the compound resulting from Example 165B, the title compound was prepared by the method Example 164D. $^1$H NMR (DMSO-d$_6$) δ7.39, 7.28, 7.13, 7.00 (all m, total 18H), 4.75 (m, 2H), 4.35–3.90 (envelope, 5H), 3.72 (m, 1H), 3.68–3.15 (envelope, 2H), 3.05–2.55 (envelope, 2H), 1.50, (m, 4H), 0.83, 0.73 (both m, total 6H). MS (FAB+) m/e 719 (M+H)$^+$. Anal cald for C$_{41}$H$_{42}$N$_4$O$_8$: C, 68.51; H, 5.89; N, 7.79. Found: C, 68.11; H, 5.81; N, 7.58.

EXAMPLE 166

(1α,2β,3β,4α)-1,2-Di[N-propyl-N-(4-phenoxybenzyl)aminocarbonyl]cyclobutane-3-(N-methanesulfonyl)carboxamido-4-carboxylic acid

EXAMPLE 166A

Benzyl (1α,2β,3β,4α)-1,2-Di[N-propyl-N-(4-phenoxybenzyl)aminocarbonyl]cyclobutane-3-(N-methanesulfonyl)carboxamido-4-carboxylate To the monoacid resulting from the first part of Example 164A (80 mg, 0.10 mmol) dissolved in THF (1 mL) was added carbonyldiimidazole (18 mg, 0.11 mmol). The reaction mixture was warmed at 45° C. for 3 hours and then cooled to room temperature. Methanesulfonamide (10 mg, 0.10 mmol) and 1,8-diazabicyclo[5.4.0]undec-7-ene (0.016 mL, 16 mg, 0.11 mmol) were added, and the reaction was stirred at room temperature overnight. The reaction was diluted with EtOAc, washed with 3× with 1M H$_3$PO$_4$ and brine, dried over Na$_2$SO$_4$, filtered and concentrated. The resulting crude residue was purified by chromatography eluting with 2% methanol in CHCl$_3$ to give the title compound (56 mg, 64%) as a mixture of diastereomers. MS (FAB–) m/e 844 (M–H)$^-$.

EXAMPLE 166B (1α,2β,3β,4α)-1,2-Di[N-propyl-N-(4-phenoxybenzyl)aminocarbonyl]cyclobutane-3-(N-methanesulfonyl)carboxamido-4-carboxylic acid Using the compound resulting from Example 166A, the title compound was prepared by the method Example 164D. $^1$H NMR (DMSO-d$_6$) δ7.39, 7.28, 7.15, 6.97, 6.86 (all m, total 18H), 5.05, 4.70 (both m, total 4H), 4.40–3.35 (envelope, 6H), 3.25 (m, 1H), 3.05–2.65 (envelope, 1H), 1.47 (m, 4H), 0.80 (m, 6H). MS (FAB+) m/e 756 (M+H)$^+$. Anal cald for C$_{41}$H$_{45}$N$_3$O$_9$S.0.75 H$_2$O: C, 64.00; H, 6.09; N, 5.46. Found: C, 64.03; H, 5.95; N, 5.37.

EXAMPLE 167

(1α,2β,3β,4α)-1,2-Di[N-propyl-N-(4-phenoxybenzyl)aminocarbonyl]cyclobutane-3-(4,6-dioxo-tetrahydropyran-2-yl)-4-carboxylic acid

EXAMPLE 167A

Benzyl (1α,2β,3β,4α)-1,2-Di[N-propyl-N-[4-phenoxybenzyl]aminocarbonyl]-4-hydroxymethyl-cyclobutane-3-carboxylate Using the monoacid resulting from the first part of Example 164A, the title compound was prepared by the method of Example 70A. MS (DCl/NH$_3$) m/e 755 (M+H)$^+$.

EXAMPLE 167B (1α,2β,3β,4α)-1,2-Di[N-propyl-N-(4-phenoxybenzyl)aminocarbonyl]-3-benzyloxycarbonylcyclobutane-4-carboxyaldehyde Using the compound resulting from Example 167A, the title compound was prepared by the method of Example 71A. MS (DCl/NH$_3$) m/e 753 (M+H)$^+$.

EXAMPLE 167C

Benzyl (1α,2β,3β,4α)-1,2-Di[N-propyl-N-(4-phenoxybenzyl)aminocarbonyl]-3-[2-(2,2-dimethyl-6-oxo-6H-[1,3]dioxin-4-yl)-1-hydroxyethyl]cyclobutane-3-carboxylate To THF (1 mL) cooled to −70° C. was added a 1.5M solution of LDA in cyclohexane (0.24 mL, 0.36 mmol) followed by 1,3-dimethyl-3,4,5,6-tetrahydro-2(1H)-pyrimidone (0.088 mL, 93 mg, 0.73 mmol). The solution was stirred at −70° C. for 30 minutes, and then 2,2,6-trimethyl-4H-1,3-dioxin-4-one (0.44 mL, 48 mg, 0.34 mmol) was added. After stirring at −70° C. for 30 minutes, a solution of the compound resulting from Example 167B (125 mg, 0.17 mmol) in THF (0.5 mL) was added dropwise. The reaction was warmed to 10° C. over 3 hours and then poured into 1N HCl and extracted with Et$_2$O. The organic layer was washed with water and brine, dried over Na$_2$SO$_4$, filtered and concentrated. The resulting crude residue was purified by chromatography eluting with 65:35 hexane-EtOAc followed by 50:50 hexane-ethyl acetate to give 62 mg of the less polar diastereomer and 25 mg of the more polar diastereomer (total of 87 mg, 57%). MS (FAB+) m/e 895 (M+H)$^+$ (for both diastereomers).

EXAMPLE 167D (1α,2β,3β,4α)-1,2-Di[N-propyl-N-(4-phenoxybenzyl)aminocarbonyl]cyclobutane-3-(4,6-dioxo-tetrahydropyran-2-yl)-4-carboxylic acid methyl ester To the less polar diastereomer resulting from Example 167C (60 mg, 0.067 mmol) dissolved in MeOH (0.25 mL) was added K$_2$CO$_3$ (15 mg, 0.091 mmol), and the reaction was stirred at room temperature overnight. The reaction was diluted with EtOAc, washed with 1M H$_3$PO$_4$ and brine, dried over Na$_2$SO$_4$, filtered and concentrated. The resulting crude residue was purified by chromatography eluting with 1:1 hexane-ethyl acetate followed by 3% methanol in chloroform to give the title compound (30 mg, 59%). MS (FAB+) m/e 761 (M+H)$^+$.

EXAMPLE 167E (1α,2β,3β,4α)-1,2-Di[N-propyl-N-(4-phenoxybenzyl)aminocarbonyl]cyclobutane-3-(4,6-dioxo-tetrahydropyran-2-yl)-4-carboxylic acid Using the compound resulting from Example 167D, the title compound was prepared by the method of Example 92B, except the reaction was stirred at room temperature overnight, and there was no chromatography. $^1$H NMR (DMSO-d$_6$) δ7.39, 7.25, 7.12, 6.97, 6.90 (all m, total 18H), 4.90, 4.77 (both m, total 2H), 4.60–3.90 (envelope, 4H), 3.60–3.20 (envelope, 5H), 3.05, 2.70, 2.45, 2.15 (all m, total 4H), 1.60, 1.40 (both m, total 4H), 0.85, 0.78 (both m, total 6H). MS (FAB+) m/e 747 (M+H)$^+$. Anal cald for C$_{44}$H$_{46}$N$_2$O$_9$.1.20 H$_2$O: C, 68.77; H, 6.35; N, 3.65. Found: C, 68.75; H, 6.08; N, 3.52.

145

EXAMPLE 168

(1α,2β,3β,4α)-1,2-Di[(N-methyl-N-(R)-α-propyl-4-phenoxybenzyl)aminocarbonyl]cyclobutane-3,4-dicarboxylic acid

EXAMPLE 168A (4S,5R)-3-(2-(4-Phenoxyphenyl)acetyl)-4-methyl-5-phenyl-1,3-oxazolidin-2-one To a solution containing 4-phenoxyphenylacetic acid (10.0 g, 43.8 mmol) in THF (62.6 mL) at −78° C. was added pivaloyl chloride (5.49 g, 45.6 mmol) followed by triethylamine (4.61 g, 45.6 mmol). The mixture was stirred at −78° C. for 15 minutes, at 0° C. for 1 hour, and then recooled to −78° C. In a separate flask, 2.5M n-butyllithium (20 mL, 50 mmol) was added to a solution of (4S,5R)-(−)-4-methyl-5-phenyl-2-oxazolidinone (8.86 g, 50 mmol) in THF (100 mL) at −78° C. This mixture was stirred for 15 minutes and then transferred to the flask containing pivalic anhydride via cannula. The mixture was stirred for 15 minutes at −78° C. then at room temperature for 18 hours. The solvent was removed, and the residue was partitioned between diethyl ether (500 mL) and 1N HCl (500 mL). The organic layer was dried (MgSO₄), filtered and concentrated to provide a light yellow solid. The solid was chromatographed with 10% ethyl acetate in hexane to yield 10.9 g (64%) of the title compound as a white solid.

EXAMPLE 168B (4S,5R)-3-{(4R)-4-(1-(4-Phenoxyphenyl)but-1-en-4-yl}-4-methyl-5-phenyl-1,3-oxazolidin-2-one A solution of the compound resulting from Example 168A (3 g, 7.4 mmol) in THF (25 mL) at −78° C. was added via cannula to a 1M solution of NaN(Si(CH₃)₃)₂ in THF (10 mL, 10 mmol) at −78° C. After 1 hour, allyl iodide (2.5 g, 15 mmol) in THF (5 mL) at −78° C. was added via cannula to the cold enolate solution. After 6 hours, the reaction was quenched with saturated ammonium chloride solution and extracted with diethyl ether. The combined organic extracts were dried (MgSO₄), filtered and concentrated to provide a yellow oil. Chromatography of the oil eluting with ethyl acetate/hexane provided 2.65 g (84%) of the title compound as a colorless oil.

EXAMPLE 168C (4R)-4-(4-Phenoxyphenyl)-1-pentenoic acid

A solution of the compound resulting from Example 168B in THF and water was treated with 30% aqueous hydrogen peroxide followed by 1M aqueous lithium hydroxide. After 2 hours, the THF was removed under reduced pressure, and the aqueous layer was extracted with CH₂Cl₂. The aqueous layer was then acidified to pH 0 with 6N HCl and extracted with diethyl ether. The combined ether extracts were dried (MgSO₄), filtered and concentrated to provide the title compound as an oil which was used without further purification.

EXAMPLE 168D (4R)-4-(4-Phenoxyphenyl)pentanoic acid

A solution of the compound resulting from Example 168C (1.4 g, 5.2 mmol) in ethyl acetate (17 mL) was hydrogenated over 18 hours using a palladium on carbon catalyst (150 mg). The solution was filtered through celite and concentrated to provide 1.41 g (100%) of the title compound as a colorless glass.

EXAMPLE 168E (1R)-N-Methoxycarbonyl-N-{1-(4-phenoxyphenyl)butyl}amine

The compound resulting from Example 168D (1.4 g, 5.2 mol), diphenylphosphoryl azide (1.58 g, 5.7 mmol) and triethylamine (1.1 g, 10.4 mmol) were warmed to 83° C. in toluene for 2 hours. Methanol (30 mL) was added, and the solution was stirred an additional 18 hours. All volatiles were removed, and the residue was chromatographed on silica gel eluting with 15% ethyl acetate in hexane to provide 1.47 g (94%) of the title compound as a white solid.

EXAMPLE 168F (1R)-N-Methyl-N-{1-(4-phenoxyphenyl)butyl}amine

The compound resulting from Example 168E (1.0 g, 3.3 mmol) in THF (10 mL) was treated with 1M lithium aluminum hydride in THF (6.6 mL). The solution was refluxed for 4 hours, cooled to 0° C., quenched with Na₂SO₄, filtered through celite and concentrated to provide 841 mg (99%) of the title compound as a colorless oil which was used directly in the next step.

EXAMPLE 168G (+)-(1α,2β,3β,4α)-1,2-Di[benzyloxycarbonyl]cyclobutane-3,4-dicarboxylic acid To a solution of 1,2,3,4-cyclobutanetetracarboxylic anhydride (21 g, 107.1 mmol) in acetonitrile (530 mL) at −7.5° C. was added benzyl alcohol (70 mL, 680 mmol) all at once. Triethylamine (30 mL, 210 mmol) was added dropwise over 3–5 minutes and the temperature rose to 2.8° C. Dimethylaminopyridine (1.3 g, 10.6 mmol) was added and the temperature returned to −5° C. The reaction mixture was stirred for 18 hours at which time the internal temperature was 9.2° C. and then concentrated in vacuo. The residue was dissolved in ethyl acetate (1 L) and washed with 2M HCl (2×375 mL). The product was then extracted into saturated NaHCO₃ solution (2×375 mL). The aqueous solution was allowed to stand at ambient temperature and then was cooled in a refrigerator overnight. The solid was collected and washed with cold saturated NaHCO₃ solution (200 mL) and then was dissolved in water (500 mL), acidified with 2M HCl (375 mL) and extracted into ethyl acetate (2×375 mL). The combined organic extracts were washed with brine, dried over sodium sulfate and concentrated in vacuo to afford (1α,2β,3β,4α)-1,2-di(benzyloxycarbonyl)cyclobutane-3,4-dicarboxylic acid (25.65 g, 58%) as a white solid. m.p. 164.5°–165.5° C.

To the above prepared compound (1.0 g, 2.4 mmol) dissolved in absolute EtOH (45 mL) was added a solution of (−)-norephedrine (0.74 g, 4.9 mmol) in absolute EtOH (5 mL). The solution was allowed to sit at room temperature overnight. The resultant crystals were filtered and then recrystallized twice from hot absolute EtOH (4.5 mg/mL), then partitioned between 1M H₃PO₄ and Et₂O. The Et₂O layer was washed with brine, dried over Na₂SO₄, filtered and concentrated to give the title compound. $[\alpha]_D$=+17.3° (c=0.92, MeOH).

EXAMPLE 168H (+)-(1α,2β,3β,4α)-1,2-Di[(N-methyl-N-(R)-α-propyl-4-phenoxybenzyl)aminocarbonyl]cyclobutane-3,4-dicarboxylic acid dibenzyl ester A solution of the compound resulting from Example 168G (85.2 mg, 0.21 mmol) in CH₂Cl₂ (1 mL) was treated with oxalyl chloride (58.6 mg, 0.46 mmol) and DMF (1 drop). After 2 hours, all volatiles were removed, and the residue was chased with toluene (2×5 mL), redissolved in CH$_2$Cl$_2$ (5 mL) and added dropwise to a slurry of the compound resulting from Example 168F (149 mg, 0.62 mmol) and NaHCO$_3$ (1.04 g, 12.4 mmol) in H$_2$O (2 mL). After 18 hours, the layers were separated, and the organic phase was dried over MgSO$_4$, filtered, concentrated and chromatographed eluting with 1:1 ethyl acetate-hexane to provide 138 mg of the title compound as a colorless glass.

EXAMPLE 168I (+)-(1α,2β,3β,4α)-1,2-Di[(N-methyl-N-(R)-α-propyl-4-phenoxybenzyl)aminocarbonyl] cyclobutane-3,4-dicarboxylic acid The compound resulting from Example 168H (130 mg, 0.15 mmol) and palladium on carbon (33 mg) were stirred in ethyl acetate (5 mL) under a hydrogen atmosphere for 18 hours. The mixture was filtered through celite and concentrated to provide 97 mg (94%) of the title compound as a white solid. $^1$H NMR (CDCl$_3$, 300 MHz) δ0.9–1.0 (m, 7H), 1.1–1.4 (envelope, 7H), 1.7–2.0 (m, 5H), 3.3–3.6 (m, 3H), 3.9–4.1 (m, 2H), 5.5–5.7 (m, 2H), 6.9–7.1 (m, 8H), 7.15–7.2 (m, 2H), 7.21–7.41 (m, 8H), 12.4–12.8 (br s, 2H). MS (FAB) m/e 707 (M+H)$^+$.

EXAMPLE 169

(1α,2β,3β,4α)-1,2-Di[N-(S)-sec-butyl-N-(4-phenoxybenzyl)aminocarbonyl]cyclobutane-3,4-dicarboxylic acid

EXAMPLE 169A

N-((S)-sec-Butyl)-N-(4-phenoxybenzyl)amine

4-Phenoxybenzaldehyde (8.13 g, 41 mmol) and (S)-sec-butylamine (3 g, 41 mmol) were dissolved in methanol (137 mL) under a nitrogen at room temperature. Sodium cyanoborohydride (2.58 g) was added, and stirring was continued for 18 hours. The solvent was removed, and the residue was suspended in ether, washed with brine and dried over Na$_2$SO$_4$. The ether was evaporated, and the crude product was chromatographed on silica gel eluting with 3% methanol in methylene chloride to provide 7.24 g (77%) of the title compound as a colorless oil.

EXAMPLE 169B (1α,2β,3β,4α)-1,2-Di[N-(S)-sec-butyl-N-(4-phenoxybenzyl)aminocarbonyl]cyclobutane-3,4-dicarboxylic acid A slurry of 1,2,3,4-cyclobutanetetracarboxylic dianhydride (457 mg, 2.33 mmol) in acetonitrile (9 mL) under a nitrogen atmosphere at room temperature was treated with a solution of the compound resulting from Example 169A (1.19 g, 4.7 mmol) in acetonitrile (8 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile, triturated with water, and lyophilized to provide 609 mg (36%) of the title compound as a white powder. $^1$H NMR (CDCl$_3$, 300 MHz) δ0.8–1.6 (envelope, 18H), 3.4–4.6 (envelope, 8H), 6.8–7.45 (envelope, 18H), 12.4 (br s, 2H). MS (FAB) m/e 707 (M+H)$^+$.

EXAMPLE 170

(1α,2β,3β,4α)-1,2-Di[N-(R)-sec-butyl-N-(4-phenoxybenzyl)aminocarbonyl]cyclobutane-3,4-dicarboxylic acid

EXAMPLE 170A

N-((R)-sec-butyl)-N-(4-phenoxybenzyl)amine

4-Phenoxybenzaldehyde (8.13 g, 41 mmol) and (R)-sec-butylamine (3 g, 41 mmol) were dissolved in methanol (137 mL) under nitrogen at room temperature. Sodium cyanoborohydride (2.58 g) was added, and stirring was continued for 18 hours. The solvent was removed, and the residue was suspended in ether, washed with brine and dried over Na$_2$SO$_4$. The ether was evaporated, and the crude product was chromatographed on silica gel eluting with 3% methanol in methylene chloride to provide 8.0 g (77%) of the title compound as a colorless oil.

EXAMPLE 170B (1α,2β,3β,4α)-1,2-Di[N-(R)-sec-butyl-N-(4-phenoxybenzyl)aminocarbonyl]cyclobutane-3,4-dicarboxylic acid A slurry of 1,2,3,4-cyclobutanecarboxylic dianhydride (457 mg, 2.33 mmol) in acetonitrile (9 mL) under nitrogen at room temperature was treated with a solution of the compound resulting from Example 170A (1.19 g, 4.7 mmol) in acetonitrile (8 mL). The resulting suspension was refluxed for 15 hours. The solvent was evaporated, and the residue was chromatographed on silica gel eluting with 98:1:1 chloroform-methanol-acetic acid to provide a wet foam. The foam was dissolved in acetonitrile, triturated with water, and lyophilized to provide 610 mg (37%) of the title compound as a white powder. $^1$H NMR (CDCl$_3$, 300 MHz) δ0.6–1.6 (envelope, 18H), 3.4–4.6 (envelope, 8H), 6.8–7.45 (envelope, 18H), 12.4 (br s, 2H). MS (FAB) m/e 707 (M+H)$^+$.

EXAMPLE 171

(1α,2β,3β,4α)-1,2-Di[N-propyl-N-(4-phenoxybenzyl)aminocarbonyl]-3-(methoxyacetyl)cyclobutane-4-acetic acid Using the compound resulting from Example 103A, the title compound was prepared by the method of Example 95 (starting with the second sentence). $^1$H NMR (DMSO-d$_6$) δ7.39, 7.28, 7.13, 6.95 (all m, total 18H), 4.68 (m, 2H), 4.22 (m, 2H), 3.95 (m, 2H), 3.60, 3.58, 3.49, 3.47 (all s, total 3H), 3.50, 3.25, 3.00, 2.65, 2.40 (all m, total 10H), 1.50, (m, 4H), 0.83, 0.76 (both m, total 6H). MS (FAB+) m/e 721 (M+H)$^+$. Anal cald for C$_{43}$H$_{48}$N$_2$O$_8$·0.5 H$_2$O: C, 70.76; H, 6.77; N, 3.84. Found: C, 70.90; H, 6.58; N, 3.84.

EXAMPLE 172

(1α,2β,3β,4α)-1,2-Di[N-propyl-N-(4-phenoxybenzyl)aminocarbonyl]-3-(5-oxo-4,5-dihydro-[1,3,4]-oxadiazol-2-ylmethyl)cyclobutane-4-acetic acid

EXAMPLE 172A (1α,2β,3β,4α)-1,2-Di[N-propyl-N-(4-phenoxybenzyl)aminocarbonyl]-3-(benzyloxycarbonylmethyl)cyclobutane-4-acetic acid To the compound resulting from Example 103B (1.0 g, 1.5 mmol) dissolved in 1:1 THF-DMF (100 mL) was added EDCI.HCl (282 mg, 1.5 mmol) and DMAP (90 mg, 0.7 mmol). After cooling to −78° C., benzyl alcohol (0.15 mL, 156 mg, 1.4 mmol) was added. The reaction was stirred at −78° C., allowed to come to room temperature overnight, stirred another day at room temperature, and then the reaction was heated at 60° C. for 3 days. After concentrating, the residue was partitioned between EtOAc and 1M $H_3PO_4$. The organic layer was washed with brine, dried over $Na_2SO_4$, filtered and concentrated to a crude residue which was purified by chromatography eluting with 1:1 hexane-EtOAc followed by 5% methanol in chloroform to give the title compound (160 mg, 14%). MS (FAB+) (M+H)$^+$ 797.

EXAMPLE 172B (1α,2β,3β,4α)-1,2-Di[N-propyl-N-(4-phenoxybenzyl)aminocarbonyl]-3-(5-oxo-4,5-dihydro-[1,3,4]-oxadiazol-2-ylmethyl)cyclobutane-4-acetic acid The compound resulting from Example 172A was treated by the procedures described in Example 165A to give (1α,2β,3β,4α)-1,2-di[N-propyl-N-(4-phenoxybenzyl)aminocarbonyl]cyclobutane-3-(hydrazinocarbonylmethyl)-4-acetic acid benzyl ester. MS (FAB+) (M+H)$^+$ 811.

The hydrazinocarbonylmethyl compound prepared above was treated by the procedures described in Example 165B to give (1α,2β,3β,4α)-1,2-di[N-propyl-N-(4-phenoxybenzyl)aminocarbonyl]-3-(5-oxo-4,5-dihydro-[1,3,4]-oxadiazol-2-ylmethyl)cyclobutane-4-acetic acid benzyl ester. MS (FAB+) (M+H)$^+$ 837.

The benzyl ester prepared above was treated by the procedures described in Example 165C to give the title compound. $^1$H NMR (DMSO-d$_6$) δ7.39, 7.24, 7.13, 6.96 (all m, total 18H), 4.70 (m, 2H), 4.22 (m, 2H), 4.00 (m, 2H), 3.50, 3.30, (both m, total 4H), 3.00 (m, 1H), 2.63 (m, 2H), 2.40, 2.35, 2.16 (all m, total 3H), 1.50, (m, 4H), 0.83, 0.77 (both m, total 6H). MS (FAB+) (M+H)$^+$ 747. Anal cald for $C_{43}H_{46}N_4O_8$: C, 69.15; H, 6.21; N, 7.50. Found: C, 68.79; H, 6.11; N, 7.31.

EXAMPLE 173

(1α,2β,3β,4α)-1,2-Di[N-propyl-N-(4-phenoxybenzyl)aminocarbonyl]-3-(2-hydroxyethyl)cyclobutane-4-acetic acid Using the compound resulting from Example 171, (1α,2β,3β,4α)-1,2-di[N-propyl-N-(4-phenoxybenzyl)aminocarbonyl]-3-(2-hydroxyethyl)cyclobutane-4-acetic acid methyl ester was prepared by the method of Example 70A. MS (DCI/NH$_3$) m/e 707 (M+H)$^+$.

Using the methyl ester prepared above, the title compound was prepared by the method of Example 72C, except chromatography was not needed. $^1$H NMR (DMSO-d$_6$) δ7.39, 7.26, 7.15, 6.98 (all m, total 18H), 4.70 (m, 2H), 4.22 (m, 2H), 3.93 (m, 2H), 3.60–3.10 (envelope, 5H), 3.00 (m, 1H), 2.68 (m, 1H), 2.30 (m, 3H), 1.50, (m, 6H), 0.83, 0.78 (both m, total 6H). MS (FAB+) m/e 693 (M+H)$^+$. Anal cald for $C_{42}H_{48}N_2O_7$: C, 72.81; H, 6.98; N, 4.04. Found: C, 72.53; H, 7.09; N, 4.04.

EXAMPLE 174

(1α,2β,3β,4α)-1,2-Di[N-propyl-N-[4-phenoxybenzyl]aminocarbonyl]-3-(2-oxo-ethyl)cyclobutane-4-acetic acid The compound resulting from the first paragraph of Example 173 was treated by the procedures described in Example 71A to give methyl (1α,2β,3β,4α)-1,2-di[N-propyl-N-[4-phenoxybenzyl]aminocarbonyl]-3-(2-oxo-ethyl)cyclobutane-4-acetic acid. MS (DCI/NH$_3$) m/e 705 (M+H)$^+$.

Using the methyl ester prepared above, the title compound was prepared by the method of Example 72C. $^1$H NMR (DMSO-d$_6$) δ9.61, 9.45 (both m, total 1H), 7.39, 7.24, 7.15, 6.98 (all m, total 18H), 4.67 (m, 2H), 4.20 (m, 2H), 3.98 (m, 2H), 3.50 (m, 1H), 3.23, 3.20, 3.07, 3.00 (all m, total 3H), 2.80–2.10 (envelope, 6H), 1.50, (m, 6H), 0.83, 0.78 (both m, total 6H). MS (FAB+) m/e 691 (M+H)$^+$. Anal cald for $C_{42}H_{46}N_2O_7$·0.4 $H_2O$: C, 72.28; H, 6.80; N, 3.94. Found: C, 72.27; H, 6.76; N, 4.01.

EXAMPLE 175

(1α,2β,3β,4α)-1,2-Di[N-propyl-N-[4-phenoxybenzyl]aminocarbonyl]-3-(5-tetrazolylmethyl)cyclobutane-4-acetic acid The compound described in the first paragraph of Example 174 was treated by the procedures described in Example 71B to give (1α,2β,3β,4α)-1,2-di[N-propyl-N-[4-phenoxybenzyl]aminocarbonyl]-3-(2-hydroxyiminoethyl)cyclobutane-4-acetic acid methyl ester. MS (DCI/NH$_3$) m/e 720 (M+H)$^+$.

The hydroxyimino compound prepared above was treated by the procedures described in Example 72A to give (1α,2β,3β,4α)-1,2-di[N-propyl-N-[4-phenoxybenzyl]aminocarbonyl]-3-cyanomethylcyclobutane-4-acetic acid methyl ester. MS (DCI/NH$_3$) m/e 702 (M+H)$^+$.

The nitrile prepared above was treated by the procedures described in Example 72B to give (1α,2β,3β,4α)-1,2-di[N-propyl-N-[4-phenoxybenzyl]aminocarbonyl]-3-(5-tetrazolylmethyl)cyclobutane-4-acetic acid methyl ester. MS (DCI/NH$_3$) m/e 745 (M+H)$^+$.

The methyl ester prepared above was treated by the procedures described in Example 72C to give the title compound. $^1$H NMR (DMSO-d$_6$) δ7.39, 7.24, 7.15, 6.98 (all m, total 18H), 4.67 (m, 2H), 4.23 (m, 2H), 4.05 (m, 2H), 3.52 (m, 1H), 3.30, 3.00, 2.80,2.35, 2.20 (all m, total 9H), 1.50, (m, 6H), 0.85, 0.77 (both m, total 6H). MS (FAB+) m/3 731 (M+H)$^+$. Anal cald for $C_{42}H_{46}N_6O_6$·0.65 $H_2O$: C, 67.93; H, 6.42; N, 11.32. Found: C, 67.92; H, 6.41; N, 11.25.

EXAMPLE 176

(1α,2β,3β,4α)-1,2-Di[N-propyl-N-(4-phenoxybenzyl)aminocarbonyl]-3-benzyloxycarbonylcyclobutane-4-carboxylic acid To the compound resulting from Example 123B (22.25 g, 25.90 mmol) in tetrahydrofuran (220 mL) at 0° C. was added LiOH monohydrate (1.092 g, 26.02 mmol). The cooling bath was removed, and the mixture was stirred at ambient temperature for 14 hours. The reaction was quenched with 2M HCl (50 mL), concentrated, and diluted with ethyl acetate. After washing with brine, the organic layer was dried over $Na_2SO_4$ and evaporated. Chromatography of the residue on silica gel with ethyl acetate in hexane and methanol in chloroform mixtures afforded 3.65 g (18%) of the title product as a foam. $^1$H NMR (CDCl$_3$, 300 MHz) δ7.40–6.80 (m, 23H), 5.22–5.02 (m, 2H), 1.65–1.30 (m, 4H), 0.92–0.72 (m, 6H). Anal calcd for $C_{47}H_{48}N_2O_8$: C, 73.42; H, 6.29; N, 3.64. Found: C, 73.22; H, 6.14; N, 3.58.

EXAMPLE 177

(1α,2β,3β,4α)-1,2-Di[N-propyl-N-(4-phenoxybenzyl)aminocarbonyl]-3-(N,N-diethylaminocarbonylmethoxycarbonyl)cyclobutane-4-carboxylic acid

EXAMPLE 177A (1α,2β,3β,4α)-1,2-Di[N-propyl-N-(4-phenoxybenzyl)aminocarbonyl]-3-(N,N-diethylaminocarbonylmethoxycarbonyl)cyclobutane-4-carboxylic acid benzyl ester The resultant compound from Example 176 (65.0 mg, 0.0845 mmol), DMAP (13.0 mg, 0.106 mmol) and glycolic acid diethyl amide (24.3 mg, 0.185 mmol) in dimethylformamide (0.8 mL) were treated with 1-(3-dimethylaminopropyl)-3-ethylcarbodiimide hydrochloride (23.0 mg, 0.120 mmol). After 20 hours, the mixture was diluted with ethyl acetate and washed sequentially with 2M HCl, saturated $NaHCO_3$ solution, and brine, and then was dried over $Na_2SO_4$ and evaporated. Chromatography of the residue on silica gel with 40% ethyl acetate in hexane afforded 40.0 mg (54%) of the title compound as an oil.

EXAMPLE 177B (1α,2β,3β,4α)-1,2-Di[N-propyl-N-(4-phenoxybenzyl)aminocarbonyl]-3-(N,N-diethylaminocarbonylmethoxycarbonyl)cyclobutane-4-carboxylic acid The resultant compound from Example 177A (37.5 mg, 0.0425 mmol) and 10% Pd/C (35 mg) in ethyl acetate were stirred under a hydrogen atmosphere for 2 hours. The mixture was filtered and evaporated to afford 30.9 mg (92%) of the title compound as a foam. $^1$H NMR ($CDCl_3$, 300 MHz) δ7.37–6.96 (m, 18H), 1.67–1.39 (m, 4H), 1.30–1.03 (m, 6H), 0.92–0.72 (m, 6H). Anal calcd for $C_{46}H_{53}N_3O_9$: C, 69.77; H, 6.74; N, 5.30. Found: C, 69.53; H, 6.62; N, 5.21.

EXAMPLE 178

(1α,2β,3β,4α)-1,2-Di[N-propyl-N-(4-phenoxybenzyl)aminocarbonyl]-3-(indan-5-yloxycarbonyl)cyclobutane-4-carboxylic acid

EXAMPLE 178A (1α,2β,3β,4α)-1,2-Di[N-propyl-N-(4-phenoxybenzyl)aminocarbonyl]cyclobutane-3-benzyloxycarbonyl-4-carboxylate Indan-5-ol Ester The resultant compound from Example 176 (75.0 mg, 0.098 mmol), DMAP (15.0 mg, 0.123 mmol) and 5-hydroxyindane (37.0 mg, 0.276 mmol) in dimethylformamide (0.8 mL) were treated with 1-(3-dimethylaminopropyl)-3-ethylcarbodiimide hydrochloride (28.0 mg, 0.146 mmol). After 40 hours, the mixture was diluted with ethyl acetate and washed sequentially with 2M HCl, saturated $NaHCO_3$ solution, and brine, and then was dried over $Na_2SO_4$ and evaporated. Chromatography of the residue on silica gel with 20% ethyl acetate in hexane afforded 59.2 mg (68%) of the title compound as a tacky foam.

EXAMPLE 178B (1α,2β,3β,4α)-1,2-Di[N-propyl-N-(4-phenoxybenzyl)aminocarbonyl]-3-(indan-5-yloxycarbonyl)cyclobutane-4-carboxylic acid The resultant compound from Example 178A (57.0 mg, 0.064 mmol) and 10% Pd/C (40 mg) in ethyl acetate were stirred under a hydrogen atmosphere for 2 hours. The mixture was filtered and evaporated to afford 48.3 mg (94%) of the title compound as waxy solid. $^1$H NMR ($CDCl_3$, 300 MHz) δ7.40–6.70 (m, 22H), 2.15–1.98 (m, 2H), 1.66–1.40 (m, 4H), 0.98–0.74 (m, 6H). Anal calcd for $C_{46}H_{53}N_3O_9$: C, 74.04; H, 6.34; N, 3.52. Found: C, 73.85; H, 6.52; N, 3.39.

EXAMPLE 179

(+)-(1α,2β,3β,4α)-1,2-Di[N-propyl-N-(trans, trans-3,7-dimethyl-2,6-octadienyl)aminocarbonyl] cyclobutane-3,4-dicarboxylic acid

EXAMPLE 179A

N-Propionyl-N-(trans, trans-3,7-dimethyl-2,6-octadienyl)amine trans, trans-3,7-Dimethyl-2,6-octadienylamine and $NaHCO_3$ in water at room temperature were treated with propionyl chloride in $CH_2Cl_2$. After 18 hours, the layers were separated and the $CH_2Cl_2$ layer was dried ($MgSO_4$), filtered and concentrated to provide a residue which was chromatographed with 25% ethyl acetate/hexane to provide 1.87 g (91%) of the title compound as a colorless oil.

EXAMPLE 179B

N-Propyl-N-(trans, trans-3,7-dimethyl-2,6-octadienyl)amine

The compound resulting from Example 179A in THF was treated with 1M LAH in THF. The solution was refluxed for 5 hours, cooled to 0° C., quenched with $Na_2SO_4.10\ H_2O$, filtered through celite and concentrated to provide the title compound as an oil which was used directly in the next step.

EXAMPLE 179C (+)-(1α,2β,3β,4α)-1,2-Di[N-propyl-N-(trans, trans-3,7-dimethyl-2,6-octadienyl)aminocarbonyl] cyclobutane-3,4-dicarboxylic acid dibenzyl ester To a solution of the compound resulting from Example 123A (412 mg, 1 mmol) in $CH_2Cl_2$ (3 mL) was added oxalyl chloride (279 mg, 2.2 mmol) followed by DMF (1 drop). After 2 hours, the solvent was removed, and the residue was chased with toluene (3×5 mL). The residue was redissolved in $CH_2Cl_2$ (5 mL) and added dropwise to a slurry of the compound resulting from Example 179B (540 mg, 2.76 mmol) and $NaHCO_3$ (585 mg, 5.5 mmol) in water (10 mL). After 18 hours, the layers were separated and the $CH_2Cl_2$ layer was dried ($MgSO_4$), filtered, concentrated and chromatographed with 25% ethyl acetate in hexane to provide 600 mg (78%) of the title compound as a colorless oil.

EXAMPLE 179D (+)-(1α,2β,3β,4α)-1,2-Di[N-propyl-N-(trans, trans-3,7-dimethyl-2,6-octadienyl)aminocarbonyl] cyclobutane-3,4-dicarboxylic acid The compound resulting from Example 179C (575 mg, 0.75 mmol) in methanol (8 mL) was treated with 1M LiOH in water (4 mL). After 18 hours, the solution was acidified to pH 1 with 1N HCl and extracted with ethyl acetate (2×20 mL). The combined extracts were dried ($MgSO_4$), filtered and concentrated to provide a residue which was chromatographed with 98:1:1 $CHCl_3:CH_3OH$: acetic acid to provide a colorless oil. $^1$H NMR (300 MHz, $CDCl_3$) δ0.8 (m, 6H), 1.3–1.7 (m, 18H), 2.0 (m, 8H), 2.9 (m, 2H), 3.3 (m, 6H), 3.5 (m, 2H), 3.6–4.0 (envelope, 6H), 5.1 (m, 4H), 12.5 (br s, 2H). MS (FAB) m/e 587 (M+H)$^+$.

EXAMPLE 180

(+)-(1α,2β,3β,4α)-1,2-Di[N-methyl-N-((1S)-1-(4-phenoxyphenyl)-1-ethyl)aminocarbonyl] cyclobutane-3,4-dicarboxylic acid

EXAMPLE 180A (4S,5R)-3-(2-(4-Phenoxyphenyl)acetyl)-4-methyl-5-phenyl-1,3-oxazolidin-2-one To a solution containing 4-phenoxyphenylacetic acid (10.0 g, 43.8 mmol) in THF (62.6 mL) at −78° C. was added pivaloyl chloride (5.49 g, 45.6 mmol) followed by triethylamine (4.61 g, 45.6 mmol). The mixture was stirred at −78° C. for 15 minutes, at 0° C. for 1 hour, then recooled to −78° C. In a separate flask, 2.5M n-butyllithium (20 mL, 50 mmol) was added to a solution of (4S,5R)-(−)-4-methyl-5-phenyl-2-oxazolidinone (8.86 g, 50 mmol) in THF (100 mL) at −78° C., stirred for 15 minutes, then transferred to the flask containing pivalic anhydride via cannula. The mixture was stirred 15 minutes at −78° C. then at room temperature for 18 hours. The solvent was removed, and the residue was partitioned between diethyl ether (500 mL) and 1N HCl (500 mL). The organic layer was dried (MgSO$_4$), filtered and concentrated to provide a light yellow solid. The solid was chromatographed with 10% ethyl acetate in hexane to yield 10.9 g (64%) of the title compound as a white solid.

EXAMPLE 180B (4S,5R,2'S)-3-(2-(4-Phenoxyphenyl)propionyl)-4-methyl-5-phenyl-1,3-oxazolidin-2-one A solution of the compound resulting from Example 180A (3.0 g, 7.44 mmol) in THF (26 mL) at −78° C. was added via cannula to a 1M solution of NaN(Si(CH$_3$)$_3$)$_2$ in THF (10 mL, 10 mmol) at −78° C. After 1 hour, methyl iodide (10 g, 77.4 mmol) in THF (4.8 mL) at −78° C. was added via cannula to the cold enolate solution. After 6 hours, the reaction was quenched with saturated ammonium chloride solution and extracted with diethyl ether. The organic extract was dried (MgSO$_4$), filtered and concentrated to provide a yellow oil. Chromatography of the oil with ethyl acetate-hexane provided 2.5 g (81%) of the title compound as a colorless oil.

EXAMPLE 180C (2S)-2-(4-Phenoxyphenyl)propionic acid

A solution of the compound resulting from Example 180B (2.5 g, 6.3 mmol) in THF (98 mL) and water (33 mL) was treated with 30% aqueous hydrogen peroxide (5.3 mL, 52 mmol) then 1M aqueous lithium hydroxide (13 mL, 13 mmol). After 2 hours, the THF was removed, and the aqueous layer was extracted with CH$_2$Cl$_2$ (3×100 mL). The water layer was then acidified to pH 0 with 6N HCl and extracted with diethyl ether. The ether was dried (MgSO$_4$), filtered and concentrated to provide the title compound as an oil (1.5 g, 99%) which was used without further purification.

EXAMPLE 180D (1S)-N-(Methoxycarbonyl)-N-(1-(4-phenoxyphenyl)ethyl)amine

The compound resulting from Example 180C (1.4 g, 5.8 mol), diphenylphosphoryl azide (1.76 g, 6.4 mmol) and triethylamine (1.2 g, 11.6 mmol) were warmed at 83° C. in toluene for 2 hours. Methanol (20 mL) was added, and the solution was stirred an additional 18 hours. All volatiles were removed, and the residue was chromatographed on silica gel with 15% ethyl acetate in hexane to provide 1.51 g (96%) of the title compound as a pale yellow oil.

EXAMPLE 180E (1S)-N-Methyl-N-(1-(4-phenoxyphenyl)ethyl)amine

The compound resulting from Example 180D (432 mg, 1.5 mmol) in THF (5 mL) was treated with 1M lithium aluminum hydride in THF (3.2 mL). The solution was refluxed for 4 hours, cooled to 0° C., quenched with sodium sulfate decahydrate, filtered through celite and concentrated to provide 344 mg (95%) of the title compound as a colorless oil used directly in the next step.

EXAMPLE 180F (+)-(1α,2β,3β,4α)-1,2-Di[N-methyl-N-((1S)-1-(4-phenoxyphenyl)-1-ethyl)aminocarbonyl] cyclobutane-3,4-dicarboxylic acid dibenzyl ester A solution of the compound resulting from Example 168G (100 mg, 0.22 mmol) in CH$_2$Cl$_2$ (1 mL) was treated with oxalyl chloride (67 mg, 0.53 mmol) and DMF (1 drop). After 2 hours, all volatiles were removed, and the residue was chased with toluene (2×5 mL), redissolved in CH$_2$Cl$_2$ (5 mL) and added dropwise to a slurry of the compound resulting from Example 180E (344 mg, 1.2 mmol) and NaHCO$_3$ (1.04 g, 12.4 mmol) in H$_2$O (2 mL). After 18 hours, the layers were separated, and the methylene chloride was dried over MgSO$_4$, filtered, concentrated and chromatographed with 1:1 ethyl acetate-hexane to provide 121 mg of the title compound as a colorless glass.

EXAMPLE 180G (+)-(1α,2β,2β,4α)-1,2-Di[N-methyl-N-((1S)-1-(4-phenoxyphenyl)-1-ethyl)aminocarbonyl] cyclobutane-3,4-dicarboxylic acid The compound resulting from Example 180F (100 mg, 0.12 mmol) and palladium on carbon (33 mg) were stirred in ethyl acetate (5 mL) under a hydrogen atmosphere for 18 hours. The mixture was filtered through celite and concentrated to provide 71 mg (91%) the title compound as a white solid. $^1$H NMR (300 MHz CDCl$_3$) δ0.9–1.0 (m, 4H), 1.1–1.4 (envelope, 4H), 1.7–2.0 (m, 3H), 3.3–3.6 (m, 3H), 3.9–4.1 (m, 2H), 5.5–5.7 (m, 2H), 6.9–7.1 (m, 8H), 7.15–7.2 (m, 2H), 7.21–7.41 (m, 8H), 12.4–12.8 (br s, 2H). MS (FAB) m/e 651 (M+H)$^+$.

EXAMPLE 181

(+)-(1α,2β,3β,4α)-1,2-Di[N-methyl-N-((1R)-1-(4-phenoxyphenyl)-1-butyl)aminocarbonyl] cyclobutane-3,4-dicarboxylic acid

EXAMPLE 181A (4R,5S,2'R)-3-(2-(4-Phenoxyphenyl)pent-4-enoyl)-4-methyl-5-phenyl-1,3-oxazolidin-2-one A solution of the compound resulting from Example 180A (3 g, 7.4 mmol) in THF (25 mL) at −78° C. was added via cannula to a 1M solution of NaN(Si(CH$_3$)$_3$)$_2$ in THF (10 mL, 10 mmol) at −78° C. After 1 hour, allyl iodide (2.5 g, 15 mmol) in THF (5 mL) at −78° C. was added via cannula to the cold enolate solution. After 6 hours, the reaction was quenched with saturated ammonium chloride solution and extracted with diethyl ether. The organic extract was dried (MgSO$_4$), filtered and concentrated to provide a yellow oil. Chromatography of the oil with ethyl acetate-hexane provided 2.65 g (84%) of the title compound as a colorless oil.

EXAMPLE 181B (2R)-2-(4-Phenoxyphenyl)pentanoic acid

A solution of the compound resulting from Example 181A was converted to (2R)-2-(4-phenoxyphenyl)-4-pentenoic acid by the procedures described in Example 180C.

A solution of the pentenoic acid prepared above (1.4 g, 5.2 mmol) in ethyl acetate (17 mL) was hydrogenated in the presence of palladium on carbon (150 mg) for 18 hours. The solution was filtered through celite and concentrated to provide 1.41 g (100%) of the title compound as a colorless glass.

EXAMPLE 181C (+)-(1α,2β,3β,4α)-1,2-Di[N-methyl-N-((1R)-1-(4-phenoxyphenyl)-1-butyl)aminocarbonyl] cyclobutane-3,4-dicarboxylic acid The compound resulting from Example 181B was treated by the procedures described in Examples 180D–G to provide 97 mg (94% for the last step) of the title compound as a white solid. $^1$H NMR (300 MHz CDCl$_3$) δ0.9– 1.0 (m, 7H), 1.1–1.4 (envelope, 7H), 1.7–2.0 (m, 5H), 3.3–3.6 (m, 3H), 3.9–4.1 (m, 2H), 5.5–5.7 (m, 2H), 6.9–7.1 (m, 8H), 7.15–7.2 (m, 2H), 7.21–7.41 (m, 8H), 12.4–12.8 (br s, 2H). MS (FAB) m/e 707 (M+H)$^+$.

EXAMPLE 182

(+)-(1α,2β,3β,4α)-1,2-Di[N-methyl-N-((1S)-1-(4-phenoxyphenyl)-1-butyl)aminocarbonyl] cyclobutane-3,4-dicarboxylic acid Following the procedures described in Example 181 but starting with the (4S,5R)-oxazolidinone described in Example 180A, the title compound (97 mg, 94% for the last step) was prepared as a white solid. $^1$H NMR (300 MHz CDCl$_3$) δ0.9–1.0 (m, 7H), 1.1–1.4 (envelope, 7H), 1.7–2.0 (m, 5H), 3.3–3.6 (m, 3H), 3.9–4.1 (m, 2H), 5.5–5.7 (m, 2H), 6.9–7.1 (m, 8H), 7.15–7.2 (m, 2H), 7.21–7.41 (m, 8H), 12.4–12.8 (br s, 2H). MS (FAB) m/e 707 (M+H)$^+$.

EXAMPLE 183

(+)-(1α,2β,3β,4α)-1,2-Di[N-((1S)-1-(4-phenoxyphenyl)-1-butyl)aminocarbonyl] cyclobutane-3,4-dicarboxylic acid

EXAMPLE 183A (2S)-2-(4-Phenoxyphenyl)pentanoic acid

A solution of (2S)-2-(4-phenoxyphenyl)-1-pentenoic acid (1.4 g, 5.2 mmol), prepared by the procedures described in Example 181 but starting with the (4S,5R)-oxazolidinone described in Example 180A, in ethyl acetate (17 mL) was hydrogenated in the presence of palladium on carbon (150 mg) for 18 hours. The solution was filtered through celite and concentrated to provide 1.41 g (100%) of the title compound as a colorless glass.

EXAMPLE 183B (1S)-N-Benzyloxycarbonyl-N-(1-(4-phenoxyphenyl) butyl)amine

The compound resulting from Example 183A (459 mg, 1.7 mmol), diphenylphosphoryl azide (515 mg, 1.9 mmol) and triethylamine (344 mg, 3.4 mmol) were warmed at 83° C. in toluene for 2 hours. Benzyl alcohol (919 mg, 8.5 mmol) was added, and the solution was stirred an additional 18 hours. All volatiles were removed, and the residue was chromatographed on silica gel eluting with 15% ethyl acetate in hexane to provide 233 mg (37%) of the title compound as a white solid.

EXAMPLE 183C (1S)-N-(1-(4-Phenoxyphenyl)butylamine

The compound resulting from Example 183B (229 mg, 0.66 mmol) in ethyl acetate (5 mL) was stirred for 18 hours under a hydrogen atmosphere, filtered through celite and concentrated to provide 149 mg (99%) of the title compound as a colorless oil which was used directly in the next step.

EXAMPLE 183D (+)-(1α,2β,3β,4α)-1,2-Di[N-((1S)-1-(4-phenoxyphenyl)-1-butyl)aminocarbonyl] cyclobutane-3,4-dicarboxylic acid The compound resulting from Example 183C was treated by the procedures described in Examples 180F and 180G to give the title compound. High resolution MS calcd for C$_{40}$H$_{42}$N$_2$O$_8$: 679.3019. Found: 679.3015.

EXAMPLE 184

(+)-(1α,2β,3β,4α)-1,2-Di[N-propyl-N-((1S)-1-(4-phenoxyphenyl)-1-butyl)aminocarbonyl] cyclobutane-3,4-dicarboxylic acid

EXAMPLE 184A

N-Propyl-N-((1S)-1-(4-phenoxyphenyl)butyl)amine

The compound resulting from Example 183C (74 mg, 0.31 mmol) and NaHCO$_3$ (260 mg, 3 mmol) in water (5 mL) at room temperature were treated with propionyl chloride (34 mg, 0.37 mmol) in CH$_2$Cl$_2$ (1 mL). After 18 hours, the CH$_2$Cl$_2$ layer was drawn off, dried (MgSO$_4$), filtered and concentrated. The residue was chromatographed on silica gel with eluting with 15% ethyl acetate in hexane to provide 81 mg (88%) of N-propionyl-N-((1S)-1-(4-phenoxyphenyl) butyl)amine as a colorless oil.

The butylamine prepared above (57 mg, 0.21 mmol) in THF (1 mL) at room temperature was treated with 1M LAH in THF (0.42 mL). The solution was warmed to reflux for 4 hours, cooled to 0° C. and quenched with sodium sulfate decahydrate. The slurry was filtered through celite and concentrated to provide 53 mg (99%) of the title compound as a colorless oil.

EXAMPLE 184B (+)-(1α,2β,2β,4α)-1,2-Di[N-propyl-N-((1S)-1-(4-phenoxyphenyl)-1-butyl)aminocarbonyl] cyclobutane-3,4-dicarboxylic acid The compound resulting from Example 184A was treated by the procedures described in Examples 180F and 180G to give 15 mg of the title compound as a white solid. MS (FAB) m/e 763 (M+H)⁺.

EXAMPLE 185

(1α,2β,3β,4α)-1,2-Di[N-propyl-N-(4-phenoxybenzyl)aminocarbonylamino]cyclobutane-3,4-dicarboxylic acid

EXAMPLE 185

(1α,2β,3β,4α)-1,2-Di[N-propyl-N-(4-phenoxybenzyl)aminocarbonylamino]cyclobutane-3,4-dicarboxylic acid dibenzyl ester To a suspension of 412 mg (1.0 mmol, 1.0 eq.) of the compound resulting from Example 123A in 10 mL of $CH_2Cl_2$ was added 0.18 mL (2.1 mmol, 1.05 eq.) of oxalyl chloride followed by 1 drop of DMF. The mixture was stirred at ambient temperature for 1 hour during which time the evolution of gas ceased, and the solid completely dissolved. The solvent was removed under reduced pressure, and the yellow solid obtained was dissolved in 5 mL of acetone. To this vigorously stirred solution was added 260 mg (4.0 mmol, 4.0 eq.) of $NaN_3$ and stirring was continued for 2.5 hours. The resulting white suspension was filtered and the filter was washed well with acetone. Toluene (10 mL) was added to the filtrate, and the acetone was removed on a rotary evaporator. The resulting toluene solution was heated in an oil bath for 1 hour (30 minutes past the completion of nitrogen evolution) and then cooled to ambient temperature. To the yellow solution was added a solution of 598 mg (2.5 mmol, 2.5 eq.) of N-propyl-N-(4-phenoxybenzyl)amine in 2 mL of $CH_2Cl_2$ and stirring was continued for 1 hour. After concentration of the solvent on a rotary evaporator, the residue was purified by column chromatography on 50 g of $SiO_2$ eluting with 30% ethyl acetate in hexanes to give 511 mg (58%) of the title compound as a thick syrup.

EXAMPLE 185B (1α,2β,3β,4α)-1,2-Di[N-propyl-N-(4-phenoxybenzyl)aminocarbonylamino]cyclobutane-3,4-dicarboxylic acid To a solution of 495 mg (0.55 mol, 1 eq.) of the compound resulting from Example 185A in 4 mL of ethanol under $N_2$ was added 125 mg of 10% Pd/C. The resulting black suspension was stirred under a balloon of $H_2$ for 2 hours and filtered through celite to remove the catalyst. The filter pad was washed with copious amounts of hot methanol, and the filtrate was concentrated. The residue was recrystallized from hot methanol to give 199 mg (51%) of the title compound as a white solid. ¹H NMR (300 MHz, DMSO-d₆) δ7.37 (m, 4H), 7.22 (d, 4H), 7.11 (m, 1H), 6.95 (m, 8H), 6.74 (bs, 1H), 4.72 (bs, 2H), 4.38 (s, 4H), 3.23 (d, 2H), 3.04 (m, 4H), 1.45 (m, 4H), 0.77 (t, 6H). MS (FAB+) m/e 731 (M+Na)⁺, 709 (M+H)⁺. MS (FAB−) m/e 707 (M−H)⁻. HRMS: calcd for $C_{40}H_{45}N_4O_8$ 709.3237. Found: 709.3233.

EXAMPLE 186

(1α,2β,3β,4α)-1,2-Di[N-propyl-N-(4-phenoxybenzylcarbonyl)amino]cyclobutane-3,4-dicarboxylic acid

EXAMPLE 186A (1α,2β,3β,4α)-1,2-Di(tert-butyloxycarbonylamino)cyclobutane-3,4-dicarboxylic acid dibenzyl ester A mixture of 507 mg (1.23 mmol) of the compound resulting from Example 123A in 10 mL of toluene was treated with 5 mL of oxalyl chloride. The mixture was heated to reflux under a nitrogen atmosphere for 0.5 hours. Volatiles were removed under reduced pressure to afford a pale yellow oil. The oil was dissolved in 5 mL of acetone and treated with 0.168 g (2.58 mmol) of sodium azide in 1 mL of water. A precipitate formed immediately. After 2 hours the mixture was filtered, and the filtrate was concentrated under reduced pressure while keeping the solution cool. The oil was dissolved in 30 mL of toluene, and the solution was heated to 60° C. until bubble formation ceased (~2 hours). Approximately half of the toluene was removed under vacuum. 1.0 mL of t-butanol and 20 mg of CuCl were added, and the solution was warmed to 70° C. for 6 hours under an atmosphere of nitrogen. All volatiles were then removed under reduced pressure to afford a white solid. Purification by flash column chromatography on silica gel eluting with 2:1 hexane-ethyl acetate afforded the title compound as a white powder (250 mg, 37%). ¹H NMR (CDCl₃) δ1.38 (s, 18H), 3.45–3.52 (m, 2H), 4.52–4.63 (m, 2H), 5.14 (s, 4H), 5.21–5.34 (m, 2H), 7.34 (b.s., 12H).

EXAMPLE 186B (1α,2β,3β,4α)-1,2-Di(N-allyl-N-tert-butyloxycarbonylamino)cyclobutane-3,4-dicarboxylic acid dibenzyl ester A solution of 200 mg (0.361 mmol) of the compound resulting from Example 186A in 8 mL of anhydrous dimethylformamide was cooled to 0° C. under an atmosphere of nitrogen. The solution was treated sequentially with 127 mg (0.758 mmol) of allyl iodide and 18.2 mg (0.758 mmol) of sodium hydride. The reaction mixture was allowed to slowly warm to ambient temperature. After 3 days the solution was quenched with 10 mL of water. The aqueous mixture was extracted with ethyl acetate, the combined extracts were dried (MgSO₄), and all volatiles were removed under reduced pressure. The resulting oil was purified by flash column chromatography on silica gel eluting with 2:1 hexane-ethyl acetate affording 110 mg (48.1%) of the desired product. ¹H NMR (CDCl₃) δ1.40 (s, 18H), 3.2–3.4 (m, 2H), 3.7–4.0 (m, 2H), 4.5–4.7 (m, 2H), 4.9–5.3 (m, 10H), 5.6–5.9 (m, 2H), 7.2–7.4 (m, 10H). MS (FAB)⁺ m/e 673 (M+K)⁺.

EXAMPLE 186C (1α,2β,3β,4α)-1,2-Di[N-allyl-N-(4-phenoxybenzylcarbonyl)amino]cyclobutane-3,4-dicarboxylic acid dibenzyl ester A solution of 110 mg (0.174 mmol) of the compound resulting from Example 186B in 10 mL of methylene chloride was cooled to 0° C. under an atmosphere of nitrogen, whereupon 1 mL of trifluoroacetic acid was added. After 10 minutes, all volatiles were removed under reduced pressure, leaving 75.5 mg (100%) of (1α,2β,3β,4α)-1,2-di(N-allylamino)cyclobutane-3,4-dicarboxylic acid dibenzyl ester as a semisolid.

The crude amine from above was dissolved in 10 mL of anhydrous tetrahydrofuran, to which was added 87.3 mg (0.382 mmol) of 4-phenoxyphenylacetic acid, 80.8 mg (0.421 mmol) 1-(3-dimethylaminopropyl)-3-ethylcarbodiimide.HCl, 56.8 mg (0.421 mmol) of 1-hydroxybenzotriazole hydrate, and 128 mg (1.26 mmol) of triethylamine. The mixture was stirred under an atmosphere of nitrogen for 3 days. A 50 mL portion of water was added, and the mixture was extracted with three 50 mL portions of ethyl acetate. The combined extracts were dried (MgSO$_4$), and all volatiles were removed under reduced pressure affording an oil. Purification of the oil by flash column chromatography on silica gel eluting with 2:1 hexane-ethyl acetate afforded 46 mg (31%) of the title compound as a clear colorless oil. $^1$H NMR (CDCl$_3$) δ3.2–3.4 (m, 2H), 3.5–3.7 (m, 4H), 3.9–4.1 (m, 2H), 4.5–4.6 (m, 2H), 4.9–5.3 (m, 10H), 5.6–5.9 (m, 2H), 6.8–7.2 (m, 14H), 7.2–7.4 (m, 14H).

EXAMPLE 186D (1α,2β,3β,4α)-1,2-Di[N-propyl-N-(4-phenoxybenzylcarbonyl)amino]cyclobutane-3,4-dicarboxylic acid A solution of 46 mg (0.054 mmol) of the compound resulting from Example 186C with 40 mg of 10% palladium on carbon was covered with 20 mL of ethyl acetate. The flask was flushed with nitrogen and the flask was filled with hydrogen. The mixture was stirred vigorously for 48 hours. The mixture was filtered, and the solvent was removed under reduced pressure, affording an oil. Purification by flash column chromatography on silica gel eluting with 18:1:1 ethyl acetate-formic acid-water afforded 6 mg (16%) of the title compound. $^1$H NMR (CDCl$_3$) δ0.7–1.0 (m, 6H), 1.1–1.6 (m, 4H), 3.2–3.4 (m, 4H), 3.5–3.8 (m, 4H), 4.0–4.2 (m, 2H), 4.8–5.0 (m, 2H), 6.8–7.4 (m, 18H). MS (FAB+) m/e 679 (M+H)$^+$.

EXAMPLE 187

(1α,2β,3β,4α)-1,2-Di[N-{(2S)-2-(4-phenoxyphenyl)pentanoylamino]cyclobutane-3,4-dicarboxylic acid A solution of 100 mg (0.180 mmol) of the compound resulting from Example 186A in 5 mL of methylene chloride under an atmosphere of nitrogen was treated with 1.0 mL of trifluoroacetic acid. After 3 hours all volatiles were removed under reduced pressure. Concurrently, a solution of (2S)-2-(4-phenoxyphenyl)pentanoic acid in 5 mL of methylene chloride was treated with 1.0 mL of oxalyl chloride. After 3 hours all volatiles were removed under reduced pressure. The products from the two reactions were combined in 5 mL of anhydrous dimethylformamide, to which was added 100 µL (0.719 mmol) of triethylamine. After 3 days, water was added, and the mixture was extracted with ethyl acetate. The combined extracts were dried (MgSO$_4$), filtered, and all volatiles were removed under reduced pressure, affording 154 mg of (1α,2β,3β,4α)-1,2-di[N-{(2S)-2-(4-phenoxyphenyl)pentanoylamino]cyclobutane-3,4-dicarboxylic acid dibenzyl ester (100%) as a solid.

This crude ester (154 mg, 0.180 mmol) was dissolved in 10 mL of ethanol to which was added 40 mg of 10% palladium on carbon. An atmosphere of hydrogen was introduced, and the mixture was stirred vigorously for 20 hours. The mixture was filtered, and all volatiles were removed under reduced pressure, affording an oil. Purification by flash column chromatography on silica gel eluting with 180:1:1 ethyl acetate-formic acid-water afforded 40 mg (33%) of the title compound. $^1$H NMR (CDCl$_3$) δ0.8–1.0 (m, 6H), 1.2–1.4 (m, 4H), 1.6–1.8 (m, 2H), 1.9–2.1 (m, 2H), 3.2–3.5 (m, 2H), 3.5–3.6 (m, 2H), 6.7–6.9 (m, 2H), 6.9–7.4 (m, 18H). MS (FAB+) m/e 679 (M+H)$^+$.

EXAMPLE 188

(1α,2β,3β,4α)-1,2-Di[N-propyl-N-(4-phenoxybenzyl)aminocarbonyl]-4-(N-hydroxy-N-trifluoroacetylaminomethyl)cyclobutane-3-carboxylic acid

EXAMPLE 188A

Benzyl (1α,2β,3β,4α)-1,2-Di[N-propyl-N-[4-phenoxybenzyl]aminocarbonyl]-4-hydroxymethyl-cyclobutane-3-carboxylate The compound described in Example 123B was converted to the monoacid by the method of Example 95, and that monoacid was converted to the title compound by the method of Example 70A. MS (DCI/NH$_3$) m/e 755 (M+H)$^+$.

EXAMPLE 188B

Benzyl (1α,2β,3β,4α)-1,2-Di[N-propyl-N-[4-phenoxybenzyl]aminocarbonyl]-4-(N-benzyloxy-N-trifluoroacetylaminomethyl)cyclobutane-3-carboxylate To a solution of diethyl azodicarboxylate (0.037 mL, 41 mg, 0.23 mmol) dissolved in THF (1 mL) and cooled to –8° C. was added triphenyl phosphine (61 mg, 0.23 mmol) in THF (0.6 mL) dropwise. After 10 minutes, the compound resulting from Example 188A (117 mg, 0.15 mmol) in THF (1 mL) was added dropwise. After 30 minutes, (N-benzyloxy)trifluoroacetamide (42 mg, 0.19 mmol) in THF (0.4 mL) was added dropwise, the cooling bath was removed, and the reaction was allowed to stir at room temperature for 36 hours. The reaction was partitioned between EtOAc and water. The organic layer was washed with brine, dried over Na$_2$SO$_4$, and concentrated in vacuo. The residue was purified by chromatography eluting with 3:1 hexane-ethyl acetate to give the title compound (49 mg, 33%). MS (FAB+) (M+H)$^+$ 956.

EXAMPLE 188C (1α,2β,3β,4α)-1,2-Di[N-propyl-N-(4-phenoxybenzyl)aminocarbonyl]-4-(N-hydroxy-N-trifluoroacetylaminomethyl)cyclobutane-3-carboxylic acid Using the compound resulting from Example 188B, the title compound was prepared by the method of Example 74B, except 1:1 EtOAc–EtOH was used for the solvent. $^1$H NMR (DMSO-d$_6$) δ7.39, 7.28, 7.15, 7.00 6.93 (all m, total 18H), 4.80, 4.60, 4.42 (all m, total 4H), 4.20, 4.00 (both m, total 4H), 3.60–2.90 (envelope, 5H), 2.70 (m, 1H), 1.50, (m, 4H), 0.83, 0.77 (both m, total 6H). MS (FAB–) (M–H)$^-$ 774. Anal calcd for C$_{42}$H$_{44}$F$_3$N$_3$O$_8$·0.65 H$_2$O: C, 64.06), H, 5.80), N, 5.34. Found: C, 64.02), H, 5.43), N, 5.09.

EXAMPLE 189

(–)-(1α,2β,3β,4α)-1,2-Di[N-propyl-N-(4-phenoxybenzyl)aminocarbonyl]-3-(methoxycarbonyl)cyclobutane-4-carboxylic acid The resultant acid from Example 37 (10.97 g, 16.16 mmol) in dichloromethane is treated with an excess of an ether solution of diazomethane. The solvent is evaporated, and the residue is dissolved in a mixture of tetrahydrofuran (135 mL) and methanol (20 mL) and cooled to –10° C. A cold solution of LiOH monohydrate (680 mg, 16.2 mmol) in water (45 mL) is added, and the reaction is stirred at –10° to 0° C. for 3 hours and then is placed in a –20° C. freezer overnight. The reaction is quenched with 2M HCl and concentrated. The residue is dissolved in ethyl acetate, washed with brine, dried over Na$_2$SO$_4$ and evaporated. Chromatography of the residue on silica gel with 2–4% methanol in chloroform affords the title compound.

EXAMPLE 190

(1α,2β,3β,4α)-1,2-Di[N-propyl-N-(4-phenoxybenzyl)aminocarbonyl]-4-formylcyclobutane-3-carboxylic acid

EXAMPLE 190A

Methyl (1α,2β,3β,4α)-1,2-di[N-propyl-N-(4-phenoxybenzyl)aminocarbonyl]-4-hydroxymethyl-cyclobutane-3-carboxylate To a stirred solution of (1α,2β,3β,4α)-1,2-di[N-propyl-N-(4-phenoxybenzy)]aminocarbonyl]cyclobutane-3,4- dicarboxylic acid mono methyl ester (0.562 g, 0.81 mmol, 1.0 eq.) in 12 mL of dry THF at −20° C. was added 0.098 mL (0.89 mmol, 1.1 eq.) of N-methylmorpholine followed by 0.115 mL (0.89 mmol, 1.1 eq.) of isobutylchloroformate. After stirring for 30 minutes, a cold (−20° C.) suspension of 0.184 g (4.86 mmol, 3 eq.) of NaBH$_4$ in 1 mL of CH$_3$OH was carefully added and the mixture stirred for 30 minutes more. The reaction was quenched by the careful addition of 2 mL of 3N aqueous HCl and then poured into 50 mL of cold 3N aqueous HCl and extracted with 3×50 mL of ethyl acetate. The combined organic extracts were washed with 50 mL of saturated aqueous NaHCO$_3$ solution, dried (MgSO$_4$), filtered and concentrated. The residue was purified by flash column chromatography on SiO$_2$ (40 g) eluting with 1:1 ethyl acetate-hexanes to give 0.507 g (92%) of the title compound as a colorless foam. $^1$H NMR (CDCl$_3$) δ6.84–7.35 (m, 18H), 2.68–5.02 (m, 18H), 1.41–1.72 (m, 4H), 0.73–0.97 (m, 6H). MS (DCI) m/e 679 (M+H)$^+$.

EXAMPLE 190B

Methyl (1α,2β,3β,4α)-1,2-di[N-propyl-N-(4-phenoxybenzyl)aminocarbonyl]-4-formylcyclobutane-3-carboxylate To a stirred solution of 0.339 g (0.5 mmol, 1.0 eq.) of the compound resulting from Example 190A in 5 mL of 10% acetonitrile in CH$_2$Cl$_2$ at room temperature was added 0.088 g (0.75 mmol, 1.5 eq.) of N-methylmorpholine-N-oxide followed by 0.50 g of powdered, activated 4 Å molecular sieves. After stirring 15 minutes at room temperature, TPAP (0.009 g, 0.025 mmol, 0.05 eq) was added, and the resulting black mixture was stirred for an additional 30 minutes. The reaction mixture was treated with ~1 g of celite and then diluted with 5 mL of ether. After 10 minutes further stirring, the mixture was filtered through a 1.5×1" pad of SiO$_2$ (pre-wetted with ether). The pad was washed well with ether (~200 mL) and the filtrate concentrated. The green residue was purified by column chromatography on SiO$_2$ (25 g) eluting with 1:1 ethyl acetate-hexanes to give 0.269 g (80%) of the title compound as a thick syrup. $^1$H NMR (CDCl$_3$) δ9.69–9.76 (m, 1H), 6.89–7.38 (m, 18H), 4.09–4.87 (m, 5H), 3.48–4.03 (m, 6H), 2.41–3.47 (m, 4H), 1.42–1.67 (m, 4H), 0.76–0.98 (m, 6H). MS (DCI) 677 (M+H)$^+$.

EXAMPLE 190C (1α,2β,3β,4α)-1,2-Di[N-propyl-N-(4-phenoxybenzyl)aminocarbonyl]-4-formylcyclobutane-3-carboxylic acid To a solution of 22 mg (0.52 mmol) of LiOH.H$_2$O in 2 mL of 1:1 THF-H$_2$O cooled to 0° C. was added a solution of the the compound resulting from Example 190B (178 mg, 0.26 mmol) in 2 mL of THF dropwise. After stirring at 0° C. for 2 hours, the mixture was treated with 5 mL of 3N aqueous HCl. The phases were separated, and the aqueous. phase was extracted with 3×10 mL of ethyl acetate. The combined organic phases were dried over MgSO$_4$, filtered and concentrated. The residue was lyophilized to give 152 mg (88%) of the title compound as a fluffy solid. $^1$H NMR (CDCl$_3$) δ9.72 (t, 1H), 6.84–7.38 (m, 18H), 3.89–4.73 (m, 6H), 2.80–3.84 (m, 6H), 1.55 (m, 4H), 0.86 (m, 6H). MS (FAB+): 663 (M+H$^+$, 30%); 479 (18%); 240 (19%); 183 (100%). MS (FAB−): 661 (M−H, 80%); 305 (20%); 199 (18%); 168 (48%); 153 (100%). Anal calcd for C$_{40}$H$_{42}$N$_2$O$_7$: C, 72.49; H, 6.39; N, 4.23. Found: C, 71.67; H, 6.39; N, 4.23.

EXAMPLE 191

(−)-(1α,2β,3β,4α)-1,2-Di{N-propyl-N-[(4-phenoxy)benzyl]aminocarbonyl}cyclobutane-3,4-diacetic acid The first EtOH filtrate from Example 129A was concentrated, acidified, and treated with two equivalents of (+)-norephedrine. The resultant crystals were recrystallized and acidified using the procedure described in Example 129A to give the (−)-diacid.

The diacid was converted to the title compound by the methods described in Examples 128B, 103A, 123C, 123B (using the amine described in Example 3), and 103B. The resultant foam was dissolved in CH$_3$CN, water was added, then after freezing and lyophilizing, the title compound was recovered as a white solid. $^1$H NMR (DMSO-d$_6$) δ7.38 (m, 4H), 7.25 (m, 5H), 7.13 (m, 2H), 6.95 (m, 7H), 4.63 (m, 2H), 4.20 (m, 2H), 3.90 (m, 2H), 3.50 (m, 2H), 2.97 (m, 1H), 2.77–2.22 (envelope, 7H), 1.50 (m, 4H), 0.83,0.77 (both m, total 6H). MS (FAB$^+$) m/e 707 (M+H)$^+$. Anal calcd for C$_{42}$H$_{46}$N$_2$O$_8$.2.0 H$_2$O: C, 67.91; H, 6.78; N, 3.45. Found: C, 67.56; H, 6.38; N, 3.66. [α]$_D$=−74.0° (c=1.17, MeOH).

EXAMPLE 192

(−)-(1α,2β,3β,4α)-1,2-Di[N-propyl-N-(4-phenoxybenzyl)aminocarbonyl]-3-(5-oxo-4,5-dihydro-[1,3,4]-oxadiazol-2-ylmethyl)cyclobutane-4-acetic acid The compound described in Example 191 was converted to the title compound by the methods described in Examples 172A, 165A, 165B, and 164D. The title compound was obtained as a lyophilized powder. $^1$H NMR (DMSO-d$_6$) δ7.39, 7.24, 7.13, 6.96 (all m, total 18H), 4.70 (m, 2H), 4.22 (m, 2H), 4.00 (m, 2H), 3.50, 3.30, (both m, total 4H), 3.00 (m,1H), 2.63 (m, 2H), 2.40, 2.35, 2.16 (all m, total 3H), 1.50, (m, 4H), 0.83, 0.77 (both m, total 6H). MS (FAB+) m/e 747 (M+H)$^+$. Anal calcd for C$_{43}$H$_{46}$N$_4$O$_8$.0.5 H$_2$O: C, 68.33; H, 6.27; N, 7.41. Found: C, 68.27; H, 6.18; N, 7.36. [α]$_D$=−98.0° (c=1.15, MeOH).

EXAMPLE 193

(−)-(1α,2β,3β,4α)-1,2-Di[N-propyl-N-(4-phenoxybenzyl)aminocarbonyl]-3,4-di(5-oxo-4,5-dihydro-[1,3,4]-oxadiazol-2-ylmethyl)cyclobutane The compound resulting from Example 191 was converted to the title compound by the methods described in Examples 165A and 165B, except 1:1 hexane-EtOAc, followed by 95:5 CHCl$_3$—MeOH was used for the chromatography. $^1$H NMR (DMSO-d$_6$) δ7.39, 7.24, 7.13, 6.96 (all m, total 18H), 4.70 (m, 2H), 4.22 (m, 2H), 4.08 (m, 2H), 3.50, 3.30, (both m, total 4H), 3.00 (m, 1H), 2.80–2.40 (envelope, total 5H), 1.45, (m, 4H), 0.83, 0.77 (both m, total 6H). MS (FAB+) m/e 787 (M+H)$^+$. Anal calcd for C$_{44}$H$_{46}$N$_6$O$_8$: C, 67.16; H, 5.89; N, 10.68. Found: C, 66.99; H, 6.09; N, 10.62. [α]$_D$=−111.9° (c=0.895, MeOH).

EXAMPLE 194

(−)-(1α,2β,3β,4α)-1,2-Di{N-cyclopentyl-N-[(4-phenoxy)benzyl]aminocarbonyl}cyclobutane-3,4-diacetic acid The diacid that was described in the first paragraph of Example 191 was converted to the title compound by the methods described in Examples 128B, 103A, 123C, 123B (using the amine described in Example 49), and 103B. The resultant foam was dissolved in CH$_3$CN, water was added, then after freezing and lyophilizing, the title compound was recovered as a white solid. $^1$H NMR (DMSO-d$_6$) δ7.38 (m, 4H), 7.25 (m, 6H), 6.93 (m,8H), 4.50, 4.22, 4.05, 3.70 (all m, total 8H), 2.65, 2.50, 2.30 (all m, total 6H), 1.82 1.50 (both m, total 16H). MS (FAB$^+$) m/e 759 (M+H)$^+$. Anal calcd for C₄₆H₅₀N₂O₈·0.7 H₂O: C, 71.61; H, 6.73; N, 3.63. Found: C, 71.64; H, 6.66; N, 3.47. [α]_D=−40.8° (c=0.855, MeOH).

EXAMPLE 195

(−)-(1α,2β,3β,4α)-1,2-Di[N-cyclopentyl-N-(4-phenoxybenzyl)aminocarbonyl]-3-(5-oxo-4,5-dihydro-[1,3,4]-oxadiazol-2-ylmethyl)cyclobutane-4-acetic acid The compound described in Example 194 was converted to the title compound by the methods described in Examples 172A, 165A, 165B, and 164D. The title compound was obtained as a lyophilized powder. ¹H NMR 500 MHz (DMSO-d₆) δ7.38, 7.20, 7.15, 7.10, 6.96, 6.88 (all m, total 18H), 4.60–4.10, 3.86, 3.80, 3.73 (envelope, m, m, m, total 8H), 2.70, 2.55, 2.30 (all m, total 6H), 1.82 1.55 (both m, total 16H). MS (DCI/NH₃) m/e 799 (M+H)⁺. Anal cald for C₄₇H₅₀N₄O₈·0.5 H₂O: C, 69.87; H, 6.36; N, 6.93. Found: C, 69.76; H, 6.22; N, 6.77. [α]_D=−60.7° (c=1.165, MeOH).

EXAMPLE 196

(−)-(1α,2β,3β,4α)-1,2-Di[N-cyclopentyl-N-(4-phenoxybenzyl)aminocarbonyl]-3,4-diacetic acid 3-methyl ester The compound resulting from Example 194 was converted to the title compound by the method described in Example 172A, then converted to the methyl ester using trimethylsilyldiazomethane and hydrogenolyzed as described in Example 164D. The title compound was obtained as a lyophilized powder. ¹H NMR (DMSO-d₆) δ7.38, 7.20,7.15, 7.10, 6.96, 6.88 (all m, total 18H), 4.60–4.10, 3.75 (envelope, m, total 8H), 3.58, 3.56, 3.54, 3.52 (all s, total 3H), 2.70–2.25 (envelope, 6H), 1.82 1.60 (both m, total 16H). MS (FAB⁺) m/e 773 (M+H)⁺. Anal cald for C₄₇H₅₂N₂O₈·0.25 H₂O: C, 72.61; H, 6.81; N, 3.60. Found: C, 72.34; H, 6.83; N, 3.48. [α]_D=−49.5° (c=0.95, MeOH).

EXAMPLES 197–347

The following compounds can be prepared according to the methods described in the previous examples, particularly Examples 149 and 163.

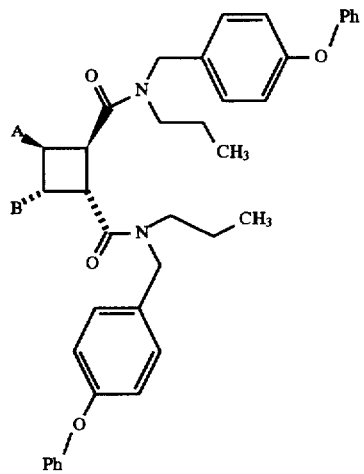

| Ex. No. | A | B |
|---|---|---|
| 197 | —COOH | (acetoxymethyl ester of pentanoic acid with CH₃) |
| 198 | (acetoxymethyl ester of butanoic acid with CH₃) | (acetoxymethyl ester of pentanoic acid with CH₃) |
| 199 | —COOH | (acetoxymethyl ester of 3-methylbutanoic acid with H₃C, CH₃) |

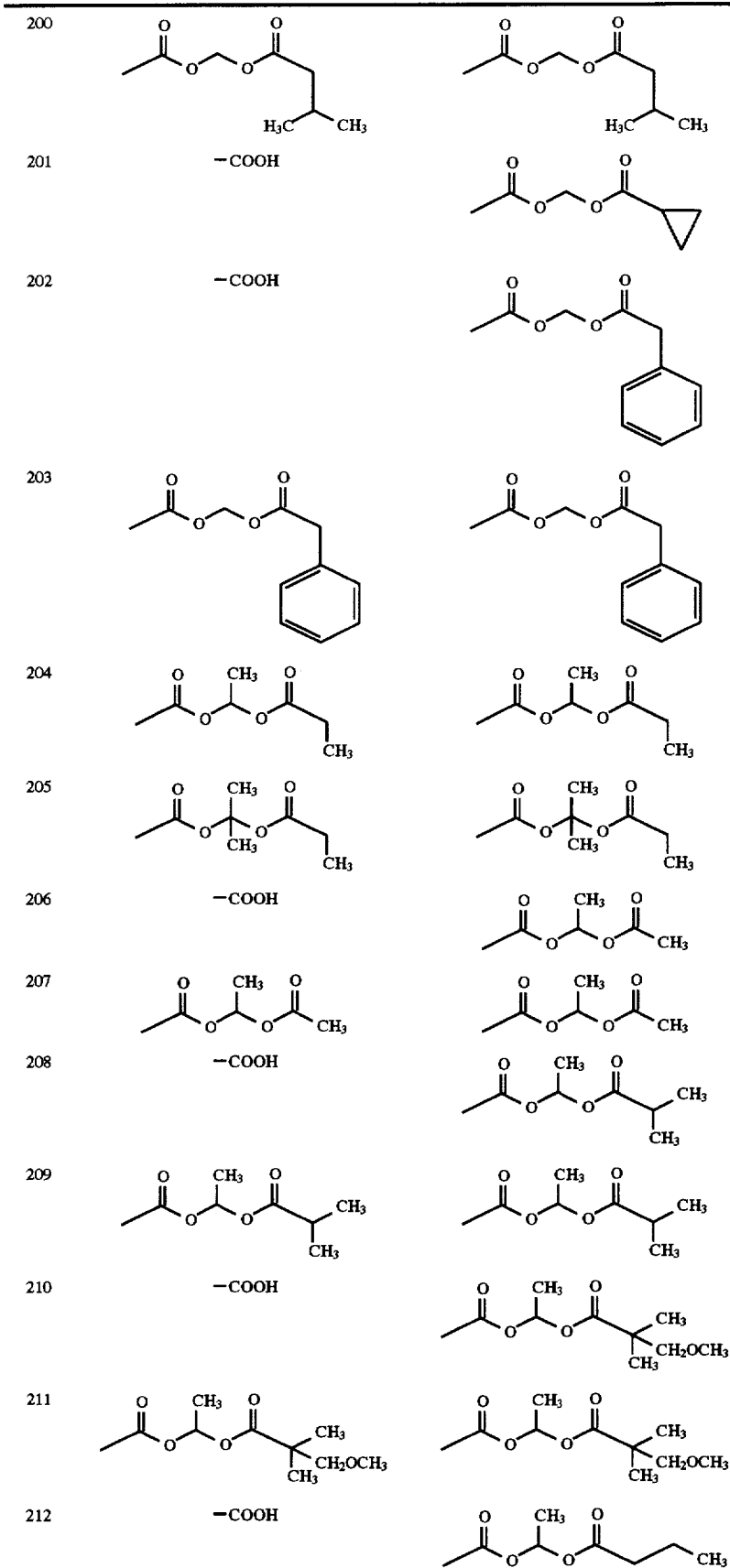

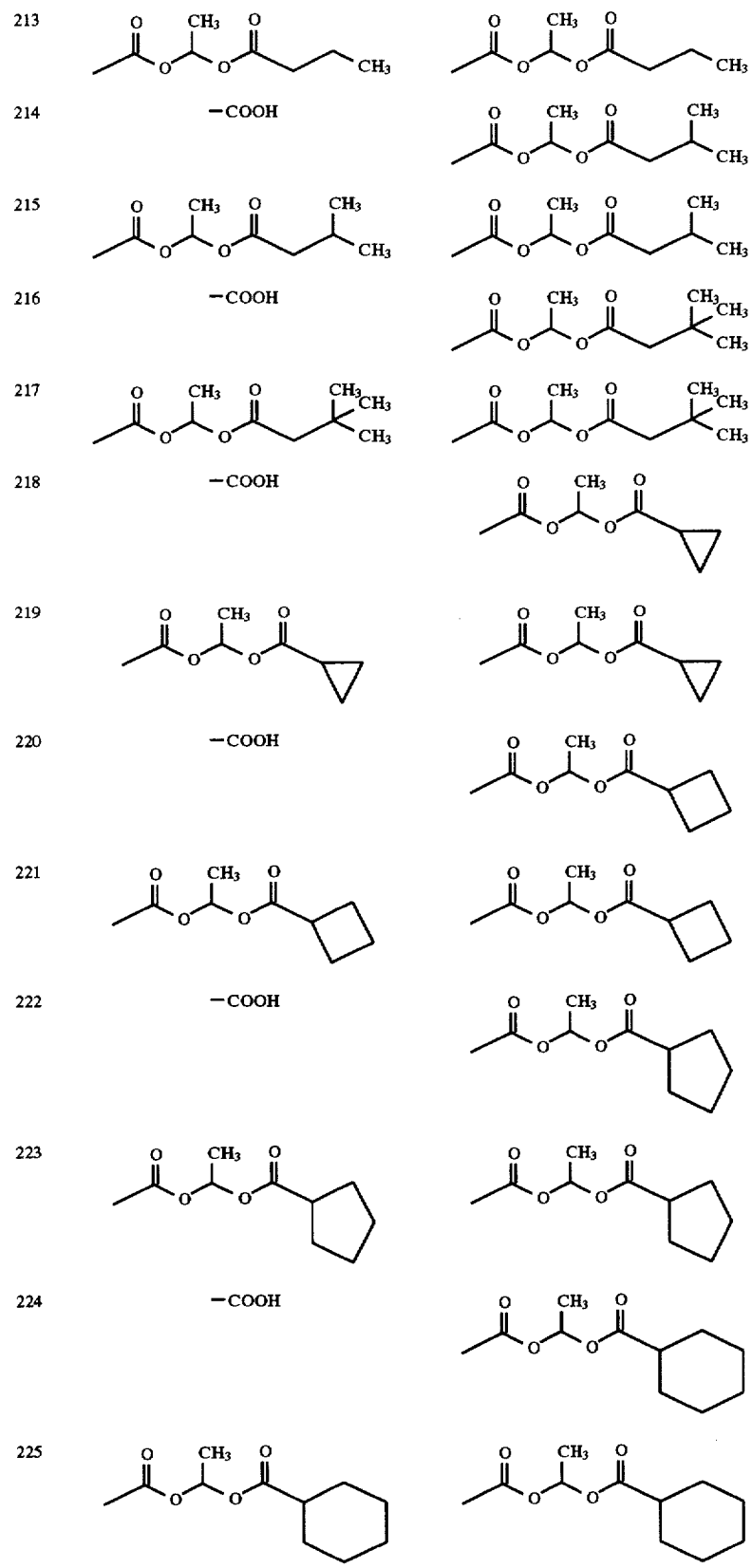

-continued
| | | |
|---|---|---|
| 226 | —COOH | 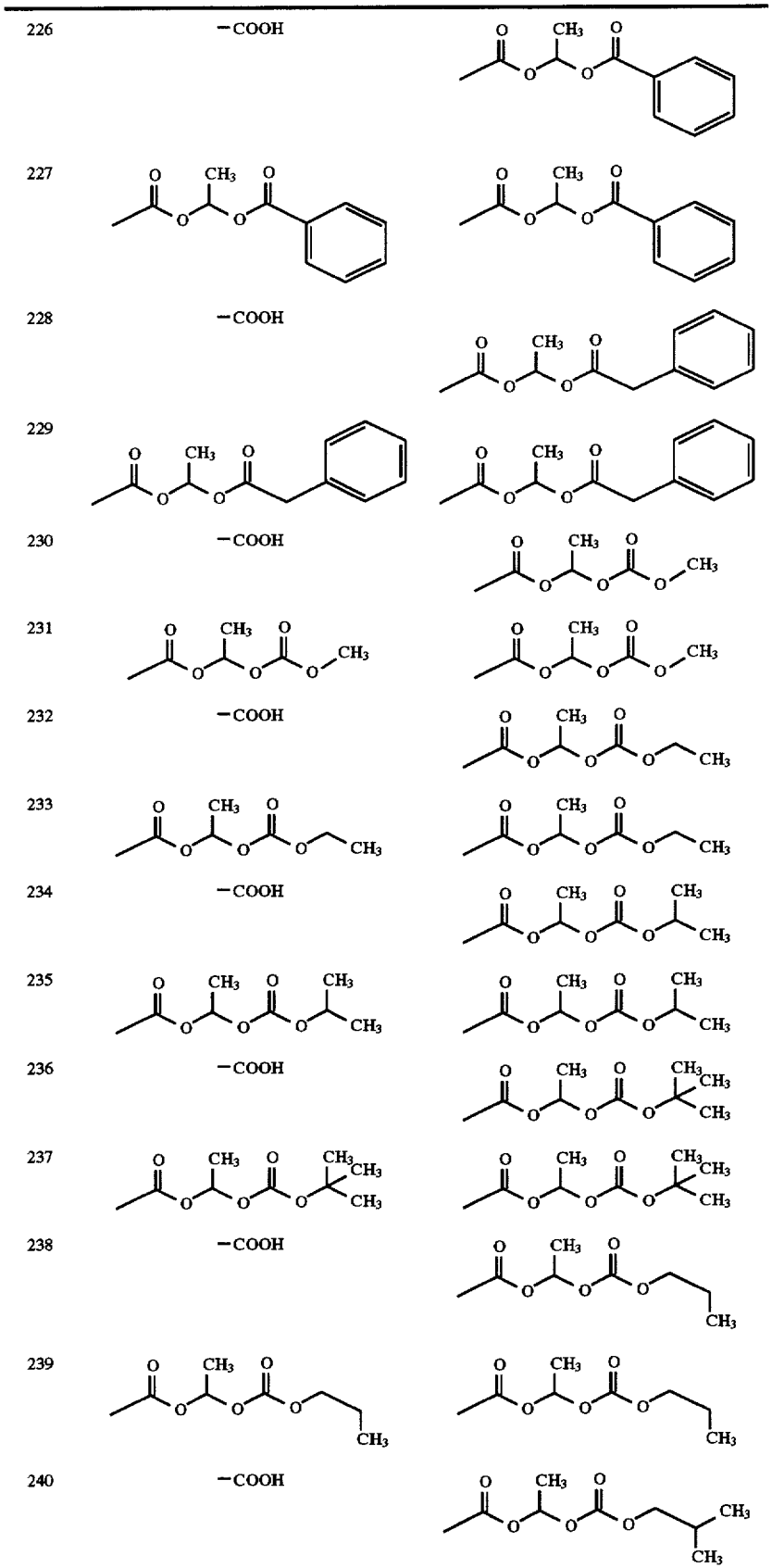 |
| 227 | | |
| 228 | —COOH | |
| 229 | | |
| 230 | —COOH | |
| 231 | | |
| 232 | —COOH | |
| 233 | | |
| 234 | —COOH | |
| 235 | | |
| 236 | —COOH | |
| 237 | | |
| 238 | —COOH | |
| 239 | | |
| 240 | —COOH | |

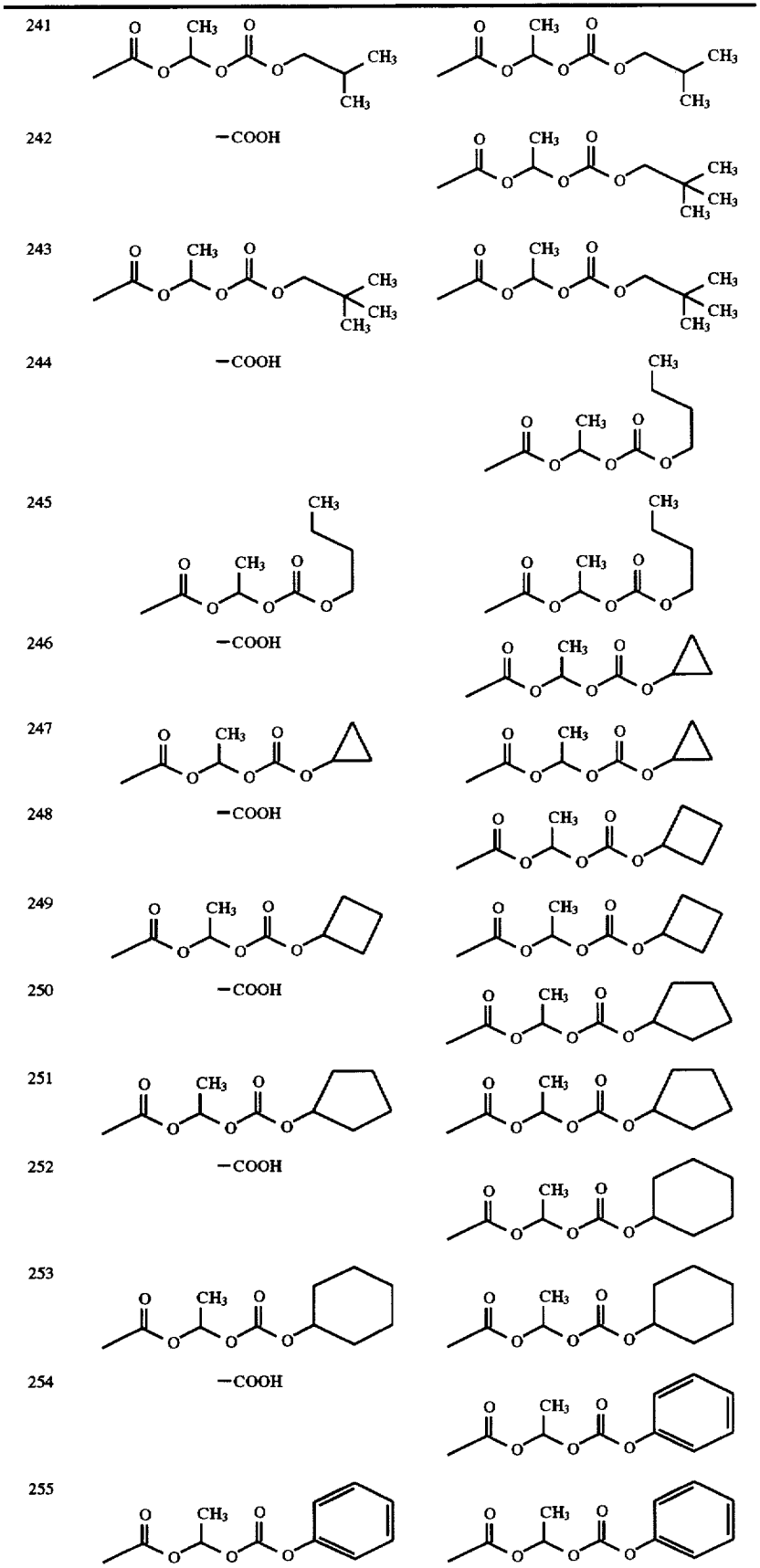

-continued
| | | |
|---|---|---|
| 256 | —COOH | 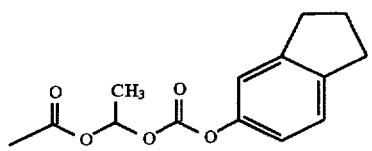 |
| 257 | 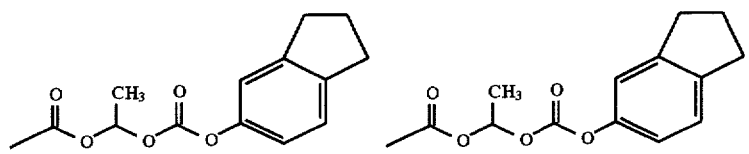 | |
| 258 | —COOH | 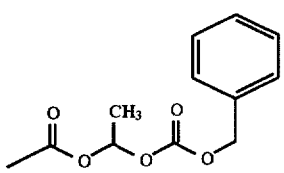 |
| 259 | 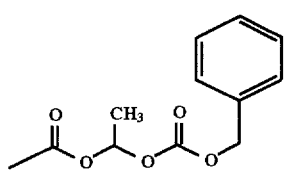 | 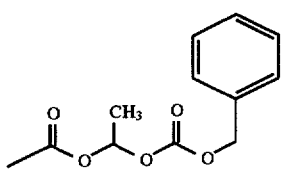 |
| 260 | —COOH | 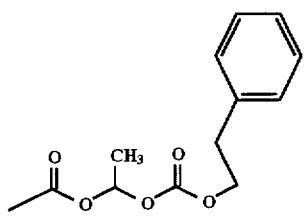 |
| 261 | 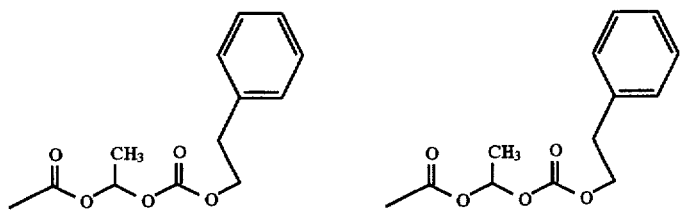 | |
| 262 | —COOH | 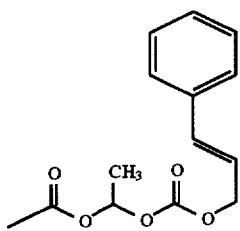 |
| 263 | 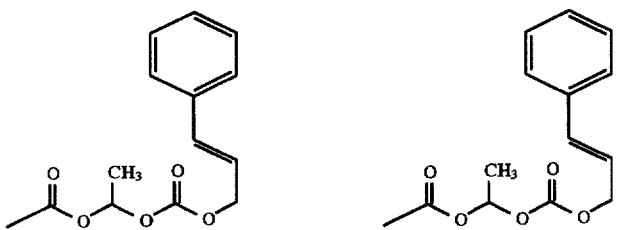 | |

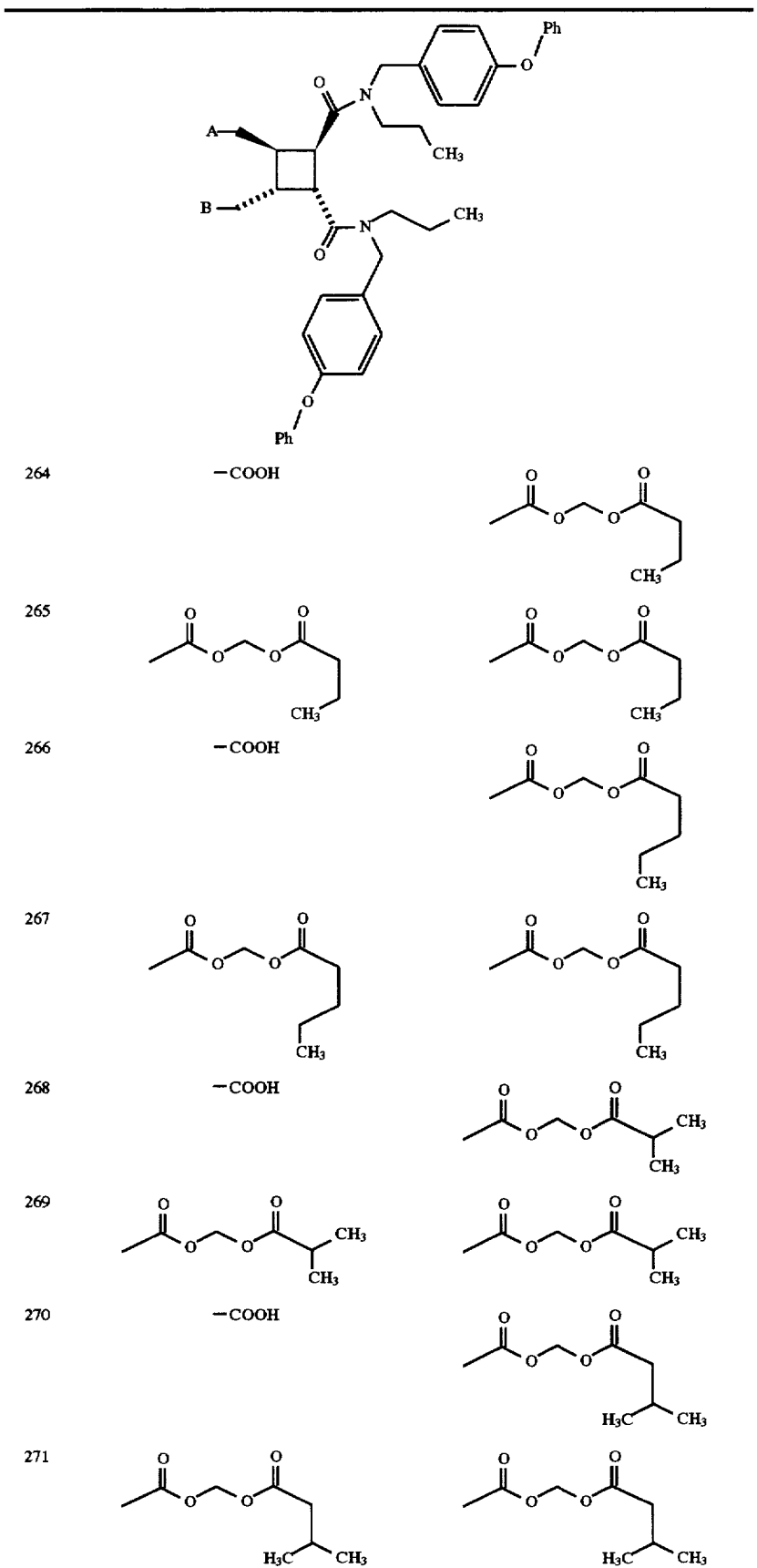

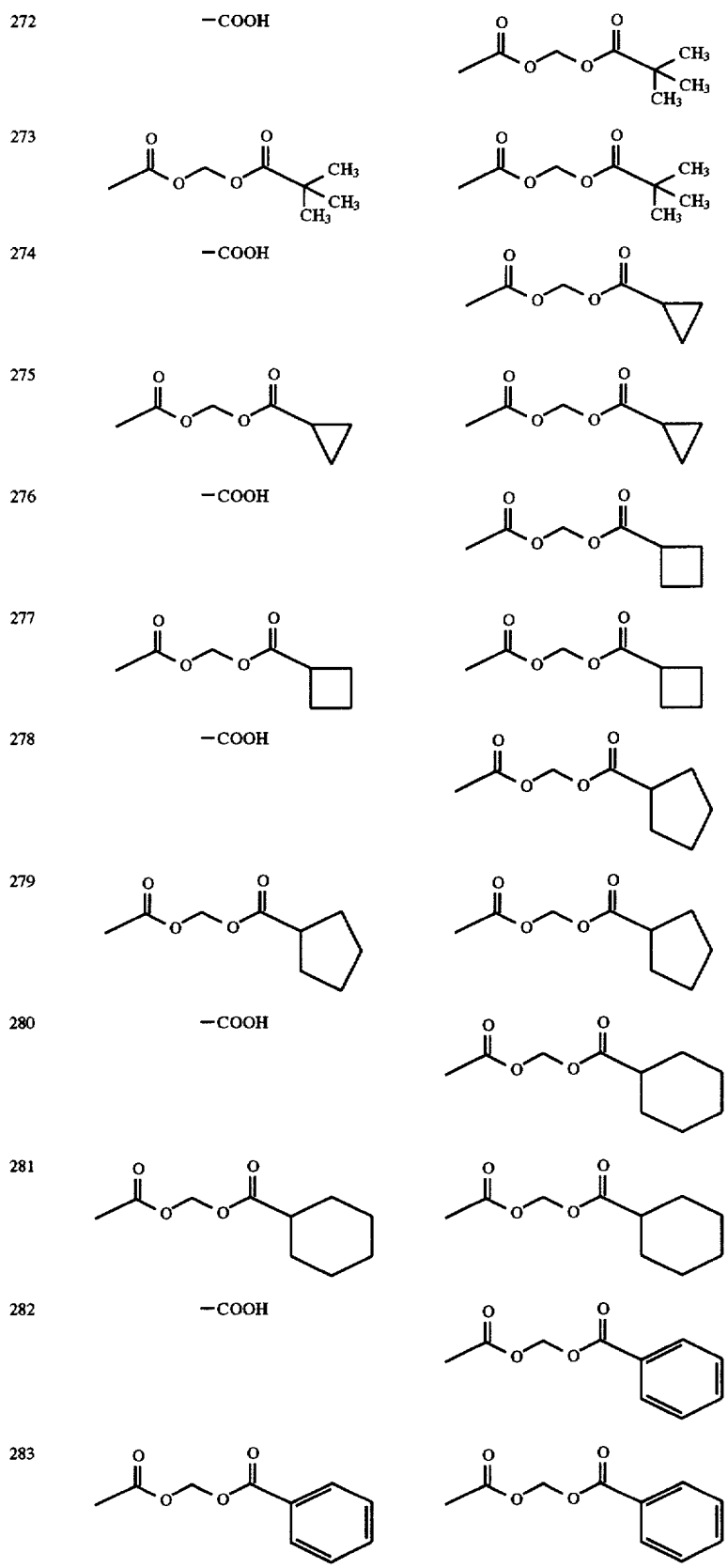

| | | |
|---|---|---|
| 284 | —COOH | 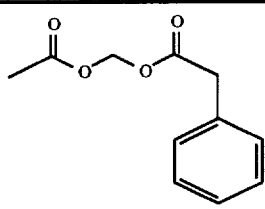 |
| 285 | 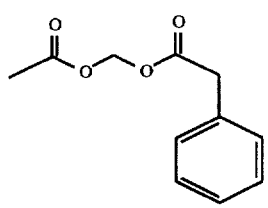 | 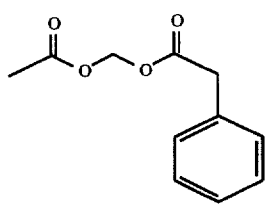 |
| 286 | —COOH | 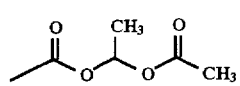 |
| 287 | 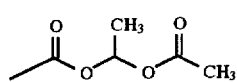 | 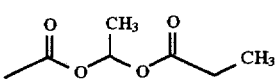 |
| 288 | —COOH | 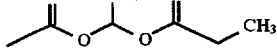 |
| 289 | 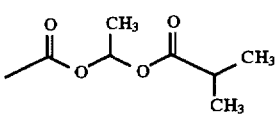 | 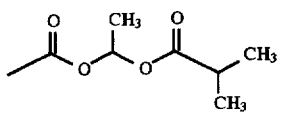 |
| 290 | —COOH | 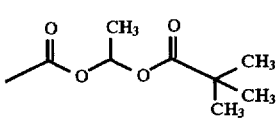 |
| 291 | 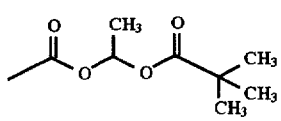 | 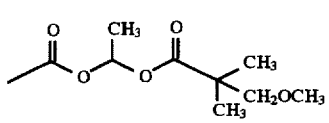 |
| 292 | —COOH | 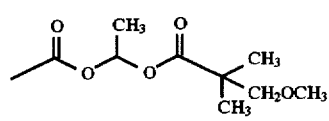 |
| 293 | 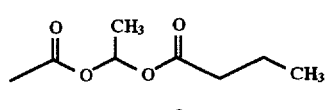 | 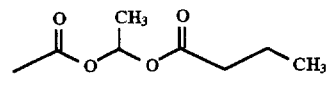 |
| 294 | —COOH | |
| 295 | | |
| 296 | —COOH | |
| 297 | | |

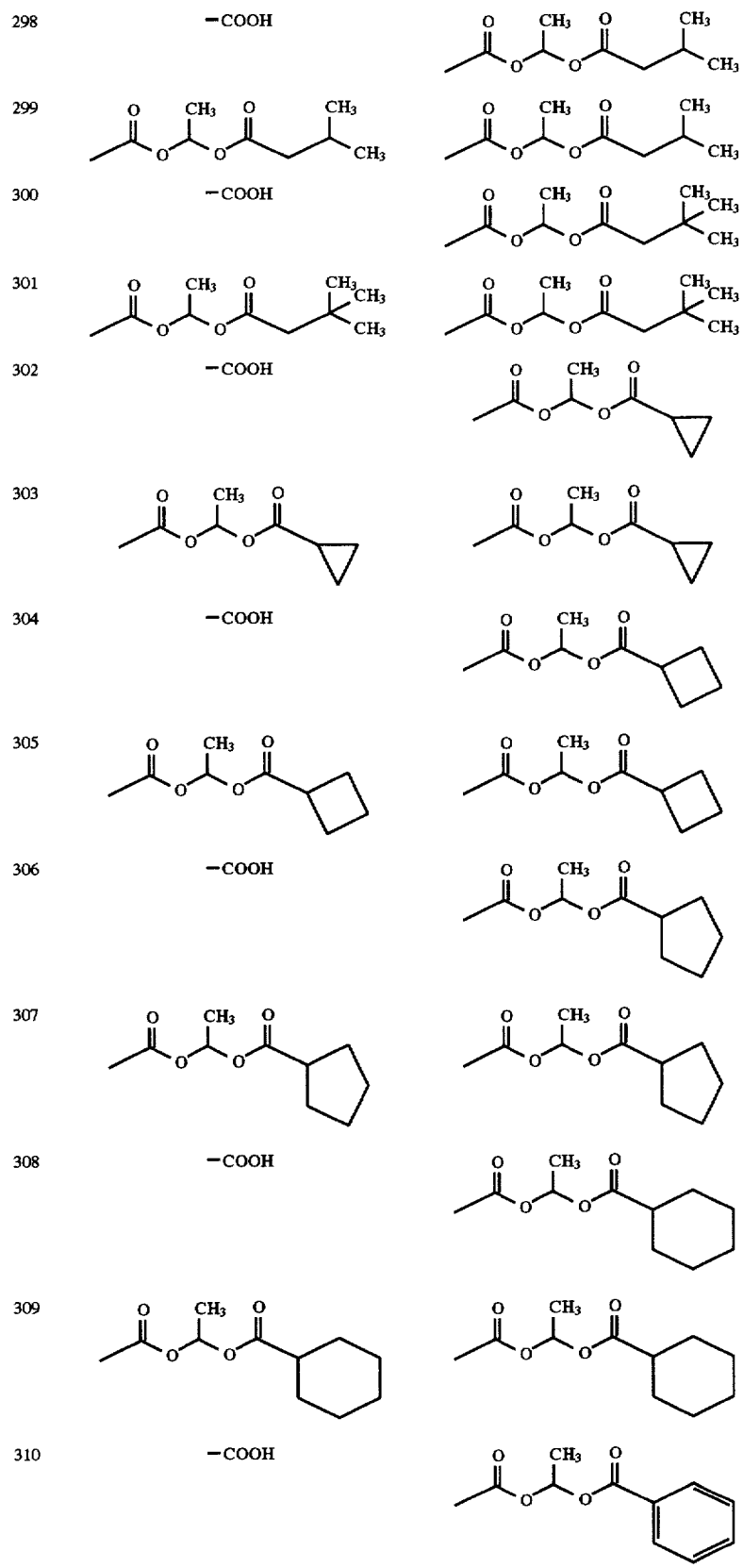

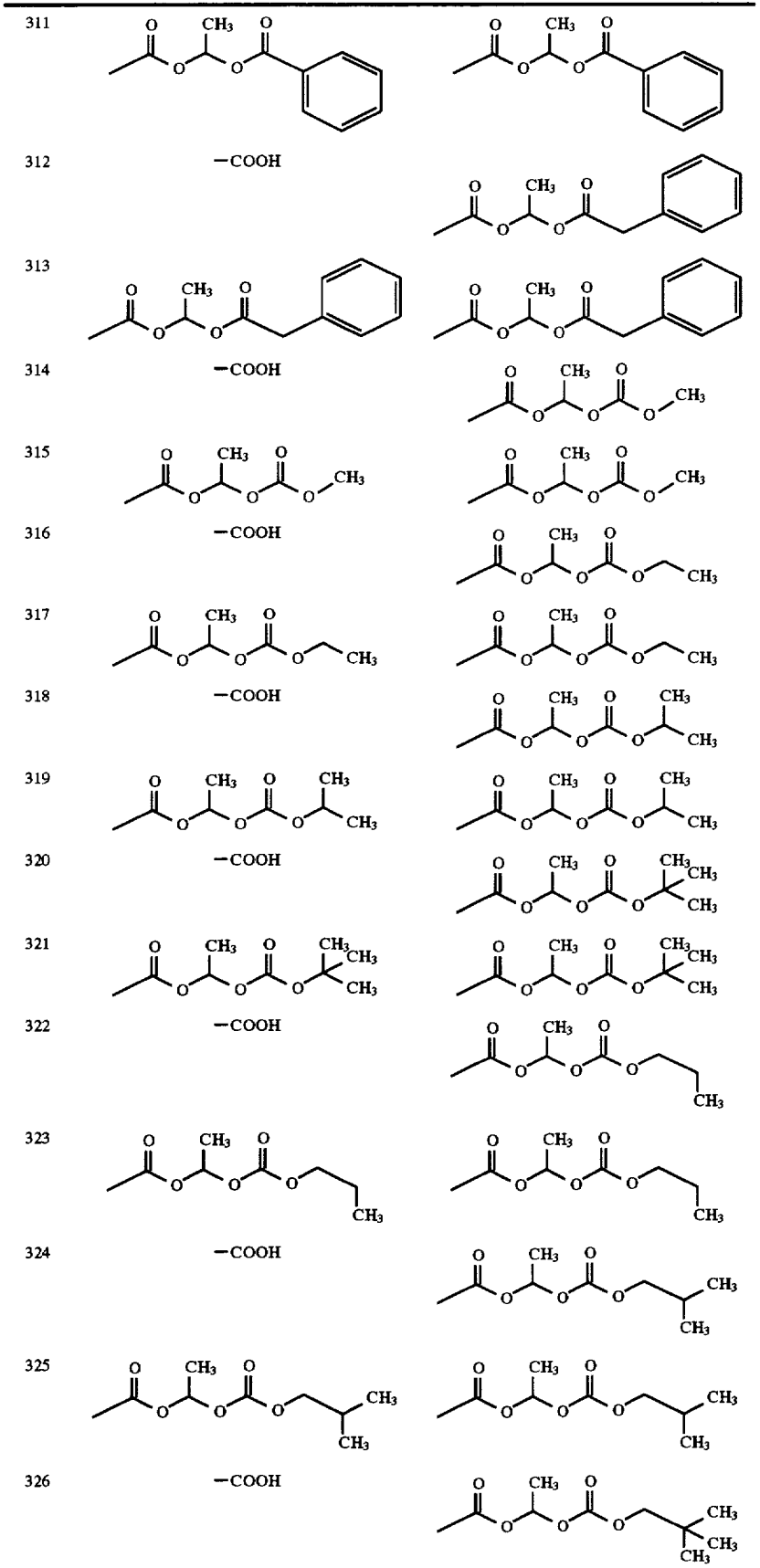

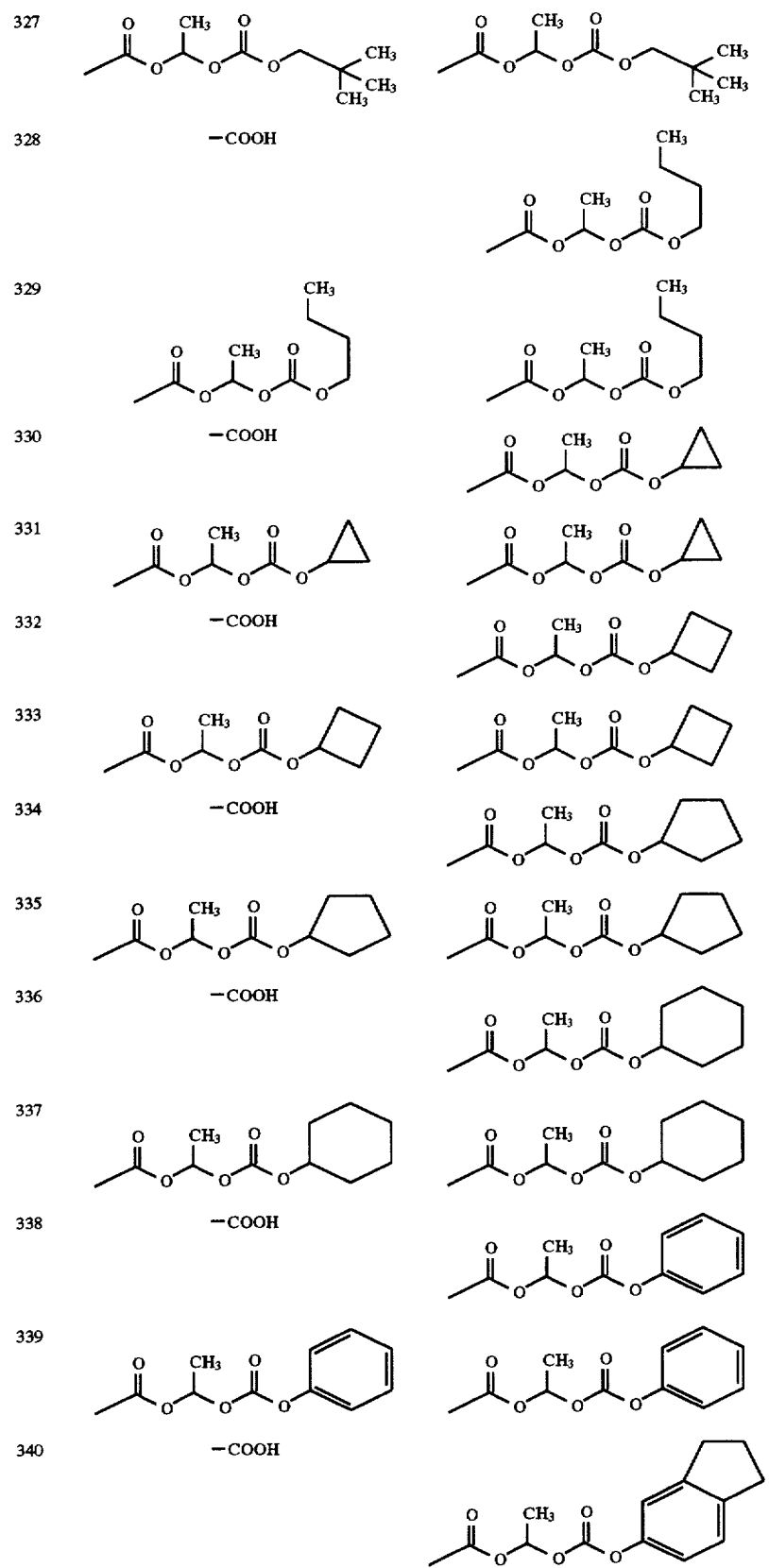

-continued
| | | |
|---|---|---|
| 341 | | 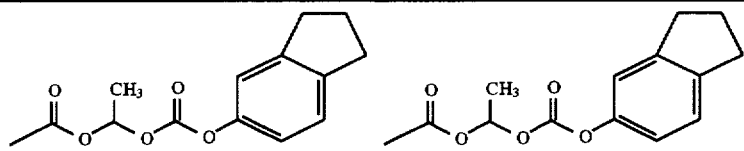 |
| 342 | —COOH | 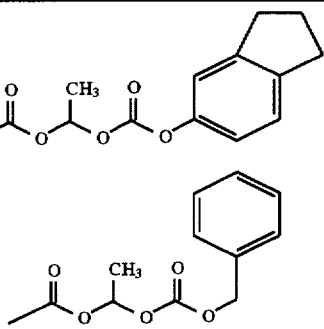 |
| 343 | 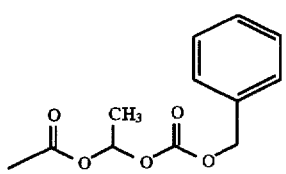 | 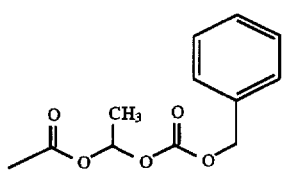 |
| 344 | —COOH | 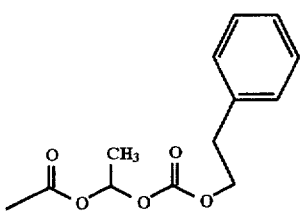 |
| 345 | 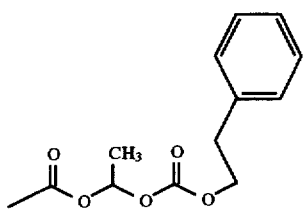 | 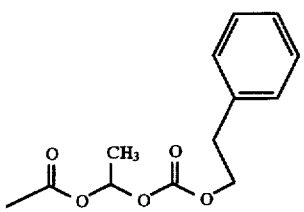 |
| 346 | —COOH | 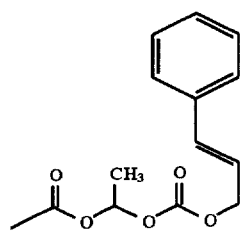 |
| 347 | 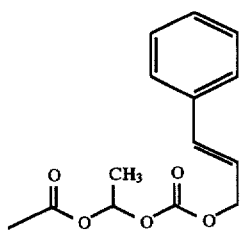 | 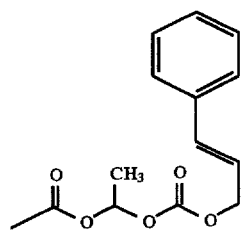 |
EXAMPLES 348–379
The following compounds can be prepared according to the methods described in the previous examples, particularly Examples 131, 132, 133 and 134.
| Ex. No. | Name |
|---|---|
| 348 | (1α,2β,3β,4α)-1,2-Di[N-(R)-α-ethylbenzyl-N-(4-phenoxyphenyl)aminocarbonyl]-cyclobutane-3,4-dicarboxylic acid |

| Ex. No. | Name |
|---|---|
| 349 | (1α,2β,3β,4α)-1,2-Di[N-(S)-α-ethylbenzyl-N-(4-phenoxyphenyl)aminocarbonyl]-cyclobutane-3,4-dicarboxylic acid |
| 350 | (1α,2β,3β,4α)-1,2-Di[N-(R)-α-propyl-(4-phenoxybenzyl)aminocarbonyl]cyclobutane-3,4-dicarboxylic acid |
| 351 | (1α,2β,3β,4α)-1,2-Di[N-(S)-α-propyl-(4-phenoxybenzyl)aminocarbonyl]cyclobutane-3,4-dicarboxylic acid |
| 352 | (1α,2β,3β,4α)-1,2-Di[N-propyl-N-(R)-α-propyl-(4-phenoxybenzyl)aminocarbonyl]-cyclobutane-3,4-dicarboxylic acid |
| 353 | (1α,2β,3β,4α)-1,2-Di[N-propyl-N-(R)-α-propyl-(4-phenoxybenzyl)aminocarbonyl]-cyclobutane-3,4 dicarboxylic acid |
| 354 | (1α,2β,3β,4α)-1,2-Di[N-benzyl-N-(R)-α-propyl-(4-phenoxybenzyl)aminocarbonyl]-cyclobutane-3,4-dicarboxylic acid |
| 355 | (1α,2β,3β,4α)-1,2-Di[N-benzyl-N-(S)-α-propyl-(4-phenoxybenzyl)aminocarbonyl]-cyclobutane-3,4 dicarboxylic acid |
| 356 | (1α,2β,3β,4α)-1,2-Di[N-(cyclopropylmethyl)-N-(R)-α propyl-(4-phenoxybenzyl)-aminocarbonyl]cyclobutane-3,4-dicarboxylic acid |
| 357 | (1α,2β,3β,4α)-1,2-Di[N-(cyclopropylmethyl)-N-(S)-α-propyl-(4-phenoxybenzyl)-aminocarbonyl]cyclobutane-3,4-dicarboxylic acid |
| 358 | (1α,2β,3β,4α)-1,2-Di[N-(R)-α-ethyl-(4-phenoxybenzyl)aminocarbonyl]cyclobutane-3,4-dicarboxylic acid |
| 359 | (1α,2β,3β,4α)-1,2-Di[N-(S)-α-ethyl-(4-phenoxybenzyl)aminocarbonyl]cyclobutane-3,4-dicarboxylic acid |
| 360 | (1α,2β,3β,4α)-1,2-Di[N-propyl-N-(R)-α-ethyl-N-(4-phenoxybenzyl)aminocarbonyl]-cyclobutane-3,4-dicarboxylic acid |
| 361 | (1α,2β,3β,4α)-1,2-Di[N-propyl-N-(3)-α-ethyl-N-(4-phenoxybenzyl)aminocarbonyl]-cyclobutane-3,4-dicarboxylic acid |
| 362 | (1α,2β,3β,4α)-1,2-Di[N-benzyl-N-(R)-α-ethyl-N-(4-phenoxybenzyl)aminocarbonyl]-cyclobutane-3,4-dicarboxylic acid |
| 363 | (1α,2β,3β,4α)-1,2-Di[N-benzyl-N-(S)-α-ethyl-N-(4 phenoxybenzyl)aminocarbonyl]-cyclobutane-3,4 dicarboxylic acid |
| 364 | (1α,2β,3β,4α)-1,2-Di[N-(cyclopropylmethyl)-N-(R)-α-ethyl-(4-phenoxybenzyl)-aminocarbonyl]cyclobutane-3,4-dicarboxylic acid |
| 365 | (1α,2β,3β,4α)-1,2-Di[N-(cyclopropylmethyl)-N-(S)-α-ethyl-(4-phenoxybenzyl)-aminocarbonyl]cyclobutane-3,4-dicarboxylic acid |
| 366 | (1α,2β,3β,4α)-1,2-Di[N-(R)-α-methyl-(4-phenoxybenzyl)aminocarbonyl]-cyclobutane-3,4 dicarboxylic acid |
| 367 | (1α,2β,3β,4α)-1,2-Di[N-(S)-α-methyl-(4 phenoxybenzyl)aminocarbonyl]-cyclobutane-3,4-dicarboxylic acid |
| 368 | (1α,2β,3β,4α)-1,2-Di[N-propyl-N-(R)-α-methyl-(4-phenoxybenzyl)aminocarbonyl]-cyclobutane-3,4-dicarboxylic acid |
| 369 | (1α,2β,3β,4α)-1,2-Di[N-propyl-N-(S)-α-methyl-(4-phenoxybenzyl)aminocarbonyl]-cyclobutane-3,4-dicarboxylic acid |
| 370 | (1α,2β,3β,4α)-1,2-Di[N-benzyl-N-(R)-α-methyl-(4-phenoxybenzy)aminocarbonyl]-cyclobutane-3,4-dicarboxylic acid |
| 371 | (1α,2β, 3β,4α)-1,2-Di[N-benzyl-N-(S)-α-methyl-(4-phenoxybenzyl)aminocarbonyl]-cyclobutane-3,4-dicarboxylic acid |
| 372 | (1α,2β,3β,4α)-1,2-Di[N-(cyclopropylmethyl)-N-(R)-α-methyl-(4-phenoxybenzyl)-aminocarbonyl]cyclobutane-3,4-dicarboxylic acid |
| 373 | (1α,2β,3β,4α)--Di[N-(cyclopropylmethyl)-N-(S)-α-methyl-(4-phenoxybenzyl)-aminocarbonyl]cyclobutane-3,4-dicarboxylic acid |
| 374 | (1α,2β,2β,4α)-1,2-Di[N-(R)-α-(cyclopropylmethyl)-(4 phenoxybenzyl)amino-carbonyl]cyclobutane-3,4 dicarboxylic acid |
| 375 | (1α,2β,3β,4α)-1,2-Di[N-(S)-α-(cyclopropylmethyl)-(4 phenoxy benzyl)amino-carbonyl]cyclobutane-3,4-dicarboxylic acid |
| 376 | (1α,213,3β,4α)-1,2-Di[N-benzyl-N-(R)-α-(cyclopropylmethyl)-(4-phenoxybenzyl)-aminocarbonyl]cyclobutane-3,4-dicarboxylic acid |
| 377 | (1α,2β,3β,4α)-1,2-Di[N-benzyl-N-(S)-α-(cyclopropylmethyl)-(4-phenoxybenzyl)-aminocarbonyl]cyclobutane-3,4-dicarboxylic acid |
| 378 | (1α,2β,3β,4α)-1,2-Di[N-(cyclopropylmethyl)-N-(R)-α-(cyclopropylmethyl)-(4-phenoxybenzyl)aminocarbonyl]cyclobutane-3,4-dicarboxylic acid |
| 379 | (1α,2β,3β,4α)-1,2-Di[N-(cyclopropylmethyl)-N-(S)-α-(cyclopropylmethyl)-(4 phenoxybenzyl)aminocarbonyl]cyclobutane-3,4 dicarboxylic acid |

Inhibition of Squalene Synthetase

In vitro inhibition of squalene synthetase may be measured by the following procedure.

Rat liver microsomal squalene synthetase activity was measured using farnesyl pyrophosphate as a substrate and quantitating squalene synthesis using labelled farnesyl pyrophosphate and counting the squalene formed.

Rat liver microsome, the source of enzyme, was prepared according to the method of Gillies, P. J., et al., Exp. Molc. Pathol. 44: 329–339 (1986), a modification of the procedure of Erickson, S. K., and Cooper, A. D., Metabolism, 29: 991–996 (1980). Approximately 30 µg of microsomal protein was incubated for 10 minutes at 37° C. with 5–11 µmol of $^3$H-farnesyl pyrophosphate, 49 mCi/mmol, and at least three concentrations of test compound in the presence of squalene (2 µL), $Mg^{++}$, KF, reduced B-nicotinamide adenine dinucleotide phosphate, dithiothreitol, and $K_2PO_4$, pH 7.35, in a total volume of 200 µL. Oxygen was excluded from the closed incubation tube by degassing with nitrogen. The reaction was terminated by the addition of ethanolic KOH and after degassing with $N_2$, the microsomal membranes were solubilized by heating at 60° C. for 30 minutes. The squalene was extracted into hexane, and the squalene was separated from all other radioactive molecules by passage over an activated alumina column. The solution was collected in scintillation vials, evaporated to dryness, liquid scintillation fluid was added, and the radioactivity was determined in a liquid scintillation counter. The per cent inhibition at a dose of 10 µM (or 1 µM) compared to controls with no test compound was determined. The % inhibition values for the compounds of the invention are shown in Table 1. The data show that compounds of the invention are inhibitors of squalene synthetase.

TABLE 1

In vitro Inhibition of Squalene Synthetase

| Ex. No. | % Inhibition at 10 µM | Ex. No. | % Inhibition at 10 µM |
|---|---|---|---|
| 13 | 54 | 14 | 31 |
| 15 | 99 | 16 | 40* |
| 17 | 88* | 18 | 55 |
| 19 | 86 | 20 | 50 |
| 21 | 52 | 22 | 20 |
| 23 | 65* | 24 | 77* |
| 25 | 84 | 26 | 89* |

TABLE 1-continued

In vitro Inhibition of Squalene Synthetase

| Ex. No. | % Inhibition at 10 μM | Ex. No. | % Inhibition at 10 μM |
|---|---|---|---|
| 27 | 79 | 28 | 91 |
| 29 | 72* | 30 | 67 |
| 31 | 37* | 34 | 89 |
| 35 | 59* | 36 | 63 |
| 37B | 91 | 38H | 51 |
| 39C | 59 | 40B | 82 |
| 41B | 72* | 42 | 81* |
| 43 | 47* | 44 | 56* |
| 45 | 50* | 47B | 87 |
| 48 | 79* | 53B | 63* |
| 54B | 74 | 55 | 78 |
| 56 | 86 | 57 | 64 |
| 58 | 63 | 59 | 50 |
| 60 | 65* | 61B | 43 |
| 62B | 83 | 63 | 90 |
| 64D | 45 | 65B | 58 |
| 66C | 33 | 67C | 87 |
| 68B | 84* | 69E | 56* |
| 70B | 80 | 71C | 77 |
| 72C | 51* | 73B | 75* |
| 74D | 55* | 75B | 73* |
| 76B | 57* | 77B | 51* |
| 78B | 82* | 79B | 83 |
| 81B | 73 | 82B | 67 |
| 83B | 85 | 84G | 89 |
| 85 | 56* | 86D | 86 |
| 87B | 72 | 88 | 86 |
| 89C | 88 | 90 | 53 |
| 91 | 62 | 92B | 80* |
| 95 | 78 | 96B | 76 |
| 97 | 72 | 98C | 84 |
| 99B | 80 | 100C | 84 |
| 101C | 86* | 102 | 58 |
| 103B | 90 | 104A | 70* |
| 104B | 71* | 105A | 48* |
| 105B | 57* | 106 | 92 |
| 107 | 75* | 108 | 59* |
| 109 | 78* | 110A | 73* |
| 110B | 69* | 111 | 49* |
| 112 | 21* | 113 | 31* |
| 115B | 75 | 116 | 79 |
| 117 | 53* | 118B | 51 |
| 119C | 45* | 120 | 54 |
| 121 | 44 | 122B | 57 |
| 127C | 68* | 128F | 80* |
| 129B | 92* | 130B | 48* |
| 153B | 35* | 155B | 19* |
| 164D | 95* | 165C | 90* |
| 166B | 87* | 167E | 88* |
| 168I | 75* | 169B | 84* |
| 170B | 57* | 171 | 33 |
| 172B | 84* | 173 | 41* |
| 174 | 28* | 175 | 74* |
| 179D | 94 | 180G | 67* |
| 181C | 54* | 182 | 75* |
| 183D | 55* | 184B | 57* |
| 185B | 95 | 186D | 39 |
| 187 | 93 | 188C | 94 |
| 190 | 83* | 191 | 80** |
| 192 | 64** | 193 | 59* |
| 194 | 95* | 195 | 87* |
| 196 | 81* | | |

*% Inhibition at 1 μM
**% Inhibition at 0.1 μM

In vivo Inhibition of Cholesterol Synthesis

Monkeys, Cynomolgus, 2 males and 2 females per group, Controls: 3.7–6.1 Kg body weight, Dosed animals: 4.8–5.6 Kg body weight) were fasted overnight and bled in the morning. Plasma samples were prepared and analyzed for total cholesterol, HDL-cholesterol and triglycerides. The treated animals were dosed with the product of Example 17, 20 mg/kg, po, while control monkeys were dosed with vehicle containing 0.2% Methocel (hydroxypropylmethyl cellulose) in water. Dosing was continued daily for a total of 5 days. Prior to the last dose the animals were fasted overnight and bled after dosing but before feeding. Plasma samples (anticoagulated with EDTA) were prepared and analyzed as before. One-sample t-tests were calculated to test for significant change within a group across the experiment. Total plasma cholesterol was lowered an average of 15.5% in the monkeys that received the product of Example 17.

Inhibition of Protein Farnesyltransferase

In vitro inhibition of protein farnesyltransferase can be measured by the following procedure. (Procedures for determination of the inhibition of farnesylation of the oncogene protein Ras are described by Goldstein, et al., J. Biol. Chem., 266: 15575–15578 (1991) and by Singh in U.S. Pat. No. 5,245,061.)

Rat brain protein farnesyltransferase activity was measured using the biotin-lamin substrate (which is known to undergo farnesylation in a manner analogous to Ras protein) and radioactive farnesyl diphosphate provided by Amersham Life Science in their commercial scintillation proximity assay kit for the determination of farnesyltransferase. Alternatively, rat brain protein farnesyltransferase activity was measured using an Amersham Life Science commercial scintillation proximity assay kit and substituting a biotin-K Ras B fragment (biotin-Lys-Lys-Ser-Lys-Thr-Lys-Cys-Val-Ile-Met-$CO_2H$), 0.1 μM final concentration, for the biotin-lamin substrate provided by Amersham. The enzyme was purified according to Reiss, Y., et al., Cell, 62: 81–88 (1990), utilizing steps one through three. The specific activity of the enzyme used is approximately 10 nmol substrate farnesylated/mg enzyme/hour. The percent inhibition of the farnesylation caused by the compounds of the invention (at $1\times10^{-5}M$) compared to an uninhibited control sample was evaluated in the same Amersham test system.

The compounds of the present invention can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, parnoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides (such as methyl, ethyl, propyl, and butyl chloride, bromides, and iodides), dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

The compounds of the invention are useful (in humans and other mammals) for inhibiting squalene synthase. The compounds of the invention are also useful for inhibiting cholesterol biosynthesis. The compounds of the invention are also useful for treating atherosclerosis and inhibiting progression of atherosclerosis. The compounds of the invention are also useful for treating hyperlipidemia. The compounds of the invention are also useful for treating fungal infections.

The compounds of the invention are also useful for treating acne in humans. Methods to demonstrate this activity, appropriate doses and means of administration are disclosed in PCT patent application WO 94/22870, published Oct. 13, 1994 which is incorporated herein by reference.

The ability of the compounds of the invention to inhibit cholesterol biosynthesis can be demonstrated in vivo according to the following method. The in vivo inhibition of cholesterol synthesis can be determined in a monkey model in which the monkeys are dosed, fasted overnight and bled in the morning. Plasma samples are prepared and analyzed for total cholesterol, HDL-cholesterol and triglycerides.

The ability of the compounds of the invention to treat fungal infections can be demonstrated according to the method described by S. Shadomy and M. A. Pfaller. 1991. Laboratory Studies with Antifungal Agents: Susceptibility Tests and Quantitation in Body Fluids, pp. 1173–1183. In A. Balows, W. J. Hausler, Jr., K. L. Herrmann, H. Isenberg and H. J. Shadomy, Eds. Manual of Clinical Microbiology, 5th Ed. American Society for Microbiology, Washington, D.C. The antifungal activity of squalene synthase inhibitors has been reported by a number of researchers including Dufresne, et al., Tetrahedron 48/47 10221–10226 (1992) and Dawson, M. J., et al., J. Antibiot. (Tokyo) 45: 639–647 (1992).

The compounds of the invention are useful (in humans and other mammals) for inhibiting protein farnesyltransferase and the farnesylation of Ras. These inhibitors of protein farnesyltransferase are also useful for inhibiting or treating cancer in humans and other mammals. Examples of the kinds of cancers which may be treated or inhibited with the compounds of the invention include, but are not limited to, carcinomas, such as lung, colorectal, exocrine pancreatic, cervical, esophageal, stomach, and small intestinal; sarcomas, such as oesteroma, osteosarcoma, lepoma, liposarcoma, hemanioma, and hemangiosarcoma; melanomas, such as amelanotic and melanotic; mixed types of cancers such as carcinosarcoma, lymphoid tissue type, follicular reticulum, cell sarcoma and Hodgkins disease; and leukemias, such as myeloid, acute lymphoblastic, chronic lymphocytic, acute myloblastic and chronic mylocytic.

The ability of the compounds of the invention to inhibit or treat carcinoma can be demonstrated according to the methods referenced below; the determination of in vitro and in vivo anti-cancer activity of several different classes of compounds is described. Mazerska Z., Woynarowska B., Stefanska B., Borowski S., Drugs Exptl. Clin. Res. 13(6): 345–351 (1987). Bissery, M.C., Guenard F., Guerritte-Voegelein F., Lavelle F., Cancer Res. 51: 4845–4852 (1991). Rose W., Anti-cancer Drugs 3: 311–321 (1992). Rygaard J., and Povisen C. O., Acta Pathol. Microbiol. Scand. 77: 758 (1969).

These inhibitors of protein farnesyltransferase are also useful for preventing restenosis in humans and other mammals. The ability of the compounds of the invention to prevent restenosis can be demonstrated according to the methods described by Kranzhofer, R. et al. Circ. Res. 73: 264–268 (1993), Mitsuka, M. et al. Circ. Res. 73: 269–275 (1993) and Santoian, E. C. et al. Circulation 88: 11–14 (1993).

For inhibition of squalene synthetase, the total daily dose administered to a host in single or divided doses may be in amounts, for example, from 0.001 to 1000 mg/kg body weight daily and more preferred from 1.0 to 30 mg/kg body weight daily. Dosage unit compositions may contain such amounts of submultiples thereof to make up the daily dose.

For use as a chemotherapeutic agent, the total daily dose administered to a host in single or divided doses may be in amounts, for example, from 0.01 to 500 mg/kg body weight daily, preferably in amounts from 0.1 to 20 mg/kg body weight daily and more preferably in amounts from 0.5 to 10 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they can also be used in combination with one or more other cardiovascular agents independently selected from HMG CoA reductase inhibitors, antihyperlipoproteinemic agents and serum cholesterol lowering agents.

Representative HMG CoA reductase inhibitors include lovastatin, pravastatin, velostatin, simvastatin and the like.

Representative antihyperlipoproteinemic agents include probucol and the like.

Representative serum cholesterol lowering agents include gemfibrozil), bile acid sequestrants such as cholestyramine, colestipol, polidexide, DEAE-Sephadex, clofibrate, nicotinic acid and its derivatives, neomycin, p-aminosalicylic acid, bezafibrate and the like.

The above compounds to be employed in combination with the squalene synthetase inhibitor of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other cardiovascular agent can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents.

While the compounds of the invention can be administered as the sole active pharmaceutical agent for the inhibition or treatment of cancer, they can also be used in combination with one or more other chemotherapeutic agents.

Representative examples of chemotherapeutic agents are described in Holleb, et al., *Clinical Oncology*, American Cancer Society, United States (1991) p 56 et seq. These agents include alkylating agents such as the nitrogen mustards (mechloethamine, melphalan, chlorambucil, cyclophosphamide and ifosfamide), nitrosoureas (carmustine, lomustine, semustine, streptozocin), alkyl sulfonates (busulfan), triazines (dacarbazine) and ethyenimines (thiotepa, hexamethylmelamine); folic acid analogues (methotrexate); pyrimidine analogues (5-fluorouracil, cytosine arabinoside); purine analogues (6-mercaptopurine, 6-thioguanine); antitumor antibiotics (actinomycin D, the anthracyclines (doxorubicin), bleomycin, mitomycin C, methramycin); plant alkaloids such as vinca alkaloids (vincristine, vinblastine) and etoposide (VP-16); hormones and hormone antagonists (tamoxifen and corticosteroids); and miscellaneous agents (cisplatin, taxol, brequinar).

The above compounds to be employed in combination with the farnesyl protein transferase inhibitor of the invention will be used in therapeutic amounts as indicated in the Physicians' Desk Reference (PDR) 47th Edition (1993), which is incorporated herein by reference, or such therapeutically useful amounts as would be known to one of ordinary skill in the art.

The compounds of the invention and the other chemotherapeutic agent can be administered at the recommended maximum clinical dosage or at lower doses. Dosage levels of the active compounds in the compositions of the invention may be varied so as to obtain a desired therapeutic response depending on the route of administration, severity of the disease and the response of the patient.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

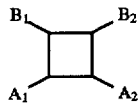

wherein $A_1$ and $A_2$ are independently selected from —C(O)—G wherein G is —N($R_1$)($R_2$) wherein at each occurrence $R_1$ is independently selected from (a) loweralkyl, (b) cycloalkyl and (c) cycloalkylalkyl and at each occurrence $R_2$ is independently selected from aryl and arylalkyl wherein the aryl group or aryl part of the arylalkyl group is substituted with —Z—$R_4$ wherein at each occurrence Z is independently selected from (i) —O— and (ii) —S— and at each occurrence $R_4$ is independently selected from (i) aryl, (ii) arylalkyl, (iii) cycloalkyl, (iv) cycloalkylalkyl, (v) heterocyclic and (vi) (heterocyclic)alkyl and $B_1$ and $B_2$ are independently selected from —Q—C(O)—$R_6$, —W—$R_5$ and

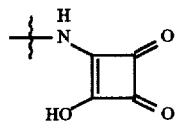

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

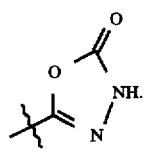

2. A compound according to claim 1 wherein $A_1$ and $A_2$ are independently selected from —C(O)—G wherein G is —N($R_1$)($R_2$) wherein at each occurrence $R_1$ is independently selected from (a) loweralkyl, (b) cycloalkyl and (c) cycloalkylalkyl and at each occurrence $R_2$ is independently selected from phenyl and benzyl wherein the phenyl group or the phenyl ring of the benzyl group is substituted with —Z—$R_4$ wherein at each occurrence Z is independently selected from (i) —O— and (ii) —S— and at each occurrence $R_4$ is independently selected from (i) aryl, (ii) arylalkyl, (iii) heterocyclic and (iv) (heterocyclic)alkyl and $B_1$ and $B_2$ are independently selected from —Q—C(O)—$R_6$, —W—$R_5$ and

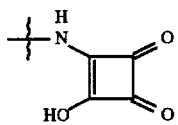

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

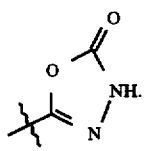

3. A compound according to claim 2 wherein $A_1$ and $A_2$ are independently selected from —C(O)—G wherein G is —N($R_1$)($R_2$) wherein at each occurrence $R_1$ is independently selected from (a) loweralkyl, (b) cycloalkyl and (c) cycloalkylalkyl and $R_2$ is benzyl wherein the phenyl ring of the benzyl group is substituted with —Z—$R_4$ wherein at each occurrence Z is independently selected from (i) —O— and (ii) —S— and $R_4$ is aryl and $B_1$ and $B_2$ are independently selected from —Q—C(O)—$R_6$, —W—$R_5$ and

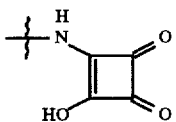

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

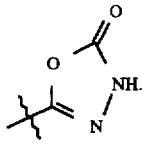

4. A compound according to claim 2 wherein $A_1$ and $A_2$ are independently selected from —C(O)—G wherein G is —N($R_1$)($R_2$) wherein at each occurrence $R_1$ is (a) loweralkyl, (b) cycloalkyl or (c) cycloalkylalkyl and $R_2$ is benzyl wherein the phenyl ring of the benzyl group is substituted with —Z—$R_4$ wherein at each occurrence Z is independently selected from (i) —O— and (ii) —S— and $R_4$ is heterocyclic and $B_1$ and $B_2$ are independently selected from —Q—C(O)—$R_6$, —W—$R_5$ and

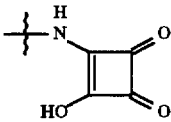

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

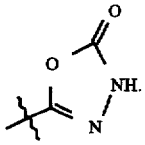

5. A compound of the formula

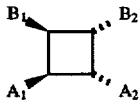

wherein $A_1$ and $A_2$ are independently selected from —C(O)—G wherein G is —N($R_1$)($R_2$) wherein at each occurrence $R_1$ is independently selected from (a) loweralkyl, (b) cycloalkyl and (c) cycloalkylalkyl and at each occurrence $R_2$ is independently selected from aryl and arylalkyl wherein the aryl group or aryl part of the arylalkyl group is substituted with —Z—$R_4$ wherein at each occurrence Z is independently selected from (i) —O— and (ii) —S— and at each occurrence $R_4$ is independently selected from (i) aryl, (ii) arylalkyl, (iii) cycloalkyl, (iv) cycloalkylalkyl, (v) heterocyclic and (vi) (heterocyclic)alkyl and $B_1$ and $B_2$ are independently selected from —Q—C(O)—$R_6$, —W—$R_5$ and

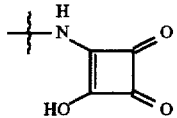

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

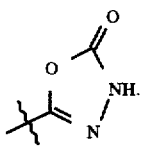

6. A compound according to claim 5 wherein $A_1$ and $A_2$ are independently selected from —C(O)—G wherein G is —N($R_1$)($R_2$) wherein at each occurrence $R_1$ is independently selected from (a) loweralkyl, (b) cycloalkyl and (c) cycloalkylalkyl and at each occurrence $R_2$ is independently selected from phenyl and benzyl wherein the phenyl group or the phenyl ring of the benzyl group is substituted with —Z—$R_4$ wherein at each occurrence Z is independently selected from (i) —O— and (ii) —S— and at each occurrence $R_4$ is independently selected from (i) aryl, (ii) arylalkyl, (iii) heterocyclic and (iv) (heterocyclic)alkyl and $B_1$ and $B_2$ are independently selected from —Q—C(O)—$R_6$, —W—$R_5$ and

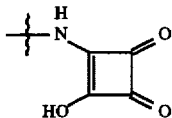

wherein at each occurrence Q and W are independently selected from a covalent bond and alkylene, $R_6$ is —$OR_7$ wherein $R_7$ is hydrogen or a carboxy-protecting group and $R_5$ is 5-tetrazolyl or

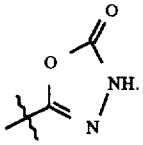

7. A compound according to claim 6 wherein $A_1$ and $A_2$ are independently selected from —C(O)—G wherein G is —N($R_1$)($R_2$) wherein at each occurrence $R_1$ is independently selected from (a) loweralkyl, (b) cycloalkyl and (c) cycloalkylalkyl and $R_2$ is benzyl wherein the phenyl ring of the benzyl group is substituted with —Z—$R_4$ wherein at each occurrence Z is independently selected from (i) —O— and (ii) —S— and $R_4$ is aryl and $B_1$ and $B_2$ are independently selected from —Q—C(O)—$R_6$, —W—$R_5$ and

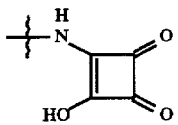

wherein at each occurrence Q and W are independently selected from a covalent bond and alkylene, R₆ is —OR₇ wherein R₇ is hydrogen or a carboxy-protecting group and R₅ is 5-tetrazolyl or

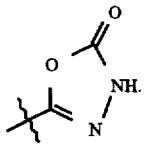

8. A compound according to claim 6 wherein

A₁ and A₂ are independently selected from —C(O)—G wherein G is —N(R₁)(R₂) wherein at each occurrence R₁ is (a) loweralkyl, (b) cycloalkyl or (c) cycloalkylalkyl and R₂ is benzyl wherein the phenyl ring of the benzyl group is substituted with —Z—R₄ wherein at each occurrence Z is independently selected from (i) —O— and (ii) —S— and R₄ is heterocyclic and B₁ and B₂ are independently selected from —Q—C(O)—R₆, —W—R₅ and

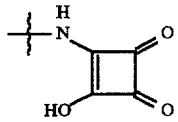

wherein at each occurrence Q and W are independently selected from a covalent bond and alkylene, R₆ is —OR₇ wherein R₇ is hydrogen or a carboxy-protecting group and R₅ is 5-tetrazolyl or

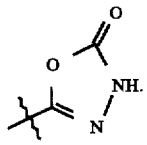

9. A compound selected from the group consisting of
(1α,2β,3β,4α)-1,2-Di(N-benzyl-N-(4-phenoxybenzyl) aminocarbonyl)cyclobutane-3,4-dicarboxylic acid;
(1α,2β,3β,4α)-1,2-Di(N-propyl-N-(4-phenoxybenzyl) aminocarbonyl)cyclobutane-3,4-dicarboxylic acid;
(−)-(1α,2β,3β,4α)-1,2-Di(N-propyl-N-(4-phenoxybenzyl) aminocarbonyl)cyclobutane-3,4-dicarboxylic acid;
(1α,2β,3β,4α)-1,2-Di(N-(2-ethylthioethyl)-N-(4-phenoxybenzyl)aminocarbonyl)cyclobutane-3,4-dicarboxylic acid;
(1α,2β,3β,4α)-1,2-Di(N-(cyclopropylmethyl)-N-(4-phenoxybenzyl)aminocarbonyl)cyclobutane-3,4-dicarboxylic acid;
(1α,2β,3β,4α)-1-(N-Propyl-N-(4-phenoxybenzyl) aminocarbonyl)-2-(N-benzyl-N-(4-phenoxybenzyl) aminocarbonyl)cyclobutane-3,4-dicarboxylic acid;
(1α,2β,3β,4α)-1,2-Di(N-propyl-N-(4-phenylthiobenzyl) aminocarbonyl)cyclobutane-3,4-dicarboxylic acid;
(1α,2β,3β,4α)-1,2-Di(N-propyl-N-(4-phenoxybenzyl) aminocarbonyl)-4-tetrazolylmethyl-cyclobutane-3-carboxylic acid;
(1α,2β,3β,4α)-1,2-Di(N-propyl-N-(4-phenoxybenzyl) aminocarbonyl)-4-(3-carboxypropionylamino) cyclobutane-3-carboxylic acid;
(1α,2β,3β,4α)-1,2-Di(N-propyl-N-(4-phenoxybenzyl) aminocarbonyl)-4-(1-carboxy-1-hydroxymethyl) cyclobutane-3-carboxylic acid;
(1α,2β,3β,4α)-1,2-Di(N-propyl-N-(4-phenoxybenzyl) aminocarbonyl)cyclobutane-3-(N-(5-tetrazolyl)) carboxamide-4-carboxylic acid;
(1α,2β,3β,4α)-4-(Carboxymethyl)-1,2-di(N-propyl-N-(4-phenoxybenzyl)aminocarbonyl)cyclobutane-3-carboxylic acid;
(1α,2β,3β,4α)-1,2-Di(-N-propyl-N-(4-phenoxybenzyl) aminocarbonyl)cyclobutane-3,4-diacetic acid;
(1α,2β,3β,4α)-1,2-Di(N-propyl-N-(4-phenoxybenzyl) aminocarbonyl)-3-(2-hydroxy-3,4-dioxocyclobut-1-enylamino)cyclobutane-4-carboxylic acid;
(1α,2β,3β,4α)-1,2-Di(N-propyl-N-(4-phenoxybenzyl) aminocarbonyl)-3-(5-oxo-4,5-dihydro-(1,3,4)oxadiazol-2-yl)cyclobutane-4-carboxylic acid;
(1α,2β,3β,4α)-1,2-Di(N-propyl-N-(4-phenoxybenzyl) aminocarbonyl)-3-(5-oxo-4,5-dihydro-(1,3,4)-oxadiazol-2-ylmethyl)cyclobutane-4-acetic acid;
(1α,2β,3β,4α)-1,2-Di(N-propyl-N-(4-phenoxybenzyl) aminocarbonyl)-3-(5-tetrazolylmethyl)cyclobutane-4-acetic acid;
(1α,2β,3β,4α)-1,2-Di(N-propyl-N-(4-phenoxybenzyl) aminocarbonyl)-3-(2-hydroxy-3,4-dioxocyclobut-1-enylamino)cyclobutane-4-carboxylic acid;
(1α,2β,3β,4α)-1,2-Di(N-propyl-N-(4-phenoxybenzyl) aminocarbonyl)-3-(5-oxo-4,5-dihydro-(1,3,4)oxadiazol-2-yl)cyclobutane-4-carboxylic acid;
(1α,2β,3β,4α)-1,2-Di(N-propyl-N-(4-phenoxybenzyl) aminocarbonyl)-3-(5-oxo-4,5-dihydro-(1,3,4)-oxadiazol-2-ylmethyl)cyclobutane-4-acetic acid;
(1α,2β,3β,4α)-1,2-Di(N-propyl-N-(4-phenoxybenzyl) aminocarbonyl)-3-(5-tetrazolylmethyl)cyclobutane-4-acetic acid;
(−)-(1α,2β,3β,4α)-1,2-Di[N-propyl-N-(4-phenoxybenzyl) aminocarbonyl]-3-(methoxycarbonyl)cyclobutane-4-carboxylic acid;
(−)-(1α,2β,3β,4α)-1,2-Di{N-propyl-N-[(4-phenoxy) benzyl]aminocarbonyl}cyclobutane-3,4-diacetic acid;
(−)-(1α,2β,3β,4α)-1,2-Di[N-propyl-N-(4-phenoxybenzyl) aminocarbonyl]-3-(5-oxo-4,5-dihydro-[1,3,4]-oxadiazol-2-ylmethyl)cyclobutane-4-acetic acid;
(−)-(1α,2β,3β,4α)-1,2-Di{N-cyclopentyl-N-[(4-phenoxy) benzyl]aminocarbonyl}cyclobutane-3,4-diacetic acid; and
(−)-(1α,2β,3β,4α)-1,2-Di[N-cyclopentyl-N-(4-phenoxybenzyl)aminocarbonyl]-3-(5-oxo-4,5-dihydro-[1,3,4]-oxadiazol-2-ylmethyl)cyclobutane-4-acetic acid;
or a pharmaceutically acceptable salt thereof.

10. (−)-(1α,2β,3β,4α)-1,2-Di[N-propyl-N-(4-phenoxybenzyl)aminocarbonyl]-3-(methoxycarbonyl) cyclobutane-4-carboxylic acid, or a pharmaceutically acceptable salt thereof.

11. A pharmaceutical composition for inhibiting squalene synthetase comprising a therapeutically effective amount of a compound according to claim 1 and a pharmaceutically acceptable carrier.

12. A pharmaceutical composition for inhibiting squalene synthetase comprising a therapeutically effective amount of a compound according to claim 5 and a pharmaceutically acceptable carrier.

13. A pharmaceutical composition for inhibiting squalene synthetase comprising a therapeutically effective amount of a compound according to claim 9 and a pharmaceutically acceptable carrier.

14. A method for inhibiting cholesterol biosynthesis in a human or lower mammal in need of such treatment comprising administering a therapeutically effective amount of a compound according to claim 1.

15. A method for inhibiting cholesterol biosynthesis in a human or lower mammal in need of such treatment comprising administering a therapeutically effective amount of a compound according to claim 5.

16. A method for inhibiting cholesterol biosynthesis in a human or lower mammal in need of such treatment comprising administering a therapeutically effective amount of a compound according to claim 9.

17. A method of treating hyperlipidaemia or atherosclerosis comprising administering to a mammal in need of such treatment a therapeutically effective amount of a compound as defined by claim 1.

18. A method of treating hyperlipidaemia or atherosclerosis comprising administering to a mammal in need of such treatment a therapeutically effective amount of a compound as defined by claim 5.

19. A method of treating hyperlipidaemia or atherosclerosis comprising administering to mammal in need of such treatment a therapeutically effective amount of a compound as defined by claim 9.

20. A method of treating a fungal infection comprising administering to a mammal in need of such treatment a therapeutically effective amount of a compound as defined by claim 1.

21. A method of treating a fungal infection comprising administering to a mammal in need of such treatment a therapeutically effective amount of a compound as defined by claim 5.

22. A method of treating a fungal infection comprising administering to a mammal in need of such treatment a therapeutically effective amount of a compound as defined by claim 9.

23. A pharmaceutical composition for inhibiting squalene synthetase comprising a therapeutically effective amount of (−)-(1α,2β,3β,4α)-1,2-Di[N-propyl-N-(4-phenoxybenzyl)-aminocarbonyl]-3-(methoxycarbonyl)cyclobutane-4-carboxylic acid, or a pharmaceutically acceptable salt thereof, and a pharmaceutically acceptable carrier.

24. A method for inhibiting cholesterol biosynthesis in a human or lower mammal in need of such treatment comprising administering a therapeutically effective amount of (−)-(1α,2β,3β,4α)-1,2-Di[N-propyl-N-(4-phenoxybenzyl) aminocarbonyl]-3-(methoxycarbonyl)cyclobutane-4-carboxylic acid, or a pharmaceutically acceptable salt thereof.

25. A method of treating hyperlipidaemia or atherosclerosis comprising administering to a mammal in need of such treatment a therapeutically effective amount of (−)-(1α,2β,3β,4α)-1,2-Di[N-propyl-N-(4-phenoxybenzyl)aminocarbonyl]-3-(methoxycarbonyl)cyclobutane-4-carboxylic acid, or a pharmaceutically acceptable salt thereof.

26. A method of treating a fungal infection comprising administering to a mammal in need of such treatment a therapeutically effective amount of (−)-(1α,2β,3β,4α)-1,2-Di[N-propyl-N-(4-phenoxybenzyl)-aminocarbonyl]-3-(methoxycarbonyl)cyclobutane-4-carboxylic acid, or a pharmaceutically acceptable salt thereof.

* * * * *

UNITED STATES PATENT AND TRADEMARK OFFICE
CERTIFICATE OF CORRECTION

PATENT NO. : 5,783,593
DATED : July 21, 1998
INVENTOR(S) : Baker et al.

It is certified that error appears in the above-identified patent and that said Letters Patent is hereby corrected as shown below:

Signed and Sealed this

Second Day of March, 1999

Attest:

Q. TODD DICKINSON

Attesting Officer

Acting Commissioner of Patents and Trademarks